(12) United States Patent
Bloksberg et al.

(10) Patent No.: US 7,087,426 B2
(45) Date of Patent: Aug. 8, 2006

(54) MATERIALS AND METHODS FOR THE MODIFICATION OF PLANT LIGNIN CONTENT

(75) Inventors: Leonard N. Bloksberg, Auckland (NZ); Ikka Havukkala, Auckland (NZ)

(73) Assignees: Agrigenesis Biosciences Ltd., Auckland (NZ); Rubicon Forests Holdings Limited, Auckland (NZ)

(*) Notice: Subject to any disclaimer, the term of this patent is extended or adjusted under 35 U.S.C. 154(b) by 161 days.

(21) Appl. No.: 10/174,693

(22) Filed: Jun. 18, 2002

(65) Prior Publication Data

US 2003/0131373 A1   Jul. 10, 2003

Related U.S. Application Data

(63) Continuation-in-part of application No. 09/615,192, filed on Jul. 12, 2000, now Pat. No. 6,410,718, and a continuation-in-part of application No. 09/169,789, filed on Oct. 9, 1998, now Pat. No. 6,653,528, which is a continuation-in-part of application No. 08/975,316, filed on Nov. 21, 1997, now Pat. No. 5,952,486, which is a continuation-in-part of application No. 08/713,000, filed on Sep. 11, 1996, now Pat. No. 5,850,020.

(60) Provisional application No. 60/143,833, filed on Jul. 14, 1999.

(51) Int. Cl.
  *C12N 15/00* (2006.01)
  *C12N 15/09* (2006.01)
  *C12N 5/04* (2006.01)
  *C12N 5/10* (2006.01)
  *C07H 21/04* (2006.01)

(52) U.S. Cl. .................. 435/320.1; 536/23.1; 435/419

(58) Field of Classification Search .............. 536/23.1; 435/230.1, 419

See application file for complete search history.

(56) References Cited

U.S. PATENT DOCUMENTS

| | | | |
|---|---|---|---|
| 5,850,020 A | 12/1998 | Bloksberg et al. | |
| 5,952,486 A | 9/1999 | Bloksberg et al. | |
| 6,420,629 B1 | 7/2002 | Xue et al. | |
| 6,455,762 B1 | 9/2002 | Chiang et al. | |

FOREIGN PATENT DOCUMENTS

| | | |
|---|---|---|
| EP | 0513884 | 11/1992 |
| EP | 0516958 | 12/1992 |
| EP | 0632128 | 1/1995 |
| JP | 4330285 | 11/1992 |
| JP | 9173069 | 7/1997 |
| JP | 9173069 A2 | 7/1997 |
| NZ | 328434 | 5/1998 |
| WO | 9008828 | 8/1990 |
| WO | 9305159 | 3/1993 |
| WO | 9305160 | 3/1993 |
| WO | 9315599 | 8/1993 |
| WO | 9324638 | 12/1993 |
| WO | 9408036 | 4/1994 |
| WO | 9421794 | 9/1994 |
| WO | 9423044 | 10/1994 |
| WO | 9507993 | 3/1995 |
| WO | 9527790 | 10/1995 |
| WO | 9620595 | 7/1996 |
| WO | 9723599 | 7/1997 |
| WO | 9745549 | 12/1997 |
| WO | 9811205 | 3/1998 |
| WO | 9839454 | 9/1998 |
| WO | 0022099 | 4/2000 |

OTHER PUBLICATIONS

Gibco Catalog 1993-1994 (7-7).*
Hu et al. Compartmentalized expression of two structurally and functionally distinct 4-coumarate: CoA ligase genes in aspen (populus tremuloides) Proc. Natl. Acad. Sci. U.S.A 95 (9), 5407-5412 1998.
Yahiaoui et al. Comparative Efficiency Of Different Constructs For Down Regulation Of Tobacco Cinnamyl Alcohol Dehydrogenase vol. 49, No. 2 pp. 295-306 1998.
Kawaoka, A. AND Chiang, V.L. The molecular cloning and expression of syringyl- and guaiacyl-specific hydroxycinnamate: CoA Ilgases from aspen (*Populus tremuloides*), Biotechnology in the Pulp and Paper Industry, Recent Advances In Applied and Fundamental Research, Proceedings of the Sixth International Conference on Biotechnology in the Pulp and Paper Industry, 1996, pp. 315-318.
Uhlmann, Annette AND Ebel, Jürgen, Molecular Cloning and Expression of 4-Coumarate:Coenzyme A Ligase, an Enzyme Involved in the Resistance Response of Soybean (*Glycine max L*) against Pathogen Attach, Plant Physiology, 1993, pp. 1147-1156, vol. 102.

(Continued)

*Primary Examiner*—James Ketter
*Assistant Examiner*—Konstantina Katcheves
(74) *Attorney, Agent, or Firm*—Speckman Law Group PLLC; Janet Sleath; Ann W. Speckman

(57) ABSTRACT

Novel isolated polynucleotides and polypeptides associated with the lignin biosynthetic pathway are provided, together with genetic constructs including such sequences. Methods for the modulation of lignin content, lignin structure and lignin composition in target organisms are also disclosed, the methods comprising incorporating one or more of the polynucleotides of the present invention into the genome of a target organism.

24 Claims, 3 Drawing Sheets

OTHER PUBLICATIONS

Zhang, Xing-Hai AND Chiang, Vincent L., Molecular Cloning of 4-Coumarate:Coenzyme A Ligase in Loblolly Pine and the Roles of This Enzyme in the Biosynthesis of Lignin in Compression Wood, Plant Physiology, 1997, pp. 65-74, vol. 113.

Voo, Kui Shin, Whetten, Ross W., O'Malley, David M., AND Sederoff, Ronald R., 4-Coumarate:Coenzyme A Ligase from Loblolly Pine Xylem, Plant Physiology, 1995, pp. 85-97, vol. 108.

Kajita, Shinya, Katayama, Yoshihiro, AND Omori, Shunji, Alterations in the Biosynthesis of Lignin in Transgenic Plants with Chimeric Genes for 4-Coumarate:Coenzyme A Ligase, Plant Cell Physiology, 1996, pp. 957-965, vol. 37(7).

Ehlting, Jürgen, Büttner, Daniela, Wang, Quing, Douglas, Carl J., Somssich, Imre E., AND Kombrink, Erich, Three 4-coumarate-coenzyme A ligase in *Arabidopsis thaliana* represent two evolutionarlly divergent classes in angiosperms. The Plant Journal, 1999, pp. 9-20, vol. 19(1).

Anterola, Aldwin, M., AND Lewis, Norman G., Trends in Lignin modification: a comprehensive analysis of the effects of genetic manipulations/mutations on lignification and vascular Integrity, Phytochemistry, 2002, pp. 221-294, vol. 61.

Lee, Diana, Ellard, Mary, Wanner, Leslie A., Davis, Keith R., AND Douglas, Carl J., The *Arabidopsis thaliana* 4-coumarate:CoA ligase (*4CL*) gene: stress and developmentally regulated expression and nucleotide sequence of its cDNA, 1995, pp. 871-884, vol. 28.

Vincent, J.R., AND Nicholson, R.L., Evidence for isoenzymes of 4-hydroxycinnamic acid: CoA ligase in maize mesocolyis and their response to infection by *helminthosporium maydis* race O, Physiological and Molecular Plant Pathology, 1987, 121-129, vol. 30.

GenBank Accession No. AW191302; Bossinger, G.; submitted Nov. 23, 1999.

GenBank Accession No. AJ244010; Rech, P., et al.; submitted Jul. 21, 1999.

GenBank Accession No. AF239686; Kumar, A., et al.; submitted Feb. 28, 2000.

GenBank Accession No. BE454671; Wing, R. A.; submitted Jul. 26, 2000.

GenBank Accession No. AF041049; Hu, W.J., et al.; submitted Jan. 6, 1998.

GenBank Accession No. AF008183; Allina, S.M., et al.; submitted Jun. 12, 1997.

GenBank Accession No. AF052223; Heath, R.L., et al.; submitted Mar. 5, 1998.

GenBank Accession No. AW244908; Walbot, V., et al.; submitted Feb. 28, 2000.

PCT Written Opinion; In re Fletcher Challenge Forests, Ltd.; International Application No. PCT/NZ99/00168, filed Oct. 6, 1999.

Hu, Wen-Jing et al., "Repression of lignin biosynthesis promotes cellulose accumulation and growth in transgenic trees," *Nature Biotechnology*, vol. 17, No. 8, pp. 808-812 (Aug. 1999).

Neustaedter, David A. et al., "A novel parsley *4CLI* cis-element is required for developmentqally regulated expression and protein-DNA complex formation," *The Plant Journal*, vol. 18, No. 1, pp. 77-88 (Apr. 1999).

Lee, Diane et al., "Antisense Suppression of 4-Coumarate:Coenzyme A Ligase Activity in Arabidopsis Leads to Altered Lignin Subunit Composition," *The Plant Cell*, vol. 9, No. 11, pp. 1985-1998 (Nov. 1997).

Kajita, Shinya et al., "Alterations in the Biosynthesis of Lignin in Transgenic Plants with Chimeric Genes for 4-Coumarate:Coenzyme A Ligase," *Plant Cell Physiol.* vol. 37, No. 7, pp. 957-965 (Oct. 1996).

Hauffe, Karl D. et al., "Combinatorial interactions between positive and negative cis-acting elements control spatial patterns of 4*CL*-1 expression in transgenic tobacco," *The Plant Journal*, vol. 4, No. 2, pp. 235-253 (Aug. 1993).

Hauffe, Karl D. et al., "A Parsley 4*CL*-1 Promoter Fragment Specifies Complex Expression Patterns in Transgenic Tobacco," *The Plant Cell*, vol. 3., No. 2, pp. 435-443 (May 1991).

Wagner, A. et al., "Isolation and Characterisation of a Cinnamyl-Alcohol Dehydrogenase Gene from *Pinus Radiata*", *Queenstown Molecular Biology Meeting*, New Zealand Forest Research Institute (Aug. 1996).

In re Genesis Research & Development Corp. and Fletcher Challenge Forests Ltd; PCT International Search Report: Int'l No. PCT/NZ99/00168 filed Oct. 6, 1999 (7 sheets).

GenBank (no EST GSS HTG STS); Accession No. Z49263 (Sep. 25, 1997).

EMBL (no EST GSS HTG STS); Accession No. L07634 (Jan. 7, 1993).

GenBank (no EST GSS HTG STS); Accession No. X92437 (Jul. 17, 1998).

EMBL (no EST GSS HTG STS); Accession No. D87520 (Sep. 8, 1996).

EMBL (no EST GSS HTG STS): Accession No. U29243 (Jul. 9, 1995).

GenBank (no EST GSS HTG STS): Accession No. U12013 (Mar. 23, 1996).

GenBank (no EST GSS HTG STS): Accession No. U12012 (Mar. 23, 1996).

GenBank (no EST GSS HTG STS): Accession No. U39405 (Feb. 7, 1997).

GenBank (no EST GSS HTG STS): Accession No. U39404 (Feb. 7, 1997).

GenBank (no EST GSS HTG STS); Accession No. AF008183 (Feb. 26, 1998).

Swiss-Prot: Accession No. P14912 (Apr. 1, 1990).

Swiss-Prot: Accession No. P14913 (Apr. 1, 1990).

GenPept: Accession No. BAA07828 (Dec. 8, 1994).

GenPept: Accession No. AAB18638 (Mar. 7, 1996).

GenPept: Accession No. AAC39366 (Jun. 12, 1997).

GenPept: Accession No. AAB18638 (Mar. 7, 1996).

GenPept: Accession No. AAC39365 (Jun. 12, 1997).

GenBank (no EST GSS HTG STS): Accession No. U38416 (Aug. 12, 1996).

GenPept: Accession No. AAA62426 (1994).

Swiss-Prot: Accession No. P93711 (Jul. 15, 1998).

EMBL (no EST GSS HTG STS): Accession No. X52623 (Jul. 9, 1990).

GenBank (no EST GSS HTG STS): Accession No. L43362 (Jul. 7, 1995).

GenPept: Accession No. AAA92669 (Jul. 7, 1994).

GenPept: Accession No. AAB18637 (Mar. 7, 1996).

Swiss-Prot: Accession No. P93711 (Jul. 15, 1998).

EMBL (no EST GSS HTG STS): Accession No. X52623 (Jul. 9, 1990).

GenBank (no EST GSS HTG STS): Accession No. L43362 (Jul. 7, 1995).

GenPept: Accession No. AAA92669 (Jul. 7, 1994).

GenPept; Accession No. AAB18637 (Mar. 7, 1996).

Swiss-Prot: Accession No. P13687 (Jul. 1, 1993).

PIR: Accession No. PQ0773 (Jul. 14, 1994).

In re Bloksberg, et al., Materials and Methods for the Modification of Plant Lignin Content Patent U.S. Appl. No. 09/211,710, filed Dec. 14, 1998; Allowed Claims.

Dixon, R. A. et al., Metabolic engineering: prospects for crop improvement through genetic manipulation of phenylpropanoid biosynthesis and defense responses—a review, *Gene Papers* 179:61-71, 1996.

Hotze, M. et al., Cinnamate 4-hydroxylase from Catharanthus roseus, and a strategy for the functional expression of plant cytochrome $P_{450}$ proteins as translational fusions with $P_{450}$ reductase in *Escherichia coli, FEBS Letters* 374:345-350, 1995.

Hotze, M., et al., C. roseus mRNA for cinnamate 4-hydroxylase (CYP73), *EMBL Sequence Database*, Rel. 39, Apr. 15, 1994, Accession No. Z32563, (XP-002054206).

Mizutani, M. et al., Molecular Cloning and Sequencing of a cDNA Encoding Mung Bean Cytochrome P450 Possessing Cinnamate 4-Hydroxylase Activity, *Biochemical and Biophysical Research Communictaions* 190:3, 875-880, 1993.

Kawai, S., et al., Populus kitakamiensis cyp73a gene for cinnamic acid 4-hydroxylase complete cds. *EMBL Sequence Database*, Rel. 46, Dec. 30, 1995, Accession No. D82812 (XP002054135).

Sewalt et al. Reduced Lignin Content and Altered Lignin Composition in Transgenic Tobacco Down-Regulated in Expression of L-Phenylalnine Ammonia-Lyase or Cinnamate 4-Hydroxylase, *Plant Physiol.* 115:41-50, 1997.

Boudet, A.M., et al., Tansley Review No. 80 Biochemistry and molecular biology of lignification, *New Phytoolgist* 129:203-236, 1995.

Boudet, A.M. et al., Lignin genetic engineering, *Molecular Breeding* 2: 25-39, 1996.

Shiokawa, T., et al., Expression analysis of a cinnamic acid 4-hydroxylase gene from a hybrid aspen, Populus kitakamiensis. Chemical Abstracts 125:13, 1996.

Poeydomenge, O., et al., A cDNA Encoding S-Adenosyl-L-Methionine: Caffeic Acid 3-0-Methyl-transferase from *Eucalyptus. Plant Physiol* 105:749-750, 1994.

Mason, M.E., et al., Pinus elliortii PEC18 mRNA, partial sequence, *EMBL Sequence Database*, Rel. 47 May 31, 1996, Accession No. U55006 (XP 002054138).

Wagner, A., et al., Pinus radiata cinnamyl alcohol dehydrogenase (CAD) mRNA, complete cds. *EMBL Sequence Database*, Rel. 48 Jul. 28, 1996, Accession No. U62394 (XP002054137).

Van Doorsselaere, J., et al., A novel lignin in poplar trees with a reduced caffeic acid/5-hydroxyferulic acid 0-methyltransferase activity, *Plant Journal* 8:6, 855-864, 1995.

Ni , Weiting et al., Reduced lignin in transgenic plants containing a caffeic acid0=methyltransferase antisense gene, *Transgenic Research* 3:120-126, 1994.

Halpin, C. et al., Manipulation of lignin quality by downregulation of cinnamyl alcohol dehydrogenase, *Plant Journal* 6:3, 339-350, 1994.

Atanassova, R. et al., Altered lignin composition in transgenic tobacco expressing O-methyltransferase sequence in sense and antisense orientation, *Plant Jnl*, 8:465-477, 1995.

Chabbert et al., Manipulation of lignin quality in transgenic poplar, *Biotechnol. Pulp. Pap. Ind. Proc. Int. Conf.* 6th pp. 319-322, 1995.

Baucher, M. et al., Higher extractability of lignin in poplar by reducing cinnamyl alcohol dehydrogenase activity, *Somatic Cell Genetics and Molecular Genetics of Trees*, ISBN 0-7923-4179-1, pp. 153-158, 1996.

Boudet A. M. et al., La lignification domestiquee *BioFutur* 158:27-31, 1996.

Bouder A. M. Genes involved in monolignol biosynthesis and their manipulation for tailoring new lignins *Am. Chem Soc. Abstracts of Paper at National Meeting*, No. 1, 1996.

Elkind Y. et al., Abnormal plant development and down-regulation of phenylpropanoid biosynthesis in transgenic tobacco containing a heterologous phenylalanine ammonia-lyase gene *Proc. Natl Acad. Sci. USA* 87:9057-9061, 1990.

Bate, N.J. et al., Quantitative relationship between phenylalanine ammonia-lyase levels and phenylpropanoid accumulation in transgenic tobacco identifies a rate-determining step in natural product biosynthesis, *Proc. Natl. Acad. Sci. USA* 91:7608-7612, 1994.

Kajita S. et al., Alterations in the biosynthesis of lignin in transgenic plants with chimeric genes for 4-coumarate:Coenzyme A ligase *Plant Cell. Physiol.* 37:957-965, 1996.

Erickson et al., Laccase as a target for decreasing the lignin content in transgenic trees through antisense genetic engineering, Biotechnol. Pulp Pap. Ind. Proc. 6th *Intl. Conf*. pp. 310-314, 1996.

Lagrimini, L. M., Wound-induced deposition of polyphenols in transgenic plants overexpressing peroxidase *Plant Physiol.* 96:577-583, 1991.

Liu, T.Y. et al., Lignin contect and composition in tobacco plants with over and under expressed peroxidase, *Supplement to Plant Physiol.* 102:103, 1993.

McIntyre, C.L. et al. Strategies for the suppression of peroxidase gene expression in tobacco. II. In vivo suppression of peroxidase activity in transgenic tobacco using ribozyme and antisense constructs *Transgenic Research* 5:263-270, 1996.

Sikorski, R.S. et al., Yeast centromere vector pRS415 with LEU2 marker, complete sequence, EMBL Accession No. U03449, Jan. 8, 1984.

Yu, L.X. et al. Lycopersicon chilense unknown protein (LC15) mRNA, complete cds, EMBL Accession No. U19099, Oct. 3, 1995.

Grima-Pettenari, J. et al., E. gunnii OMT mRNA for O-methyltransferase, EMBL Accession No. X74814, Dec. 31, 1993.

Poeydomenge O. et al., A cDNA encoding S-adenosyl-L-methioninecaffeic acid 3-O-methyltransferase from eucalyptus, *Plant Physiol*, 105:749-750, 1994.

Raynal et al. A. thaliana transcribed sequence; clone PAP790; 5' end similar to cinnamyl alcohol dehydrogenase; Stylosanthes hmilis, EMBL Accession No. Z46703, Nov. 18, 1994.

Goffner D. et al., E. gunnii mRNA for cinnamyl alcohol dehydrogenase, EMBL Accession No. X88797, Dec. 31, 1995.

Newman T., et al., 10030 Arabidopsis thaliana cDNA clone 143C13T7, EMBL Accession No. T46767, Feb. 11, 1995.

Zhang, X.H. et al., Pinus taedae phenylalanine ammonia-lyase (IpPAL) gene complete cds, EMBL Accession No. U39792, Jan. 1, 1996.

Voo, K.S. et al. Pinus taeda PT4CL2 4-coumarate-CoA ligase enzyme, mRNA complete cds, EMBL Accession No. U12013, Jul. 27, 1994.

Zhang X.H. et al., Pinus taeda xylem 4-coumarate:CoA ligase (1p4CL-1) gene, complete cds, EMBL Accession No. U39405, Jan. 1, 1996.

Davies, K.M. et al. Malus sp. mRNA for anthocyanim hydroxylase, EMBL Accession No. X71360, Apr. 27, 1993.

Hrmova M. et al., Hordeum vulgare beta-d-glucan exohydrolase, isoenzyme exoII, mRNA, complete cds. EMBL Accession No. U46003, Feb. 29, 1996.

Willekens, H.D. N. plumoaginifolia mRNA for caralase (car3 gene), EMBL Accession No. Z36977, Sep. 7, 1994.

Ritter D. et al., Gossypium hirsutum peroxidase mRNA, complete cds, EMBL Accession No. L08199, Dec. 24, 1992.

Meyer K. et al., Arabidopsis thaliana ferulate-5-hydroxylase (FAH1) mRNA, completed cds, EMBL Accession No. U38416, Aug. 13, 1996.

Meyer K. et al., Ferulate-5-hydroxylase from Arabidopsis thaliana defines a new family of cytochrome P450-dependent monooxygenases *Proc. Natl. Acad. Sci. USA* 93:6869-6874, 1996.

Sewalt, V.J.H., et al. Reduced lignin content and altered lignin composition in transgenic tobacco down-regulated in expression of L-phenylalanine ammonia-lyase or cinnamate 4-hydroxylase *Plant Physiol.* 115:41-50, 1997.

Rech, P. et al., E. gunii mRNA for caffeoyl-CoA O-methyltransferase, EMBL Accession No. Y12228, Apr. 8, 1997.

Bachem, C.W.B., et al. Antisense expression of polyphenol oxidase genes inhibits enzymatic browning in potato tubers, *Biotechnology* 12:1101-1105, 1994.

Udagama-Randeniya, P.V. et al., Coniferyl alcohol oxidase: A catechol oxidase? *Trees* 10:102-108, 1995.

Dharmawardhana, D.P. et al., A beta-glycosidase from lodgepole pine xylem specific for the lignin precursor coniferin *Plant Physiol* 107:331-339, 1995.

Database Dissabs, AN97:45741 Dissabs Order No. AARNN14739, Dharmawardhanz, D.P. et al. A biochemical and molecular study of lignin biosynthesis (Pinus contorta, glucosidase, conferin, xylem).

Bao W. et al. A laccase associated with lignification in loblolly pine xylem *Science* 260:672-674, 1993.

Shiokawa, T. et al., Expression analysis of a cinnamic acid 4-hydroxylase gene from a hybrid aspen, Populus kitakamiensis, *Chem. Abstracts*, vol. 125, No. 13, abstract No. 163462, Sep. 23, 1996.

Leonard Nathan Bloksberg, Studies on the Biology of Phenylalanine Ammonia Lyase and Plant Pathogen Interaction, *Genetics*, Abstract iii, Dec. 1991.

D. Palitha Dharmawardhana et al., A β-Glucosidase from Lodgepole Pine Xylem Specific for the Lignin Precursor Coniferin, *Plant Physiol*, 107:331-339, 1995.

G. Schmid et al., Enzymic synthesis of lignin precursors. Purification and properties of UDP glucose: coniferyl-alcohol glucosyltransferase from cambial sap of spruce (Picea abies L.), *Eur J. Biochem* 123:363-70, 1982.

U. N. Dwivedi et al., Modification of lignin biosynthesis in transgenic *Nicotiana* through expression of an antisense O-methyltransferase gene from *Populus, Plant Molecular Biology* 26:61-71, 1994.

Carolyn Napoli et al., Introduction of a Chimeric Chalcone Synthase Gene into Petunia Results in Reversible Co-Suppression of Homologous Genes *in trans. The Plant Cell* 2: 279-289, Apr. 1990.

Ross Whetten et al., Lignin Biosynthesis, *The Plant Cell* 7: 1001-1013, Jul. 1995.

J. Prima-Pettenati et al., Molecular cloning and expression of a Eucalyptus gunnii cDNA clone encoding cinnamyl alcohol dehydrogenase. *Plant Mol Biol* 21: 1085-95, 1993.

C. Feuillet et al., Tissue- and cell-specific expression of cinnamyl alcohol dehydrogenase promoter in transgenic poplar plants, *Plant Mol Biol* 27: 651-667, 1995.

H. Wengenmayer et al., Enzymic synthesis of lignin precursors. Purification and properties of a cinnamoyl-CoA: NADPH reductase from cell suspension cultures of soybean (Glycinemax), *Eur J. Biochem* 65: 529-536, 1976.

T. Ludertiz et al., Enzymic synthesis of lignin precursors. Comparison of cinnamoyl-CoA reductase and cinnamyl alcohol: NADP+ dehydrogenase from spruce S(Picea abies L.) and soybean )Glycine max L.), *Eur J. Biochem* 119: 115-124, 1981.

F. Sarni et al., Purification and properties of cinnamoyl-CoA reductase and cinnamyl alcohol dehydrogenase from poplar stems (Populus X euramericana) *Eur J. Biochem* 139:259-265, 1984.

R.C. Bugos, et al., Characterization of bispecific caffeic acid/5-hydroxyferulic acid O-methyltransferase from aspen, *Phytochemistry* 31: 1495-1498, 1992.

C. Hermann et al., Enzymatic synthesis of lignin: purification to homogeneity of the three O-methyltransferases of tobacco and production of specific antibodies, *Arch Biochem Biophys* 253:367-376, 1987.

J. Van Doorsselaere et al., One-step purification and characterization of a lignin-specific O-methyltransferase from poplar, *Gene* 133:213-317, 1993.

R.C. Bugos et al., cDNA cloning, sequence analysis and seasonal expression of lignin-bispecific caffeic acid/5-hydroxyferulic acid O-methyltransferase of aspen, *Plant Mol Biol* 17: 1203-1215, 1991.

P. Collazo et al., Structure and expression of the lignin O-methyltransferase gene from Zea mays L., *Plant Mol Biol* 20:857-867, 1992.

W. Hosel et al., Characterization of beta-glucosidase isoenzymes possibly involved in lignification from chick pea (Cicer arietinum L. ) cell suspension cultures, *Eur J Biochem* 84:487-492, 1978.

* cited by examiner

SEQUENCE LISTING

```
<160> NUMBER OF SEQ ID NOS: 407

<210> SEQ ID NO 1
<211> LENGTH: 535
<212> TYPE: DNA
<213> ORGANISM: Eucalyptus grandis
<220> FEATURE:
<221> NAME/KEY: unsure
<222> LOCATION: (110)...(110)

<400> SEQUENCE: 1
cttcgcgcta ccgcatactc caccaccgcg tgcagaagat gagctcggag ggtgggaagg      60
aggattgcct cggttgggct gcccgggacc cttctgggtt cctctccccn tacaaattca     120
cccgcaggcc gtgggaagcg aagacgtctc gattaagatc acgcactgtg gagtgtgcta     180
cgcagatgtg gcttggacta ggaatgtgca gggacactcc aagtatcctc tggtgccggg     240
gcacgagata gttggaattg tgaaacaggt tggctccagt gtccaacgct tcaaagttgg     300
```

```
cgatcatgtg ggggtgggaa cttatgtcaa ttcatgcaga gagtgcgagt attgcaatga      360
caggctagaa gtccaatgtg aaaagtcggt tatgactttt gatggaattg atgcagatgg      420
tacagtgaca aagggaggat attctagtca cattgtcgtc catgaaaggt attgcgtcag      480
gattccagaa aactacccga tggatctagc agcgcattgc tctgtgctgg atcac          535

<210> SEQ ID NO 2
<211> LENGTH: 671
<212> TYPE: DNA
<213> ORGANISM: Pinus radiata

<400> SEQUENCE: 2
gcgcctgcag gtcgacacta gtggatccaa agaattcggc acgaggttgc aggtcgggga       60
tgatttgaat cacagaaacc tcagcgattt tgccaagaaa tatggcaaaa tctttctgct      120
caagatgggc cagaggaatc ttgtggtagt ttcatctccc gatctcgcca aggaggtcct      180
gcacacccag ggcgtcgagt ttgggtctcg aacccggaac gtggtgttcg atatcttcac      240
gggcaagggg caggacatgg tgttcaccgt ctatggagat cactggagaa agatgcgcag      300
gatcatgact gtgcctttct ttacgaataa agttgtccag cactacagat cgcgtgggga      360
agacgagatc agccgcgtgg tcgcggatgt gaaatcccgc gccgagtctt ccacctcggg      420
cattgtcatc cgtagcgcct ccagctcatg atgtataata ttatgtatag gatgatgttc      480
gacaggagat tcgaatccga ggacgacccg cttttcctca agctcaaggc cctcaacgga      540
gagcgaagtc gattggccca gagctttgag tacaattatg gggatttcat tcccagtctt      600
aggcccttcc tcagaggtta tcacagaatc tgcaatgaga ttaaagagaa acggctctct      660
cttttcaagg a                                                          671

<210> SEQ ID NO 3
<211> LENGTH: 940
<212> TYPE: DNA
<213> ORGANISM: Pinus radiata
<220> FEATURE:
<221> NAME/KEY: unsure
<222> LOCATION: (463)...(463)

<400> SEQUENCE: 3
cttcaggaca agggagagat caatgaggat aatgttttgt acatcgttga gaacatcaac       60
gttgcagcaa ttgagacaac gctgtggtcg atggaatggg gaatagcgga gctggtgaac      120
caccaggaca ttcagagcaa ggtgcgcgca gagctggacg ctgttcttgg accaggcgtg      180
cagataacgg aaccagacac gacaaggttg ccctaccttc aggcggttgt gaaggaaacc      240
cttcgtctcc gcatggcgat cccgttgctc gtcccccaca tgaatctcca cgacgccaag      300
ctcgggggct acgatattcc ggcagagagc aagatcctgg tgaacgcctg gtggttggcc      360
aacaaccccg ccaactggaa gaaccccgag gagttccgcc ccgagcggtt cttcgaggag      420
gagaagcaca ccgaagccaa tggcaacgac ttcaaattcc tgncccttcgg tgtggggagg      480 aggagctgcc cggaatcat tctggcgctg ctctcctcgc actctccatc ggaagacttg      540
ttcagaactt ccaccttctg ccgccgcccg ggcagagcaa agtggatgtc actgagaagg      600
gcgggcaatt cagccttcac attctcaacc attctctcat cgtcgccaag cccatagctt      660
ctgcttaatc ccaacttgtc agtgactggt atataaatgc gcgcacctga acaaaaaaca      720
ctccatctat catgactgtg tgtcgtgtc cactgtcgag tctactaaga gctcatagca      780
cttcaaaagt ttgctaggat ttcaataaca gacaccgtca attatgtcat gtttcaataa      840
```

| aagtttgcat aaattaaatg atatttcaat atactatttt gactctccac caattgggga | 900 |
| atttactgc taaaaaaaaa aaaaaaaaaa aaaaaaaaa | 940 |

<210> SEQ ID NO 4
<211> LENGTH: 949
<212> TYPE: DNA
<213> ORGANISM: Pinus radiata
<220> FEATURE:
<221> NAME/KEY: unsure
<222> LOCATION: (1)...(949)
<223> OTHER INFORMATION: n at all occurrences indicates unsure

<400> SEQUENCE: 4

| nngctcnacc gacggtggac ggtccgctac tcagtaactg agtgggatcc cccgggctga | 60 |
| caggcaattc gatttagctc actcattagg caccccaggc tttacacttt atgcttccgg | 120 |
| ctcgtatgtt gtgtggaatt gtgagcggat aacaatttca cacaggaaac agctatgacc | 180 |
| atgattacgc caagcgcgca attaaccctc actaaaggga acaaaagctg gagctccacc | 240 |
| gcggtggcgg ccgctctaga actagtggat ccaaagaatt cggcacgaga cccagtgacc | 300 |
| ttcaggcctg agagatttct tgaggaagat gttgatatta agggccatga ttacaggcta | 360 |
| ctgccattgg tgcagggcgc aggatctgcc ctggtgcaca attgggtatt aatttagttc | 420 |
| agtctatgtt gggacacctg cttcatcatt tcgtatgggc acctcctgag ggaatgaagg | 480 |
| cagaagacat agatctcaca gagaatccag ggcttgttac tttcatggcc aagcctgtgc | 540 |
| aggccattgc tattcctcga ttgcctgatc atctctacaa gcgacagcca ctcaattgat | 600 |
| caattgatct gatagtaagt ttgaattttg ttttgataca aaacgaaata acgtgcagtt | 660 |
| tctccttttc catagtcaac atgcagcttt cttctctga gcgcatgca gctttctttc | 720 |
| tctgaagccc aacttctagc aagcaataac tgtatatttt agaacaaata cctattcctc | 780 |
| aaattgagwa tttctctgta ggggnngnta attgtgcaat ttgcaagnaa tagtaaagtt | 840 |
| tantttaggg nattttaata gtcctangta anangnggna atgntagngg gcattnagaa | 900 |
| anccctaata gntgttggng gnngntaggn ttttnacca aaaaaaaaa | 949 |

<210> SEQ ID NO 5
<211> LENGTH: 959
<212> TYPE: DNA
<213> ORGANISM: Pinus radiata
<220> FEATURE:
<221> NAME/KEY: unsure
<222> LOCATION: (697)...(697)

<400> SEQUENCE: 5

| gaattcggca cgagaaagcc ctagaatttt ttcagcatgc tatcacagcc ccagcgacaa | 60 |
| ctttaactgc aataactgtg gaagcgtaca aaaagtttgt cctagtttct ctcattcaga | 120 |
| ctggtcaggt tccagcattt ccaaaataca cacctgctgt tgtccaaaga aatttgaaat | 180 |
| cttgcactca gccctacatt gatttagcaa acaactacag tagtgggaaa atttctgtat | 240 |
| tggaagcttg tgtcaacacg aacacagaga agttcaagaa tgatagtaat ttggggttag | 300 |
| tcaagcaagt tttgtcatct ctttataaac ggaatattca gagattgaca cagacatatc | 360 |
| tgaccctctc tcttcaagac atagcaagta cggtacagtt ggagactgct aagcaggctg | 420 |
| aactccatgt tctgcagatg attcaagatg gtgagatttt tgcaaccata aatcagaaag | 480 |
| atgggatggt gagcttcaat gaggatcctg aacagtacaa aacatgtcag atgactgaat | 540 |
| atatagatac tgcaattcgg agaatcatgg cactatcaaa gaagctcacc acagtagatg | 600 |

| | |
|---|---:|
| agcagatttc gtgtgatcat tcctacctga gtaaggtggg gagagagcgt tcaagatttg | 660 |
| acatagatga ttttgatact gttccccaga agttcanaaa tatgtaacaa atgatgtaaa | 720 |
| tcatcttcaa gactcgctta tattcattac tttctatgtg aattgatagt ctgttaacaa | 780 |
| tagtactgtg gctgagtcca gaaaggatct ctcggtatta tcacttgaca tgccatcaaa | 840 |
| aaaatctcaa atttctcgat gtctagtctt gattttgatt atgaatgcga cttttagttg | 900 |
| tgacatttga gcacctcgag tgaactacaa agttgcatgt taaaaaaaaa aaaaaaaa | 959 |

<210> SEQ ID NO 6
<211> LENGTH: 1026
<212> TYPE: DNA
<213> ORGANISM: Pinus radiata

<400> SEQUENCE: 6

| | |
|---|---:|
| gaattcggca cgagctttga ggcaacctac attcattgaa tcccaggatt tcttcttgtc | 60 |
| caaacaggtt taaggaaatg gcaggcacaa gtgttgctgc agcagaggtg aaggctcaga | 120 |
| caacccaagc agaggagccg gttaaggttg tccgccatca agaagtggga cacaaaagtc | 180 |
| ttttgcagag cgatgccctc tatcagtata tattggaaac gagcgtgtac cctcgtgagc | 240 |
| ccgagccaat gaaggagctc cgcgaagtga ctgccaagca tccctggaac ctcatgacta | 300 |
| cttctgccga tgagggtcaa tttctgggcc tcctgctgaa gctcattaac gccaagaaca | 360 |
| ccatggagat tggggtgtac actggttact cgcttctcag cacagccctt gcattgcccg | 420 |
| atgatggaaa gattctagcc atggacatca acagagagaa ctatgatatc ggattgccta | 480 |
| ttattgagaa agcaggagtt gcccacaaga ttgacttcag agagggccct gctctgccag | 540 |
| ttctggacga actgcttaag aatgaggaca tgcatggatc gttcgatttt gtgttcgtgg | 600 |
| atgcggacaa agacaactat ctaaactacc acaagcgtct gatcgatctg gtgaaggttg | 660 |
| gaggtctgat tgcatatgac aacaccctgt ggaacggatc tgtggtggct ccacccgatg | 720 |
| ctcccctgag gaaatatgtg agatattaca gagatttcgt gatggagcta aacaaggccc | 780 |
| ttgctgtcga tccccgcatt gagatcagcc aaatcccagt cggtgacggc gtcacccttt | 840 |
| gcaggcgtgt ctattgaaaa caatccttgt ttctgctcgt ctattgcaag cataaaggct | 900 |
| ctctgattat aaggagaacg ctataatata tggggttgaa gccatttgtt ttgtttagtg | 960 |
| tattgataat aaagtagtac agcatatgca agtttgtat caaaaaaaaa aaaaaaaaaa | 1020 |
| aaaaaa | 1026 |

<210> SEQ ID NO 7
<211> LENGTH: 1454
<212> TYPE: DNA
<213> ORGANISM: Pinus radiata

<400> SEQUENCE: 7

| | |
|---|---:|
| gaattcggca cgaggccaac tgcaagcaat acagtacaag agccagacga tcgaatcctg | 60 |
| tgaagtggtt ctgaagtgat gggaagcttg gaatctgaaa aaactgttac aggatatgca | 120 |
| gctcgggact ccagtggcca cttgtcccct tacacttaca atctcagaaa gaaaggacct | 180 |
| gaggatgtaa ttgtaaaggt catttactgc ggaatctgcc actctgattt agttcaaatg | 240 |
| cgtaatgaaa tggacatgtc tcattaccca atggtccctg gcatgaagt ggtgggatt | 300 |
| gtaacagaga ttggcagcga ggtgaagaaa ttcaaagtgg agagcatgt aggggttggt | 360 |
| tgcattgttg ggtcctgtcg cagttgcggt aattgcaatc agagcatgga acaatactgc | 420 |
| agcaagagga tttggaccta caatgatgtg aaccatgacg gcacacctac tcaggcggga | 480 |

```
tttgcaagca gtatggtggt tgatcagatg twtgtggttc gaatcccgga gaatcttcct      540
ctggaacaag cggcccctct gttatgtgca ggggttacag ttttcagccc aatgaagcat      600
ttcgccatga cagagcccgg gaagaaatgt gggattttgg gtttaggagg cgtggggcac      660
atgggtgtca agattgccaa agcctttgga ctccacgtga cggttatcag ttcgtctgat      720
aaaaagaaag aagaagccat ggaagtcctc ggcgccgatg cttatcttgt tagcaaggat      780
actgaaaaga tgatggaagc agcagagagc ctagattaca taatggacac cattccagtt      840
gctcatcctc tggaaccata tcttgccctt ctgaagacaa atggaaagct agtgatgctg      900
ggcgttgttc cagagtcgtt gcacttcgtg actcctctct taatacttgg gagaaggagc      960
atagctggaa gtttcattgg cagcatggag gaaacacagg aaactctaga tttctgtgca     1020
gagaagaagg tatcatcgat gattgaggtt gtgggcctgg actacatcaa cacggccatg     1080
gaaaggttgg agaagaacga tgtccgttac agatttgtgg tggatgttgc tagaagcaag     1140
ttggataatt agtctgcaat caatcaatca gatcaatgcc tgcatgcaag atgaatagat     1200
ctggactagt agcttaacat gaaagggaaa ttaaattttt atttaggaac tcgtactggg     1260
tttttgttac tttagtttag cttttgtgag gttgaaacaa ttcagatgtt tttttaactt     1320
gtatatgtaa agatcaattt ctcgtgacag taaataataa tccaatgtct tctgccaaat     1380
taatatatgt attcgtattt ttatatgaaa aaaaaaaaaa aaaaaaaaaa aaaaaaaaaa     1440
aaaaaaaaaa aaaa                                                       1454

<210> SEQ ID NO 8
<211> LENGTH: 740
<212> TYPE: DNA
<213> ORGANISM: Pinus radiata

<400> SEQUENCE: 8
gaattcggca cgagaccatt tccagctaat attggcatag caattggtca ttctatcttt       60 gtcaaggag atcaaacaaa ttttgaaatt ggacctaatg gtgtggaggc tagtcagcta       120
tacccagatg tgaaatatac cactgtcgat gagtacctca gcaaatttgt gtgaagtatg      180
cgagattctc ttccacatgc ttcagagata cataacagtt tcaatcaatg tttgtcctag      240
gcatttgcca aattgtgggt tataatcctt cgtaggtgtt tggcagaaca gaacctcctg      300
tttagtatag tatgacgagc taggcactgc agatccttca cacttttctc ttccataaga      360
aacaaatact cacctgtggt ttgttttctt tctttctgga actttggtat ggcaataatg      420
tctttggaaa ccgcttagtg tggaatgcta agtactagtg tccagagttc taagggagtt      480
ccaaaatcat ggctgatgtg aactggttgt tccagagggt gtttacaacc aacagttgtt      540
cagtgaataa ttttgttaga gtgtttagat ccatctttac aaggctattg agtaaggttg      600
gtgttagtga acggaatgat gtcaaatctt gatgggctga ctgactctct tgtgatgtca      660
aatcttgatg gattgtgtct ttttcaatgg taaaaaaaaa aaaaaaaaaa aaaaaaaaaa      720
aaaaaaaaaa aaaaaaaaaa                                                 740

<210> SEQ ID NO 9
<211> LENGTH: 624
<212> TYPE: DNA
<213> ORGANISM: Pinus radiata

<400> SEQUENCE: 9
gaattcctgc agcccggggg atccactagt tctagagcgg ccgccaccgc ggtggagctc       60
```

-continued

```
gcgcgcctgc aggtcgacac tagtggatcc aaagaattcg gcacgaggcc cgacggccac      120
ttgttggacg ccatggaagc tctccggaaa gccgggattc tggaaccgtt taaactgcag      180
cccaaggaag gactggctct cgtcaacggc acagcggtgg gatccgccgt ggccgcgtcc      240
gtctgtgttg acgccaacgt gctgggcgtg ctggctgaga ttctgtctgc gctcttctgc      300
gaggtgatgc aagggaaacc ggagttcgta gatccgttaa cccaccagtt gaagcaccac      360
ccagggcaga tcgaagccgc ggccgtcatg gagttcctcc tcgacggtag cgactacgtg      420
aaagaagcag cgcggcttca cgagaaagac ccgttgagca aaccgaaaca agaccgctac      480
gctctgcgaa catcgccaca gtggttgggg cctccgatcg aagtcatccg cgctgcyact      540
cactccatcg agcgggagat caattccgtc aacgacaatc cgttaatcga tgtctccagg      600
gacatggctg tccacggcgg caac                                             624

<210> SEQ ID NO 10
<211> LENGTH: 278
<212> TYPE: DNA
<213> ORGANISM: Pinus radiata

<400> SEQUENCE: 10
gaattcctgc agcccggggg atccactagt tctagagcgg ccgccaccgc ggtggagctc       60
cagtacctgg ccaaccccgt cacgactcac gtccagagcg ccgaacaaca caaccaggat      120
gtcaattccc tcggcttgat ctccgccaga aagactgccg aggccgttga gattttaaag      180
ctgatgttcg ctacatatct ggtggcctta tgccaggcga tcgatctccg gcacctggaa      240
gaaaacatgc gatccgttgt gaagcacgta gtcttgca                              278

<210> SEQ ID NO 11
<211> LENGTH: 765
<212> TYPE: DNA
<213> ORGANISM: Pinus radiata

<400> SEQUENCE: 11
gagctcctgc aagtcatcga tcatcagccc gttttctcgt acatcgacga tcccacaaat       60
ccatcatacg cgcttatgct ccaactcaga gaagtgctcg tagatgaggc tctcaaatca      120
tcttgcccag acgggaatga cgaatccgat cacaatttgc agcccgctga gagcgctgga      180
gctgctggaa tattacccaa ttgggtgttt agcaggatcc ccatatttca agaggagttg      240
aaggcccgtt tagaggaaga ggttccgaag gcgagggaac gattcgataa tgggacttc       300 ccaattgcaa acagaataaa caagtgcagg acatatccca tttacagatt cgtgagatca      360
gagttgggaa ccgatttgct aacagggccc aagtggagaa gccccggcga agatatagaa      420
aaggtatttg agggcatttg ccaagggaaa attggaaacg tgatcctcaa atgtctggac      480
gcttggggtg ggtgcgctgg accattcact ccacgtgcat atcctgcgtc tcctgcagcg      540
ttcaatgcct catattgggc atggtttgat agcaccaaat caccctctgc aacgagcggc      600
agaggtttct ggagcgccca acaacaacaa gttctttgat ttaactgact cttaagcatt      660
cctaaacagc ttgttcttcg caataacgaa tctttcatct tcgttacttt gtaaaagatg      720
gggttccaac aaaatagaag aaatattttc gatccaaaaa aaaaa                      765

<210> SEQ ID NO 12
<211> LENGTH: 453
<212> TYPE: DNA
<213> ORGANISM: Pinus radiata
```

```
<400> SEQUENCE: 12
tgattatgcg gatccttggg cagggatacg gcatgacaga agcaggcccg gtgctggcaa    60
tgaacctagc cttcgcaaag aatcctttcc ccgccaaatc tggctcctgc ggaacagtcg   120
tccggaacgc tcaaataaag atcctcgatt acaggaactg gcgagtctct cccgcacaat   180
caagccggcg aaatctgcat ccgcggaccc gaaataatga aaggatatat taacgacccg   240
gaatccacgg ccgctacaat cgatgaagaa ggctggctcc acacaggcga cgtcgggtac   300
attgacgatg acgaagaaat cttcatagtc gacagagtaa aggagattat caatataaag   360
gcttccaggt ggatcctgct aatcgaattc ctgcagcccg ggggtccact agttctagag   420
cggccgccac cgcggtggag ctccagcttt tgt                                453

<210> SEQ ID NO 13
<211> LENGTH: 278
<212> TYPE: DNA
<213> ORGANISM: Pinus radiata

<400> SEQUENCE: 13
tcttcgaatt ctcttttcacg actgcttcgt taatggctgc gatggctcga tattgttaga    60
tgataactca acgttcaccg gagaaaagac tgcaggccca atgttaatt ctgcgagagg    120 attcgacgta atagacacca tcaaaactca agttgaggca gcctgcagtg gtgtcgtgtc   180
agttgccgac attctcgcca ttgctgcacg cgattcagtc gtccaactgg ggggcccaac   240
atggacggta cttctgggag aaaagacgga tccgatca                           278

<210> SEQ ID NO 14
<211> LENGTH: 23
<212> TYPE: DNA
<213> ORGANISM: Pinus radiata

<400> SEQUENCE: 14
cttcgaattc wyttycayga ytg                                            23

<210> SEQ ID NO 15
<211> LENGTH: 22
<212> TYPE: DNA
<213> ORGANISM: Pinus radiata

<400> SEQUENCE: 15
gatcggatcc rtcyykycty cc                                             22

<210> SEQ ID NO 16
<211> LENGTH: 472
<212> TYPE: DNA
<213> ORGANISM: Eucalyptus grandis

<400> SEQUENCE: 16
aattcggcac gagacgacct cttgtatcgg acccggatcc gctatcgtta acgtacacac    60
gttctagtgc tgaatggaga tggagagcac caccggcacc ggcaacggcc ttcacagcct   120
ctgcgccgcc gggagccacc atgccgaccc actgaactgg ggggcggcgg cagcagccct   180
cacagggagc cacctcgacg aggtgaagcg gatggtcgag gagtaccgga ggccggcggt   240
gcgcctcggc ggggagtccc tcacgatagc ccaggtggcg gcggtggcga gtcaggaggg   300 ggtagggggtc gagctctcgg aggcggcccg tcccagggtc aaggccagca gcgactggt   360 catggagagc atgaacaagg gaactgacag ctacggggtc accaccgggt tcggcggcaa   420
cttctcaaac cggaggccga agcaaggcgg tccttttcag aaggaactta ta           472
```

<210> SEQ ID NO 17
<211> LENGTH: 622
<212> TYPE: DNA
<213> ORGANISM: Eucalyptus grandis

<400> SEQUENCE: 17

```
ccaaagctcc tagtgcctca tgagtctgct gaggattgca caattggcgg gttcgacgtg      60
cccccgaggca ccatgatcct ggttaatgcg tgggcaattc aaagagaccc aaaagtgtgg    120
gacgatccca caattttaa accggagagg tacgagggat tggaaggtga tcatgcctac      180
cgactattgc cgtttgggat ggggaggaga agttgtcctg gtgctggcct tgccaataga    240
gtggtgagct tggtcctggc ggcgcttatt cagtgcttcg aatgggaacg agttggcgaa    300
gaattggtgg acttgtccga ggggacggga ctcacaatgc aaagagaga gccattggag    360
gccttgtgca aagcgcgtga atgcatgata gctaatgttc ttgcgcacct ttaagaaggt    420
cgttgtctaa tgaatttaca ttggtgatgt atctccaatg tttttgaata atcaaataga    480
ctgaaaatag gccagtgcag ctttaggaat gatcgtgagc atcaatagca tcctgaggag    540
gccaatgcag ctttaggcct ttctcttagg agaaaaatga tggtttatat aggtactggc    600
aacattgttc aaaaaaaaaa aa                                             622
```

<210> SEQ ID NO 18
<211> LENGTH: 414
<212> TYPE: DNA
<213> ORGANISM: Eucalyptus grandis

<400> SEQUENCE: 18

```
cacgctcgac gaattcggta ccccgggttc gaaatcgata agcttggatc caaagcaaca     60
cattgaactc tctctctctc tctctctctc tctctctctc tcccccaccc cccttccca    120
accccaccca catacagaca agtagatacg cgcacacaga agaagaaaag atggggttt     180
caatgcagtc aatcgcacta gcgacggttc tggccgtcct aacgacatgg gcgtggaggg    240
cggtgaactg ggtgtggctg aggccgaaga ggctcgagag gcttctgaga cagcaaggtc    300
tctccggcaa gtcctacacc ttcctggtcg gcgacctcaa ggagaacctg cggatgctca    360
aggaagccaa gtccaagccc atcgccgtct ccgatgacat caagcctcgt ctct          414
```

<210> SEQ ID NO 19
<211> LENGTH: 469
<212> TYPE: DNA
<213> ORGANISM: Eucalyptus grandis

<400> SEQUENCE: 19

```
gaattcggca cgagtgtctc tctctctctc tctctctgta aaccaccatg ctcttcctca     60
ctcatctcct agcagttcta ggggttgtgt tgctcctgct aattctatgg agggcaagat    120
cttctccgaa caaacccaaa ggtactgcct taccccggga gctgccgggc gcatggccga    180
tcataggcca catccacttg ctgggcggcg agacccgct ggccaggacc ctggccgcca    240
tggcggacaa gcagggcccg atgtttcgga tccgtctcgg agtccacccg gcgaccatca    300
taagcagccg tgaggcggtc cgggagtgct tcaccaccca cgacaaggac ctcgcttctc    360
gccccaaatc caaggcggga atccacttgg gctacgggta tgccggtttt ggcttcgtag    420
aatacgggga cttttggcgc gagatgagga agatcaccat gctcgagct              469
```

<210> SEQ ID NO 20

<211> LENGTH: 341
<212> TYPE: DNA
<213> ORGANISM: Eucalyptus grandis

<400> SEQUENCE: 20

```
cgggctcgtg gctcggctcc ggcgcaacgc ccttcccacc gggcccgagg ggcctccgg      60
tcatcgggaa catgctcatg atgggcgagc tcacccaccg cggcctcgcg agtctggcga    120
agaagtatgg cggatcttc cacctccgca tgggcttcct gcacatggtt gccgtgtcgt    180
cccccgacgt ggcccgccag gtcctccagg tccacgacgg gatcttctcg aaccggcctg    240
ccaccatcgc gatcagctac ctcacgtatg accgggccga catggccttc gcgcactacg    300
gcccgttctg gcggcagatg cggaagctgt gcgtgatgaa a                        341
```

<210> SEQ ID NO 21
<211> LENGTH: 387
<212> TYPE: DNA
<213> ORGANISM: Eucalyptus grandis

<400> SEQUENCE: 21

```
gaattcggca cgagcgggct cgtggctcgg ctccggcgca acgcccttcc caccgggccc    60
gaggggcctc ccggtcatcg ggaacatgct catgatgggc gagctcaccc accgcggcct   120
cgcgagtctg gcgaagaagt atggcgggat cttccacctc gcatgggct tcctgcacat    180
ggttgccgtg tcgtcccccg acgtggcccg ccaggtcctc caggtccacg acgggatctt   240
ctcgaaccgg cctgccacca tcgcgatcag ctacctcacg tatgaccggg ccgacatggc   300
cttcgcgcac tacggcccgt tctggcggca gatgcggaag ctgtgcgtga tgaaagctct   360
tcagcggaag cgggctgagt cgtggga                                       387
```

<210> SEQ ID NO 22
<211> LENGTH: 443
<212> TYPE: DNA
<213> ORGANISM: Eucalyptus grandis

<400> SEQUENCE: 22

```
cacgagctcg tgagccttcc cggagacaag gccatcttac ttcgcaacaa attgcgtccg    60
cactcctttc tcaagaaacc tagtcatcca agaagcagag cattgcaact gcaaacagcc   120
aaagcccaaa ctcgtacaga aggagagaga gagagagaat agaagcatga gtgcatgcac   180
gaaccaagca atcacgacgg ccagtgaaga tgaagagttc ttgttcgcca tggaaatgaa   240
tgctctgata gcactcccct tggtcttgaa ggccaccatc gaactgggga tcctcgaaat   300
actggccgag tgcgggccta tggctccact ttcgcctgct cagattgcct cccgtctctc   360
cgcaaagaac ccggaagccc ccgtaaccct tgaccggatc ctccggtttc tcgccagcta   420
ctccatcctc tcttgcactc tcg                                           443
```

<210> SEQ ID NO 23
<211> LENGTH: 607
<212> TYPE: DNA
<213> ORGANISM: Eucalyptus grandis

<400> SEQUENCE: 23

```
gaattcggca cgagccaacc ctggaccagg tacttttggc aggcggtcca ttgcccttca    60
aaccggtcca aaccggacca tcactgtcct tatatacgtt gcatcatgcc tgctcataga   120
acttaggtca actgcaacat ttcttgatca caacatatta caatattcct aagcagagag   180
agagagagag agagagagag agagagagag agagtttgaa tcaatggcca ccgccggaga   240
```

-continued

```
ggagagccag acccaagccg ggaggcacca ggaggttggc cacaagtctc tccttcagag    300
tgatgctctt taccaatata ttttggagac cagcgtgtac ccaagagagc ctgagcccat    360
gaaggagctc agggaaataa cagcaaaaca tccatggaac ataatgacaa catcagcaga    420
cgaagggcag ttcttgaaca tgcttctcaa gctcatcaaa gccaagaaca ccatggagat    480
tggtgtcttc actggctact ctctcctcgc accgctctt gctcttcctg atgacggaaa     540
gattttggct atggacatta acagagagag ctatgaactt ggcctgccgg catccaaaaa    600
gccggtg                                                              607
```

<210> SEQ ID NO 24
<211> LENGTH: 421
<212> TYPE: DNA
<213> ORGANISM: Eucalyptus grandis

<400> SEQUENCE: 24

```
gaattcggca cgagccgttt tatttcctct gatttccttt gctcgagtct cgcggaagag    60
agagaagaga ggagaggaga gaatgggttc gaccggatcc gagacccaga tgaccccgac   120
ccaagtctcg gacgaggagg cgaacctctt cgccatgcag ctggcgagcg cctccgtgct   180
ccccatggtc ctcaaggccg ccatcgagct cgacctcctc gagatcatgg ccaaggccgg   240
gccgggcgcg ttcctctccc cgggggaagt cgcggcccag ctcccgaccc agaaccccga   300
ggcacccgta atgctcgacc ggatcttccg gctgctggcc agctactccg tgctcacgtg   360
caccctccgc gacctccccg atggcaaggt cgagcggctc tacggcttag cgccggtgtg   420
c                                                                    421
```

<210> SEQ ID NO 25
<211> LENGTH: 760
<212> TYPE: DNA
<213> ORGANISM: Eucalyptus grandis

<400> SEQUENCE: 25

```
ggaagaagcc gagcaaacga attgcagacg ccattgaaaa aagacacgaa agagatcaag    60
aaggagctta gaagcatca tcaatggcag ccaacgcaga gcctcagcag acccaaccag    120
cgaagcattc ggaagtcggc cacaagagcc tcttgcagag cgatgctctc taccagtata   180
tattggagac cagcgtctac ccaagagagc cagagcccat gaaggagctc agggaaataa   240
cagccaaaca tccatggaac ctgatgacca catcggcgga tgaagggcag ttcctgaaca   300
tgctcctcaa gctcatcaac gccaagaaca ccatggagat cggcgtctac accggctact   360
ctctcctcgc aaccgccctt gctcttcccg atgacggaaa gatcttggcc atggccatca   420
atagggagaa cttcgagatc gggctgcccg tcatccagaa ggccggcctt gcccacaaga   480
tcgatttcag agaaggccct gccctgccgc tccttgatca gctcgtgcaa gatgagaaga   540
accatggaac gtacgacttc ttctcaatcc ttaatcgttc atttgaatac aaatacatgc   600
tcaatggttc aaagacaaca taagacagaa gatggaaaaa atagaaagga aggaaagtat   660
taagggtagt ttctcatttc atcaatgctt gatttttgaga tctcctttct ggtgcgatca   720
gctgacccgg cggcacaggt gatgccatcc ccgacgggaa                          760
```

<210> SEQ ID NO 26
<211> LENGTH: 508
<212> TYPE: DNA
<213> ORGANISM: Eucalyptus grandis

```
<400> SEQUENCE: 26
gaattcggta cccgggttcg aaatcgataa gcttggatcc aaagaattcg gcacgagatc    60
actaaccatc tgcctttctt catcttcttt cttctgcttc tcctccgttt cctcgtttcg   120
atatcgtgaa aggagtccgt cgacgacaat ggccgagaag agcaaggtcc tgatcatcgg   180
agggacgggc tacgtcggca agttcatcgt ggaagcgagt gcaaaagcag ggcatcccac   240
gttcgcgctg gttaggcaga gcacggtctc cgaccccgtc aagggccagc tcgtcgagag   300
cttcaagaac ttgggcgtca ctctgctcat cggtgatctg tacgatcatg agagcttggt   360
gaaggcaatc aagcaagccg acgtggtgat atcgacagtg gggcacatgc aaatggcgga   420
tcagaccaaa gaatcgtcga cgccattaaa ggaagctggc aacgttaagg tttgttggtt   480
ggttcatttg atctggtttg ggggggtc                                      508

<210> SEQ ID NO 27
<211> LENGTH: 495
<212> TYPE: DNA
<213> ORGANISM: Eucalyptus grandis

<400> SEQUENCE: 27
gaattcggca cgaggttaat ggcagtgcag cctcaacacc acccaccttc ctccatctct    60
ctcctccctt cttctttctc tgacttcaat ggcagccgac tccatgcttg cgttcagtat   120
aagaggaagg tggggcagcc taaggggca ctgcgggtca ctgcatcaag caataagaag   180
atcctcatca tgggaggcac ccgtttcatc ggtgtgtttt tgtcgagact acttgtcaaa   240
gaaggtcatc aggtcacttt gtttaccaga ggaaaagcac ccatcactca acaattgcct   300
ggtgagtcgg acaaggactt cgctgatttt tcatccaaga tcctgcattt gaaaggagac   360
agaaaggatt ttgattttgt taaatctagt cttgctgcag aaggctttga cgttgtttat   420
gacattaacg gcgagaggcg gatgaagtcg caccaatttt ggatgcctgc caaaccttga   480
accagtcaac tactg                                                    495

<210> SEQ ID NO 28
<211> LENGTH: 472
<212> TYPE: DNA
<213> ORGANISM: Eucalyptus grandis

<400> SEQUENCE: 28
gaattcggca cgagcataag ctctcccgta atcctcacat cacatggcga agagcaaggt    60
cctcgtcgtt ggcggcactg gctacctcgg gcggaggttc gtgagggcga gcctggacca   120
gggccacccc acgtacgtcc tccagcgtcc ggagaccggc ctcgacattg agaagctcca   180
gacgctactg cgcttcaaga ggcgtggcgc ccaactcgtc gaggcctcgt tctcagacct   240
gaggagcctc gtcgacgctg tgaggcgggt cgatgtcgtc gtctgtgcca tgtcggggt    300 ccacttccgg agccacaaca tcctgatgca gctcaagctc gtggaggcta tcaaagaagc   360
tggaaatgtc aagcggtttt tgccgtcaga gttcggaatg acccggccc tcatgggtca   420 tgcaattgag ccgggaaggg tcacgttcga tgagaaatgg aggtgagaaa ag           472

<210> SEQ ID NO 29
<211> LENGTH: 396
<212> TYPE: DNA
<213> ORGANISM: Eucalyptus grandis

<400> SEQUENCE: 29
gaattcggca cgaggaggca cctcctcgaa acgaagaaga agaaggacga aggacgaagg    60
```

-continued

```
agacgaaggc gagaatgagc gcggcgggcg gtgccgggaa ggtcgtgtgc gtgaccgggg      120
cgtccggtta catcgcctcg tggctcgtca agctcctcct ccagcgcggc tacaccgtca      180
aggccaccgt ccgcgatccg aatgatccaa aaaagactga acatttgctt ggacttgatg      240
gagcgaaaga tagacttcaa ctgttcaaag caaacctgct ggaagagggt tcatttgatc      300
ctattgttga gggttgtgca ggcgtttttc aaactgcctc tcccttttat catgatgtca      360
aggatccgca ggcagaatta cttgatccgg ctgtaa                                396

<210> SEQ ID NO 30
<211> LENGTH: 592
<212> TYPE: DNA
<213> ORGANISM: Eucalyptus grandis

<400> SEQUENCE: 30
gaattcggca cgaggttgaa cctcccgtcc tcggctctgc tcggctcgtc accctcttcg       60
cgctcccgca tactccacca ccgcgtacag aagatgagct cggagggtgg gaaggaggat     120
tgcctcggtt gggctgcccg ggacccttct gggttcctct ccccctacaa attcacccgc     180
agggccgtgg aagcgaaga cgtctcgatt aagatcacgc actgtggagt gtgctacgca      240
gatgtggctt ggactaggaa tgtgcaggga cactccaagt atcctctggt gccagggcac      300
gagatagttg gaattgtgaa acaggttggc tccagtgtcc aacgcttcaa agttggcgat      360
catgtggggg tgggaactta tgtcaattca tgcagagagt gcgagtattg caatgacagg      420
ctagaagtcc aatgtgaaaa gtcggttatg acttttgatg gaattgatgc agatggtaca      480
gtgacaaagg gaggatattc tagtcacatt gtcgtccatg aaaggtattg cgtcaggatt      540
ccagaaaact acccgatgga tctagcagcg catttgctct gtgctggatc ac             592

<210> SEQ ID NO 31
<211> LENGTH: 468
<212> TYPE: DNA
<213> ORGANISM: Eucalyptus grandis

<400> SEQUENCE: 31
gaattcggca cgagaactca tcttgaaatg tcattggagt catcatcctc tagtgagaag       60
aaacaaatgg gttccgccgg attcgaatcg gccacaaagc cgcacgccgt ttgcattccc     120
taccctgcac aaagccacat ggcgccatg ctcaagctag caaagctcct ccatcacaag      180
ggcttccaca tctccttcgt caacaccgag ttcaaccacc ggcggctcgc cagggctcga     240
ggccccgagt tcacaaatgg aatgctgagc gactttcagt tcctgacaat ccccgatggt     300
cttcctcctt cggacttgga tgcgatccaa gacatcaaga tgctctgcga atcgtccagg     360
aactatatgg tcagccccat caacgatctt gtatcgagcc tgggctcgaa cccgagcgtc     420
cctccggtga cttgcatcaa tctcggatgg tttcatgaca ctcgtgac                  468

<210> SEQ ID NO 32
<211> LENGTH: 405
<212> TYPE: DNA
<213> ORGANISM: Eucalyptus grandis

<400> SEQUENCE: 32
ctttactccg ccaagaagat ccaatcgcag ttttcgcaat ggcccatta cacaaatgcg        60 gtccatcttc atcgggaagt ctcttggcag aagaccggag ttgcatttcc tggctggaca     120
agcaagcccc taactcagtg gtctatgtga gtcttgggag catcgcctct gtgaacgagt     180
```

```
cggaatttc  cgaaatagct  ttaggtttag  ccgatagcca  gcagccattc  ttgtgggtgg        240
ttcgacccgg  gtcagtgagc  ggctcggaac  tcttagagaa  tttgcccggt  tgctttctgg        300
aggcattaca  ggagaggggg  aagattgtga  aatgggcgcc  tcaacatgaa  gtgctggctc        360
atcgggctgt  cggagcgttt  tggactcaca  atggatggaa  ctcca                        405
```

<210> SEQ ID NO 33
<211> LENGTH: 380
<212> TYPE: DNA
<213> ORGANISM: Eucalyptus grandis

<400> SEQUENCE: 33

```
ggcaaacacg  cccgttttcg  ttttactaag  agaagatggt  gagcgttgtg  gctggtagag         60
tcgagagctt  gtcgagcagt  ggcattcagt  cgatcccgca  ggagtatgtg  aggccgaagg        120
aggagctcac  aagcattggc  gacatcttcg  aggaggagaa  gaagcatgag  ggccctcagg        180
tcccgaccat  cgacctcgag  gacatagcgt  ctaaagaccc  cgtggtgagg  gagaggtgcc        240
acgaggagct  caggaaggct  gccaccgact  ggggcgtcat  gcacctcgtc  aaccatggga        300
tccccaacga  cctgattgag  cgtgtaaaga  aggctggcga  ggtgttcttc  aacctcccga        360
tcgaggagaa  ggacaagcat                                                       380
```

<210> SEQ ID NO 34
<211> LENGTH: 305
<212> TYPE: DNA
<213> ORGANISM: Eucalyptus grandis

<400> SEQUENCE: 34

```
ttgtacccga  agatctccgg  gaccgttcga  cggcgacatc  gccgtcggcc  gggaacccgt         60
cgaggccgcc  gccggaggcc  ggggagaagc  tggagtagcc  gccgtagccg  agaaggcgc         120 cgtcgtggtc  ggcggcggcg  gcgtggtgga  cctcatcgcc  gtccatgctg  aaggcgtcga        180
aggaagcgga  catggctggg  ggatcgatcg  accgatccga  tcggccggag  gatttcgaga        240
tcggagatgg  agagatggaa  atgaaagaga  gagagagaga  gagatccggt  ggactggtgg        300
tgttt                                                                        305
```

<210> SEQ ID NO 35
<211> LENGTH: 693
<212> TYPE: DNA
<213> ORGANISM: Eucalyptus grandis

<400> SEQUENCE: 35

```
gaattcggca  cgagctaaga  gaggagagga  gaggagcaag  atggcactag  caggagctgc         60
actgtcagga  accgtggtga  gctccccctt  tgtgaggatg  cagcctgtga  acagactcag        120
ggcattcccc  aatgtgggtc  aggccctgtt  tggtgtcaac  tctggccgtg  gcagagtgac        180
tgccatggcc  gcttacaagg  tcaccctgct  caccccctgaa  ggcaaagtcg  aactcgacgt        240
ccccgacgat  gtttacatct  tggactacgc  cgaggagcaa  ggcatcgact  tgccctactc        300
ctgccgtgcc  ggctcttgct  cctcctgcgc  gggcaaggtc  gtggcgggga  gcgtcgacca        360
gagcgacggc  agcttcctgg  atgatgatca  gattgaggaa  ggttgggtcc  tcacttgtgt        420
cgcctaccct  aagtctgagg  tcaccattga  gacccacaag  gaagaggagc  tcactgcttg        480 aagtctcct  atatttgctt  ttgcataaat  cagtctcact  ctacgcaact  ttctccactc        540
tctcccccct  tcactacatg  tttgttagtt  cctttagtct  cttcctttt  tactgtacga        600 gggatgattt  gatgttattc  tgagtctaat  gtaatggctt  ttcttttcc  tatttctgta        660 tgaggaaata  aaactcatgc  tctaaaaaaa  aaa                                      693
```

<210> SEQ ID NO 36
<211> LENGTH: 418
<212> TYPE: DNA
<213> ORGANISM: Eucalyptus grandis

<400> SEQUENCE: 36

```
aggactttat tataagcatt gtaaaaagag tcaaactaat acatcgcaag aattgggtta      60
tccaataatc tacaaaaaga aaaagtttg atgcattgag atggtaactg cttaattcaa      120
atgccttagt ttgaaaaatt aaccaactat taaaattaat gatgatgaat atggattatg     180
tgtgaaaaac tatatagact taaaattgac tcagaagaca ttcttttctt cttattttat    240
gatatgatga attcggtcta aacaggcaaa tggtgtcaaa cgggaagtcg caaaactct     300
tcctcggcag tgactaccgg gcgggcgatg atgcggatcc ggggggccggg tcgctggaga    360
acatcccgca cggaccggtc cacgtttggt gcggtgacaa caggcagccc aacctgga      418
```

<210> SEQ ID NO 37
<211> LENGTH: 777
<212> TYPE: DNA
<213> ORGANISM: Eucalyptus grandis

<400> SEQUENCE: 37

```
gaattcggca cgagcataca actacactgc gacgccgccg cagaacgcga gcgtgccgac      60
catgaacggc accaaggtct accggttgcc gtataacgct acggtccagc tcgtttttaca    120
ggacaccggg ataatcgcgc cggagaccca ccccatccat ctgcacggat tcaacttctt     180
cggtgtgggc aaaggagtgg ggaattatga cccaaagaag gatcccaaga agttcaatct    240
ggttgaccca gtggagagga acaccattgg aatcccatct ggtggatgga tagccatcag    300
attcacagca gacaatccag gagtttggtt cctgcactgc catctggaag tgcacacaac    360
ttggggactg aagatggcat tcttggtgga caatgggaag gggcctaaag agaccctgct    420
tccacctcca agtgatcttc caaaatgttg atcatttgat catgaggacg acaagcgatt    480
actaatgaca ccaagttagt ggaatcttct ctttgaaaaa gaagaagaag agcaagaaga    540
ataagaaaga tgaggagaga agccatagaa gatttgacca agaagagaga gggcaataaa    600
ccaaagagac ccttgagatc acgacatccc gcaattgttt ctagagtaat agaaggattt    660
actccgacac tgctacaata aattaaggaa gacaaggaat ttggttttttt tcattggagg    720
agtgtaattt gttttttggc aagctcatca catgaatcac atggaaaaaa aaaaaaa       777
```

<210> SEQ ID NO 38
<211> LENGTH: 344
<212> TYPE: DNA
<213> ORGANISM: Eucalyptus grandis

<400> SEQUENCE: 38

```
atatgttcag aatttcaaat gtgggaatgt caacctcctt gaacttcaga attcagggcc      60
atacgttgaa gctagtcgag gttgaaggat ctcacaccgt ccagaacatg tatgattcaa    120
tcgatgttca cgtgggccaa tccatggctg tcttagtgac cttaaatcag cctccaaagg    180
actactacat tgtcgcatcc acccggttca ccaagacggt tctcaatgca actgcagtgc    240
tacactacac caactcgctt accccagttt ccgggccact accagctggt ccaacttacc    300
aaaaacattg gtccatgaag caagcaagaa caatcaggtg gaac                     344
```

<210> SEQ ID NO 39
<211> LENGTH: 341

```
<212> TYPE: DNA
<213> ORGANISM: Eucalyptus grandis

<400> SEQUENCE: 39
gccgcaactg caattctctt cgtaaaacat gacggctgtc ggcaaaacct ctttcctctt      60
gggagctctc ctcctcttct ctgtggcggt gacattggca gatgcaaaag tttactacca     120
tgattttgtc gttcaagcga ccaaggtgaa gaggctgtgc acgacccaca acaccatcac     180
ggtgaacggg caattcccgg gtccgacttt ggaagttaac gacggcgaca ccctcgttgt     240
caatgtcgtc aacaaagctc gctacaacgt caccattcac tggcacggcg tccggcaggt     300
gagatctggt tgggctgatg gggcggaatt tgtgactcaa t                        341

<210> SEQ ID NO 40
<211> LENGTH: 358
<212> TYPE: DNA
<213> ORGANISM: Eucalyptus grandis

<400> SEQUENCE: 40
gaattcggca cgagatatgt tcagaatttc aaatgtggga atgtcaacct ccttgaactt      60
cagaattcag ggccatacgt tgaagctagt cgaggttgaa ggatctcaca ccgtccagaa     120
catgtatgat tcaatcgatg ttcacgtggg ccaatccatg ctgtcttag tgaccttaaa      180 tcagcctcca aaggactact acattgtcgc atccacccgg ttcaccaaga cggttctcaa     240
tgcaactgca gtgctacact acaccaactc gcttacccca gtttccgggc cactaccagc     300
tggtccaact taccaaaaac attggtccat gaagcaagca agaacaatca ggtggaac      358

<210> SEQ ID NO 41
<211> LENGTH: 409
<212> TYPE: DNA
<213> ORGANISM: Eucalyptus grandis

<400> SEQUENCE: 41
atcaagagtt tgagtctaaa ccttgtctaa tcctctctcg catagtcatt tggagacgaa      60
tgctgatcgg ccgcagctgc attctcttcg taaaacatga cggctgtcgg caaaacctct     120
ttcctcttgg gagctctcct cctcttctct gtggcggtga cattggcaga tgcaaaagtt     180
tactaccatg attttgtcgt tcaagcgacc aaggtgaaga ggctgtgcac gacccacaac     240
accatcacgg tgaacgggca attcccgggt ccgactttgg aagttaacga cggcgacacc     300
ctcgttgtca atgtcgtcaa caaagctcgc tacaacgtca ccattcactg gcacggcgtc     360
cggcaggtga gatctggttg ggctgatggg gcggaatttg tgactcaat                409

<210> SEQ ID NO 42
<211> LENGTH: 515
<212> TYPE: DNA
<213> ORGANISM: Eucalyptus grandis

<400> SEQUENCE: 42
ctctctctct ctctctctct gtgtgttcat tctcgttgag ctcgtggtcg cctcccgcca      60
tggatccgca caagtaccgt ccatccagtg ctttcaacac ttctttctgg actacgaact     120
ctggtgctcc tgtctggaac aataactctt cgttgactgt tggaagcaga ggtccaattc     180
ttcttgagga ttatcacctc gtggagaaac ttgccaactt tgatagggag aggattccag     240
agcgtgtggt gcatgccaga ggagccagtc aaagggatt ctttgaggtc actcatgaca      300
tttcccagct tacctgtgct gatttccttc gggcaccagg agttcaaaca cccgtgattg     360
```

```
tccgtttctc cactgtcatc cacgaaaggg gcagccctga aaccctgagg gaccctcgag     420
gttttgctgt gaagttctac acaagagagg gtaactttga tctggtggga aacaatttcc     480
ctgtcttctt tgtccgtaat gggataaatt ccccg                                515

<210> SEQ ID NO 43
<211> LENGTH: 471
<212> TYPE: DNA
<213> ORGANISM: Eucalyptus grandis

<400> SEQUENCE: 43
gaattcggca cgaggctccc tctcgtactg ccatactcct gggacgggat tcggatagg       60 atttgcggcg atccatttct cgattcaagg ggaagaatca tggggaagtc ctacccgacc    120
gtaagccagg agtacaagaa ggctgtcgag aaatgcaaga agaagttgag aggcctcatc    180
gctgagaaga gctgcgctcc gctcatgctc cgcatcgcgt ggcactccgc cggtaccttc    240
gatgtgaaga cgaagaccgg aggcccgttc ggaccatga  agcacgccgc ggagctcagc    300
cacggggcca acagcgggct cgacgttgcc gatcaggtct tgcagccgat caaggatcag    360
ttccccgtca tcacttatgc tgatttctac cagctggctg gcgtcgttgc tgtggaagtt    420
actggtggac ctgaagttgc ttttcacccg gaagagaggc aaaccacaac c             471

<210> SEQ ID NO 44
<211> LENGTH: 487
<212> TYPE: DNA
<213> ORGANISM: Eucalyptus grandis

<400> SEQUENCE: 44
gaattcggca cgagctccca cttctgtctc gccaccatta ctagcttcaa agcccagatc     60
tcagtttcgt gctctcttcg tcatctctgc ctcttgccat ggatccgtac aagtatcgcc    120
cgtccagcgc ttacgattcc agcttttgga caaccaacta cggtgctccc gtctggaaca    180
atgactcatc gctgactgtt ggaactagag gtccgattct cctggaggac taccatctga    240
ttgagaaact tgccaacttc gagagagaga ggattcctga gcgggtggtc catgcacggg    300
gagccagcgc gaaagggttc ttcgaggtca cccacgacat ctctcacttg acctgtgctg    360
atttcctccg ggctcctgga gtccagacgc ccgtaatcgt ccgtttctcc accgtcatcc    420
acgagcgcgg cagcccgaac ctcagggacc ctcgtggttt tgcagtgaag ttctacacca    480
gagaggg                                                             487

<210> SEQ ID NO 45
<211> LENGTH: 684
<212> TYPE: DNA
<213> ORGANISM: Pinus radiata

<400> SEQUENCE: 45
gaattcctgc agcccggggg atccactagt tctagagcgg ccgccaccgc ggtggagctc     60
gcgcgcctgc aggtcgacac tagtggatcc aaagaattcg gcacgaggcc cgacggccac    120
ttgttggacg ccatggaagc tctccggaaa gccgggattc tggaaccgtt taaactgcag    180
cccaaggaag gactggctct cgtcaacggc acagcggtgg gatccgccgt ggccgcgtcc    240
gtctgttttg acgccaacgt gctgggcgtg ctggctgaga ttctgtctgc gctcttctgc    300
gaggtgatgc aagggaaacc ggagttcgta gatccgttaa cccaccagtt gaagcaccac    360
ccagggcaga tcgaagccgc ggccgtcatg gagttcctcc tcgacggtag cgactacgtg    420
aaagaagcag cgcggcttca cgagaaagac ccgttgagca aaccgaaaca agaccgctac    480
```

```
gctctgcgaa catcgccaca gtggttgggg cctccgatcg aagtcatccg cgctgctact    540
cactccatcg agcgggagat caattccgtc aacgacaatc cgttaatcga tgtctccagg    600
gacatggctc tccacggcgg caacttccag ggaacaccca tcggagtttc catggacaac    660
atgcgaatct ctttggcagc cgtc                                          684

<210> SEQ ID NO 46
<211> LENGTH: 418
<212> TYPE: DNA
<213> ORGANISM: Pinus radiata

<400> SEQUENCE: 46
gaattcggca cgaggacaag gtcataggcc ctctcttcaa atgcttggat gggtggaaag     60
gaactcctgg cccattctga ataaataat cttccaagat cgcctttata caacgactgc    120
tatgatttga gtcctcggat cttttttgttg atgcagttgt ttaccgatct ggaatttgat    180
tggtcataaa gcttgatttt gttttctctt cttttgtttt atactgctgg atttgcatcc    240
cattggattt gccagaaata tgtaaggtgg gcagatcatt tgggtgatct gaaacatgta    300
aaagtggcgg atcatttggg tagcatgcag atcagttggg tgatcgtgta ctgctttcac    360
tattacttac atatttaaag atcgggaata aaaacatgat tttaattgaa aaaaaaa      418

<210> SEQ ID NO 47
<211> LENGTH: 479
<212> TYPE: DNA
<213> ORGANISM: Pinus radiata

<400> SEQUENCE: 47
gatatcccaa cgaccgaaaa cctgtatttt cagggcgcca tggggatccg gaattcggca     60
cgagcaagga agaaaatatg gttgcagcag cagaaattac gcaggccaat gaagttcaag    120
ttaaaagcac tgggctgtgc acggacttcg gctcgtctgg cagcgatcca ctgaactggg    180
ttcgagcagc caaggccatg gaaggaagtc actttgaaga agtgaaagcg atggtggatt    240
cgtatttggg agccaaggag atttccattg aagggaaatc tctgacaatc tcagacgttg    300
ctgccgttgc tcgaagatcg caagtgaaag tgaaattgga tgctgcggct gccaaatcta    360
gggtcgagga gagttcaaac tgggttctca cccagatgac caaggggacg gatacctatg    420
gtgtcactac tggtttcgga gccacttctc acaggagaac gaaccaggga gccgagctt     479

<210> SEQ ID NO 48
<211> LENGTH: 1785
<212> TYPE: DNA
<213> ORGANISM: Pinus radiata

<400> SEQUENCE: 48
tatcgataag cttgatatcg aattcctgca gcccggggga tccactagtt ctagagcggc     60
cgccaccgcg gtggagctcg cgcgcctgca ggtcgacact agtggatcca agaattcgg    120 cacgaggttg caggtcgggg atgatttgaa tcacagaaac ctcagcgatt ttgccaagaa    180
atatggcaaa atctttctgc tcaagatggg ccagaggaat cttgtggtag tttcatctcc    240
cgatctcgcc aaggaggtcc tgcacaccca gggcgtcgag tttgggtctc gaacccggaa    300
cgtggtgttc gatatcttca cgggcaaggg gcaggacatg tgttcaccg tctatggaga    360 tcactggaga aagatgcgca ggatcatgac tgtgcctttc tttacgaata agttgtcca    420 gcactacaga ttcgcgtggg aagacgagat cagccgcgtg gtcgcggatg tgaaatcccg    800
```

```
tagatgctca ggacaaggga gagatcaatg aggataatgt tttgtacatc gttgagaaca    900
tcaacgttgc agcaattgag acaacgctgt ggtcgatgga atggggaata gcggagctgg    960
tgaaccacca ggacattcag agcaaggtgc gcgcagagct ggacgctgtt cttggaccag   1020
gcgtgcagat aacggaacca gacacgacaa ggttgcccta ccttcaggcg gttgtgaagg   1080
aaacccttcg tctccgcatg gcgatcccgt tgctcgtccc ccacatgaat ctccacgacg   1140
ccaagctcgg gggctacgat attccggcag agagcaagat cctggtgaac gcctggtggt   1200
tggccaacaa ccccgccaac tggaagaacc ccgaggagtt ccgccccgag cggttcttcg   1260
aggaggagaa gcacaccgaa gccaatggca acgacttcaa attcctgcct tcggtgtggg   1320
gaggaggagc tgcccgggaa tcattctggc gctgcctctc ctcgcactct ccatcggaag   1380
acttgttcag aacttccacc ttctgccgcc gcccgggcag agcaaagtgg atgtcactga   1440
gaagggcggg cagttcagcc ttcacattct caaccattct ctcatcgtcg ccaagcccat   1500
agcttctgct taatcccaac ttgtcagtga ctggtatata aatgcgcgca cctgaacaaa   1560
aaacactcca tctatcatga ctgtgtgtgc gtgtccactg tcgagtctac taagagctca   1620
tagcacttca aaagtttgct aggatttcaa taacagacac cgtcaattat gtcatgtttc   1680
aataaaagtt tgcataaatt aaatgatatt tcaatatact attttgactc tccaccaatt   1740
ggggaatttt actgctaaaa aaaaaaaaaa aaaaaaaaa aaaaa                    1785

<210> SEQ ID NO 49
<211> LENGTH: 475
<212> TYPE: DNA
<213> ORGANISM: Pinus radiata

<400> SEQUENCE: 49
gaattcggca cgagatttcc atggacgatt ccgtttggct tcaattcgtt tcctctggct     60
gtcctcgtcc tcgttttcct tgttcttcct ccgacttttt ctctggaagc tatggcgtaa    120
taggaacctg ccgccaggac ccccggcatg gccgatcgta gggaacgtcc ttcagattgg    180
attttccagc ggcgcgttcg agacctcagt gaagaaattc catgagagat acggtccaat    240
attcactgtg tggctcggtt cccgccctct gctgatgatc accgaccgcg agcttgccca    300
cgaggcgctc gtacagaagg gctccgtctt cgctgaccgc ccgccgccc tcggatgca     360 gaaaatcttc agtagcaacc agcacaacat cacttcggct gaatacggcc cgctgtggcg    420
gagccttcgc aggaatctgg ttaaagaagc cctgagactt cggcgatgaa ggctt         475

<210> SEQ ID NO 50
<211> LENGTH: 801
<212> TYPE: DNA
<213> ORGANISM: Pinus radiata

<400> SEQUENCE: 50
gctccaccga cggtggacgg tccgctactc agtaactgag tgggatcccc cgggctgaca     60
ggcaattcga tttagctcac tcattaggca ccccaggctt tacactttat gcttccggct    120
cgtatgttgt gtggaattgt gagcggataa caatttcaca caggaaacag ctatgaccat    180
gattacgcca agcgcgcaat taaccctcac taaagggaac aaaagctgga gctccaccgc    240
ggtggcggcc gctctagaac tagtggatcc aaagaattcg gcacgagacc cagtgacctt    300
caggcctgag agatttcttg aggaagatgt tgatattaag ggccatgatt acaggctact    360
gccattcggt gcagggcgca ggatctgccc tggtgcacaa ttgggtatta atttagttca    420
gtctatgttg ggacacctgc ttcatcattt cgtatgggca cctcctgagg gaatgaaggc    480
```

```
agaagacata gatctcacag agaatccagg gcttgttact ttcatggcca agcctgtgca      540
ggccattgct attcctcgat tgcctgatca tctctacaag cgacagccac tcaattgatc      600
aattgatctg atagtaagtt tgaattttgt tttgatacaa aacgaaataa cgtgcagttt      660 ctcctttcc atagtcaaca tgcagctttc tttctctgaa gcgcatgcag ctttctttct       720
ctgaagccca acttctagca agcaataact gtatatttta gaacaaatac ctattcctca      780
aattgagtat ttctctgtag g                                                801

<210> SEQ ID NO 51
<211> LENGTH: 744
<212> TYPE: DNA
<213> ORGANISM: Pinus radiata

<400> SEQUENCE: 51 gggccccct tcgaggtgga cactagtgga tccaaagaat tcggcacgag gtttatctg        60 aaggacgctg tgcttgaagg ctcccagcca ttcaccaaag cccatggaat gaatgcgttc      120
gagtacccgg ccatcgatca gagattcaac aagattttca acaggctat gtctgagaat      180 tctaccatgt tgatgaacaa gattttggat acttacgagg ttttaagga ggttcaggag      240 ttggtggatg tgggaggagg tattgggtcg actctcaatc tcatagtgtc taggtatccc     300
cacatttcag gaatcaactt cgacttgtcc catgtgctgg ccgatgctcc tcactaccca     360
gctgtgaaac atgtgggtgg agacatgttt gatagtgtac caagtggcca agctattttt     420
atgaagtgga ttctgcatga ttggagcgat gatcattgca ggaagctttt gaagaattgt     480
cacaaggcgt tgccagagaa ggggaaggtg attgcggtgg acaccattct cccagtggct     540
gcagagacat ctccttatgc tcgtcaggga tttcatacag atttactgat gttggcatac     600
aacccagggg gcaaggaacg cacagagcaa gaatttcaag atttagctaa ggagacggga    660
tttgcaggtg tgtgttgaacc tgtatgttgt gtcaatggaa tgtgggtaat ggaattcctg   720
cagcccgggg gatccactag ttct                                            744

<210> SEQ ID NO 52
<211> LENGTH: 426
<212> TYPE: DNA
<213> ORGANISM: Pinus radiata

<400> SEQUENCE: 52
gtggccctgg aagtagtgtg cgcgacatgg attccttgaa tttgaacgag tttatgttgt     60
ggtttctctc ttggcttgct ctctacattg gatttcgtta tgttttgaga tcgaacttga     120
agctcaagaa gaggcgcctc ccgccgggcc catcggatg gccagtggtg ggaagtctgc      180
cattgctggg agcgatgcct cacgttactc tctacaacat gtataagaaa tatggccccg     240
ttgtctatct caaactgggg acgtccgaca tggttgtggc ctccacgccc gctgcagcta     300
aggcgtttct gaagactttg gatataaact ctccaaccg gccgggaaat gcaggagcca     360
cgtacatcgc ctacgattct caggacatgg tgtgggcagc gtatggagga cggtggaaga    420
tgggagc                                                              426

<210> SEQ ID NO 53
<211> LENGTH: 562
<212> TYPE: DNA
<213> ORGANISM: Pinus radiata

<400> SEQUENCE: 53
```

```
cagttcgaaa ttaacctcac taaagggaac aaaagctgga gttcgcgcgc ctgcaggtcg     60
acactagtgg atccaaagaa ttcggcacga gctttgaggc aacctacatt cattgaatcc    120
caggatttct tcttgtccaa acaggtttaa ggaaatggca ggcacaagtg ttgctgcagc    180
agaggtgaag gctcagacaa cccaagcaga ggagccggtt aaggttgtcc gccatcaaga    240
agtgggacac aaaagtcttt tgcagagcga tgccctctat cagtatatat tggaaacgag    300
cgtgtaccct cgtgagcccg agccaatgaa ggagctccgc gaagtgactg ccaagcatcc    360
ctggaacctc atgactactt ctgccgatga gggtcaattt ctgggcctcc tgctgaagct    420
cattaacgcc aagaacacca tggagattgg ggtgtacact ggttactcgc ttctcagcac    480
agcccttgca ttgcccgatg atggaaagat tctagccatg acatcaaca gagagaacta    540 tgatatcgga ttgcctataa tt                                              562

<210> SEQ ID NO 54
<211> LENGTH: 1074
<212> TYPE: DNA
<213> ORGANISM: Pinus radiata

<400> SEQUENCE: 54
tcgtgccgct cgatcctcac aggccctttt tatttccctg gtgaacgata cgatgggctc     60
gcacgctgag aatggcaacg gggtggaggt tgttgatcca acggacttaa ctgacatcga    120
gaatgggaaa ccaggttatg acaagcgtac gctgcctgcg gactggaagt ttggagtgaa    180
gcttcaaaac gttatggaag aatccattta caagtacatg ctggaaacat tcacccgcca    240
tcgagaggac gaggcgtcca aggagctctg gaacgaaca tggaacctga cacagagagg    300
ggagatgatg acattgccag atcaggtgca gttcctgcgc ttgatggtaa agatgtcagg    360
tgctaaaaag gcattggaga tcggagtttt cactggctat tcattgctca atatcgctct    420
cgctcttcct tctgatggca aggtggtagc tgtggatcca ggagatgacc ccaaatttgg    480
ctggccctgc ttcgttaagg ctggagttgc agacaaagtg gagatcaaga aaactacagg    540
gttggactat ttggattccc ttattcaaaa gggggagaag gattgcttcg actttgcatt    600
cgtggacgca gacaaagtga actacgtgaa ctatcatcca cggctgatga gttagtgcg    660 cgtgggggc gtcataattt acgacgacac cctctggttt ggtctggtgg aggaaaggga    720
tccccacaac ctgcttaaga atgattacat gaggacttct ctggagggta tcaaggccat    780
caactccatg gtagccaacg accccaactt ggaggtcgcc acagtctta tgggatatgg    840 tgtcactgtt tgttaccgca ctgcttagtt agctagtcct ccgtcattct gctatgtatg    900
tatatgataa tggcgtcgat ttctgatata ggtggttttt caatgtttct atcgtcatgt    960
tttctgttta gccagaatgt ttcgatcgtc atggtttctg ttaaagccag aataaaatta   1020
gccgcttgca gttcaaaaaa aaaaaaaaa aaaaactcga gactagttct cttc           1074

<210> SEQ ID NO 55
<211> LENGTH: 1075
<212> TYPE: DNA
<213> ORGANISM: Pinus radiata

<400> SEQUENCE: 55
tcggagctct cgaatcctca caggcccttt ttatttccct ggtgaacgat acgatgggct     60
cgcacgctga gaatggcaac ggggtggagg ttgttgatcc aacggactta actgacatcg    120
aagaatggga aaccaggtta tgacaagcgt cgctgcctgc ggactggaag tttggagtga    180
agcttcaaaa cgttatggaa gaatccattt acaagtacat gctggaaaca ttcacccgcc    240
```

-continued

```
atcgagagga cgaggcgtcc aaggagctct gggaacgaac atggaacctg acacagagag        300
gggagatgat gacattgcca gatcaggtgc agttcctgcg cttgatggta agatgtcag         360 gtgctaaaaa ggcattggag atcggagttt tcactggcta ttcattgctc aatatcgctc        420
tcgctcttcc ttctgatggc aaggtggtag ctgtggatcc aggagatgac cccaaatttg        480
gctggccctg cttcgttaag gctggagttg cagacaaagt ggagatcaag aaaactacag        540
ggttggacta tttggattcc cttattcaaa aggggagaa ggattgcttc gactttgcat         600
tcgtggacgc agacaaagtg aactacgtga actatcatcc acggctgatg aagttagtgc        660
gcgtgggggg cgtcataatt tacgacgaca ccctctggtt tggtctggtg ggaggaaagg       720
atccccacaa cctgcttaag aatgattaca tgaggacttc tctggagggt atcaaggcca        780
tcaactccat ggtagccaac gaccccaact tggaggtcgc cacagtcttt atgggatatg        840
gtgtcactgt ttgttaccgc actgcttagt tagctagtcc tccgtcattc tgctatgtat        900
gtatatgata atggcgtcga tttctgatat aggtggtttt tcaatgtttc tatcgtcatg        960 tttctgttt agccagaatg tttcgatcgt catggtttct gttaaagcca gaataaaatt       1020
agccgcttgc agttcaaaaa aaaaaaaaaa aaaaaactcg agactagttc tcttc           1075
```

<210> SEQ ID NO 56
<211> LENGTH: 1961
<212> TYPE: DNA
<213> ORGANISM: Pinus radiata

<400> SEQUENCE: 56

```
gtttttccgcc attttttcgcc tgtttctgcg gagaatttga tcaggttcgg attgggattg       60
aatcaattga aaggttttta ttttcagtat ttcgatcgcc atggccaacg gaatcaagaa       120
ggtcgagcat ctgtacagat cgaagcttcc cgatatcgag atctccgacc atctgcctct       180
tcattcgtat tgctttgaga gagtagcgga attcgcagac agaccctgtc tgatcgatgg       240
ggcgacagac agaacttatt gcttttcaga ggtggaactg atttctcgca aggtcgctgc       300
cggtctggcg aagctcgggt tgcagcaggg gcaggttgtc atgcttctcc ttccgaattg       360
catcgaattt gcgtttgtgt tcatggggc ctctgtccgg ggcgccattg tgaccacggc       420
caatcctttc tacaagccgg gcgagatcgc caaacaggcc aaggccgcgg gcgcgcgcga       480
tcatagttac cctggcagct tatgtggaga aactggccga tctgcagagc acgatgtgc       540 tcgtcatcac aatcgatgat gctcccaagg aaggttgcca acatatttcc gttctgaccg       600
aagccgacga aacccaatgc ccggccgtga caatccaccc ggacgatgtc gtggcgttgc       660
cctattcttc cggaaccacg gggctcccca agggcgtgat gttaacgcac aaaggcctgg       720
tgtccagcgt tgcccagcag gtcgatggtg aaaatcccaa tctgtatttc cattccgatg       780
acgtgatact ctgtgtcttg cctcttttcc acatctattc tctcaattcg gttctcctct       840
gcgcgctcag agccggggct gcgaccctga ttatgcagaa attcaacctc acgacctgtc       900
tggagctgat tcagaaatac aaggttaccg ttgccccaat tgtgcctcca attgtcctgg       960
acatcacaaa gagccccatc gtttcccagt acgatgtctc ggccgtccgg ataatcatgt      1020
ccggcgctgc gcctctcggg aaggaactcg aagatgccct cagagagcgt tttcccaagg      1080
ccattttcgg gcagggctac ggcatgacag aagcaggcc ggtgctggca atgaacctag      1140
ccttcgcaaa gaatccttt cccgtcaaat ctggctcctg cggaacagtc gtccggaacg      1200
ctcaaataaa gatcctcgat acagaaactg gcgagtctct cccgcacaat caagccggcg      1260
```

-continued

| | |
|---|---|
| aaatctgcat ccgcggaccc gaaataatga aaggatatat taacgacccg gaatccacgg | 1320 |
| ccgctacaat cgatgaagaa ggctggctcc acacaggcga cgtcgggtac attgacgatg | 1380 |
| acgaagaaat cttcatagtc gacagagtaa aggagattat caaatataag ggcttccagg | 1440 |
| tggctcctgc tgagctggaa gctttacttg ttgctcatcc gtcaatcgct gacgcagcag | 1500 |
| tcgttcctca aaagcacgag gaggcgggcg aggttccggt ggcgttcgtg gtgaagtcgt | 1560 |
| cggaaatcag cgagcaggaa atcaaggaat tcgtggcaaa gcaggtgatt ttctacaaga | 1620 |
| aaatacacag agtttacttt gtggatgcga ttcctaagtc gccgtccggc aagattctga | 1680 |
| gaaaggattt gagaagcaga ctggcagcaa atgaaaatg aatttccata tgattctaag | 1740 |
| attcctttgc cgataattat aggattcctt tctgttcact tctatttata taataaagtg | 1800 |
| gtgcagagta agcgccctat aaggagagag agagcttatc aattgtatca tatggattgt | 1860 |
| caacgcccta cactcttgcg atcgctttca atatgcatat tactataaac gatatatgtt | 1920 |
| ttttttataa atttactgca cttctcgttc aaaaaaaaaa a | 1961 |

<210> SEQ ID NO 57
<211> LENGTH: 1010
<212> TYPE: DNA
<213> ORGANISM: Pinus radiata

<400> SEQUENCE: 57

| | |
|---|---|
| gacaaacttg gtcgtttgtt taggttttgc tgcaggtgaa cactaatatg gaaggccaga | 60 |
| ttgcagcatt aagcaaagaa gatgagttca ttttttcacag cccttttcct gcagtacctg | 120 |
| ttccagagaa tataagtctt ttccagtttg ttctggaagg tgctgagaaa taccgtgata | 180 |
| aggtggccct cgtggaggcc tccacaggga aggagtacaa ctatggtcag gtgatttcgc | 240 |
| tcacaaggaa tgttgcagct gggctcgtgg acaaaggcat tcaaaagggc gatgttgtat | 300 |
| ttgttctgct tccaaatatg gcagaatacc ccattattgt gctgggaata atgttggccg | 360 |
| gcgcagtgtt ttctggggca aatccttctg cacacatcaa tgaagttgaa aaacatatcc | 420 |
| aggattctgg agcaaagatt gttgtgacag ttgggtctgc ttatgagaag gtgaggcaag | 480 |
| tgaaactgcc tgttattatt gcagataacg agcatgtcat gaacacaatt ccattgcagg | 540 |
| aaatttttga gagaaactat gaggccgcag ggccttttgt acaaatttgt caggatgatc | 600 |
| tgtgtgcact cccttattcc tctggcacca caggggcctc taaaggtgtc atgctcactc | 660 |
| acagaaatct gattgcaaat ctgtgctcta gcttgtttga tgtccatgaa tctcttgtag | 720 |
| gaaatttcac cacgttgggg ctgatgccat tctttcacat atatggcatc acgggcatct | 780 |
| gttgcgccac tcttcgcaac ggaggcaagg tcgtggtcat gtccagattc gatctccgac | 840 |
| actttatcag ttctttgatt acttatgagg tcaacttcgc gcctattgtc ccgcctataa | 900 |
| tgctctccct ccggtttaaa aatcctatcg ttaacgagtt cgatctcagc cgcttgaaac | 960 |
| tccaaagctg ttcatgactg cggctgctcc actggcgccg gatctactgc | 1010 |

<210> SEQ ID NO 58
<211> LENGTH: 741
<212> TYPE: DNA
<213> ORGANISM: Pinus radiata

<400> SEQUENCE: 58

| | |
|---|---|
| gaattcggca cgagaccatt tccagctaat attggcatag caattggtca ttctatcttt | 60 |
| gtcaaaggag atcaaacaaa ttttgaaatt ggacctaatg gtgtggaggc tagtcagcta | 120 |
| tacccagatg tgaaatatac cactgtcgat gagtacctca gcaaatttgt gtgaagtatg | 180 |

```
cgagattctc ttccacatgc ttcagagata cataacagtt tcaatcaatg tttgtcctag    240
gcatttgcca aattgtgggt tataatcctt cgtaggtgtt tggcagaaca gaacctcctg    300
tttagtatag tatgacgagc taggcactgc agatccttca cacttttctc ttccataaga    360
aacaaatact cacctgtggt ttgttttctt tctttctgga actttggtat ggcaataatg    420
tctttggaaa ccgcttagtg tggaatgcta agtactagtg tccagagttc taagggagtt    480
ccaaaatcat ggctgatgtg aactggttgt tccagagggt gtttacaacc aacagttgtt    540
cagtgaataa ttttgttaga gtgtttagat ccatctttac aaggctattg agtaaggttg    600
gtgttagtga acggaatgat gtcaaatctt gatgggctga ctgactctct tgtgatgtca    660
aatcttgatg gattgtgtct ttttcaatgg taaaaaaaaa aaaaaaaaaa aaaaaaaaa     720 aaaaaaaaaa aaaaaaaaaa a                                              741

<210> SEQ ID NO 59
<211> LENGTH: 643
<212> TYPE: DNA
<213> ORGANISM: Pinus radiata

<400> SEQUENCE: 59
ctcatctcgg agttgcaggc tgcagctttt ggcccaaagc atgatatcag atcaaacgac     60
gcagatgaag caaacggatc aaacagtttg cgttactgga gcagcgggtt tcattgcctc    120
atggcttgtc aagatgctcc tcatcagagg ttacactgtc agagcagcag ttcggaccaa    180
cccagctgat gataggtgga agtatgagca tctgcgagag ttggaaggag caaaagagag    240
gcttgagctt gtgaaagctg atattctcca ttaccagagc ttactcacag tcatcagagg    300
ttgccacggt gtctttcaca tggcttcagt tctcaatgat gaccctgagc aagtgataga    360
accagcagtc gaagggacga ggaatgtgat ggaggcctgc gcagaaactg gggtgaagcg    420
cgttgttttt acttcttcca tcggcgcagt ttacatgaat cctcatagag acccgctcgc    480
gattgtccat gatgactgct ggagcgattt gactactgcg tacaaaccaa gaattggtat    540
tgctatgcaa aaaccttggc agagaaatct gcatgggata ttgctaaggg aaggaattta    600
gagcttgcag tgataaatcc aggcctggcc ttaggtccct tga                      643

<210> SEQ ID NO 60
<211> LENGTH: 441
<212> TYPE: DNA
<213> ORGANISM: Pinus radiata

<400> SEQUENCE: 60
gaattcggca cgagaatttt tctgtggtaa gcatatctat ggctcaaacc agagagaagg     60
acgatgtcag cataacaaac tccaaaggat tggtatgcgt gacaggagcg gctggttact    120
tggcatcttg gctatcaag cgtctcctcc agtgtggtta ccaagtgaga ggaactgtgc     180
gggatcctgg caatgagaaa aagatggctc atttatggaa gttagatggg gcgaaagaga    240
gactgcaact aatgaaagct gatttaatgg acgagggcag cttcgatgag gtcatcagag    300
gctgccatgg tgttttttcac acagcgtctc cagtcgtggg tgtcaaatca gatcccaaga    360
tatggtatgc tctggccaag actttagcag aaaaagcagc atgggatttt gcccaagaaa    420
accatctgga catggttgca g                                              441

<210> SEQ ID NO 61
<211> LENGTH: 913
<212> TYPE: DNA
```

<213> ORGANISM: Pinus radiata

<400> SEQUENCE: 61

```
gaattcggca cgaggaaaac atcatccagg cattttggaa atttagctcg ccggttgatt      60
caggatcctg caatggcttt tggcgaagag cagactgcct tgccacaaga aacgcctttg     120
aatcctccgg tccatcgagg aacagtgtgc gttacaggag ctgctgggtt catagggtca     180
tggctcatca tgcgattgct tgagcgagga tatagtgtta gagcaactgt gcgagacact     240
ggtaatcctg taaagacaaa gcatctgttg gatctgccgg gggcaaatga gagattgact     300
ctctggaaag cagatttgga tgatgaagga agctttgatg ctgccattga tgggtgtgag     360
ggtgttttcc atgttgccac tcccatggat ttcgagtccg aggatcccga gaatgagata     420
attaagccaa caatcaacgg ggtcttgaat gttatgagat cgtgtgcaaa agccaagtcc     480
gtgaagcgag ttgttttcac gtcatctgct gggactgtga attttacaga tgatttccaa     540
acaccaggca agttttttga cgaatcatgc tggaccaacg tggatctttg cagaaaagtt     600
aaaatgacag gatggatgta ctttgtatcg aagacattag cagagaaagc tgcttgggat     660
tttgcagagg agaacaagat cgatctcatt actgttatcc ccacattggt cgttggacca     720
ttcattatgc agaccatgcc accgagcatg atcacagcct ggcactgtt aacgcggaat     780
gaaccccact acatgatact gagacaggta cagctggttc acttggatga tctctgtatg     840
tcacatatct ttgtatatga acatcctgaa gcaaagggca gatacatctc ttccacatgt     900
gatgctaccc att                                                        913
```

<210> SEQ ID NO 62
<211> LENGTH: 680
<212> TYPE: DNA
<213> ORGANISM: Pinus radiata

<400> SEQUENCE: 62

```
gaattcggca cgagatcaat ttttgcatat tattaaaaag taagtgtatt cgttctctat      60
attgatcagt cacagagtca tggccagttg tggttccgag aaagtaagag ggttgaatgg     120
agatgaagca tgcgaagaga caagagagt ggtttgtgta actggggcaa atgggtacat     180
cggctcttgg ctggtcatga gattactgga acatggctat tatgttcatg gaactgttag     240
ggacccagaa gacacaggga aggttgggca tttgctgcgg ctcccagggg caagtgagaa     300
gctaaagctg ttcaaggcag agcttaacga cgaaatggcc tttgatgatg ctgtgagcgg     360
ttgtcaaggg gttttccacg ttgccaagcc tgttaatctg gactcaaacg ctcttcaggg     420
ggaggttgtt ggtcctgcgg tgagggaac agtaaatctg cttcgagcct gcgaacgatc     480
gggcactgtg aaacgagtga tacatacctc gtccgtttca gcagtgagat tcactgggaa     540
acctgacccc cctgatactg tgctggatga atctcattgg acttcggtcg agtattgcag     600
aaagacaaag atggtcggat ggatgtacta catcgccaac acttatgcag aagagggagc     660
ccataagttc ggatcagaga                                                 680
```

<210> SEQ ID NO 63
<211> LENGTH: 492
<212> TYPE: DNA
<213> ORGANISM: Pinus radiata

<400> SEQUENCE: 63

```
gaattcggca cgaggctggt tcaagtgtca gcccaatggc ctcccctaca gagaatcccc      60
agatttcaga agagctgcta aatcatgaga tccatcaagg aagtacagta tgtgtgacag     120
```

```
gagctgctgg cttcatagga tcatggctcg tcatgcgttt gcttgagcga ggatatactg    180
ttagaggaac tgtgcgagac actggtaatc cggtgaagac gaagcatcta ttggatctgc    240
ctggggcgaa tgagaggtta actctctgga aagcagattt ggatgatgaa ggaagctttg    300
acgccgccat tgatggttgt gagggagttt ccatgttgc cactcccatg gatttttgaat    360 ccgaggaccc cgagaacgag ataattaaac ccgctgtcaa tgggatgttg aatgttttga    420
gatcgtgtgg gaaaaccaag tctatgaagc gagttgtttt cacgtcgtct gctgggactc    480 tgcttttttac gg                                                       492
```

<210> SEQ ID NO 64
<211> LENGTH: 524
<212> TYPE: DNA
<213> ORGANISM: Pinus radiata

<400> SEQUENCE: 64

```
gaattcggca cgagcttgtt caaagtcaca tatcttattt tctttgtgat atctgcaatt    60
tccaagcttt tcgtctacct ccctgaaaag atgagcgagg tatgcgtgac aggaggcaca    120
ggcttcatag ctgcttatct cattcgtagt cttctccaga aaggttacag agttcgcact    180
acagttcgca acccagataa tgtggagaag tttagttatc tgtgggatct gcctggtgca    240
aacgaaagac tcaacatcgt gagagcagat ttgctagaga aaggcagttt tgatgcagca    300
gtagatggtg tagatggagt attccatact gcatcacctg tcttagtccc atataacgag    360
cgcttgaagg aaaccctaat agatccttgt gtgaagggca ctatcaatgt cctcaggtcc    420
tgttcaagat caccttcagt aaagcgggtg gtgcttacat cctcctgctc atcaataccg    480
atacgactat aatagcttag agcgttccct gctggactga gtca                     524
```

<210> SEQ ID NO 65
<211> LENGTH: 417
<212> TYPE: DNA
<213> ORGANISM: Pinus radiata

<400> SEQUENCE: 65

```
tcctaattgt tcgatcctcc cttttaaagc ccttccctgg ccttcattcc aggtcacaga    60
gttgttcatg cagtgctagc aggaggagca gcgttgcaat tggggaaaat tccaaaatca    120
ataacgagag gacagaagta agtttgtgga aatagcaacc atgccggtgt ttccttctgg    180
tctggacccc tctgaggaca atggcaagct cgtttgtgtc atggatgcgt ccagttatgt    240
aggtttgtgg attgttcagg gccttcttca acgaggctat tcagtgcatg ccacggtgca    300
gagagacgct ggcgaggttg agtctctcag aaaattgcat gggatcgat tgcagatctt    360 ctatgcagat gtcttggatt atcacagcat tactgatgcg ctcaagggct gttctgg      417
```

<210> SEQ ID NO 66
<211> LENGTH: 511
<212> TYPE: DNA
<213> ORGANISM: Pinus radiata

<400> SEQUENCE: 66

```
atgacacgaa tttgtgcctc tctctgacca gagcttgaag ctctgtcttc tctgatatcg    60
cttcattcca tcatccagga gcttctgtta tatccatttc ctcaaaatgg atgcctacct    120
tgaagaaaat ggatacggcg cttccaattc tcggaaatta atgtgcctta ccgggggctg    180
gagtttcctg gggattcata tcgcaagaat gctgctcggc cggggttact cagtccgttt    240
```

```
cgcaattccg gtaacgccag aagaggcagg ctcacttatg gaatccgaag aagcattatc    300
ggggaagctg gagatatgcc aagccgatct cttggattat cgcagcgttt tcggcaacat    360
caatggttgc tccggagtct tccacgtccc tgcgccctgt gatcatctgg atggattaca    420
ggagtatccg gtatgattag tttaatagat tgacggggta tcctgtatga attagtttat    480
gaatttaagg ttttcttaga atttggatac t                                   511
```

<210> SEQ ID NO 67
<211> LENGTH: 609
<212> TYPE: DNA
<213> ORGANISM: Pinus radiata

<400> SEQUENCE: 67

```
cattgatagt tgatggaaga ccatcagtaa agcatgaaaa agaaattgtt ccaaggtgaa     60
gaagtcagtt gctccagcag aacctttta gcaattgttt ttgtatcctt tttgcctttg    120
aatatgtaat ccataaactt atgcaggaag tgcctcgtgc cgaattcggc acgagaatca    180
ctgaccttca catatttatt ccaattctaa tatctctact cgctgtctac ctgattttc    240 agtggcgaac caacttgaca ggttggaca tggccaacag cagcaagatt ctgattattg    300
gaggaacagg ctacattggt cgtcatataa ccaaagccag ccttgctctt ggtcatccca    360
cattccttct tgtcagagag acctccgctt ctaatcctga aaggctaag cttctggaat    420 ccttcaaggc ctcaggtgct attatactcc atggatcttt ggaggaccat gcaagtcttg    480
tggaggcaat caagaaagtt gatgtagtta tctcggctgt caagggacca cagctgacgg    540
ttcaaacagg atatttatcc aggtatttta aagggagggt tggaacccat caagaagggt    600
tttggccaa                                                            609
```

<210> SEQ ID NO 68
<211> LENGTH: 474
<212> TYPE: DNA
<213> ORGANISM: Pinus radiata

<400> SEQUENCE: 68

```
gcaagatagg ttttattctt ctggagttgg gtgaggcttg gaaatttaag taaaagggt     60 gcatagcaat taagcagttg cagccatggc ggtctgtgga actgaagtag ctcatactgt    120
gctctatgta gctgcagaca tggtggaaaa caacacgtct attgtgacca cctctatggc    180
tgcagcaaat tgtgagatgg agaagcctct tctaaattcc tctgccacct caagaatact    240
ggtgatggga gccacaggtt acattggccg ttttgttgcc caagaagctg ttgctgctgg    300
tcatcctacc tatgctctta acgcccgtt tgctgcttgt gacctggcca agcacagcg    360 cgtccaacaa ttgaaggatg ccggggtcca tatcctttat gggtctttga gtgatcacaa    420
cctcttagta aatacattga aggacatggg ccgttgttat ctctaccatt ggag           474
```

<210> SEQ ID NO 69
<211> LENGTH: 474
<212> TYPE: DNA
<213> ORGANISM: Pinus radiata

<400> SEQUENCE: 69

```
gcaagatagg ttttattctt ctggagttgg gtgaggcttg gaaatttaag taaaagggt     60 gcatagcaat taagcagttg cagccatggc ggtctgtgga actgaagtag ctcatactgt    120
gctctatgta gctgcagaca tggtggaaaa caacacgtct attgtgacca cctctatggc    180
tgcagcaaat tgtgagatgg agaagcctct tctaaattcc tctgccacct caagaatact    240
```

```
ggtgatggga gccacaggtt acattggccg ttttgttgcc caagaagctg ttgctgctgg    300
tcatcctacc tatgctctta tacgcccgtt tgctgcttgt gacctggcca agcacagcg    360 cgtccaacaa ttgaaggatg ccggggtcca tatcctttat gggtctttga gtgatcacaa    420
cctcttagta aatacattga aggacatggg ccgttgttat ctctaccatt ggag         474

<210> SEQ ID NO 70
<211> LENGTH: 608
<212> TYPE: DNA
<213> ORGANISM: Pinus radiata

<400> SEQUENCE: 70
cattgatagt tgatggaaga ccatcagtaa agcatgaaaa agaaattgtt ccaaggtgaa     60
gaagtcagtt gctccagcag aaccttttta gcaattgttt ttgtatcctt tttgcctttg    120
aatatgtaat ccataaactt atgcaggaag tgcctcgtgc cgaattcggc acgagaatca    180
ctgaccttca atatttatt ccaattctaa tatctctact cgctgtctac ctgattttc    240 agtggcgaac caacttgaca gggttggaca tggccaacag cagcaagatt ctgattattg    300
gaggaacagg ctacattggt cgtcatataa ccaaagccag ccttgctctt ggtcatccca    360
cattccttct tgtcagagag acctccgctt ctaatcctga aaggctaag cttctggaat    420 ccttcaaggc ctcaggtgct attatactcc atggatcttt ggaggaccat gcaagtcttg    480
tggaggcaat caagaaagtt gatgtagtta tctcggctgt caagggacca cagctgacgg    540
atcaaacagg atatttatcc agggtattta agggaggtt ggaacccatc aagaagggtt    600
ttggccaa                                                            608

<210> SEQ ID NO 71
<211> LENGTH: 1474
<212> TYPE: DNA
<213> ORGANISM: Pinus radiata

<400> SEQUENCE: 71
gaattcggca cgagaaaacg tccatagctt ccttgccaac tgcaagcaat acagtacaag     60
agccagacga tcgaatcctg tgaagtggtt ctgaagtgat gggaagcttg gaatctgaaa    120
aaactgttac aggatatgca gctcgggact ccagtggcca cttgtcccct tacacttaca    180
atctcagaaa gaaaggacct gaggatgtaa ttgtaaaggt catttactgc ggaatctgcc    240
actctgattt agttcaaatg cgtaatgaaa tggacatgtc tcattaccca atggtccctg    300 gcatgaagt ggtgggatt gtaacagaga ttggcagcga ggtgaagaaa ttcaaagtgg    360
gagagcatgt aggggttggt tgcattgttg ggtcctgtcg cagttgcggt aattgcaatc    420
agagcatgga acaatactgc agcaagagga tttggaccta caatgatgtg aaccatgacg    480
gcacacctac tcagggcgga tttgcaagca gtatggtggt tgatcagatg tttgtggttc    540
gaatcccgga gaatcttcct ctggaacaag cggcccctct gttatgtgca ggggttacag    600
ttttcagccc aatgaagcat ttcgccatga cagagcccgg gaagaaatgt gggattttgg    660
gtttaggagg cgtggggcac atgggtgtca agattgccaa agcctttgga ctccacgtga    720
cggttatcag ttcgtctgat aaaaagaaag aagaagccat ggaagtcctc ggcgccgatg    780
cttatcttgt tagcaaggat actgaaaaga tgatggaagc agcagagagc ctagattaca    840
taatggacac cattccagtt gctcatcctc tggaaccata tcttgccctt ctgaagacaa    900
atggaaagct agtgatgctg ggcgttgttc cagagccgtt gcacttcgtg actcctctct    960
```

-continued

| | |
|---|---|
| taatacttgg gagaaggagc atagctggaa gtttcattgg cagcatggag gaaacacagg | 1020 |
| aaactctaga tttctgtgca gagaagaagg tatcatcgat gattgaggtt gtgggcctgg | 1080 |
| actacatcaa cacggccatg gaaaggttgg agaagaacga tgtccgttac agatttgtgg | 1140 |
| tggatgttgc tagaagcaag ttggataatt agtctgcaat caatcaatca gatcaatgcc | 1200 |
| tgcatgcaag atgaatagat ctggactagt agcttaacat gaaagggaaa ttaaatttt | 1260 |
| atttaggaac tcgatactgg tttttgttac tttagtttag cttttgtgag gttgaaacaa | 1320 |
| ttcagatgtt tttttaactt gtatatgtaa agatcaattt ctcgtgacag taaataataa | 1380 |
| tccaatgtct tctgccaaat taatatatgt attcgtattt ttatatgaaa aaaaaaaaa | 1440 |
| aaaaaaaaaa aaaaaaaaaa aaaaaaaaaa aaaa | 1474 |

<210> SEQ ID NO 72
<211> LENGTH: 1038
<212> TYPE: DNA
<213> ORGANISM: Pinus radiata

<400> SEQUENCE: 72

| | |
|---|---|
| gaattcggca cgagagaggg ttatatatct tgattctgac ctgattgtcg tcgacgacat | 60 |
| tgccaagctc tgggccacgg atttggaatc tcgtgtcctc ggggcaccag agtactgcaa | 120 |
| ggcgaatttc acaaagtatt tcaccgataa tttctggtgg gatcccgcat tatccaagac | 180 |
| cttttgaggga aaaaaaccct gctacttcaa cacaggcgta atggtgatcg atcttgaaaa | 240 |
| atggcgggca gggaattcaa caagaaagat cgaaatctgg atggacatac agaaggaacg | 300 |
| ccgtatctat gagctcggat cattaccgcc atttttactg gtatttgctg gtttggttaa | 360 |
| gcaagtcgat catcgttgga atcagcacgg tttaggcgga gataatttgc aaggcctttg | 420 |
| ccgagatctt caccctggac ctgtcagttt gttgcattgg agtggtaagg gcaaaccttg | 480 |
| gctacgcctg gaatgccaag cggacttgcc ctctggatac tttatgggct ccttatgatc | 540 |
| tttatcgatc aacgtattac ctaaatgggt gagagagcct ctctcctcgg ggtgcttttt | 600 |
| atcgaattaa acctgatttg ataaaatgcc aaatagaact ttacgcctat gcatctttca | 660 |
| gttttgaatt tcaattctgg taacgaatag aagaaaacaa tagcacagcc acaggcagga | 720 |
| caaatccatc atgagggacc aatcgtttga atttagtatt aataaggttg ttccatataa | 780 |
| cgcctgtgaa gaatgatatt gtggactgat ctatttatat ttgtactgcc atgccatcct | 840 |
| cagccagcag agaggcaagc aatgccgctg caagtcatgt agggaaggcg ttgtgaactc | 900 |
| aattttcggc gactgtacag gatgtaaatt tttggaacat taatatcatt atgataagtt | 960 |
| cctgaaccaa caactgtata ataccttata aatgtatctg caactccatt tttgcataaa | 1020 |
| aaaaaaaaaa aaaaaaaa | 1038 |

<210> SEQ ID NO 73
<211> LENGTH: 372
<212> TYPE: DNA
<213> ORGANISM: Pinus radiata

<400> SEQUENCE: 73

| | |
|---|---|
| ctagggtct tgggggttc ctgatgccca attgttgctg tgcttggcat gaacccaaaa | 60 |
| catgcaagag atctgtagtc agtagtcttg ttggatctat agcttttaga aaagagtcac | 120 |
| gtccttttag ggtaacatca ttccaaccat atccagttcc accaccggct acaccttcaa | 180 |
| cgggaggagg agcaagatat tcagcattgc tttgggcacc agatggatag gcattatttt | 240 |
| ccatcggaat tcagccgagc tcgcccctc agtccaatcg tcgtgaaaat ccctcaaaat | 300 |

```
tgggcaattc tggctcgaaa tcgccaaatt atgggctaca acaggattaa aattgcacag      360
aaatctgcca gt                                                         372
```

<210> SEQ ID NO 74
<211> LENGTH: 545
<212> TYPE: DNA
<213> ORGANISM: Pinus radiata

<400> SEQUENCE: 74

```
aaagaattcg gcacgagggc aatccgagcc tagccaacca acttggcagc aaggagcaca       60
gggagttggc gagagaagct gttaggaaat ctttggtatt gttgaaaaat gggaagtcag      120
ccaacaagcc tttgctccct ttggagaaga atgcttccaa ggttcttgtt gcaggaaccc      180
atcctgataa tctgggttat cagtgtggtg gatggacgat ggaatggcaa ggattaagtg      240
gaaacataac cgtaggaact acaattctgg aagctatcaa actagctgtc agccctcta      300 ctgaagtggt ttatgagcaa atccagatg ctaactatgt caaggacaa gggttttcat       360 atgccattgt ggttgtgggt gaggcaccat acgcagaaac gtttgagac atcttaatt        420 tgaccattcc cctaggcgga ggggacacga ttaagacggt ctgtggctcc ttgaaatgcc      480
ttgtaatctt gatatctgga aggccacttg ttattgaacc ttatcttcca ttggtggatc      540
gtttt                                                                 545
```

<210> SEQ ID NO 75
<211> LENGTH: 463
<212> TYPE: DNA
<213> ORGANISM: Pinus radiata

<400> SEQUENCE: 75

```
gcaggtcgac actagtggat ccaaagaatt cggcacgaga aaaacaaat gttagctagc        60 ctagtgatga gctttacgta tacctggcct tttatacatg gatctgagtt tttatgcagg      120
tgtagagcct tttgttactc tgtatcactg ggacttgcca caagctctgg aggacgaata     180
cggtggattt cgtagcaaaa aagttgtgga tgactttggc atattctcag aagaatgctt      240 tcgtgcttt ggagaccgtg tgaagtactg ggtaactgtt aacgaaccgt tgatcttctc       300
atatttttct tacgatgtgg ggcttcacgc accgggccgc tgttcgcctg gatttggaaa      360
ctgcactgcg ggaaattcag cgacagagcc ttatattgta gcccataaca tgcttcttgc      420
acatagtacc gctgttaaaa atatatagca taaataccca ggg                       463
```

<210> SEQ ID NO 76
<211> LENGTH: 435
<212> TYPE: DNA
<213> ORGANISM: Pinus radiata

<400> SEQUENCE: 76

```
acactagtgg atccaaagaa ttcggcacga ggctaccatc ttccctcata atattgggct        60
tggagctacc agggatcctg atctggctag aagaataggg gctgctacgg ctttggaagt      120
tcgagctact ggcattcaat acacatttgc tccatgtgtt gctgtttgca gagatcctcg      180
atggggccgc tgctatgaga gctacagtga ggatccaaaa attgtcaagg ccatgactga      240
gattatcgtt ggcctgcaag ggaatcctcc tgctaattct acaaaagggg ggccttttat      300
agctggacag tcaaatgttg cagcttgtgc taagcatttt gtgggttatg gtggaacaac      360
caaaggtatc gatgagaata atactgttat caactatcaa gggttattc aacattccaa       420
```

| attaccccca attttt | 435 |

<210> SEQ ID NO 77
<211> LENGTH: 451
<212> TYPE: DNA
<213> ORGANISM: Pinus radiata

<400> SEQUENCE: 77

| gaattcggca cgagcctaga attctatggt gaaaattgtt gggacaaggc tgcccaagtt | 60 |
| tacaaaggaa cagtcccaaa tggttaaagg ttcaatagac tatctaggcg ttaaccaata | 120 |
| cactgcttat tacatgtatg atcctaaaca acctaaacaa aatgtaacag attaccagac | 180 |
| tggactggaa tacaggcttt gcatatgctc gcaatggagt gcctattgga ccaagggcga | 240 |
| actccaattg gctttacatt gtgccttggg gtctatacaa ggccgtcaca tacgtaaaag | 300 |
| aacactatgg aaatccaact atgattctct ctgaaaatgg aatggacgac ctggaaacgt | 360 |
| gacacttcca gcaggactgc atgataccat caggggtaac tactataaaa gctatttgca | 420 |
| aaatttgatt aatgcacgtg aatgaccggg g | 451 |

<210> SEQ ID NO 78
<211> LENGTH: 374
<212> TYPE: DNA
<213> ORGANISM: Pinus radiata

<400> SEQUENCE: 78

| ctgctctgca agcagtacta tgcacagcaa ggcctgctta actgaaaaca gagcgctgag | 60 |
| cttgaggaaa cgctcaagca ttgctgaggc caccgtttat ctaaatagcg caacataggg | 120 |
| cttcagaaaa atggcaatgg cacaagcatt cagaggccgt gtcttgcaag ctgcccgttt | 180 |
| gctccgccgc aacattctgc cggaggataa aagctttgga tccgctgctt ctcctagacg | 240 |
| agctcttagc ctgctctcat caaaagcctt catctctttc tctgttgaac ggcatcggct | 300 |
| agctgctaca aattcaacaa ttgtgttgca atctcgaaac ttttctgcaa aaggtaaaaa | 360 |
| gacaggacaa tctg | 374 |

<210> SEQ ID NO 79
<211> LENGTH: 457
<212> TYPE: DNA
<213> ORGANISM: Pinus radiata

<400> SEQUENCE: 79

| gaagaatgga agagattaat ggtgataacg cagtaaggag gagctgcttt cctccaggtt | 60 |
| tcatgtttgg gatagcaact tctgcttatc agtgtgaagg agctgccaac gaaggtggaa | 120 |
| aaggcccaag catctgggac tcattttcac gaacaccagg caaaattctt gatgaagca | 180 |
| acggtgatgt agcagtggat cagtatcatc gttataaggc agatgtaaaa ctgatgaaag | 240 |
| atatgggcgt ggctacctac agattctcga tttcatggcc tcgtatattt ccaaagggaa | 300 |
| aaggagagat caatgaggaa ggagtagcct attacaataa cctcatcaat gaactcctcc | 360 |
| agaatggaat ccaagcgtct gtcaactttg tttcactggg atactcccca gtctctggag | 420 |
| gatgaatatg gcggatttct gaggccaacc attgtga | 457 |

<210> SEQ ID NO 80
<211> LENGTH: 346
<212> TYPE: DNA
<213> ORGANISM: Pinus radiata

<400> SEQUENCE: 80

-continued

```
ggtgtgatgg caggaattcc agtcctaagg ccattttgca tctgtttgct ttcagtctac      60
atgctgcaca ttgtagctgc agtagcttca ccaaggctag gtagaagcag cttcccaagg     120
ggtttcaaat ttggtgcagg gtcatctgct tatcaggcgg aaggagctgc tcatgagggt     180
ggcaaaggcc caagcatttg ggatacattc tcccacactc caggtaaaat cgctgatggg     240
aatattggga tgttgcagta gatcaatacc accgttataa ggaagatgtg cagcttctca     300
aatacatggg aatggacgtc tatcgtttct ctatctcctg gtcacg                    346
```

<210> SEQ ID NO 81
<211> LENGTH: 957
<212> TYPE: DNA
<213> ORGANISM: Pinus radiata

<400> SEQUENCE: 81

```
gaattcggca cgagaaagcc ctagaatttt ttcagcatgc tatcacagcc ccagcgacaa      60
ctttaactgc aataactgtg gaagcgtaca aaaagtttgt cctagtttct ctcattcaga     120
ctggtcaggt tccagcattt ccaaaataca cacctgctgt tgtccaaaga aatttgaaat     180
cttgcactca gccctacatt gatttagcaa acaactacag tagtgggaaa atttctgtat     240
tggaagcttg tgtcaacacg aacacagaga agttcaagaa tgatagtaat ttggggttag     300
tcaagcaagt tttgtcatct ctttataaac ggaatattca gagattgaca cagacatatc     360
tgaccctctc tcttcaagac atagcaagta cggtacagtt ggagactgct aagcaggctg     420
aactccatgt tctgcagatg attcaagatg gtgagatttt tgcaaccata aatcagaaag     480
atgggatggt gagcttcaat gaggatcctg aacagtacaa aacatgtcag atgactgaat     540
atatagatac tgcaattcgg agaatcatgg cactatcaaa gaagctcacc acagtagatg     600
agcagatttc gtgtgatcat tcctacctga gtaaggtggg gagagagcgt tcaagatttg     660
acatagatga ttttgatact gttccccaga agttcacaaa tatgtaacaa atgatgtaaa     720
tcatcttcaa gactcgctta tattcattac tttctatgtg aattgatagt ctgttaacaa     780
tagtactgtg gctgagtcca gaaaggatct ctcggtatta tcacttgaca tgccatcaaa     840
aaaatctcaa atttctcgat gtctagtctt gattttgatt atgaatgcga cttttagttg     900
tgacatttga gcacctcgag tgaactacaa agttgcatgt taaaaaaaaa aaaaaaa      957
```

<210> SEQ ID NO 82
<211> LENGTH: 489
<212> TYPE: DNA
<213> ORGANISM: Pinus radiata

<400> SEQUENCE: 82

```
gcaggtcgac actagtggat ccaaagaatt cggcacgaga taagactaat tttccagaca      60
atcctccatt cccattcaat tacactggta ctccacccaa taatacacag gctgtgaatg     120
ggactagagt aaaagtcctt cccttttaaca caactgttca attgattctt caagacacca     180
gcatcttcag cacagacagc caccctgtcc atctccatgg tttcaatttc tttgtggtgg     240
gccaaggtgt tggaaactac aatgaatcaa cagatgcacc aaattttaac ctcattgacc     300
ctgtcgagag aaaacactgtg ggagttccca aggaggttg gctgctata agatttcgtg     360 cagacaatcc aggggtttgg ttcatgcact gtcatttgga ggttcacaca tcgtggggac     420
tgaaaatggc gtgggtagta agaacggaa aagggcccat cgattttcca cccgggtggg     480
taccagtaa                                                              489
```

<210> SEQ ID NO 83
<211> LENGTH: 471
<212> TYPE: DNA
<213> ORGANISM: Pinus radiata

<400> SEQUENCE: 83

| | | | | | |
|---|---|---|---|---|---|
| gaattcggca | cgagaaaacc | ttttcagacg | aatgttctga | tgctcggccc | cggccagaca | 60 |
| acagacatac | ttctcactgc | caatcaggct | acaggtagat | actacatggc | tgctcgagca | 120 |
| tattccaacg | ggcaaggagt | tcccttcgat | aacaccacta | ccactgccat | tttagaatac | 180 |
| gagggaagct | ctaagacttc | aactccagtc | atgcctaatc | ttccattcta | taacgacacc | 240 |
| aacagtgcta | ctagcttcgc | taatggtctt | agaagcttgg | gctcacacga | ccacccagtc | 300 |
| ttcgttcctc | agagtgtgga | ggagaatctg | ttctacacca | tcggtttggg | gttgatcaaa | 360 |
| tgtccggggc | agtcttgtgg | aggtccaacg | gatcaagatt | tgcagcaagt | atgaatacat | 420 |
| atcatttgtc | ccgcaaccac | ttcttccaat | ccttcaagct | cagcattttg | g | 471 |

<210> SEQ ID NO 84
<211> LENGTH: 338
<212> TYPE: DNA
<213> ORGANISM: Pinus radiata

<400> SEQUENCE: 84

| | | | | | |
|---|---|---|---|---|---|
| gttcggcact | gagagatcca | tttctttcaa | tgttgagaca | gtgagtagta | ttagtttgat | 60 |
| atctctttca | ggaatatatc | gtgcttgcag | gatctttagt | ttctgcaaca | atgtcgttgc | 120 |
| aatcagtgcg | tctatcttct | gctctccttg | ttttgctact | agcatttgtt | gcttacttag | 180 |
| ttgctgtaac | aaacgcagat | gtccacaatt | ataccttcat | tattagaaag | agacagttac | 240 |
| caggctatgc | aataagcgta | taatcgccac | cgtcaatggc | agctaccagg | cccaactatt | 300 |
| catgtacgtg | atggagacgt | tgttaattat | caaagctt | | | 338 |

<210> SEQ ID NO 85
<211> LENGTH: 1229
<212> TYPE: DNA
<213> ORGANISM: pinus radiata

<400> SEQUENCE: 85

| | | | | | |
|---|---|---|---|---|---|
| agagaaataa | ttatatttgt | aaatttaagt | ctacgtttat | taaaaaacta | caaccctaaa | 60 |
| tgcaggagaa | aaaacaagca | tgctgtctac | tgaagcttac | aaatcaaatc | cctgcgatat | 120 |
| gtcttttctc | gtgccgaatt | cggcacgaga | agatcttggt | tcgagtctct | cagctctctc | 180 |
| caaaggaatt | ttgtgggtca | tttgcaggtg | aagacaccat | ggtgaaggct | tatcccaccg | 240 |
| taagcgagga | gtacaaggct | gccattgaca | aatgcaagag | gaagctccga | gctctcattg | 300 |
| cagagaagaa | ctgtgcgccg | atcatggttc | gaatcgcatg | gcacagcgct | gggacttacg | 360 |
| atgtcaagac | caagaccgga | gggcccttcg | ggacgatgag | atatgggcc | gagcttgccc | 420 |
| acggtgctaa | cagtggtctg | gacatcgcag | ttaggctcct | ggagccaatc | aaggaacagt | 480 |
| tccccataat | cacctatgct | gacctttatc | agttggctgg | tgtggtggct | gttgaagtga | 540 |
| ccggggacc | tgacattccg | ttccatcctg | aagagaaga | caagcctgag | cctccagaag | 600 |
| aaggccgcct | tcctgatgct | acaaaaggac | ctgatcatct | gagggatgtt | tttggtcaca | 660 |
| tggggttgaa | tgataaggaa | attgtggcct | tgtctggtgc | ccacaccttg | gggagatgcc | 720 |
| acaaggagag | atctggtttt | gaaggaccat | ggacctctaa | ccccttatc | tttgacaact | 780 |
| cttacttcac | agagcttgtg | actggagaga | aggaaggcct | gcttcagttg | ccatctgata | 840 |

```
aggcactgct tgctgatcct agttttgcag tttatgttca gaagtatgca caggacgaag    900
acgctttctt tgctgactat gcggaagctc acctgaagct ttctgaactt gggtttgctg    960
atgcgtagat tcataccttc tgcagagaca attccttgct agatagcttc gttttgtatt   1020
tcatctaatc ttttcgatta tatagtcaca tagaagttgg tgttatgcgc catagtgata   1080
cttgaaccta catgttttg aaaagtatcg atgttcttta aatgaacat tgaatacaac    1140 attttggaat ctggttgtgt tctatcaagc gcatatttta atcgaatgct tcgttcctgt   1200
taaaaaaaaa aataaaataa aaaaaaaa                                      1229
```

<210> SEQ ID NO 86
<211> LENGTH: 1410
<212> TYPE: DNA
<213> ORGANISM: Pinus radiata

<400> SEQUENCE: 86

```
gaagatgggg ctgtgggtgg tgctggcttt ggcgctcagt gcgcactatt gcagtctcag     60
gcttacaatg tggtaagttc aagcaatgct actgggagtt acagtgagaa tggattggtg    120
atgaattact atgggactc ttgccctcag gctgaagaga tcattgctga acaagtacgc    180
ctgttgtaca aaagacacaa gaacactgca ttctcatggc ttagaaatat tttccatgac    240
tgtgctgtgg agtcatgtga tgcatcgctt ctgttggact caacaaggaa cagcatatca    300
gaaaaggaca ctgacaggag cttcggcctc cgcaacttta ggtatttgga taccatcaag    360
gaagccgtgg agagggagtg ccccggggtc gtttcctgtg cagatatact cgttctctct    420
gccagagatg gcgttgtatc gttgggagga ccatacattc ccctgaagac gggaagaaga    480
gatggacgga agagcagagc agatgtggtg gagaattacc tgcccgatca caatgagagc    540
atctccactg ttctgtctcg cttcaaagcc atgggaatcg cacccgtgg ggttgttgca    600 ctgctggggg ctcacagcgt ggggaggact cactgcgtga agctggtgca caggctgtac    660
ccggaagtag atccgacact ggaccctggg cacgtggagc acatgaagca caagtgcccg    720
gacgcgatcc ccaacccgaa ggcagtgcag tatgtgcgga cgaccgggga acgcctatg    780 aagctggaca caactacta cgtgaacctg atgaacaaca aggggctcct aatagtggac    840
cagcaactgt atgcagattc gaggaccagg ccgtatgtga agaagatggc aaaaagccag    900
gaatacttct tcaaatactt ctcccgggcg ctcaccatcc tctctgagaa caatcctctc    960
accggcgctc gaggagaaat ccgtcggcag tgctcgctca aaaacaaatt gcacacaaaa   1020
agcaagcgtt gagcgatagc tcaatgccgc agtggtggga gtgatagcgt gatgccacag   1080
tggtgggcat ttcatatata aattgcagtt tgcgttttta ttagataatc ataatggtgt   1140
ggtgtgacta tgccctgcga atcacatcga tgaaccacaa ccgaaccgtg aacagtagg    1200 cttattccct tatgtaagca gaacctttta ttataagcaa aaagacaat cctgtctgtt   1260 attctagtat aattttgtca tcagttaaag ttgctcatct gataataact ggaaacggta   1320
aaatatgaca actacgtatc ttctttggtc atctgataat aaccggaaac gataaaatat   1380
gacaactaca tatattcttt aaaaaaaaaa                                   1410
```

<210> SEQ ID NO 87
<211> LENGTH: 687
<212> TYPE: DNA
<213> ORGANISM: Pinus radiata

<400> SEQUENCE: 87

```
gtagtttcgt tttacaacaa tctcaggttt tgaatctcag aatagttgcg aaaggaagcg     60
```

```
atgacgaagt acgtgatcgt tagctccatt gtgtgtttct ttgtatttgt ttctgcgtgc    120
ataatttctg tcaatggatt agttgtccat gaagatgatc tgtcaaagcc tgtgcatggg    180
ctttcgtgga cattttataa ggacagttgc cccgacttgg aggccatagt gaaatcggta    240
cttgagccgg cgttggacga agatatcact caggccgcag gcttgctgag acttcatttc    300
catgactgtt ttgtgcaggg ttgcgatggg tccgtgttgc tgacaggaac taaaagaaac    360
cccagtgagc aacaggctca gccaaactta acactaagag cccgggcctt gcagctgatc    420
gacgaaatta aaaccgctgt agaagctagc tgcagtgggg ttgtaacttg tgcagacatt    480
ctggctttgg ctgctcgtga ctccgtccgc tcaggaggcc caaaattcc agtaccactt    540
ggccgcagag atagcctaaa gtttgccagt caatccgtag ttctcgccaa tataccaact    600
ccaactttaa atttgacaca gctgatgaac attttttggct ccaaaggatt cagtttggcc    660
gaaatggttg ctcttcaggt ggcacac                                          687
```

<210> SEQ ID NO 88
<211> LENGTH: 688
<212> TYPE: DNA
<213> ORGANISM: Pinus radiata

<400> SEQUENCE: 88

```
gtagtttcgt tttacaacaa tctacaggtt ttgaatctca gaatagttgc gaaaggaagc     60
gatgacgaag tacgtgatcg ttagctccat tgtatgtttc tttgtatttg tttctgcgtg    120
cataatttct gtcaatggat tagttgtcca tgaagatgat ctgtcaaagc ctgtgcatgg    180
gctttcgtgg acattttata aggacagttg ccccgacttg gaggccatag tgaaatcggt    240
acttgagccg cgttggacg aagatatcac tcaggccgca ggttgctgag acttcatttc    300
catgactgtt ttgtgcaggg ttgcgatggg tccgtgttgc tgacaggaac taaaagaaac    360
ccccgagtga gcaacaggct cagccaaact taacactaag agcccgggcc ttgcagctga    420
tcgacgaaat taaaaccgct gtagaagcta gctgcagtgg ggttgtaact tgtgcagaca    480
ttctggcttt ggctgctcgt gactccgtcg ctcaggaggc ccaaaatttc cagtaccact    540
tggccgcaga gatagcctaa agtttgccag tcaatccgta gttctcgcca atataccaac    600
tccaacttta aatttgacac agctgatgaa cattttttgc tccaaaggat tcagtttggc    660
cgaaatggtt gctcttcagg tggcacac                                        688
```

<210> SEQ ID NO 89
<211> LENGTH: 278
<212> TYPE: DNA
<213> ORGANISM: Pinus radiata

<400> SEQUENCE: 89

```
tcttcgaatt ctcttttcacg actgcttcgt taatggctgc gatggctcga tattgttaga     60
tgataactca acgttcaccg gagaaaagac tgcaggccca atgttaatt ctgcgagagg    120
attcgacgta atagacacca tcaaaactca agttgaggca gcctgcagtg gtgtcgtgtc    180
atgtgccgac attctcgcca ttgctgcacg cgattcagtc gtccaactgg ggggcccaac    240
atggacggta cttctgggag aaaagacgga tccgatca                              278
```

<210> SEQ ID NO 90
<211> LENGTH: 1960
<212> TYPE: DNA
<213> ORGANISM: Pinus radiata

<400> SEQUENCE: 90

```
gttttccgcc attttcgcc tgtttctgcg gagaatttga tcaggttcgg attgggattg      60
aatcaattga aaggttttta ttttcagtat ttcgatcgcc atggccaacg gaatcaagaa    120
ggtcgagcat ctgtacagat cgaagcttcc cgatatcgag atctccgacc atctgcctct    180
tcattcgtat tgctttgaga gagtagcgga attcgcagac agaccctgtc tgatcgatgg    240
ggcgacagac agaacttatt gcttttcaga ggtggaactg atttctcgca aggtcgctgc    300
cggtctggcg aagctcgggt tgcagcaggg gcaggttgtc atgcttctcc ttccgaattg    360
catcgaattt gcgtttgtgt tcatgggggc tctgtccgg ggcgccattg tgaccacggc     420
caatcctttc tacaagccgg gcgagatcgc caaacaggcc aaggccgcgg gcgcgcgcat    480
catagttacc ctggcagctt atgtggagaa actggccgat ctgcagagcc acgatgtgct    540
cgtcatcaca atcgatgatg ctcccaagga aggttgccaa catatttccg ttctgaccga    600
agccgacgaa acccaatgcc cggccgtgac aatccaccg gacgatgtcg tggcgttgcc     660
ctattcttcc ggaaccacgg ggctccccaa gggcgtgatg ttaacgcaca aaggcctggt    720
gtccagcgtt gcccagcagg tcgatggtga aaatcccaat ctgtatttcc attccgatga    780
cgtgatactc tgtgtcttgc ctcttttcca catctattct ctcaattcgg ttctcctctg    840
cgcgctcaga gccggggctg cgaccctgat tatgcagaaa ttcaacctca cgacctgtct    900
ggagctgatt cagaaataca aggttaccgt tgccccaatt gtgcctccaa ttgtcctgga    960
catcacaaag agccccatcg tttcccagta cgatgtctcg gccgtccgga taatcatgtc   1020
cggcgctgcg cctctcggga aggaactcga agatgccctc agagagcgtt tcccaaggc    1080
cattttcggg cagggctacg gcatgacaga agcaggcccg gtgctggcaa tgaacctagc   1140
cttcgcaaag aatcctttcc ccgtcaaatc tggctcctgc ggaacagtcg tccggaacgc   1200
tcaaataaag atcctcgata cagaaactgg cgagtctctc ccgcacaatc aagccggcga   1260
aatctgcatc cgcggacccg aaataatgaa aggatatatt aacgaccgg aatccacggc    1320
cgctacaatc gatgaagaag gctggctcca cacaggcgac gtcgggtaca ttgacgatga   1380
cgaagaaatc ttcatagtcg acagagtaaa ggagattatc aaatataagg gcttccaggt   1440
ggctcctgct gagctggaag ctttacttgt tgctcatccg tcaatcgctg acgcagcagt   1500
cgttcctcaa aagcacgagg aggcgggcga ggttccggtg gcgttcgtgg tgaagtcgtc   1560
ggaaatcagc gagcaggaaa tcaaggaatt cgtggcaaag caggtgattt tctacaagaa   1620
aatacacaga gtttactttg tggatgcgat tcctaagtcg ccgtccggca agattctgag   1680
aaaggatttg agaagcagac tggcagcaaa atgaaaatga atttccatat gattctaaga   1740
ttcctttgcc gataattata ggattccttt ctgttcactt ctatttatat aataaagtgg   1800
tgcagagtaa gcgccctata aggagagaga gagcttatca attgtatcat atggattgtc   1860
aacgccctac actcttgcga tcgctttcaa tatgcatatt actataaacg atatatgttt   1920
tttttataaa tttactgcac ttctcgttca aaaaaaaaa                          1960
```

<210> SEQ ID NO 91
<211> LENGTH: 701
<212> TYPE: DNA
<213> ORGANISM: Pinus radiata

<400> SEQUENCE: 91

```
gtagtttcgt tttacaacaa tctcaggttt tgaatctcag aatagttgcg aaaggaagcg      60
atgacgaagt acgtgatcgt tagctccatt gtatgtttct ttgtatttgt ttctgcgtgc    120
```

```
ataatttctg tcaatggatt agttgtccat gaagatgatc tgtcaaagcc tgtgcatggg    180
ctttcgtgga cattttataa ggacagttgc cccgacttgg aggccatagt gaaatcggta    240
cttgagccgg cgttggacga agatatcact caggccgcag gttgctgaga cttcatttcc    300
atgactgttt tgtgcagggt tgcgatgggt ccgtgttgct gacaggaact aaaagaaacc    360
ccgagtgagc aacaggctca gccaaactta acactaagag cccgggcctt gcagctgatc    420
gacgaaatta aaccgctgt agaagctagc tgcagtgggg ttgtaacttg tgcagacatt    480
ctggctttgg ctgctcgtga ctccgtcgct caggaggccc aaaatttcca gtaccacttg    540
gccgcagaga tagcctaaag tttgccagtc aatccgtagt tctcgccaat ataccaactc    600
caactttaaa tttgacacag ctgatgaaca ttttttggctc caaggattc agtttggccg    660 aaatggttgc tctttcaggt ggacacacaa tcggcattgg t                       701

<210> SEQ ID NO 92
<211> LENGTH: 626
<212> TYPE: DNA
<213> ORGANISM: Pinus radiata

<400> SEQUENCE: 92
gttgcaggtc ggggatgatt tgaatcacag aaacctcagc gattttgcca agaaatatgg     60
caaaatcttt ctgctcaaga tgggccagag gaatcttgtg gtagtttcat ctcccgatct    120
cgccaaggag gtcctgcaca cccagggcgt cgagtttggg tctcgaaccc ggaacgtggt    180
gttcgatatc ttcacgggca aggggcagga catggtgttc accgtctatg gagatcactg    240
gagaaagatg cgcaggatca tgactgtgcc tttctttacg aataaagttg tccagcacta    300
cagattcgcg tgggaagacg agatcagccg cgtggtcgcg gatgtgaaat cccgcgccga    360
gtcttccacc tcgggcattg tcatccgtag cgcctccagc tcatgatgta taatattatg    420
tataggatga tgttcgacag gagattcgaa tccgaggac accccgctttt cctcaagctc    480 aaggccctca acggagagcg aagtcgattg gcccagagct ttgagtacaa ttatggggat    540
ttcattccca gtcttaggcc cttcctcaga ggttatcaca gaatctgcaa tgagattaaa    600
gagaaacggc tctctctttt caagga                                        626

<210> SEQ ID NO 93
<211> LENGTH: 660
<212> TYPE: DNA
<213> ORGANISM: Pinus radiata
<220> FEATURE:
<221> NAME/KEY: unsure
<222> LOCATION: (1)...(660)
<223> OTHER INFORMATION: n at all occurrences indicates unsure

<400> SEQUENCE: 93
acccagtgac cttcaggcct gagagatttc ttgaggaaga tgttgatatt aagggccatg     60
attacaggct actgccattg gtgcagggcg caggatctgc cctggtgcac aattgggtat    120
taatttagtt cagtctatgt tgggacacct gcttcatcat ttcgtatggg cacctcctga    180
gggaatgaag gcagaagaca tagatctcac agagaatcca gggcttgtta ctttcatggc    240
caagcctgtg caggccattg ctattcctcg attgcctgat catctctaca gcgacagcc    300 actcaattga tcaattgatc tgatagtaag tttgaatttt gttttgatac aaaacgaaat    360
aacgtgcagt ttctccttttt ccatagtcaa catgcagctt tctttctctg aagcgcatgc    420
agctttcttt ctctgaagcc caacttctag caagcaataa ctgtatatttt tagaacaaat    480
```

| | |
|---|---:|
| acctattcct caaattgagw atttctctgt aggggnngnt aattgtgcaa tttgcaagna | 540 |
| atagtaaagt ttantttagg gnatttaat agtcctangt aanangnggn aatgntagng | 600 |
| ggcattnaga aancctaat agntgttggn ggnngntagg nttttnacc aaaaaaaaaa | 660 |

<210> SEQ ID NO 94
<211> LENGTH: 1012
<212> TYPE: DNA
<213> ORGANISM: Pinus radiata

<400> SEQUENCE: 94

| | |
|---|---:|
| ctttgaggca acctacattc attgaatccc aggatttctt cttgtccaaa caggtttaag | 60 |
| gaaatggcag gcacaagtgt tgctgcagca gaggtgaagg ctcagacaac ccaagcagag | 120 |
| gagccggtta aggttgtccg ccatcaagaa gtgggacaca aaagtctttt gcagagcgat | 180 |
| gccctctatc agtatatatt ggaaacgagc gtgtaccctc gtgagcccga gccaatgaag | 240 |
| gagctccgcg aagtgactgc caagcatccc tggaacctca tgactacttc tgccgatgag | 300 |
| ggtcaatttc tgggcctcct gctgaagctc attaacgcca agaacaccat ggagattggg | 360 |
| gtgtacactg gttactcgct tctcagcaca gcccttgcat gcccgatga tggaaagatt | 420 |
| ctagccatgg acatcaacag agagaactat gatatcggat tgcctattat tgagaaagca | 480 |
| ggagttgccc acaagattga cttcagagag gcccctgctc tgccagttct ggacgaactg | 540 |
| cttaagaatg aggacatgca tggatcgttc gattttgtgt tcgtggatgc ggacaaagac | 600 |
| aactatctaa actaccacaa gcgtctgatc gatctggtga aggttggagg tctgattgca | 660 |
| tatgacaaca ccctgtggaa cggatctgtg gtggctccac ccgatgctcc cctgaggaaa | 720 |
| tatgtgagat attacagaga tttcgtgatg gagctaaaca aggcccttgc tgtcgatccc | 780 |
| cgcattgaga tcagccaaat cccagtcggt gacggcgtca ccctttgcag gcgtgtctat | 840 |
| tgaaaacaat ccttgtttct gctcgtctat tgcaagcata aaggctctct gattataagg | 900 |
| agaacgctat aatatatggg gttgaagcca tttgttttgt ttagtgtatt gataataaag | 960 |
| tagtacagca tatgcaaagt ttgtatcaaa aaaaaaaaa aaaaaaaaaa aa | 1012 |

<210> SEQ ID NO 95
<211> LENGTH: 1460
<212> TYPE: DNA
<213> ORGANISM: Pinus radiata

<400> SEQUENCE: 95

| | |
|---|---:|
| aaaacgtcca tagcttcctt gccaactgca agcaatacag tacaagagcc agacgatcga | 60 |
| atcctgtgaa gtggttctga agtgatggga agcttggaat ctgaaaaaac tgttacagga | 120 |
| tatgcagctc gggactccag tggccacttg tccccttaca cttacaatct cagaaagaaa | 180 |
| ggacctgagg atgtaattgt aaaggtcatt tactgcggaa tctgccactc tgatttagtt | 240 |
| caaatgcgta atgaaatgga catgtctcat tacccaatgg tccctgggca tgaagtggtg | 300 |
| gggattgtaa cagagattgg cagcgaggtg aagaaattca agtgggaga gcatgtaggg | 360 |
| gttggttgca ttgttgggtc ctgtcgcagt tgcggtaatt gcaatcagag catggaacaa | 420 |
| tactgcagca agaggatttg gacctacaat gatgtgaacc atgacggcac acctactcag | 480 |
| ggcggatttg caagcagtat ggtggttgat cagatgtttg tggttcgaat cccggagaat | 540 |
| cttcctctgg aacaagcggc ccctctgtta tgtgcagggg ttacagtttt cagcccaatg | 600 |
| aagcatttcg ccatgacaga gcccgggaag aaatgtggga ttttgggttt aggaggcgtg | 660 |
| gggcacatgg gtgtcaagat tgccaaagcc tttggactcc acgtgacggt tatcagttcg | 720 |

-continued

```
tctgataaaa agaaagaaga agccatggaa gtcctcggcg ccgatgctta tcttgttagc      780
aaggatactg aaaagatgat ggaagcagca gagagcctag attacataat ggacaccatt      840
ccagttgctc atcctctgga accatatctt gcccttctga agacaaatgg aaagctagtg      900
atgctgggcg ttgttccaga gccgttgcac ttcgtgactc ctctcttaat acttgggaga      960
aggagcatag ctggaagttt cattggcagc atggaggaaa cacaggaaac tctagatttc     1020
tgtgcagaga agaaggtatc atcgatgatt gaggttgtgg gcctggacta catcaacacg     1080
gccatggaaa ggttggagaa gaacgatgtc cgttacagat ttgtggtgga tgttgctaga     1140
agcaagttgg ataattagtc tgcaatcaat caatcagatc aatgcctgca tgcaagatga     1200
atagatctgg actagtagct aacatgaaag ggaaattaa attttttattt aggaactcga     1260
tactggttttt tgttactttta gtttagctttt tgtgaggttg aaacaattca gatgttttttt    1320
taacttgtat atgtaaagat caatttctcg tgacagtaaa taataatcca atgtcttctg     1380
ccaaattaat atatgtattc gtattttttat atgaaaaaaa aaaaaaaaaa aaaaaaaaaa    1440
aaaaaaaaaa aaaaaaaaaa                                                  1460
```

<210> SEQ ID NO 96
<211> LENGTH: 788
<212> TYPE: DNA
<213> ORGANISM: Pinus radiata

<400> SEQUENCE: 96

```
ataagactct cgagaaggtc tatgtccccg aggagggggt tctcaactta atcgcagaga       60
caccatttcc agctaatatt ggcatagcaa ttggtcattc tatctttgtc aaaggagatc      120
aaacaaattt tgaaattgga cctaatggtg tggaggctag tcagctatac ccagatgtga      180
aatataccac tgtcgatgag tacctcagca aatttgtgtg aagtatgcga gattctcttc      240
cacatgcttc agagatacat aacagtttca atcaatgttt gtcctaggca tttgccaaat      300
tgtgggttat aatccttcgt aggtgtttgg cagaacagaa cctcctgttt agtatagtat      360
gacgagctag gcactgcaga tccttcacac ttttctcttc cataagaaac aaatactcac      420
ctgtggtttg ttttctttct ttctggaact ttggtatggc aataatgtct ttggaaaccg      480
cttagtgtgg aatgctaagt actagtgtcc agagttctaa gggagttcca aaatcatggc      540
tgatgtgaac tggttgttcc agagggtgtt tacaaccaac agttgttcag tgaataattt      600
tgttagagtg tttagatcca tctttacaag gctattgagt aaggttggtg ttagtgaacg      660
gaatgatgtc aaatcttgat gggctgactg actctcttgt gatgtcaaat cttgatggat      720
tgtgtctttt tcaatggtaa aaaaaaaaaa aaaaaaaaaa aaaaaaaaaa aaaaaaaaaa      780
aaaaaaaa                                                               788
```

<210> SEQ ID NO 97
<211> LENGTH: 577
<212> TYPE: DNA
<213> ORGANISM: Pinus radiata

<400> SEQUENCE: 97

```
gcccgacggc cacttgttgg acgccatgga agctctccgg aaagccggga ttctggaacc       60
gtttaaactg cagcccaagg aaggactggc tctcgtcaac ggcacagcgg tgggatccgc      120
cgtggccgcg tccgtctgtt ttgacgccaa cgtgctgggc gtgctggctg agattctgtc      180
tgcgctcttc tgcgaggtga tgcaagggaa accggagttc gtagatccgt taacccacca      240
```

| | |
|---|---:|
| gttgaagcac cacccagggc agatcgaagc cgcggccgtc atggagttcc tcctcgacgg | 300 |
| tagcgactac gtgaaagaag cagcgcggct tcacgagaaa gacccgttga gcaaaccgaa | 360 |
| acaagaccgc tacgctctgc gaacatcgcc acagtggttg gggcctccga tcgaagtcat | 420 |
| ccgcgctgct actcactcca tcgagcggga gatcaattcc gtcaacgaca atccgttaat | 480 |
| cgatgtctcc agggacatgg ctctccacgg cggcaacttc cagggaacac ccatcggagt | 540 |
| ttccatggac aacatgcgaa tctctttggc agccgtc | 577 |

<210> SEQ ID NO 98
<211> LENGTH: 492
<212> TYPE: DNA
<213> ORGANISM: Pinus radiata

<400> SEQUENCE: 98

| | |
|---|---:|
| tacctggcca accccgtcac gactcacgtc cagagcgccg aacaacacaa ccaggatgtc | 60 |
| aattccctcg gcttgatctc cgccagaaag actgccgagg ccgttgagat tttaaagctg | 120 |
| atgttcgcta catatctggt ggccttatgc caggcgatcg atctccggca cctggaagaa | 180 |
| aacatgcgat ccgttgtgaa gcacgtagtc ttgcaggccg caagaaagac actgtgcact | 240 |
| gcagaagacg gaagcctcca cgacaccgga ttttgcgaga aggagctcct gcaagtcatc | 300 |
| gatcatcagc ccgttttctc gtacatcgac gatcccacaa atccatcata cgcgcttatg | 360 |
| ctccaactca gagaagtgct cgtagatgag gctctcaaat catcttgccc agacgggaat | 420 |
| gacgaatccg atcacaattt gcagcccgct gagagcgctg gagctgctgg aatattaccc | 480 |
| aattgggtgt tt | 492 |

<210> SEQ ID NO 99
<211> LENGTH: 391
<212> TYPE: DNA
<213> ORGANISM: Pinus radiata

<400> SEQUENCE: 99

| | |
|---|---:|
| cgttttccca aaggccattt tcgggcaggg ctacggcgca tgacagaagc aggcccggtg | 60 |
| ctggcaatga acctagcctt cgcaaagaat cctttccccg ccaaatctgg ctcctgcgga | 120 |
| acagtcgtcc ggaacgctca aataaagatc ctcgattaca ggaactggcg agtctctccc | 180 |
| gcacaatcaa gccggcgaaa tctgcatccg cggacccgaa ataatgaaag gatatattaa | 240 |
| cgacccggaa tccacggccg ctacaatcga tgaagaaggc tggctccaca caggcgacgt | 300 |
| cgggtacatt gacgatgacg aagaaatctt catagtcgac agagtaaagg agattatcaa | 360 |
| tataaaggct tccaggtgga tcctgctaat c | 391 |

<210> SEQ ID NO 100
<211> LENGTH: 567
<212> TYPE: DNA
<213> ORGANISM: Eucalyptus grandis

<400> SEQUENCE: 100

| | |
|---|---:|
| ctgaattttc cctaactaga aataaagaga ttatatacat acacgagcaa agcgctctcc | 60 |
| tccagttgtc ttccttcgtt cgctcatctc tcctcgtaca ttattagcat acgacctctt | 120 |
| gtatcggacc cggatccgct atcgttaacg tacacacgtt ctagtgctga atggagatgg | 180 |
| agagcaccac cggcaccggc aacggccttc acagcctctg cgccgccggg agccaccatg | 240 |
| ccgacccact gaactggggg gcggcggcag cagccctcac agggagccac ctcgacgagg | 300 |
| tgaagcggat ggtcgaggag taccggaggc cggcggtgcg cctcggcggg gagtccctca | 360 |

```
cgatagccca ggtggcggcg gtggcgagtc aggaggggt aggggtcgag ctctcggagg    420
cggcccgtcc cagggtcaag gccagcagcg actgggtcat ggagagcatg aacaagggaa    480
ctgacagcta cggggtcaca ccgggttcgg cggcaacttc tcaaccggag ccgaagcaa    540 ggcggtcctt ttcagaagga acttata                                        567

<210> SEQ ID NO 101
<211> LENGTH: 612
<212> TYPE: DNA
<213> ORGANISM: Eucalyptus grandis

<400> SEQUENCE: 101
aaagcaacac attgaactct ctctctctct ctctctctct ctctctctct cccccacccc    60
cccttcccaa ccccacccac atacagacaa gtagatacgc gcacacagaa gaagaaaaga   120
tgggggtttc aatgcagtca atcgcactag cgacggttct ggccgtccta acgacatggg   180
cgtggagggc ggtgaactgg gtgtggctga ggccgaagag gctcgagagg cttctgagac   240
agcaaggtct ctccggcaag tcctacacct tcctggtcgg cgacctcaag gagaacttgc   300
ggatgctcaa ggaagccaag tccaagccca tcgccgtctc cgatgacatc aagcctcgtc   360
tcttgccttt cttgcatcaa tccttccaaa cctatggcaa agactcgttc acatggatgg   420
gcccaacacc aagagtgaac attacgaacc cggaacaaat aaaggaggta ttctctaaga   480
tatatgacta tcccaagcca gcctccaatc ccctggtgaa gttgctcgct gatggactcg   540
cgaaccatga gggcgagaaa tgggctcggc accgaaagat tatcaatcca gcattccaca   600
tggagaagtt ga                                                         612

<210> SEQ ID NO 102
<211> LENGTH: 455
<212> TYPE: DNA
<213> ORGANISM: Eucalyptus grandis

<400> SEQUENCE: 102
tgtctctctc tctctctctc tctgtaaacc accatgctct tcctcactca tctcctagca    60
gttctagggg ttgtgttgct cctgctaatt ctatggaggg caagatcttc tccgaacaaa   120
cccaaaggta ctgccttacc cccggagctg ccgggcgcat ggccgatcat aggccacatc   180
cacttgctgg gcggcgagac cccgctggcc aggaccctgg ccgccatggc ggacaagcag   240
ggcccgatgt ttcggatccg tctcggagtc cacccggcga ccatcataag cagccgtgag   300
gcggtccggg agtgcttcac cacccacgac aaggacctcg cttctcgccc caaatccaag   360 gcggaatcc acttgggcta cgggtatgcc ggttttggct tcgtagaata cggggacttt   420
tggcgcgaga tgaggaagat caccatgctc gagct                               455

<210> SEQ ID NO 103
<211> LENGTH: 1866
<212> TYPE: DNA
<213> ORGANISM: Eucalyptus grandis

<400> SEQUENCE: 103
cgggctcgtg gctcggctcc ggcgcaagcc gcccttccca ccgggcccga ggggcctccc    60
ggtcatcggg aacatgctca tgatgggcga gctcacccac cgcggcctcg cgagtctggc   120
gaagaagtat ggcggatct tccacctccg catgggcttc ctgcacatgg ttgccgtgtc   180
gtcccccgac gtggcccgcc aggtcctcca ggtccacgac gggatcttct cgaaccggcc   240
```

-continued

```
tgccaccatc gcgatcagct acctcacgta tgaccgggcc gacatggcct tcgcgcacta      300
cggcccgttc tggcggcaga tgcggaagct gtgcgtgatg aagctcttca gccggaagcg      360
ggctgagtcg tgggagtcgg tccgcgatga ggtggacacg atggtgcgca ccgtcgcggg      420
cagcgagggg accgccgtga acatcggcga gctcgtgttc gagctcacgc gggacatcat      480
ctaccgcgcg gccttcgcac gagctcgacc gagggccagg acgagttcat cagcatactg      540
caggagttct cgaaattatt tggcgccttc aacatagccg attttatccc gtacctgagc      600
tggatcgatc cgcaagggct caccgccagg cttgtcaagg cgcgccagtc gctggacggg      660
ttcatcgacc acattataga tgatcacatg gacaagaaga gaaacaagac gagttccggt      720
ggaggcgatc aagatgtcga taccgacatg gtcgacgatc tgctggcctt ctacagcgac      780
gaagcgaagg tgaacgagtc cgacgatttg cagaactcga tcaggctaac gagagacaac      840
atcaaggcca tcatcatgga cgtgatgttc ggcgggacgg agactgtggc gtcggctatc      900
gagtgggcca tggcggagct catgcgaagc cccgaggacc tgaagaaggt ccagcaagaa      960
ctcgcggatg tcgtgggcct agaccggaga gtcgaggaga gcgacttcga gaagctgacc     1020
tatctcaagt gctgcctcaa agagaccctc cgcctccacc cgccgatccc gctgctcctc     1080
cacgagacgg cagaggacgc cgtgatctcc ggctaccgca tccccgcacg gtcccgggtc     1140
atgatcaatg catgggccat cggcgtgac  cccggctcgt ggaccgaacc tgacaagttc     1200
aaaccgtccc ggttcctgga gtcaggcatg cccgactaca aggggagcaa cttcgagttc     1260
atcccttttcg ggtcgggccg gaggtcgtgc cagggatgc agctcgggct ctacgcgctc     1320
gacatggccg tggcccacct cctgcactgc ttcacgtggg aactgcccga cgggatgaag     1380
ccgagcgaga tggacatggg cgacgtcttc gggctcaccg cgccgaggtc cacccggctc     1440
gtggcggtgc cgactccgag gttggtgggg gctctatatt gagcaagcaa atggagggtc     1500
gggttggggg gtgcgaggag gggaacgtat ttttcagctc ctggagggct gcaagatttg     1560
gagtgcataa acccatccat acaagggcaa agagggtgg tgccaaaatg atttgcatgg     1620
attttttcgat ttttgttttg tattataaaa aaggtcaaat aaccgaagag acaagaaag     1680
acaagaaaaa gaattgagac ggaacttgaa tcaatgttgt tctgttctct ctttctattt     1740
ctttgtggat attacaagac ttatctcatt tggtgggctt ttcttttctt gtgatttctt     1800
tgatcttgtc atacacaaat aaatatggaa tgaagaaacc tttccatcaa aaaaaaaaa     1860
aaaaaa                                                               1866
```

<210> SEQ ID NO 104
<211> LENGTH: 519
<212> TYPE: DNA
<213> ORGANISM: Eucalyptus grandis

<400> SEQUENCE: 104

```
cacgagctcg tgagccttcc cggagacaag gccatcttac ttcgcaacaa attgcgtccg       60
cactcctttc tcaagaaacc tagtcatcca agaagcagag cattgcaact gcaaacagcc      120
aaagcccaaa ctcgtacaga aggagagaga gagagagaat agaagcatga gtgcatgcac      180
gaaccaagca atcacgacgg ccagtgaaga tgaagagttc ttgttcgcca tggaaatgaa      240
tgctctgata gcactcccct tggtcttgaa ggccaccatc gaactgggga tcctcgaaat      300
actggccgag tgcgggccta tggctccact ttcgcctgct cagattgcct cccgtctctc      360
cgcaaagaac ccggaagccc ccgtaaccct tgaccggatc ctccggtttc tcgccagcta      420
ctccatcctc tcttgcactc tcgcccaaga cacagaaggc aaccccctga ggctttacgg      480
```

-continued

```
tttgggaccc aaaagcaaac acttcgtcag agcccatgg                            519

<210> SEQ ID NO 105
<211> LENGTH: 594
<212> TYPE: DNA
<213> ORGANISM: Eucalyptus grandis

<400> SEQUENCE: 105
ccaaccctgg accaggtact tttggcaggc ggtccattgc ccttcaaacc ggtccaaacc     60
ggaccatcac tgtccttata tacgttgcat catgcctgct catagaactt aggtcaactg    120
caacatttct tgatcacaac atattacaat attcctaagc agagagagag agagagagag    180
agagagagag agagagagag tttgaatcaa tggccaccgc cggagaggag agccagaccc    240
aagccgggag gcaccaggag gttggccaca agtctctcct tcagagtgat gctctttacc    300
aatatatttt ggagaccagc gtgtacccaa gagagcctga gcccatgaag gagctcaggg    360
aaataacagc aaaacatcca tggaacataa tgacaacatc agcagacgaa gggcagttct    420
tgaacatgct tctcaagctc atcaacgcca agaacaccat ggagattggt gtcttcactg    480
gctactctct cctcgccacc gctcttgctc ttcctgatga cggaaagatt ttggctatgg    540
acattaacag agagagctat gaacttggcc tgccggtcat ccaaaaagcc ggtg          594

<210> SEQ ID NO 106
<211> LENGTH: 407
<212> TYPE: DNA
<213> ORGANISM: Eucalyptus grandis

<400> SEQUENCE: 106
ccgttttatt tcctctgatt tcctttgctc gagtctcgcg gaagagagag aagagaggag     60
aggagagaat gggttcgacc ggatccgaga cccagatgac cccgacccaa gtctcggacg    120
aggaggcgaa cctcttcgcc atgcagctgg cgagcgcctc cgtgctcccc atggtcctca    180
aggccgccat cgagctcgac ctcctcgaga tcatggccaa ggccggggcg ggcgcgttcc    240
tctccccggg ggaagtcgcg gcccagctcc cgacccagaa ccccgaggca cccgtaatgc    300
tcgaccggat cttccggctg ctggccagct actccgtgct cacgtgcacc ctccgcgacc    360
tccccgatgg caaggtcgag cggctctacg gcttagcgcc ggtgtgc                  407

<210> SEQ ID NO 107
<211> LENGTH: 1630
<212> TYPE: DNA
<213> ORGANISM: Eucalyptus grandis

<400> SEQUENCE: 107
ccgttttatt tcctctgctt tcctttgctc gagtctcgcg gaagagagag aagagaggag     60
aggagagaat gggttcgacc ggatccgaga cccagatgac cccgacccaa gtctcggacg    120
aggaggcgaa cctcttcgcc atgcagctgg cgagcgcctc cgtgctcccc atggtcctca    180
aggccgccat cgagctcgac ctcctcgaga tcatggccaa ggccggggcg ggcgcgttcc    240
tctccccggg ggaagtcgcg gcccagctcc cgacccagaa ccccgaggca cccgtcatgc    300
tcgaccggat cttccggctg ctggccagct actccgtgct cacgtgcacc ctccgcgacc    360
tccccgatgg caaggtcgag cggctctacg gcttagcgcc ggtgtgcaag ttcttggtca    420
agaacgagga cggggtctcc atcgccgcac tcaacttgat gaaccaggac aaaatcctca    480
tggaaagctg gtattacctg aaagatgcgg tccttgaagg cggaatccca ttcaacaagg    540
```

```
cgtacgggat gaccgcgttc gagtatcatg gcaccgaccc gcgattcaac aagatcttta    600 accgggaat  gtctgatcac tccaccatta ctatgaagaa gatactggaa acatacaagg    660
gcttcgaggg cctcgagacc gtggtcgatg tcggaggcgg cactgggggcc gtgctcagca    720 tgatcgttgc caaataccca tcgatgaaag ggatcaactt cgacctgcct cacgtgattg    780
aagacgctcc accccttcct ggtgtcaagc acgtcggagg cgacatgttc gtcagcgttc    840
caaagggaga tgccattttc atgaagtgga tatgccatga ctggagtgac gaccattgcg    900
cgaagttcct caagaactgc tacgatcgc  tcccaacaa  tggaaaggtg atcgttgcag    960
agtgcgtact ccctgtgtac ccagacacga gcctagcgac caagaatgtg atccacatcg   1020
actgcatcat gttggcccac aacccaggcg ggaagagag  acacagaag  gagttcgagg   1080 cattggccaa agggggccgga tttcagggct tccaagtcat gtgctgcgct tcggcactc   1140 acgtcatgga gttcctgaag accgcttgat ctgctcctct gtggtgatgt tcatggttct   1200
tggatttgaa aggtcgtgaa ggagccctt  tctcacagtt ggcttcggca taccaagttc   1260
ttctcataaa aggaaacaat aagaagcgac tgtatgatgg cgcaagtgga agttacaaga   1320
tttgttgttt tatgtctata aagttttgag tcttctgcat actgatttca cagaatgtgt   1380
aacgaaacgg cgtatatgga tgtgcctgaa tgatggaaat tgtgatattc tgtcttcttt   1440
ttcagtaaat cacttcgaac aaaagttgtg ttgctcgtgg caaccaggaa aaaatctgtg   1500
ggtgactttg agttaaagcc tgtcattcac aaaccccatg gcattgcctt tggtcagggg   1560
tcagccaagc cggaagcgtc aacgtgaaaa gatcctcaag ggtccattaa atccccaca    1620 aacccagagc                                                          1630

<210> SEQ ID NO 108
<211> LENGTH: 1248
<212> TYPE: DNA
<213> ORGANISM: Eucalyptus grandis

<400> SEQUENCE: 108
atcactaacc atctgccttt cttcatcttc tttcttctgc ttctcctccg tttcctcgtt     60
tcgatatcgt gaaggagtc  cgtcgacgac aatggccgag aagagcaagg tcctgatcat    120
cggagggacg ggctacatcg gcaagttcat cgtggaagcg agtgcaaaag cagggcatcc    180
cacgttcgcg ctggttaggc agagcaccggt ctccgacccc gtcaagggcc agctcgtcga    240
gagcttcaag aacttgggcg tcactctgct catcggtgat ctgtacgatc atgagagctt    300
ggtgaaggca atcaagcaag ccgacgtggt gatatcgaca gtggggcaca tgcaaatggc    360
ggatcagacc aagatcgtcg acgccattaa ggaagctggc aacgttaaga gattctttcc    420
ttccgaattc ggcaatgatg tggacagggt gcatgctgtg gagccagcga gtctgctttt    480
tgaattgaag gcccagatcc gccgtgccgt ggaggcggca ggcatcccctt acacctacgt    540 cccatgtggc tgcttcgccg gctacttcct cccaacactg cgcagcagg  aggtcactgc    600 tcctccgaag gacaaagtca ccgtcatggg tgacggaaat gcaaaggcaa ttttcaacaa    660
ggaagatgac attgcggcct tcaccatcaa ggctgtggat gatccgagat cgctgaacaa    720
gatcctttac atcaggcctc ctaagaacgt ttactcattc aatgagcttg ttgccttgtg    780
ggagaagaaa attggcaaga ccctcgaaga gatttacctt cctgaagagc aaatcctgaa    840
gcaaatccag gagtccccaa ttcccatcaa tgtcatatta gcagtgaacc attcaatctt    900
tgttaagggc gacggtgcca attttgagat cgaggagtct tttggtgtcg aggcttctga    960
gctgtaccca gatgtgaagt acactacagt ggaagaatac ctcgaaaatt ttgtctaaat   1020
```

```
taaggccatg cgtctcctgt tcttcaagga gtgagttacc gtgactctgg tggacagtcg   1080
atatgtatta aaaggctgta cacctaaaga atatcaaagg tcacggtctt atttagaatt   1140
gtctctgatg tcatattctt cttggtcttc ttggacatgt atttgctttc ctttgccgtg   1200
gtatccatga atttcccagg ttgttgaaat taaaaaaaaa aaaaaaaa                 1248

<210> SEQ ID NO 109
<211> LENGTH: 481
<212> TYPE: DNA
<213> ORGANISM: Eucalyptus grandis

<400> SEQUENCE: 109
gttaatggca gtgcagcctc aacaccaccc accttcctcc atctctctcc tcccttcttc    60
tttctctgac ttcaatggca gccgactcca tgcttgcgtt cagtataaga ggaaggtggg   120
gcagcctaaa ggggcactgc gggtcactgc atcaagcaat aagaagatcc tcatcatggg   180
aggcacccgt tcatcggtg tgttttttgtc gagactactt gtcaaagaag gtcatcaggt   240
cactttgttt accagaggaa aagcacccat cactcaacaa ttgcctggtg agtcggacaa   300
ggacttcgct gattttttcat ccaagatcct gcatttgaaa ggagacagaa aggattttga   360
ttttgttaaa tctagtcttg ctgcagaagg ctttgacgtt gtttatgaca ttaacggcga   420
gaggcggatg aagtcgcacc aattttggat gcctgccaaa ccttgaacca gtcaactact   480
g                                                                    481

<210> SEQ ID NO 110
<211> LENGTH: 458
<212> TYPE: DNA
<213> ORGANISM: Eucalyptus grandis

<400> SEQUENCE: 110
cataagctct cccgtaatcc tcacatcaca tggcgaagag caaggtcctc gtcgttggcg    60
gcactggcta cctcgggcgg aggttcgtga gggcgagcct ggaccagggc cacccacgt    120 acgtcctcca gcgtccggag accggcctcg acattgagaa gctccagacg ctactgcgct   180
tcaagaggcg tggcgcccaa ctcgtcgagg cctcgttctc agacctgagg agcctcgtcg   240
acgctgtgag gcgggtcgat gtcgtcgtct gtgccatgtc gggggtccac ttccggagcc   300
acaacatcct gatgcagctc aagctcgtgg aggctatcaa agaagctgga atgtcaagc   360 ggttttttgcc gtcagagttc ggaatggacc cggccctcat gggtcatgca attgagccgg   420
gaagggtcac gttcgatgag aaatggaggt gagaaaag                            458

<210> SEQ ID NO 111
<211> LENGTH: 448
<212> TYPE: DNA
<213> ORGANISM: Eucalyptus grandis

<400> SEQUENCE: 111
aggaggcacc tcctcgaaac gaagaagaag aaggacgaag gacgaaggag acgaaggcga    60
gaatgagcgc ggcgggcggt gccgggaagg tcgtgtgcgt gaccggggcg tccggttaca   120
tcgcctcgtg gctcgtcaag ctcctcctcc agcgcggcta caccgtcaag gccaccgtcc   180
gcgatccgaa tgatccaaaa aagactgaac atttgcttgg acttgatgga gcgaaagata   240
gacttcaact gttcaaagca aacctgctgg aagagggttc atttgatcct attgttgagg   300
gttgtgcagg cgttttttcac actgcctctc ccttttatca tgatgtcaag gatccgcagg   360
```

```
cagaattact tgatccggct gtgaagggaa cactcaatgt cctgaagtca tgttccaaag    420
accttctctg cagcgtgtgg cttgacat                                       448
```

<210> SEQ ID NO 112
<211> LENGTH: 578
<212> TYPE: DNA
<213> ORGANISM: Eucalyptus grandis

<400> SEQUENCE: 112

```
gttgaacctc ccgtcctcgg ctctgctcgg ctcgtcaccc tcttcgcgct cccgcatact     60
ccaccaccgc gtacagaaga tgagctcgga gggtgggaag gaggattgcc tcggttgggc    120
tgcccgggac ccttctgggt tcctctcccc ctacaaattc acccgcaggg ccgtgggaag    180
cgaagacgtc tcgattaaga tcacgcactg tggagtgtgc tacgcagatg tggcttggac    240
taggaatgtg cagggacact ccaagtatcc tctggtgcca gggcacgaga tagttggaat    300
tgtgaaacag gttggctcca gtgtccaacg cttcaaagtt ggcgatcatg tggggtgggg    360
aacttatgtc aattcatgca gagagtgcga gtattgcaat gacaggctag aagtccaatg    420
tgaaaagtcg gttatgactt tgatggaat tgatgcagat ggtacagtga caaagggagg    480
atattctagt cacattgtcg tccatgaaag gtattgcgtc aggattccag aaaactaccc    540
gatggatcta gcagcgcatt tgctctgtgc tggatcac                            578
```

<210> SEQ ID NO 113
<211> LENGTH: 454
<212> TYPE: DNA
<213> ORGANISM: Eucalyptus grandis

<400> SEQUENCE: 113

```
aactcatctt gaaatgtcat tggagtcatc atcctctagt gagaagaaac aaatgggttc     60
cgccggattc gaatcggcca caaagccgca cgccgtttgc attccctacc ctgcacaaag    120
ccacattggc gccatgctca agctagcaaa gctcctccat cacaagggct tccacatctc    180
cttcgtcaac accgagttca accaccgcg gctcgccagg gctcgaggcc ccgagttcac    240
aaatggaatg ctgagcgact ttcagttcct gacaatcccc gatggtcttc ctccttcgga    300
cttggatgcg atccaagaca tcaagatgct ctgcgaatcg tccaggaact atatggtcag    360
ccccatcaac gatcttgtat cgagcctggg ctcgaacccg agcgtccctc cggtgacttg    420
catcaatctc ggatggtttc atgacactcg tgac                                454
```

<210> SEQ ID NO 114
<211> LENGTH: 479
<212> TYPE: DNA
<213> ORGANISM: Eucalyptus grandis

<400> SEQUENCE: 114

```
catgattgag ggaatcaagg actcttcagg actcatcctg aacacatttg aagatctcga     60
gcagcccgct ctttctttac tccgccaaga agatccaatc gcagttttcg caattggccc    120
attacacaaa tgcggtccat cttcatcggg aagtctcttg gcagaagacc ggagttgcat    180
ttcctggctg acaagcaag cccctaactc agtggtctat gtgagttttg ggagcatcgc    240
ctctgtgaac gagtcggaat tttccgaaat agctttaggt ttagccgata gccagcagcc    300
attcttgtgg gtggttcgac ccgggtcagt gagcggctcg gaactcttag agaatttgcc    360
cggttgcttt ctgaggcat acaggagag ggggaagatt gtgaaatggg cgcctcaaca    420
tgaagtgctg gctcatcggg gtgtcggagc gttttggact cacaatggat ggaactcca    479
```

<210> SEQ ID NO 115
<211> LENGTH: 420
<212> TYPE: DNA
<213> ORGANISM: Eucalyptus grandis

<400> SEQUENCE: 115

| | | | | | | |
|---|---|---|---|---|---|---|
| caacattgtg | tttagagaga | ggagagagaa | ggcaaacacg | cccgttttcg | ttttactaag | 60 |
| agaagatggt | gagcgttgtg | gctggtagag | tcgagagctt | gtcgagcagt | ggcattcagt | 120 |
| cgatcccgca | ggagtatgtg | aggccgaagg | aggagctcac | aagcattggc | gacatcttcg | 180 |
| aggaggagaa | gaagcatgag | ggccctcagg | tcccgaccat | cgacctcgag | gacatagcgt | 240 |
| ctaaagaccc | cgtggtgagg | gagaggtgcc | acgaggagct | caggaaggct | gccaccgact | 300 |
| ggggcgtcat | gcacctcgtc | aaccatggga | tccccaacga | cctgattgag | cgtgtcaaga | 360 |
| aggctggcga | ggtgttcttc | aacctcccga | tcgaggagaa | ggagaagcat | gccaacgacc | 420 |

<210> SEQ ID NO 116
<211> LENGTH: 679
<212> TYPE: DNA
<213> ORGANISM: Eucalyptus grandis

<400> SEQUENCE: 116

| | | | | | | |
|---|---|---|---|---|---|---|
| ctaagagagg | agaggagagg | agcaagatgg | cactagcagg | agctgcactg | tcaggaaccg | 60 |
| tggtgagctc | cccctttgtg | aggatgcagc | ctgtgaacag | actcagggca | ttccccaatg | 120 |
| tgggtcaggc | cctgtttggt | gtcaactctg | gccgtggcag | agtgactgcc | atggccgctt | 180 |
| acaaggtcac | cctgctcacc | cctgaaggca | agtcgaact | cgacgtcccc | gacgatgttt | 240 |
| acatcttgga | ctacgccgag | gagcaaggca | tcgacttgcc | ctactcctgc | cgtgccggct | 300 |
| cttgctcctc | ctgcgcgggc | aaggtcgtgg | cggggagcgt | cgaccagagc | gacggcagct | 360 |
| tcctggatga | tgatcagatt | gaggaaggtt | gggtcctcac | ttgtgtcgcc | taccctaagt | 420 |
| ctgaggtcac | cattgagacc | cacaaggaag | aggagctcac | tgcttgaagc | tctcctatat | 480 |
| ttgcttttgc | ataaatcagt | ctcactctac | gcaactttct | ccactctctc | ccccttcac | 540 |
| tacatgtttg | ttagttcctt | tagtctcttc | ctttttact | gtacgaggga | tgatttgatg | 600 |
| ttattctgag | tctaatgtaa | tggcttttct | ttttcctatt | tctgtatgag | gaaataaaac | 660 |
| tcatgctcta | aaaaaaaaa | | | | | 679 |

<210> SEQ ID NO 117
<211> LENGTH: 763
<212> TYPE: DNA
<213> ORGANISM: Eucalyptus grandis

<400> SEQUENCE: 117

| | | | | | | |
|---|---|---|---|---|---|---|
| catacaacta | cactgcgacg | ccgccgcaga | acgcgagcgt | gccgaccatg | aacggcacca | 60 |
| aggtctaccg | gttgccgtat | aacgctacgg | tccagctcgt | tttacaggac | accgggataa | 120 |
| tcgcgccgga | gacccacccc | atccatctgc | acggattcaa | cttcttcggt | gtgggcaaag | 180 |
| gagtggggaa | ttatgaccca | agaaggatc | ccaagaagtt | caatctggtt | gacccagtgg | 240 |
| agaggaacac | cattggaatc | ccatctggtg | gatggatagc | catcagattc | acagcagaca | 300 |
| atccaggagt | ttggttcctg | cactgccatc | tggaagtgca | cacaacttgg | ggactgaaga | 360 |
| tggcattctt | ggtggacaat | gggaagggc | ctaaagagac | cctgcttcca | cctccaagtg | 420 |
| atcttccaaa | atgttgatca | tttgatcatg | aggacgacaa | gcgattacta | atgacaccaa | 480 |

```
gttagtggaa tcttctcttt gaaaaagaag aagaagagca agaagaataa gaaagatgag    540
gagagaagcc atagaagatt tgaccaagaa gagagagggc aataaaccaa agagacccCtt   600 gagatcacga catcccgcaa ttgtttctag agtaatagaa ggatttactc cgacactgct    660
acaataaatt aaggaagaca aggaatttgg ttttttttcat tggaggagtg taattttgttt  720 tttggcaagc tcatcacatg aatcacatgg aaaaaaaaaa aaa                      763
```

<210> SEQ ID NO 118
<211> LENGTH: 538
<212> TYPE: DNA
<213> ORGANISM: Eucalyptus grandis

<400> SEQUENCE: 118

```
atcaagagtt tgagtctaaa ccttgtctaa tcctctctcg catagtcatt tggagacgaa    60
gtgctgatcg gccgcagctg cattctcttc gtaaaacatg acggctgtcg gcaaaacctc   120
tttcctcttg ggagctctcc tcctcttctc tgtggcggtg acattggcag atgcaaaagt   180
ttactaccat gattttgtcg ttcaagcgac caaggtgaag aggctgtgca cgacccacaa   240
caccatcacg gtgaacgggc aattcccggg tccgactttg gaagttaacg acggcgacac   300
cctcgttgtc aatgtcgtca acaaagctcg ctacaacgtc accattcact ggcacggcgt   360
ccggcaggtg agatctggtt gggccgatgg gccggaattt gtgactcaat gcccgattag   420
acccggcgga agttacacgt accgtttcac catccaagga caggtaggaa cgctgtggtg   480
gcatgcacat agctcttggc taagagcgac tgtgtatggt gctctggcat tcgtccaa    538
```

<210> SEQ ID NO 119
<211> LENGTH: 515
<212> TYPE: DNA
<213> ORGANISM: Eucalyptus grandis

<400> SEQUENCE: 119

```
ctctctctct ctctctctct gtgtgttcat tctcgttgag ctcgtggtcg cctcccgcca    60
tggatccgca caagtaccgt ccatccagtg ctttcaacac ttctttctgg actacgaact   120
ctggtgctcc tgtctggaac aataactctt cgttgactgt tggaagcaga ggtccaattc   180
ttcttgagga ttatcacctc gtggagaaac ttgccaactt gatagggag aggattccag    240 agcgtgtggt gcatgccaga ggagccagtg caaagggatt ctttgaggtc actcatgaca   300
tttcccagct tacctgtgct gatttccttc gggcaccagg agttcaaaca cccgtgattg   360
tccgtttctc cactgtcatc cacgaaaggg gcagccctga aaccctgagg gaccctcgag   420
gttttgctgt gaagttctac acaagagagg gtaactttga tctggtggga aacaatttcc   480
ctgtcttctt tgtccgtaat gggataaaatt ccccg                             515
```

<210> SEQ ID NO 120
<211> LENGTH: 458
<212> TYPE: DNA
<213> ORGANISM: Eucalyptus grandis

<400> SEQUENCE: 120

```
gctccctctc gtactgccat actcctgggc cgggattcgg atagggtttt gcggcgatcc    60
atttctcgat tcaaggggaa gaatcatggg gaagtcctac ccgaccgtga gcaggagta   120 caagaaggct gtcgagaaat gcaagaagaa gttgagaggc ctcatcgctg agaagagctg   180
cgctccgctc atgctccgca tcgcgtggca ctccgccggt accttcgatg tgaagacgaa   240
gaccggaggc ccgttcggga ccatgaagca cgccgcggag ctcagccacg gggccaacag   300
```

```
cgggctcgac gttgccgatc aggtcttgca gccgatcaag gatcagttcc ccgtcatcac    360
ttatgctgat ttctaccagc tggctggcgt cgttgctgtg gaagttactg gtggacctga    420
agttgctttt cacccaggaa gagaggcaaa ccacaacc                            458
```

<210> SEQ ID NO 121
<211> LENGTH: 1243
<212> TYPE: DNA
<213> ORGANISM: Eucalyptus grandis

<400> SEQUENCE: 121

```
ctcccacttc tgtctcgcca ccattactag cttcaaagcc cagatctcag tttcgtgctc     60
tcttcgtcat ctctgcctct tgccatggat ccgtacaagt atcgcccgtc cagcgcttac    120
gattccagct tttggacaac caactacggt gctcccgtct ggaacaatga ctcatcgctg    180
actgttggaa ctagaggtcc gattctcctg gaggactacc atctgattga aaacttgcc     240 aacttcgaga gagagaggat tcctgagcgg gtggtccatg cacggggagc cagcgcgaaa    300
gggttcttcg aggtcaccca cgacatctct cacttgacct gtgctgattt cctccgggct    360
cctggagtcc agacgcccgt catcgtccgt ttctccaccg tcatccacga gcgcggcagc    420
cccgaaaccc tcagggaccc tcgtggtttt gcagtgaagt tctacaccag agagggaaac    480
tttgatctgg tggggaacaa tttcccagtc ttcttcgttc gcgatgcaat gaaattcccg    540
gacgcgatcc atgcgttcaa gccgaacccg aagtctaaca tccaggagat gtggagaatc    600
atcgatttct tctcccacca gcccgagagt ctgtccacgt tcgcgtggtt cttcgatgat    660
gtgggcattc ctcaggacta caggcacatg gagggattcg gtgtgcacgc tttcaccttc    720
atcaacaaga ccgaaagac gaattacgtt aaattccact ggaagccaac ttgcggggtg    780
aagtgcttgc tggaggagga ggcgatcctc attggaggat cgaaccacag ccatgcgacc    840
aaggatcttt atgactcgat cgctgctggc aactacccgg agtggaagct ctacatccaa    900
gtgatggatc cwgctcttga agacagcttc gacttcgatc cgctggatat gacgaaggaa    960
tggcctgagg acatcttgcc tctgcaacca gtaggccgct tggtgctgaa caaaaacgtc   1020
gataacttct tcgctgagaa tgagcagcta gcgtttaacc cagcatttgt ggtccctggc   1080
atctattact ccaatgataa gcttctccaa gctaggattt tcgcctattc tgatactcac   1140
cgatatcgcc ttggaccaaa ctaccttcaa ctccccgtta atgtcccaag tgcgtcatca   1200
caacaaccac catgatggtt tcatgaatat catgcacagg gat                     1243
```

<210> SEQ ID NO 122
<211> LENGTH: 404
<212> TYPE: DNA
<213> ORGANISM: Pinus radiata

<400> SEQUENCE: 122

```
gacaaggtca taggccctct cttcaaatgc ttggatgggt ggaaaggaac tcctggccca     60
ttctgaaata aataatcttc caagatcgcc tttatacaac gactgctatg atttgagtcc    120
tcggatcttt tgttgatgc agttgtttac cgatctggaa tttgattggt cataaagctt    180 gatttttgttt ttcttttcttt tgtttttatac tgctggattt gcatcccatt ggatttgcca    240
gaaatatgta agggtggcag atcatttggg tgatctgaaa catgtaaaag tggcggatca    300
tttgggtagc atgcagatca gttgggtgat cgtgtactgc tttcactatt acttacatat    360
ttaaagatcg ggaataaaaa catgatttta attgaaaaaa aaaa                     404
```

<210> SEQ ID NO 123
<211> LENGTH: 415
<212> TYPE: DNA
<213> ORGANISM: Pinus radiata

<400> SEQUENCE: 123

| | | | | | |
|---|---|---|---|---|---|
| caaggaagaa | aatatggttg | cagcagcaga | aattacgcag | gccaatgaag | ttcaagttaa | 60 |
| aagcactggg | ctgtgcacgg | acttcggctc | gtctggcagc | gatccactga | actgggttcg | 120 |
| agcagccaag | gccatggaag | gaagtcactt | tgaagaagtg | aaagcgatgg | tggattcgta | 180 |
| tttgggagcc | aaggagattt | ccattgaagg | gaaatctctg | acaatctcag | acgttgctgc | 240 |
| cgttgctcga | agatcgcaag | tgaaagtgaa | attggatgct | gcggctgcca | aatctagggt | 300 |
| cgaggagagt | tcaaactggg | ttctcaccca | gatgaccaag | gggacggata | cctatggtgt | 360 |
| cactactggt | ttcggagcca | cttctcacag | gagaacgaac | cagggagccg | agctt | 415 |

<210> SEQ ID NO 124
<211> LENGTH: 1659
<212> TYPE: DNA
<213> ORGANISM: Pinus radiata

<400> SEQUENCE: 124

| | | | | | |
|---|---|---|---|---|---|
| gttgcaggtc | ggggatgatt | tgaatcacag | aaacctcagc | gattttgcca | agaaatatgg | 60 |
| caaaatcttt | ctgctcaaga | tgggccagag | gaatcttgtg | gtagtttcat | ctcccgatct | 120 |
| cgccaaggag | gtcctgcaca | cccagggcgt | cgagtttggg | tctcgaaccc | ggaacgtggt | 180 |
| gttcgatatc | ttcacgggca | aggggcagga | catggtgttc | accgtctatg | agatcactg | 240 |
| gagaaagatg | cgcaggatca | tgactgtgcc | tttctttacg | aataaagttg | tccagcacta | 300 |
| cagattcgcg | tgggaagacg | agatcagccg | cgtggtcgcg | gatgtgaaat | cccgcgccga | 360 |
| gtcttccacc | tcgggcattg | tcatccgtag | gcgcctccag | ctcatgatgt | ataatattat | 420 |
| gtataggatg | atgttcgaca | ggagattcga | atccgaggac | gacccgcttt | tcctcaagct | 480 |
| caaggccctc | aacggagagc | gaagtcgatt | ggcccagagc | tttgagtaca | attatgggga | 540 |
| tttcattccc | attcttaggc | ccttcctcag | aggttatctc | agaatctgca | atgagattaa | 600 |
| agagaaacgg | ctctctcttt | tcaaggacta | cttcgtggaa | gagcgcaaga | agctcaacag | 660 |
| taccaagact | agtaccaaca | ccgggagagct | caagtgtgca | atggaccata | ttttagatgc | 720 |
| tcaggacaag | ggagagatca | atgaggataa | tgttttgtac | atcgttgaga | acatcaacgt | 780 |
| tgcagcaatt | gagacaacgc | tgtggtcgat | ggaatgggga | atagcggagc | tggtgaacca | 840 |
| ccaggacatt | cagagcaagg | tgcgcgcaga | gctggacgct | gttcttggac | caggcgtgca | 900 |
| gataacggaa | ccagacacga | caaggttgcc | ctaccttcag | gcggttgtga | aggaaaccct | 960 |
| tcgtctccgc | atggcgatcc | cgttgctcgt | cccccacatg | aatctccacg | acgccaagct | 1020 |
| cgggggctac | gatattccgg | cagagagcaa | gatcctggtg | aacgcctggt | ggttggccaa | 1080 |
| caaccccgcc | aactggaaga | accccgagga | gttccgcccc | gagcggttct | cgaggagga | 1140 |
| gaagcacacc | gaagccaatg | gcaacgactt | caaattcctg | ccttgcggtg | tggggaggag | 1200 |
| gagctgcccg | ggaatcattc | tggcgctgcc | tctcctcgca | ctctccatcg | gaagacttgt | 1260 |
| tcagaacttc | caccttctgc | cgccgcccgg | gcagagcaaa | gtggatgtca | ctgagaaggg | 1320 |
| cgggcagttc | agccttcaca | ttctcaacca | ttctctcatc | gtcgccaagc | ccatagcttc | 1380 |
| tgcttaatcc | caacttgtca | gtgactggta | tataaatgcg | cgcacctgaa | caaaaaacac | 1440 |
| tccatctatc | atgactgtgt | gtgcgtgtcc | actgtcgagt | ctactaagag | ctcatagcac | 1500 |

-continued

```
ttcaaaagtt tgctaggatt tcaataacag acaccgtcaa ttatgtcatg tttcaataaa    1560
agtttgcata aattaaatga tatttcaata tactattttg actctccacc aattggggaa    1620
ttttactgct aaaaaaaaaa aaaaaaaaaa aaaaaaaa                            1659
```

<210> SEQ ID NO 125
<211> LENGTH: 461
<212> TYPE: DNA
<213> ORGANISM: Pinus radiata

<400> SEQUENCE: 125

```
atttccatgg cgattccgtt tggcttcaat tcgtttcctc tggctgtcct cgtcctcgtt     60
ttccttgttc ttcctccgac tttttctctg gaagatatgg cgtaatagga acctgccgcc    120 aggaccccg gcatggccga tcgtagggaa cgtccttcag attggatttt ccagcggcgc    180
gttcgagacc tcagtgaaga aattccatga gagatacggt ccaatattca ctgtgtggct    240
cggttcccgc cctctgctga tgatcaccga ccgcgagctt gcccacgagg cgctcgtaca    300
gaagggctcc gtcttcgctt gaccgcccgc ccgccctcgg gatgcagaaa atcttcagta    360
gcaaccagca caacatcact tcggctgaat acggcccgct gtggcggagc ttcgcaggaa    420
tctggttaaa gaagccctga gcttcggcg atgaaggctt t                        461
```

<210> SEQ ID NO 126
<211> LENGTH: 569
<212> TYPE: DNA
<213> ORGANISM: Pinus radiata

<400> SEQUENCE: 126

```
acccagtgac cttcaggcct gagagatttc ttgaggaaga tgttgatatt aagggccatg     60
attacaggct actgccattc ggtgcagggc gcaggatctg ccctggtgca caattgggta    120
ttaatttagt tcagtctatg ttgggacacc tgcttcatca tttcgtatgg gcacctcctg    180
agggaatgaa ggcagaagac atagatctca cagagaatcc agggcttgtt actttcatgg    240
ccaagcctgt gcaggccatt gctattcctc gattgcctga tcatctctac aagcgacagc    300
cactcaattg atcaattgat ctgatagtaa gtttgaattt tgttttgata caaaacgaaa    360
taacgtgcag tttctccttt tccatagtca acatgcagct ttctttctct gaagcgcatg    420
cagctttctt tctctgaagc ccaacttcta gcaagcaata actgtatatt ttagaacaaa    480
tacctattcc tcaaattgag tatttctctg taggcgatgt tcacttgtgc aatttgcaag    540
atatagtaaa gtttactcta aaaaaaaaa                                     569
```

<210> SEQ ID NO 127
<211> LENGTH: 661
<212> TYPE: DNA
<213> ORGANISM: Pinus radiata

<400> SEQUENCE: 127

```
gttttatctg aaggacgctg tgcttgaagg ctcccagcca ttcaccaaag cccatggaat     60
gaatgcgttc gagtacccgg ccatcgatca gagattcaac aagatttca acagggctat    120 gtctgagaat tctaccatgt tgatgaacaa gattttggat acttacgagg gttttaagga    180
ggttcaggag ttggtggatg tgggaggagg tattgggtcg actctcaatc tcatagtgtc    240
taggtatccc cacatttcag gaatcaactt cgacttgtcc catgtgctgg ccgatgctcc    300
tcactaccca gctgtgaaac atgtgggtgg agacatgttt gatagtgtac caagtggcca    360
```

| | |
|---|---|
| agctattttt atgaagtgga ttctgcatga ttggagcgat gatcattgca ggaagctttt | 420 |
| gaagaattgt cacaaggcgt tgccagagaa ggggaaggtg attgcggtgg acaccattct | 480 |
| cccagtggct gcagagacat ctccttatgc tcgtcaggga tttcatacag atttactgat | 540 |
| gttggcatac aacccagggg gcaaggaacg cacagagcaa gaatttcaag atttagctaa | 600 |
| ggagacggga tttgcaggtg tgttgaacc tgtatgttgt gtcaatggaa tgtgggtaat | 660 |
| g | 661 |

<210> SEQ ID NO 128
<211> LENGTH: 427
<212> TYPE: DNA
<213> ORGANISM: Pinus radiata

<400> SEQUENCE: 128

| | |
|---|---|
| aatttttctg tggtaagcat atctatggct caaaccagag agaaggacga tgtcagcata | 60 |
| acaaactcca aaggattggt atgcgtgaca ggagcggctg gttacttggc atcttggctt | 120 |
| atcaagcgtc tcctccagtg tggttaccaa gtgagaggaa ctgtgcggga tcctggcaat | 180 |
| gagaaaaaga tggctcattt atggaagtta gatggggcga agagagact gcaactaatg | 240 |
| aaagctgatt taatggacga gggcagcttc gatgaggtca tcagaggctg ccatggtgtt | 300 |
| tttcacacag cgtctccagt cgtgggtgtc aaatcagatc ccaagatatg gtatgctctg | 360 |
| gccaagactt tagcagaaaa agcagcatgg gattttgccc aagaaaacca tctggacatg | 420 |
| gttgcag | 427 |

<210> SEQ ID NO 129
<211> LENGTH: 1412
<212> TYPE: DNA
<213> ORGANISM: Pinus radiata

<400> SEQUENCE: 129

| | |
|---|---|
| gaaaacatca tccaggcatt ttggaaattt agctcgccgg ttgattcagg atcctgcaat | 60 |
| ggcttttggc gaagagcaga ctgccttgcc acaagaaacg cctttgaatc ctccggtcca | 120 |
| tcgaggaaca gtgtgcgtta caggagctgc tgggttcata gggtcatggc tcatcatgcg | 180 |
| attgcttgag cgaggatata gtgttagagc aactgtgcga gacactggta atcctgtaaa | 240 |
| gacaaagcat ctgttggatc tgccggggggc aaatgagaga ttgactctct ggaaagcaga | 300 |
| tttggatgat gaaggaagct tgatgctgc cattgatggg tgtgagggtg ttttccatgt | 360 |
| tgccactccc atggatttcg agtccgagga tcccgagaat gagataatta agccaacaat | 420 |
| caacggggtc ttgaatgtta tgagatcgtg tgcaaaagcc aagtccgtga agcgagttgt | 480 |
| tttcacgtca tctgctggga ctgtgaattt tacagatgat ttccaaacac caggcaaagt | 540 |
| ttttgacgaa tcatgctgga ccaacgtgga tctttgcaga aaagttaaaa tgacaggatg | 600 |
| gatgtacttt gtatcgaaga cattagcaga gaaagctgct tggggattttg cagaggagaa | 660 |
| caagatcgat ctcattactg ttatccccac attggtcgtt ggaccattca ttatgcagac | 720 |
| catgccaccg agcatgatca cagccttggc actgttaacg cggaatgaac cccactacat | 780 |
| gatactgaga caggtacagc tggttcactt ggatgatctc tgtatgtcac atatctttgt | 840 |
| atatgaacat cctgaagcaa agggcagata catctcttcc acatgtgatg ctaccattgt | 900 |
| ccaagtggcc aagatgctgg ctcagaaata cccagagtac aatgtaccaa ccacgttcaa | 960 |
| ggatgcggat gagtccctgc cggccgtgcc attttcgtca aagaagctcc ttgatttggg | 1020 |
| cttcaagttc aactacacca tggaagagat gtttgatggg gccattaagt gctgcagaga | 1080 |

```
gaaaggattg ctgcctgaga aagcatcttt ctgataagta tctactgatg cagcatacac   1140
acaccgttgg catgtgtggt ttgtgtaaga catggtggca gtggagaaat aatggatcaa   1200
atttggttta tagaaaacag caggaattac tacttgcaag agtgacttat gtgacatgat   1260
atagaaataa gaagaatacc ggctgatcgc tgttgtttat taatgcgaat tttattgatg   1320
ttgacaaggt cataccaggg ctcctggaat gctacatatg tacggctgat tctagctcca   1380
gtaatataat ttttcaaatt ctaaaaaaaa aa                                 1412

<210> SEQ ID NO 130
<211> LENGTH: 666
<212> TYPE: DNA
<213> ORGANISM: Pinus radiata

<400> SEQUENCE: 130
atcaattttt gcatattatt aaaaagtaag tgtattcgtt ctctatattg atcagtcaca     60
gagtcatggc cagttgtggt tccgagaaag taagagggtt gaatggagat gaagcatgcg    120
aagagaacaa gagagtggtt tgtgtaactg gggcaaatgg gtacatcggc tcttggctgg    180
tcatgagatt actggaacat ggctattatg ttcatggaac tgttagggac ccagaagaca    240
cagggaaggt tgggcatttg ctgcggctcc caggggcaag tgagaagcta aagctgttca    300
aggcagagct taacgacgaa atggcctttg atgatgctgt gagcggttgt caaggggttt    360
tccacgttgc caagcctgtt aatctggact caaacgctct tcaggggag gttgttggtc    420 ctgcggtgag gggaacagta atctgcttc gagcctgcga acgatcgggc actgtgaaac    480
gagtgataca tacctcgtcc gtttcagcag tgagattcac tgggaaacct gaccccctg     540 atactgtgct ggatgaatct cattggactt cggtcgagta ttgcagaaag acaaagatgg    600
tcggatggat gtactacatc gccaacactt atgcagaaga gggagcccat aagttcggat    660
cagaga                                                              666

<210> SEQ ID NO 131
<211> LENGTH: 478
<212> TYPE: DNA
<213> ORGANISM: Pinus radiata

<400> SEQUENCE: 131
gctggttcaa gtgtcagccc aatggcctcc cctacagaga atccccagat tcagaagag     60 ctgctaaatc atgagatcca tcaaggaagt acagtatgtg tgacaggagc tgctggcttc    120
ataggatcat ggctcgtcat gcgtttgctt gagcgaggat atactgttag aggaactgtg    180
cgagacactg gtaatccggt gaagacgaag catctattgg atctgcctgg ggcgaatgag    240
aggttaactc tctggaaagc agatttggat gatgaaggaa gctttgacgc cgccattgat    300
ggttgtgagg gagttttcca tgttgccact cccatggatt ttgaatccga ggaccccgag    360
aacgagataa ttaaacccgc tgtcaatggg atgttgaatg ttttgagatc gtgtgggaaa    420
accaagtcta tgaagcgagt tgttttcacg tcgtctgctg ggactctgct ttttacgg     478

<210> SEQ ID NO 132
<211> LENGTH: 510
<212> TYPE: DNA
<213> ORGANISM: Pinus radiata

<400> SEQUENCE: 132
cttgttcaaa gtcacatatc ttatttctt tgtgatatct gcaatttcca agcttttcgt      60
```

```
ctacctccct gaaaagatga gcgaggtatg cgtgacagga ggcacaggct tcatagctgc    120
ttatctcatt cgtagtcttc tccagaaagg ttacagagtt cgcactacag ttcgcaaccc    180
agataatgtg gagaagttta gttatctgtg ggatctgcct ggtgcaaacg aaagactcaa    240
catcgtgaga gcagatttgc tagaggaagg cagttttgat gcagcagtag atggtgtaga    300
tggagtattc catactgcat cacctgtctt agtcccatat aacgagcgct tgaaggaaac    360
cctaatagat ccttgtgtga agggcactat caatgtcctc aggtcctgtt caagatcacc    420
ttcagtaaag cgggtggtgc ttacatcctc ctgctcatca ataccgatac gactataata    480
gcttagagcg ttccctgctg gactgagtca                                     510

<210> SEQ ID NO 133
<211> LENGTH: 890
<212> TYPE: DNA
<213> ORGANISM: Pinus radiata

<400> SEQUENCE: 133
tcctaattgt tcgatcctcc cttttaaagc ccttccctgg ccttcattcc aggtcacaga     60
gttgttcatg cagtgctagc aggaggagca gcgttgcaat tggggaaaat tccaaaatca    120
ataacgagag gacagaagta agtttgtgga aatagcaacc atgccggtgt ttccttctgg    180
tctggacccc tctgaggaca atggcaagct cgtttgtgtc atggatgcgt ccagttatgt    240
aggtttgtgg attgttcagg gccttcttca acgaggctat tcagtgcatg ccacggtgca    300
gagagacgct ggcgaggttg agtctctcag aaaattgcat ggggatcgat tgcagatctt    360
ctatgcagat gtcttggatt atcacagcat tactgatgcg ctcaagggct gttctggtct    420 gtctataccct ttgagcaccc tcagagtgct gcaggctatg atgaagtgat ggcagaaatt    480
gaagtacaag cagcccacaa tgcactggaa gcgtgtgctc agactgagac cattgagaaa    540
gttgtgttca cttcttctgt ggctgcagca atttggagag aagatggaga ctacaaggtt    600
aatgcccttg acgagaggca ttggagtgat gcaaatcttt gcaggaaatt gaagttgtgg    660
tacgcattag ccaagacact gtcagagaag gctgcatggg cgctggcaat ggacagaggg    720
ttgaatatgg tgacaatcaa cgcatctctg attgtaggac ctggcatcac atacaaaagc    780
tcaggatcta ccattgcata tcttaaaggg gctgcacaaa tgtatgagaa gggcacttta    840
gctagtgtgg acataaggtt tctagcggat gcacatatat gcgcttatga                890

<210> SEQ ID NO 134
<211> LENGTH: 955
<212> TYPE: DNA
<213> ORGANISM: Pinus radiata

<400> SEQUENCE: 134
aatcactgac cttcacatat ttattccaat tctaatatct ctactcgctg tctacctgat     60
ttttcagtgg cgaaccaact tgacagggtt ggacatggcc aacagcagca agattctgat    120
tattggagga acaggctaca ttggtcgtca tataaccaaa gccagccttg ctcttggtca    180
tcccacattc cttcttgtca gagagacctc cgcttctaat cctgagaagg ctaagcttct    240
ggaatccttc aaggcctcag gtgctattat actccatgga tctttggagg accatgcaag    300
tcttgtggag gcaatcaaga agttgatgt agttatctcg gctgtcaagg gaccacagct    360
gacggatcaa cagaatatta tcaaggctat taaggaggtt ggaaccatca agaggttttt    420
gccatctgag ttcgggaatg acgttgatag aacccatgca gtggagcctg caaagaccat    480
gtttgctacc aaagcgaaaa ttcgcagggc cattgaggca gaaggcatcc cttacacatt    540
```

-continued

```
tgtctctagc aactgttttg ctggttgtt cttgccaagt ttggggcagc caggccttac      600
cgccccgcca agggataaag ttgtgatatc tggagatgga aatgccaaag ttgttttttgt    660 gaaggaggag gatataggga cattcaccat caaggcagtg gatgaccta gaactctaaa      720 caagatcctg tatttgaggc ttcctgccaa cacatattct cttaacgagc ttgtagctgt     780
gtgggagaag aagattggca agtctctgga agacctat ataccagagg aagaggtcct      840
gaaaaaaatt gcagagtcgc cattcccact caatgctata atgtcaaccg gccactctat     900
ttttgtgaaa ggggatcaaa caaattttga aatcggacct gatggtgtgg aggct          955

<210> SEQ ID NO 135
<211> LENGTH: 1024
<212> TYPE: DNA
<213> ORGANISM: Pinus radiata

<400> SEQUENCE: 135
agagggttat atatcttgat tctgacctga ttgtcgtcga cgacattgcc aagctctggg      60
ccacggattt ggaatctcgt gtcctcgggg caccagagta ctgcaaggcg aatttcacaa     120
agtatttcac cgataatttc tggtgggatc ccgcattatc caagaccttt gagggaaaaa    180
aaccctgcta cttcaacaca ggcgtaatgg tgatcgatct tgaaaatgg cgggcagggg     240 aattcacaag aaagatcgaa atctggatgg acatacagaa ggaacgccgt atctatgagc    300
tcggatcatt accgccattt ttactggtat ttgctggttt ggttaagcaa gtcgatcatc    360
gttggaatca gcacggttta gcggagata atttgcaagg cctttgccga gatcttcacc    420
ctggacctgt cagtttgttg cattggagtg gtaagggcaa accttggcta cgcctggaat    480
gccaagcgga cttgccctct ggatacttta tgggctcctt atgatcttta tcgatcaacg    540
tattacctaa atgggtgaga gagcctctct cctcggggtg cttttttatcg aattaaacct    600 gatttgataa aatgccaaat agaactttac gcctatgcat ctttcagttt tgaatttcaa    660
ttctggtaac gaatagaaga aaacaatagc acagccacag gcaggacaaa tccatcatga    720
gggaccaatc gtttgaattt agtattaata aggttgttcc atataacgcc tgtgaagaat    780
gatattgtgg actgatctat ttatatttgt actgccatgc catcctcagc cagcagagag    840
gcaagcaatg ccgctgcaag tcatgtaggg aaggcgttgt gaactcaatt ttcggcgact    900
gtacaggatg taaattttg gaacattaat atcattatga taagttcctg aaccaacaac      960
tgtataatac cttataaatg tatctgcaac tccatttttg cataaaaaaa aaaaaaaaa    1020 aaaa                                                                  1024

<210> SEQ ID NO 136
<211> LENGTH: 497
<212> TYPE: DNA
<213> ORGANISM: Pinus radiata

<400> SEQUENCE: 136
agaacataaa tccgaacaat gaacttgcaa atttcctgca ttgccatcgc cagcccaaga     60 aactttggc cgcaaagcaa tctgtacact ttctctctca ttccttgcta caagcatgga    120
tataggttct aggggtcttg ggggctcctg atgcccaatt gttgctgtgc ttggcatgac    180
ccaaacatgc aagagatctg tagtcagtag tcttgttgga tctatagctt ttagaaaaga   240
gtcacgtcct tttagggtaa catcattcca accatatcca gttccaccac cggctacacc    300
ttcaacggga ggaggagcaa gatattcagc attgctttgg gcaccagatg gataggcatt    360
```

```
attttccatc ggaattcagc cgagctcgcc ccctcagtcc aatcgtcgtg aaaatccctc    420
aaaattgggc aattctggct cgaaatcgcc aaattatggg ctacaacagg attaaaattg    480
cacagaaatc tgccagt                                                   497
```

<210> SEQ ID NO 137
<211> LENGTH: 528
<212> TYPE: DNA
<213> ORGANISM: Pinus radiata

<400> SEQUENCE: 137

```
ggcaatccga gcctagccaa ccaacttggc agcaaggagc acagggagtt ggcgagagaa     60
gctgttagga aatctttggt attgttgaaa atgggaagt cagccaacaa gcctttgctc    120
cctttggaga agaatgcttc caaggttctt gttgcaggaa cccatcctga taatctgggt    180
tatcagtgtg gtggatggac gatggaatgg caaggattaa gtggaaacat aaccgtagga    240
actacaattc tggaagctat caaactagct gtcagcccct ctactgaagt ggtttatgag    300
caaaatccag atgctaacta tgtcaaagga caagggtttt catatgccat tgtggttgtg    360
ggtgaggcac catacgcaga aacgtttgga gacaatctta atttgaccat tcccctaggc    420 ggagggggaca cgattaagac ggtctgtggc tccttgaaat gccttgtaat cttgatatct    480
ggaaggccac ttgttattga accttatctt ccattggtgg atcgtttt                 528
```

<210> SEQ ID NO 138
<211> LENGTH: 424
<212> TYPE: DNA
<213> ORGANISM: Pinus radiata

<400> SEQUENCE: 138

```
aaaaaacaaa tgttagctag cctagtgatg agctttacgt ataccctggcc ttttatacat    60 ggatctgagt ttttatgcag gtgtagagcc ttttgttact ctgtatcact gggacttgcc    120
acaagctctg gaggacgaat acggtggatt tcgtagcaaa aaagttgtgg atgactttgg    180
catattctca gaagaatgct tcgtgctttt tggagaccgt gtgaagtact gggtaactgt    240
taacgaaccg ttgatcttct catattttc ttacgatgtg gggcttcacg caccgggccg     300
ctgttcgcct ggatttggaa actgcactgc gggaaattca gcgacagagc cttatattgt    360
agcccataac atgcttcttg cacatagtac cgctgttaaa aatatatagc ataaataccc    420
aggg                                                                  424
```

<210> SEQ ID NO 139
<211> LENGTH: 404
<212> TYPE: DNA
<213> ORGANISM: Pinus radiata

<400> SEQUENCE: 139

```
gctaccatct tccctcataa tattgggctt ggagctacca gggatcctga tctggctaga     60
agaatagggg ctgctacggc tttggaagtt cgagctactg gcattcaata cacatttgct    120
ccatgtgttg ctgtttgcag agatcctcga tggggccgct gctatgagag ctacagtgag    180
gatccaaaaa ttgtcaaggc catgactgag attatcgttg gcctgcaagg gaatcctcct    240
gctaattcta caaaaggggg gccttttata gctggacagt caaatgttgc agcttgtgct    300
aagcattttg tgggttatgg tggaacaacc aaaggtatcg atgagaataa tactgttatc    360
aactatcaag ggttatttca acattccaaa ttacccccaa tttt                     404
```

<210> SEQ ID NO 140
<211> LENGTH: 437
<212> TYPE: DNA
<213> ORGANISM: Pinus radiata

<400> SEQUENCE: 140

| | | | | | |
|---|---|---|---|---|---|
| cctagaattc | tatggtgaaa | attgttggga | caaggctgcc | caagtttaca | aaggaacagt | 60 |
| cccaaatggt | taaaggttca | atagactatc | taggcgttaa | ccaatacact | gcttattaca | 120 |
| tgtatgatcc | taaacaacct | aaacaaaatg | taacagatta | ccagactgga | ctggaataca | 180 |
| ggctttgcat | atgctcgcaa | tggagtgcct | attggaccaa | gggcgaactc | caattggctt | 240 |
| tacattgtgc | cttggggtct | atacaaggcc | gtcacatacg | taaaagaaca | ctatggaaat | 300 |
| ccaactatga | ttctctctga | aaatggaatg | gacgacctgg | aaacgtgaca | cttccagcag | 360 |
| gactgcatga | taccatcagg | ggtaactact | ataaaagcta | tttgcaaaat | ttgattaatg | 420 |
| cacgtgaatg | accgggg | | | | | 437 |

<210> SEQ ID NO 141
<211> LENGTH: 470
<212> TYPE: DNA
<213> ORGANISM: Pinus radiata

<400> SEQUENCE: 141

| | | | | | |
|---|---|---|---|---|---|
| gatacatcca | agctgagaat | ggaagagatt | aatggtgata | acgcagtaag | gaggagctgc | 60 |
| tttcctccag | gtttcatgtt | tgggatagca | acttctgctt | atcagtgtga | aggagctgcc | 120 |
| aacgaaggtg | aaaaggccc | aagcatctgg | gactcatttt | cacgaacacc | aggcaaaatt | 180 |
| cttgatggaa | gcaacggtga | tgtagcagtg | gatcagtatc | atcgttataa | ggcagatgta | 240 |
| aaactgatga | agatatggg | cgtggctacc | tacagattct | cgatttcatg | gcctcgtata | 300 |
| tttccaaagg | gaaaaggaga | gatcaatgag | gaaggagtag | cctattacaa | taacctcatc | 360 |
| aatgaactcc | tccagaatgg | aatccaagcg | tctgtcaact | ttgtttcact | gggatactcc | 420 |
| ccagtctctg | gaggatgaat | atggcggatt | tctgaggcca | accattgtga | | 470 |

<210> SEQ ID NO 142
<211> LENGTH: 413
<212> TYPE: DNA
<213> ORGANISM: Pinus radiata

<400> SEQUENCE: 142

| | | | | | |
|---|---|---|---|---|---|
| ataagactaa | ttttccagac | aatcctccat | tcccattcaa | ttacactggt | actccaccca | 60 |
| ataatacaca | ggctgtgaat | gggactagag | taaaagtcct | tccctttaac | acaactgttc | 120 |
| aattgattct | tcaagacacc | agcatcttca | gcacagacag | ccaccctgtc | catctccatg | 180 |
| gtttcaattt | ctttgtggtg | ggccaaggtg | ttggaaacta | caatgaatca | acagatgcac | 240 |
| caaattttaa | cctcattgac | cctgtcgaga | gaaacactgt | gggagttccc | aaaggaggtt | 300 |
| gggctgctat | aagatttcgt | gcagacaatc | caggggtttg | gttcatgcac | tgtcatttgg | 360 |
| aggttcacac | atcgtgggga | ctgaaaatgg | cgtgggtagt | aaagaacgga | aaa | 413 |

<210> SEQ ID NO 143
<211> LENGTH: 457
<212> TYPE: DNA
<213> ORGANISM: Pinus radiata

<400> SEQUENCE: 143

| | | | | | |
|---|---|---|---|---|---|
| aaaacctttt | cagacgaatg | ttctgatgct | cggccccggc | cagacaacag | acatacttct | 60 |

| | |
|---|---|
| cactgccaat caggctacag gtagatacta catggctgct cgagcatatt ccaacgggca | 120 |
| aggagttccc ttcgataaca ccactaccac tgccatttta gaatacgagg gaagctctaa | 180 |
| gacttcaact ccagtcatgc ctaatcttcc attctataac gacaccaaca gtgctactag | 240 |
| cttcgctaat ggtcttagaa gcttgggctc acacgaccac ccagtcttcg ttcctcagag | 300 |
| tgtggaggag aatctgttct acaccatcgg tttggggttg atcaaatgtc cggggcagtc | 360 |
| ttgtggaggt ccaacggatc aagatttgca gcaagtatga atacatatca tttgtcccgc | 420 |
| aaccacttct tccaatcctt caagctcagc attttgg | 457 |

<210> SEQ ID NO 144
<211> LENGTH: 598
<212> TYPE: DNA
<213> ORGANISM: Pinus radiata

<400> SEQUENCE: 144

| | |
|---|---|
| gttcggcact gagagatcca tttctttcaa tgttgagaca gtgagtagta ttagtttgat | 60 |
| atctctttca ggaatatatc gtgcttgcag gatctttagt ttctgcaaca atgtcgttgc | 120 |
| aatcagtgcg tctatcttct gttctccttg ttttgctact agcatttgtt gcttacttag | 180 |
| ttgctgtaac aaacgcagat gtccacaatt ataccttcat tattagaaag aagacagtta | 240 |
| ccaggctatg caataagcgt ataatcgcca ccgtcaatgg acagctacca ggcccaacta | 300 |
| ttcatgtacg tgatggagac gttgttaata tcaaagctta taacaaagct gggtacaatg | 360 |
| ccactcttca ctggcatgga gtcgagcagt tgcgtacagg atgggccgat ggacctgcat | 420 |
| atgttacaca gtgccccatt ccaccaggtg gtcgttatac atacagattc accatttctg | 480 |
| aacaggaagg caccgtgtgg tggcacgctc atgtgtcatg gctccgagct acggtgcatg | 540 |
| gagctttcgt aatccttcct aagagaggca accatatcc ctttcctaaa ccccgtgc | 598 |

<210> SEQ ID NO 145
<211> LENGTH: 1080
<212> TYPE: DNA
<213> ORGANISM: Pinus radiata

<400> SEQUENCE: 145

| | |
|---|---|
| aagatcttgg ttcgagtctc tcagctctct ccaaaggaat tttgtgggtc atttgcaggt | 60 |
| gaagacacca tggtgaaggc ttatcccacc gtaagcgagg agtacaaggc tgccattgac | 120 |
| aaatgcaaga ggaagctccg agctctcatt gcagagaaga actgtgcgcc gatcatggtt | 180 |
| cgaatcgcat ggcacagcgc tgggacttac gatgtcaaga ccaagaccgg agggcccttc | 240 |
| gggacgatga gatatggggc cgagcttgcc cacggtgcta acagtggtct ggacatcgca | 300 |
| gttaggctcc tggagccaat caaggaacag ttccccataa tcacctatgc tgacctttat | 360 |
| cagttggctg gtgtggtggc tgttgaagtg accgggggac ctgacattcc gttccatcct | 420 |
| ggaagagaag acaagcctga gcctccagaa gaaggccgcc ttcctgatgc tacaaaagga | 480 |
| cctgatcatc tgagggatgt ttttggtcac atggggttga atgataagga aattgtggcc | 540 |
| ttgtctggtg cccacacctt ggggagatgc acaaggaga gatctggttt tgaaggacca | 600 |
| tggacctcta accccttat ctttgacaac tcttacttca cagagcttgt gactggagag | 660 |
| aaggaaggcc tgcttcagtt gccatctgat aaggcactgc ttgctgatcc tagttttgca | 720 |
| gtttatgttc agaagtatgc acaggacgaa gacgctttct tgctgactat gcggaagct | 780 |
| cacctgaagc tttctgaact tgggtttgct gatgcgtaga ttcataccct ctgcagagac | 840 |

-continued

| | | |
|---|---|---|
| aattccttgc tagatagctt cgttttgtat ttcatctaat cttttcgatt atatagtcac | 900 | |
| atagaagttg gtgttatgcg ccatagtgat acttgaacct acatgttttt gaaaagtatc | 960 | |
| gatgttcttt aaaatgaaca ttgaatacaa cattttggaa tctggttgtg ttctatcaag | 1020 | |
| cgcatatttt aatcgaatgc ttcgttcctg ttaaaaaaaa aaataaaata aaaaaaaaa | 1080 | |

<210> SEQ ID NO 146
<211> LENGTH: 701
<212> TYPE: DNA
<213> ORGANISM: Pinus radiata

<400> SEQUENCE: 146

| | | |
|---|---|---|
| gtagtttcgt tttacaacaa tctcaggttt tgaatctcag aatagttgcg aaaggaagcg | 60 | |
| atgacgaagt acgtgatcgt tagctccatt gtatgtttct ttgtatttgt ttctgcgtgc | 120 | |
| ataatttctg tcaatggatt agttgtccat gaagatgatc tgtcaaagcc tgtgcatggg | 180 | |
| cttcgtgga cattttataa ggacagttgc cccgacttgg aggccatagt gaaatcggta | 240 | |
| cttgagccgg cgttggacga agatatcact caggccgcag gttgctgaga cttcatttcc | 300 | |
| atgactgttt tgtgcagggt tgcgatgggt ccgtgttgct gacaggaact aaaagaaacc | 360 | |
| ccgagtgagc aacaggctca gccaaactta acactaagag cccgggcctt gcagctgatc | 420 | |
| gacgaaatta aaaccgctgt agaagctagc tgcagtgggg ttgtaacttg tgcagacatt | 480 | |
| ctggctttgg ctgctcgtga ctccgtcgct caggaggccc aaaatttcca gtaccacttg | 540 | |
| gccgcagaga tagcctaaag tttgccagtc aatccgtagt tctcgccaat ataccaactc | 600 | |
| caactttaaa tttgacacag ctgatgaaca tttttggctc caaaggattc agtttggccg | 660 | |
| aaatggttgc tctttcaggt ggacacacaa tcggcattgg t | 701 | |

<210> SEQ ID NO 147
<211> LENGTH: 338
<212> TYPE: DNA
<213> ORGANISM: Pinus radiata

<400> SEQUENCE: 147

| | | |
|---|---|---|
| ctcaattctg tgctgctctg ctcgctcagg gccgggtctg ctattctgct catgcacaag | 60 | |
| tttgagatcg ggagcctgct ggatctggtg cagaggttca aggtcacggt agcgcctgtc | 120 | |
| gtgcctccca ttgttctcgc ctttgccaag aacgcgctcg tggaaagcta tgatctgtcg | 180 | |
| tccattaggg ttgtgctgtc cggtgccgcg cctctcggaa aggagctgga ggatgcatta | 240 | |
| aggctacgac ttcccaaagc cacttttggt cagggatacg gtatgacaga ggcaggaccg | 300 | |
| gtgctatcaa tgtgtctggc cttcgctaag gagcccctt | 338 | |

<210> SEQ ID NO 148
<211> LENGTH: 357
<212> TYPE: DNA
<213> ORGANISM: Pinus radiata

<400> SEQUENCE: 148

| | | |
|---|---|---|
| ctcaattctg tgctgctctg ctcgctcagg gccgggtctg ctattctgct catgcacaag | 60 | |
| tttgagatcg ggagcctgct ggatctggtg cagaggttca aggtcacggt agcgcctgtc | 120 | |
| gtgcctccca ttgttctcgc ctttgccaag aacgcgctcg tggaaagcta tgatctgtcg | 180 | |
| tccattaggg ttgtgctgtc cggtgccgcg cctctcggaa aggagctgga ggatgcatta | 240 | |
| aggctacgac ttcccaaagc cacttttggt cagggatacg gtatgacaga ggcaggaccg | 300 | |
| gtgctatcaa tgtgtctggc cttcgctaag gagccctttc cgatgaagtc cgggtcg | 357 | |

<210> SEQ ID NO 149
<211> LENGTH: 470
<212> TYPE: DNA
<213> ORGANISM: Eucalyptus grandis
<220> FEATURE:
<221> NAME/KEY: unsure
<222> LOCATION: (437)...(437)

<400> SEQUENCE: 149

| | | | | | |
|---|---|---|---|---|---|
| gagaaattca | caagcttcac | agcacgagag | ttaaagagcg | agacacggtt | tgatccagtg | 60 |
| aagggccggc | ccccggagat | ggcgaagacg | ctcaccgcgc | tggctggggg | agaagaccct | 120 |
| ccagtccaaa | gttcgtccgc | gataaggatg | agcgccccac | ggtggcctac | aaccagttca | 180 |
| gcaacgtgat | ccccgtgata | tccctggcgg | ggattgacga | ggccggcggc | cggaagggcc | 240 |
| gagatctgca | agaagatcgt | ggaggcgtgc | gaggactggg | gcgtcttcca | ggtggttgac | 300 |
| cacggggttg | atacggggct | catcactgac | atgacccggc | tcgcgcgtaa | gtncttcgct | 360 |
| ctgccctcgg | aggaaaagct | ccggttcgac | atgactggcg | aaaaagggg | gggttatcgt | 420 |
| ctccagcatc | tcaaggngaa | caagttcagg | actggtgcaa | aagtacgaac | | 470 |

<210> SEQ ID NO 150
<211> LENGTH: 380
<212> TYPE: DNA
<213> ORGANISM: Eucalyptus grandis

<400> SEQUENCE: 150

| | | | | | |
|---|---|---|---|---|---|
| ggaggtcggt | gacagagcag | tacagcgaga | agctcatggc | cctcgcttgc | aagctcttgg | 60 |
| aggtcctctc | ggaggcaatg | ggactggaga | aggaggcact | gaccaaggca | tgcgtggaca | 120 |
| tggaccagaa | ggtggtggtc | aactactacc | ccaaatgccc | gcagcccgac | ctcacgctcg | 180 |
| ggctgaagcg | ccacactgac | ccgggaacca | tcactcttct | gctccaggac | caggtggggg | 240 |
| gcctccaggc | caccagagat | ggcggcaaga | gctggatcac | cgtccagcct | gtggaagggg | 300 |
| cttttgtggt | caacctaggc | gatcatggtc | atttcctgag | caacgggagg | ttcaagaacg | 360 |
| cggaccacca | ggcggtggtg | | | | | 380 |

<210> SEQ ID NO 151
<211> LENGTH: 349
<212> TYPE: DNA
<213> ORGANISM: Pinus radiata
<220> FEATURE:
<221> NAME/KEY: unsure
<222> LOCATION: (212)...(212)

<400> SEQUENCE: 151

| | | | | | |
|---|---|---|---|---|---|
| ttggactcca | tacctctcgt | ggacctccaa | ggtcttttac | gcgattctgc | tagagcccac | 60 |
| gttattcaac | aaattggccg | ggcctgcgct | gaatatggct | tcttccagat | aatcaatcat | 120 |
| ggcatcccag | atgcagttat | caacaggatg | ctggaagtag | cgaaggagtt | tttcagaatg | 180 |
| cctgtggagg | accgaatgga | atactattcc | gncgatccgt | ccagaaaaac | acgtttgtcg | 240 |
| acgagcttca | acatccataa | agaacaagtc | ttcaactggg | gggctatctc | agacatcatt | 300 |
| gttatccgtt | agaagatcat | gttcacactt | ggccttcaaa | acctgcggg | | 349 |

<210> SEQ ID NO 152
<211> LENGTH: 427
<212> TYPE: DNA
<213> ORGANISM: Pinus radiata
<220> FEATURE:

```
<221> NAME/KEY: unsure
<222> LOCATION: (234)...(234)
<220> FEATURE:
<221> NAME/KEY: unsure
<222> LOCATION: (240)...(240)

<400> SEQUENCE: 152
atggtctggg cagcatacgg aggacgatgg aagatggaac gcaaggtgtg caacatgcac      60
atgttgggag ggaaggcgtt ggaagattgg cagccggtga gggacgccga aatgggcttc     120
atgctccgga atattctcag tcactcgcag cgcggcgaga cggtgaatgt gccggacctc     180
ctgaacatct gcgccgccaa catgatcggg cagatcattc taagcaagcg ggtnttcgan     240
acagaagggg acgaggccaa cgagttcaag gacatggtgg tggaactcat gacctgcgct     300
ggatacttca atatcggaga cttcattcca tcgctagcgt ggatggactt gcagggcatt     360
cagcggggta tgaagaagct ccacaagaaa tgggacgcac tcatacagag gattattgat     420
taacacc                                                                427

<210> SEQ ID NO 153
<211> LENGTH: 298
<212> TYPE: DNA
<213> ORGANISM: Eucalyptus grandis
<220> FEATURE:
<221> NAME/KEY: unsure
<222> LOCATION: (214)...(214)

<400> SEQUENCE: 153
gttaccaaag ggcagcaacg tattcttaaa catgggttct atccacaggg atcccaagat      60
ttgggacaaa ccgttggagt ttagacccga gaggttcttg gaaggtccta gcaagtatga     120
tttctcaggt aacaacttcg catacatgcc attcggttct ggtcgaaggg tgtgtgcagg     180
gcttgcgctg cagagagga tgctaccata tgtnttggcc tctcttttgc actcattcaa      240
gtgggaaata ccaccagggt ctgagctgga tttacctgga caagttcggc cttgtggt       298

<210> SEQ ID NO 154
<211> LENGTH: 251
<212> TYPE: DNA
<213> ORGANISM: Eucalyptus grandis

<400> SEQUENCE: 154
gacttcaaag ggcaggattt tgagctgata cccttcggtg caggtagaag gagctgcccg      60
gctattgcat ttggaaatgc cagtgttgag cttgctttag ctcaacttct tcacagtttc     120
gattgggagc ttcctgatgg gatccagcct agggacttgg atatgaccga agttttggc      180 atcacaatgc acagaattgc caacctcatg gttgtagcca aacccgctt ctcctagacg      240 atactcgtgc c                                                           251

<210> SEQ ID NO 155
<211> LENGTH: 411
<212> TYPE: DNA
<213> ORGANISM: Pinus radiata
<220> FEATURE:
<221> NAME/KEY: unsure
<222> LOCATION: (198)...(198)

<400> SEQUENCE: 155
acggggctcc ggtgacgaga tactggcagg tcgttgaagc tggttggagg ttcgaatatc      60
cgagagggat cctgtttctt gtccccttac cttggttttc ctcatccttc cgaatgcagt     120
ctaattcgaa gaccgtggaa gagcggcgcc cggggcctgg gtaagagctt gctggagata     180
```

```
tctcggcttg actatgtnttt ggctcttttc gtgaatggca aggggatct aggggcgatg      240 atgggtcgg ctgtcgtttt gagggaaaat tcgcaactgt tgatggtctt gactacatct      300
ctggccgtct tgattggttg cgttttgttc tttgtttggc ggagaggggg atcggctccc     360
tcgaagcagc cggagaagcc aactcccctg gtgaaagaag aggaagagga g              411

<210> SEQ ID NO 156
<211> LENGTH: 404
<212> TYPE: DNA
<213> ORGANISM: Pinus radiata

<400> SEQUENCE: 156
gctgaagtta ataaaactaa gtacattgag gttgacatgg aggcagaatt ttcaaatcta     60
gctttggaca ttattggatt gtgtgtattt aactatgatt ttggatccgt tactcgagaa     120
tcaccagtaa tcaaggcagt ctatggtaca ttgtttgaag ctgagcatag atcaaccttt    180
tacataccat actggaaatt ccgctggca agatggttag ttcctcgcca acgaaagttc      240
catgaagacc taaaggtcat taatgaatgt cttgataatc tgatagcagg ggccaaggaa    300
acaagacagg aagacgatat cgaggctctt caaggaagag attactctaa agtgaaatat   360
gcaagtttgc tcagatttct agttgatatg agggagaaga tgtt                     404

<210> SEQ ID NO 157
<211> LENGTH: 259
<212> TYPE: DNA
<213> ORGANISM: Pinus radiata
<220> FEATURE:
<221> NAME/KEY: unsure
<222> LOCATION: (116)...(116)
<220> FEATURE:
<221> NAME/KEY: unsure
<222> LOCATION: (246)...(246)

<400> SEQUENCE: 157
ccaatcatcg gcaatttcca ccaagtgaga cttcctcttc accgtgctct caaaaatctt    60
gctgagaaat atggtcccat tttgtttctg cgctttggct ctgtaccac tgtggntgtt     120 tcttcatctg agatggccaa acactttctt aaaactcatg atttgatatt tgccagccga   180
cctccaacat cggtaggaaa atatttcttc tataacttca agatattgc cttcagtcct   240 tatggngatc actggagga                                                 259

<210> SEQ ID NO 158
<211> LENGTH: 338
<212> TYPE: DNA
<213> ORGANISM: Pinus radiata

<400> SEQUENCE: 158
aatggcagtt gggggtcaag gaaatgtggt ctcagcttgc aggcagccat ggaagctaca    60
atcgtctggt gggtgttttg gtagtaatag tttctctggc agttttttat ttgaagagta   120
gaggttcgaa gaagcgtctg cctccagggc cgaaggtgg cctctggttg gaaatttgtt    180
tcaggttgca ttctccggga agcccttcat gtatgtggtg cgagatctga gggagcagtt   240
tggctcgatt ttcacgctcc aaatggggca aaaacgccc caaattacca cctcccccgaa  300 atttccaaca cggggcctct taaaaagag ggggcccc                             338

<210> SEQ ID NO 159
<211> LENGTH: 539
<212> TYPE: DNA
```

<213> ORGANISM: Pinus radiata
<220> FEATURE:
<221> NAME/KEY: unsure
<222> LOCATION: (1)...(539)
<223> OTHER INFORMATION: n at all occurrences indicates unsure

<400> SEQUENCE: 159

| | | | | |
|---|---|---|---|---|
| aatgtggccg | aggagttcct | gnaagactca | tggatctggc | tttcgccagc agacctccaa | 60 |
| ccatcggtaa | cgaatatttt | ggtataattc | ctccgacgtc | gcattttccc cctatggtcc | 120 |
| ttactggagg | cagatgcgta | aaatctgtgt | gttaaagttg | ctgagctcaa gacgcataga | 180 |
| ttccttccgc | cacataagag | aagaggaagt | ctcttctatg | gttcgctcta ttgctaattc | 240 |
| ggatctgcat | cctgtgaaca | ttagcagggc | cgtgtcagcc | cttgggattg atataatctg | 300 |
| caggatggcc | ttcggtaaaa | agtactgtga | ccaagaccta | attggtggca ttgggatnaa | 360 |
| gtcaatgata | aaggaaacgt | ttgtgtnagc | agggtcnttg | aacatgggag atttatacc | 420 |
| atacttggca | tggattgatc | ttcaaggtct | caaccgtcga | ttgaagaaca tacacaagat | 480 |
| ccaagacgac | ttgttagggg | aagatactag | aggcacacgc | ttcgccaacc gcagaataa | 539 |

<210> SEQ ID NO 160
<211> LENGTH: 310
<212> TYPE: DNA
<213> ORGANISM: Pinus radiata
<220> FEATURE:
<221> NAME/KEY: unsure
<222> LOCATION: (16)...(16)

<400> SEQUENCE: 160

| | | | | |
|---|---|---|---|---|
| cgaatgggtg | gtcggnaaag | accgcacagt | aaaggagtct | gatttggtaa gtctgaaata | 60 |
| ccttcagtgt | gtggtgaaag | agacgctacg | attatacccg | ggaggacctc tagcacttcc | 120 |
| ccatgagtct | gtggaggctg | tgacagtaga | agggtactat | ataccctaaga agacgatgct | 180 |
| gttggtgaat | gtgtgggcta | taggaaggga | ccccaaagtg | tgggggattg atgcttcaga | 240 |
| attcaagcca | gagagattta | tggaggaatt | aggtgggcat | ctgcatgata atgtcatgga | 300 |
| tttagcaggc | | | | | 310 |

<210> SEQ ID NO 161
<211> LENGTH: 412
<212> TYPE: DNA
<213> ORGANISM: Eucalyptus grandis

<400> SEQUENCE: 161

| | | | | |
|---|---|---|---|---|
| cgccacctcc | ctcctcctct | tcccctcct | cctgctcctc | ctggtcgccc cgcaaaagcc | 60 |
| ctccgcctct | gtccgcagtc | accgccagcc | atggatctcc | tcctcctgga gaagacccta | 120 |
| ctgggcctct | tcgccgccgc | catcgtggcc | atcgcggtct | ccaagctccg gggcaagcgg | 180 |
| ttccgcctcc | ccccgggccc | cctccccgtg | cccatcttcg | gcaactggct ccaggtcggc | 240 |
| gacgacctca | accaccgcaa | cctcaccgac | ctcgccaaga | ggttcggcga catcctcctc | 300 |
| ctccgcatgg | ggcagcgcaa | cctcgtggtc | gtctcgtccc | cggacctctc caaggaggtg | 360 |
| ctccacacgc | agggcgtcga | gttcgggtcc | cgcacccgga | acgtcgtctt ct | 412 |

<210> SEQ ID NO 162
<211> LENGTH: 329
<212> TYPE: DNA
<213> ORGANISM: Pinus radiata

<400> SEQUENCE: 162

```
acttttacaa tgagtgatca caaacaattt tttccaaaat tcataacaaa attttggata      60
cagtgcatat tcgggcaaac aatctgacgg acttcaaaac tactgacaac aaaacaaacc    120
atctggggat gaattacaat ggaaatccac acttcatttg ctgcaactg tatatataaa     180 gtgtttattg cttccagctc ctccagactt tggaagaaat tctatatttt ttttcagga    240 tctgagcttc aggctattgg tttggccaca acaacggagt ggttgagaat gtgcaggctg    300
aattgccctc ctttctctgt cacatccac                                      329
```

<210> SEQ ID NO 163
<211> LENGTH: 475
<212> TYPE: DNA
<213> ORGANISM: Pinus radiata

<400> SEQUENCE: 163

```
atttgcgtca gtctctacct ttgcctgcaa cattcacagt cgctgatgga gggcctcccg      60
cagcaactgt cctgtgctta ctctgggctt tcttcatgat atggttttg ggcaagagaa     120 gaactagtgc cacgctgcca ccaggaccct atgcatggcc catcatagga aacctctacc    180
aattaatact gcccgctcac cgttctctta gaggccttgc tgacaaatat ggtcccatta    240
tgtttctgcg cttaggctct gtccctaccg tcgtcgtttc ttcttctgag acggccaaag    300
agtttctcaa aactcatgac ttgattttg ccagccgacc cccaacagcc gctgggagat     360
tgatgttttc caactctaaa gacgtggtgt tcgctccgta tggagatcac tggaggcaaa    420
tgagaaaaat atgcgtgtta gaactactga ctgccaaaag aatcgagctc gtgcc         475
```

<210> SEQ ID NO 164
<211> LENGTH: 372
<212> TYPE: DNA
<213> ORGANISM: Pinus radiata
<220> FEATURE:
<221> NAME/KEY: unsure
<222> LOCATION: (22)...(22)

<400> SEQUENCE: 164

```
tggaaataca gttcgactct gngatttcat aaaatatgat gaggaaagga gaatcaggtg      60
gatttgaggt taagggatgg gctgccatgg atgactccgg cgtcctctcg cctttcaact    120
ttactcgcag gaaaacggga tcccacgatg tactttcaag gtagcatact gtggaatctg    180
tcactccgat ctgcatcaaa ttcggaatga atggaaaaat tccctatacc caaatgggtt    240
ccaggccacg aaatcgtagg aactgttgct tgaagttcgg tcagaagtga agaattttgg    300
ctggctggag aatcggcggt gggtgtaagg gttgcatggg tttggaggtg ccagccaatt    360
ggtgaattct tg                                                        372
```

<210> SEQ ID NO 165
<211> LENGTH: 307
<212> TYPE: DNA
<213> ORGANISM: Eucalyptus grandis

<400> SEQUENCE: 165

```
tctctctctc tctccctctt gagagtgttg aagtgttagg atgaggattc gagtgccgtc      60
gatgctgttg ttgtggtcac tgttgggcct cgtggcgagg tcgacaatgg ccgaagagac    120
ggtgatcccc gagacaacgc gtttcgacac cggtgggctg agcagatcgg ccttcccgaa    180
gggcttcgtc tgggggacgg cgacctcggc ttatcaagtc gaaggcatgg ccgacaaaga    240
gggacgcggg cctagcatct gggacgtctt cgtcaagatt ccaggaattg tggccggtaa    300
```

```
tgcaact                                                             307

<210> SEQ ID NO 166
<211> LENGTH: 454
<212> TYPE: DNA
<213> ORGANISM: Eucalyptus grandis

<400> SEQUENCE: 166
gaagaaatta ggtttcttgt tgcggctttt ggtagtgggt ctggtgatag cagagacggt   60
ccatggtgct tatgagttca gcagatacga ctttcctcct ggctttgtgt ttggtgctgg  120
cacttcagct tatcaggtcg aaggagcagc aaatgaggat gggaagactc caagtataat  180
ggacacctgg gcccactctg actcagggat acaagcggga gcaaatggag atattgcctg  240
tgatcaatat cacaaataca aggtagatgt ccaactcatg gcagaaatgg gattagacgc  300
ataccggttt tccatctcat ggtcaaggct catcccaaat gggagaggct ctgtgaatcc  360
gaagggattg cagtactaca acaacctcat caatgaactg atcagccatg ggattgaacc  420
cgcacgtgac cctgcaccat tttgatctgc caca                              454

<210> SEQ ID NO 167
<211> LENGTH: 433
<212> TYPE: DNA
<213> ORGANISM: Pinus radiata

<400> SEQUENCE: 167
gagaagcaat aggaaaatat ggccctggag aatggtgaaa gaagcagagt actgatcatt   60
ggaggaaccg gttattttgg cagaaggtta gtgaaggcca gccttgcctt cggacatgag  120
acttatgtcc agtatcgtgc ccaggcagcc tctgatatca caaagtggga gacgcttatt  180
tccttcaaat ctcaaggagc cacctggtg gatgcttcca ttgacaatca cacaagcctc  240
gtaaatgccg tgaaacgagt ggaagttgta atatcggcga tgggtgccga gggtctgaga  300
gaggggcagc tgaaagtgat cgaggccatt aaagaggcag gaaccgtcaa gcgcttcctt  360
ccttctgagt tcgggatggc ccagacagaa tggtgcacgc catctatccg ggcaacgagg  420
ttttctctga taa                                                     433

<210> SEQ ID NO 168
<211> LENGTH: 330
<212> TYPE: DNA
<213> ORGANISM: Pinus radiata

<400> SEQUENCE: 168
cggggagctt gacttgggac tggaaagcag cgggcatcgt ttcctgtggg ttctccgcgg   60
tcatccttcc aatccaaact tatctgcgct gctgccccg ggtttcgaac agcggaccaa  120
agatcgtggt ctcgtggtta cctcatgggc tccgcaggtt tctatccttg cacacccgtc  180
aacaggaggt tttgtgagtc actgcggttg gaactcgatg ctggagagca tttggtttgg  240 agttccccatt atcgcttggc ccctccaagc tgaccaaagg ccgatcgggt tactttctgg  300
tgaatgatag tagaatagac ggtaggcttg                                   330

<210> SEQ ID NO 169
<211> LENGTH: 398
<212> TYPE: DNA
<213> ORGANISM: Eucalyptus grandis

<400> SEQUENCE: 169
ggaaaatttg gtatcggtag agagatcctg tgagatcgac gcgtgggtcg accttcaaaa   60
```

```
tttgacccgt gaggtgatct ctcgaacagc gtttggcagt agcttcgaag aaggcaaaag    120
gatctccgaa cttcaggggg aacaagccca gctcacgata atagcccttc aatcggtcta    180
catccctggt tggaggtttg tgccaactaa gatgaacagg aggatgaaga gcatagataa    240
ggaagtgcgg gctctgctca tggacatcat ccgcagaaga gagaaagcaa taagggaagg    300
ggaagctgct ggcgatgatc tgctggggct gttgctggag tcaaacatga aggagaatgt    360
cgggatgagc cttcacgatg tgatggacgg agttgcag                            398

<210> SEQ ID NO 170
<211> LENGTH: 432
<212> TYPE: DNA
<213> ORGANISM: Eucalyptus grandis
<220> FEATURE:
<221> NAME/KEY: unsure
<222> LOCATION: (214)...(214)

<400> SEQUENCE: 170
gttaccaaag ggcagcaacg tattcttaaa catgggttct atccacaggg atcccaagat     60
ttgggacaaa ccgttggagt ttagacccga gaggttcttg gaaggtccta gcaagtatga    120
tttctcaggt aacaacttcg catacatgcc attcggttct ggtcgaaggg tgtgtgcagg    180
gcttgcgctg gcagagagga tgcaaccata tgtnttggcc tctcttttgc actcattcaa    240
gtgggaaata ccaccagggt ctgagctgga tttactggac aagttcggcc ttgtggtcaa    300
gaaaatgaag cccttgtcg ccattccaag accaagattg tccactctgg agctctacat     360
gtcgagatag atatttcatt agagtcccaa agctcttcat ttcaattcta gaaataaac    420 gtatcctgcc ag                                                       432

<210> SEQ ID NO 171
<211> LENGTH: 303
<212> TYPE: DNA
<213> ORGANISM: Eucalyptus grandis
<220> FEATURE:
<221> NAME/KEY: unsure
<222> LOCATION: (105)...(105)

<400> SEQUENCE: 171
ccatcgcggc cctggcccgg acctacgggc cgctcatgca cctgcggctc gggttcgtac     60
gacgtggtgg tggccgcgtc ggcctccgtg ccgccgagt tcctnaagac ccacgacgcc    120
aacttctcga gccggccgcc caactccggg gcgaacacat cgcgtacaac taccaggacc    180
tgatgttcgc gccctacggc ccgcggtggc ggatgctaag gaagataagc tccgtccacc    240
tcttctccgg caaggctctt aagcattaca gacacgttcg ccagaaaaag gtcgcaatcc    300
tca                                                                 303

<210> SEQ ID NO 172
<211> LENGTH: 518
<212> TYPE: DNA
<213> ORGANISM: Pinus radiata

<400> SEQUENCE: 172
cattagatat atatatatag acacgcattt acgatatcat tgcaacaatg tcattggtag     60
gctgggttgt ttttctaatc gctttgattt cgtatttggc tgccatcaca aatgcagcaa    120
tcgtcaatta taccttcatc attgaagcga agacagttac caggctatgc aaggagaata    180
caataatcac cgtcaatggg cagctaccag gtccgaccat ctatgtccat gacggagaca    240
```

```
ctgttattgt tgaaacttat aacaaggccg agtacaatgc cactcttcac tggcatggag      300
tggagcagtt gcgtacacca tgggctgatg gacctgcata tgttactcaa tgtcccattc      360
caccaggtgg tcgttataca tacagattca acatctctgg acaagaagga accgtgtggt      420
ggcatgccca ttactcatgg ctccgagcta cggtccatgg agcttttgta atccttccta      480
aggaaggaag ctcatatccc ttttctaaac ccaatgcc                              518

<210> SEQ ID NO 173
<211> LENGTH: 309
<212> TYPE: DNA
<213> ORGANISM: Eucalyptus grandis
<220> FEATURE:
<221> NAME/KEY: unsure
<222> LOCATION: (284)...(284)
<220> FEATURE:
<221> NAME/KEY: unsure
<222> LOCATION: (294)...(294)

<400> SEQUENCE: 173
gccgctgatc ctaggattga gatctgcatg ctccccgtgg gtgatggcat cactctctgc      60
cgtcggatca gctgagcatc taatctcaag tccttatgat cagggttcat tcttaatgta     120
gaacccacga aaagagagg gatttatgta tatcttgttg ctgtttcttt tccatgaacc      180
tagaaacggg attcgcaatt aaatgccaaa ttatgttgct gtttctcttt agtgctctcg      240
atttcttttt atttttttaat tttttgatc agtttcttcg aatnatctca agtncttcca     300
aaaaaaaaa                                                              309

<210> SEQ ID NO 174
<211> LENGTH: 381
<212> TYPE: DNA
<213> ORGANISM: Eucalyptus grandis

<400> SEQUENCE: 174
taagacgaag aaatggaaac aacggccaag ccatcgcgaa acgcctttcc gcatatggaa      60
tgcactatat ttgatcttcc gcatgtggtg gccaatttag aagttagcga aacgtgaga     120 tgtgttcctg gggacatgtt tgagtccata ccaccagcag atgcaataat attgaagtgg     180
atactccatg attggagcga tgaagacgct gtgaagatac tgaagcgatg caaggaggcc     240
ttaggcaagg gcaagggcaa gaaacagaag gtaattataa ttgacatggt gatggacaac     300
acgaagagcg ccaaagagac ggtcgaaacc cagctcttct atgacatgtt gattgatgaa     360
ccctcgccgt cgggaaaggg g                                                381

<210> SEQ ID NO 175
<211> LENGTH: 236
<212> TYPE: DNA
<213> ORGANISM: Pinus radiata
<220> FEATURE:
<221> NAME/KEY: unsure
<222> LOCATION: (37)...(37)

<400> SEQUENCE: 175
tgaattacca catgcggctg atagatctgg tgaaggncgg aggattgatt gcgtatgaca      60
atactctgtg gcaaggatcc gttgcgcttc ccccagaagt cgccatgagc gaaggcatga     120
gttatgggga agacagagag catatgttgg aactaaacag ggcccttgct gcagaccctc     180
gcatcgagat tgctcagatc ccaattgccg atggagtgac gctgtgcagg cgcctt         236

<210> SEQ ID NO 176
```

<211> LENGTH: 404
<212> TYPE: DNA
<213> ORGANISM: Pinus radiata
<220> FEATURE:
<221> NAME/KEY: unsure
<222> LOCATION: (1)...(404)
<223> OTHER INFORMATION: n at all occurrences indicates unsure

<400> SEQUENCE: 176

| | | | | | |
|---|---|---|---|---|---|
| gtcgggaatt | ccacttacca | gaccattaat | tcacgattca | tcccacctca | gcctggaaat | 60 |
| ttggtctgaa | tctggagccc | aatactgtac | aagtagcctt | ggtctcttcg | ggaatccgtg | 120 |
| tntgaaaga | agaaattgag | atccggccaa | agatggttgc | agggtcagac | ctgggcgctg | 180 |
| tgcaggccaa | tggaaatcaa | aatggaaatg | gatttcatca | tgtgcattct | gttgatctct | 240 |
| gcattcagaa | tggnccagac | cctctgaact | ggggggcaggc | tgccaaggcc | ctgcagggct | 300 |
| cccactttga | agaagtgaag | ctcatggtgg | ngtcctattt | cggatccgng | gaagtttcca | 360 |
| ttgaaggcaa | atcngtcaca | atcgcggatg | tgaccgcagt | tgcc | | 404 |

<210> SEQ ID NO 177
<211> LENGTH: 415
<212> TYPE: DNA
<213> ORGANISM: Pinus radiata
<220> FEATURE:
<221> NAME/KEY: unsure
<222> LOCATION: (20)...(20)

<400> SEQUENCE: 177

| | | | | | |
|---|---|---|---|---|---|
| cccaacgcta | tgcgtctgan | caggcaactt | tcttcagtgc | atttgtggcg | gccatggata | 60 |
| aattgggcag | tgtgggtgta | aaaactggca | cacaggggga | ggtcaggagg | agatgtgatg | 120 |
| cgttcaattg | agaagagtaa | agttcaaatt | ctctccatta | ttaaggtggg | attgtatgca | 180 |
| tggttgagat | taatgaacgg | aacaaagaaa | atttaatgtt | ttgtaactag | tgagattgat | 240 |
| gaattgaata | aagaattttt | cctgtcctct | gattcaacct | gttttgcact | ctgtgaagca | 300 |
| cttttacagtc | tggactctgg | aaggaatcca | tcaaatcgtg | actaagaaaa | gggtaatgat | 360 |
| tttaaagaga | ttccgttgcg | ctcattccat | tgggggattc | ctgaaaatat | ctgcc | 415 |

<210> SEQ ID NO 178
<211> LENGTH: 409
<212> TYPE: DNA
<213> ORGANISM: Pinus radiata

<400> SEQUENCE: 178

| | | | | | |
|---|---|---|---|---|---|
| gatgggcgcg | caattctttt | cagccggctg | gtgtagttgc | tgttgaggtt | acgggaggtc | 60 |
| ccacaattga | gtttgtccct | ggtcgtaagg | attcactggc | atcaccacga | gaagggcggc | 120 |
| ttcctgatgc | gaagaaaggt | tcacaacacc | taagggatat | cttttatagg | atgggcctat | 180 |
| ctgacaagga | tatagttgct | cttttctggag | cgcacaccat | tgggaaaagc | acatccagaa | 240 |
| aggtcaggct | ttgatggagc | atggaccgag | cagcctctga | agtttgataa | ttcatatttt | 300 |
| gtagagcttc | tcaaaggcga | gtctgaagga | ttactccaat | tgcctacgga | caaatgcttg | 360 |
| gtagaggatc | ccagtttccg | cccttatgtg | gatctttatg | ccaaggatg | | 409 |

<210> SEQ ID NO 179
<211> LENGTH: 411
<212> TYPE: DNA
<213> ORGANISM: Eucalyptus grandis
<220> FEATURE:
<221> NAME/KEY: unsure
<222> LOCATION: (393)...(393)

<400> SEQUENCE: 179

```
agagcttctc ccagagaggc ctctctatgg aagatctcgt cgctctttcg ggaggccaca      60
cactaggatt ttcccactgc tcctccttcg caggcaggat ccgcaacttc aacaccacgc     120
acgacatcga cccatcgatg cacccatccc tggcagcgag cctaagaggc gtgtgcccga     180
gcaagaacag gccaaaaaac gcagggacca ccatggaccc ttcctcgacc accttcgaca     240
acacgtacta cgggctgatc ctccagggga agggcctgtt ctcttcggac caggccctcc     300
tggcagtgcc caagacgaag gatctggtcg agaagttcgc aggctcgcac aaggaattca     360
cggatgcatt cgtcaagtcc atgatcaaga ttnagcagca tcacaggcgg a              411
```

<210> SEQ ID NO 180
<211> LENGTH: 334
<212> TYPE: DNA
<213> ORGANISM: Pinus radiata

<400> SEQUENCE: 180

```
gcatcatggg aagtacaact gggaagaaga gacagcctaa cagcaagcaa acagcagca      60
aataacaaca ttccagcccc cacatcaaat gttgcaacac ttaactccaa gtttcagaat    120
gtaggcctca ctgaacaaga catggtcaca ctctcaggag cccatacaat aggaaaggcg    180
cgttgtgcaa cattcaactc taggctcacg ggacaaccgg atcccactct tcagaaagag    240
tttttgacat cgctccaaca aatctgcttt caagggctag ccagtaataa caacaccgta    300
acttcactgg atgtggagac tcccgtcatt tttg                                334
```

<210> SEQ ID NO 181
<211> LENGTH: 343
<212> TYPE: DNA
<213> ORGANISM: Pinus radiata

<400> SEQUENCE: 181

```
atttcgctga actggatctg gatcgaagaa ggtattgcat atcaaagaaa gaggcaaata      60
tgactccggc cactgttttg ctttctatat ttgtgattgt atatggtagt gctgtgaacg    120
ctctgccaac tcccgtggcg ggtctttcgt ggacgttcta caacacaagt gcccgtcat     180
tggagtcgat agtgcggaag cgcatggaag cctatttgag tgcagacatc acacaagctg    240
caggattgct gaggctccac ttccacgact gttttgtcca gggatgcgac gggtctgtgt    300
tgctgaactc aacatcgggg gagcaaacag ttgcgcccaa ctt                       343
```

<210> SEQ ID NO 182
<211> LENGTH: 443
<212> TYPE: DNA
<213> ORGANISM: Pinus radiata
<220> FEATURE:
<221> NAME/KEY: unsure
<222> LOCATION: (164)...(164)

<400> SEQUENCE: 182

```
atttcgctga actggatctg gatcgaagaa ggtattgcat atcaaagaaa gacgcaaata      60
tgactccggc cactgttttg ctttctatat ttgtgattgt atatggtagt gctgtgaacg    120
ctctgccaat tcccgtggcg ggtctttcgt ggaccgtttt acancacaag ttgcccgtca    180
ttggagtcga tagtgcggaa gcgcatggaa gcctatttga gtgcagacat cacacaagct    240
gcaggattgc tgaggctcca cttccacgac tgttttgtcc agggatgcga cgggtctgtg    300
ttgctgaact caacatcggg ggagcaaaca gttgcgccca acttatcact cagagcggag    360
```

```
gctctgaaaa tcatcaatga catcaaagag aacgtagaag cggcgtgcag cggaactgtg    420
tcgtgtgcag acattcttgc ctt                                            443
```

<210> SEQ ID NO 183
<211> LENGTH: 243
<212> TYPE: DNA
<213> ORGANISM: Pinus radiata

<400> SEQUENCE: 183

```
acattgatga ttgtgctacg cgtattttt tcaatctcta gcacttggga aggtctggag    60
gaggcggctc caaggttgcc tgagggccgt gaccgttctt cactataaac accatattca   120
gtccccatac taaatggtcg tctaaatggc agtggagaaa ccacactcct ggattgtcag   180 cttttgaatct tatcgcaacc caaccgctca caggagctat tactgtgttg cgtagtgggg   240
atc                                                                  243
```

<210> SEQ ID NO 184
<211> LENGTH: 473
<212> TYPE: DNA
<213> ORGANISM: Pinus radiata

<400> SEQUENCE: 184

```
ggtggcccct agaagaaaca cactcagaga gtttgatcta taagaggaga gattcactcc    60
aaaatgcaca gggagattca ctccaccatc aaattttaat cattggcctt tttcctctca   120
acggccgatg gcgtaaacac gcgtaagcaa acaccaagat cctgaaacag tcgactgatc   180
gattcagaat aatttgaaag gaaactggac tactcaatca atttgttgac atttatcaag   240
aaatggatga ttcagtacag gaggtatcca aggaaggcaa tcaatgggca ggattcattg   300
agggtgagaa tgtaatccga agaggaaggg agattcttct acagcatgat aaccgggagg   360
cacataactg ggagtcacat aaacataagt ggtggccaca tttggaagaa aaaatcccgc   420
acattgccaa agcaggattt acatctatat ggctgccgcc tgcttttgat tcg          473
```

<210> SEQ ID NO 185
<211> LENGTH: 641
<212> TYPE: DNA
<213> ORGANISM: Pinus radiata

<400> SEQUENCE: 185

```
ggcaccgagc tgggataccc ctgctgcgac ttgatcccct ttgaacagga attatttaat    60
tttcctaatt attttagttt gcaaggaaac ttgactactc catcaatttg tttacagtttt   120 tcgaaaaatg ggctatccag ttcaggaggt atccaaggaa cacgatcaat gggcaggatt   180
tgttgaaggt gaaagtgtgc ttcaaagagg aagggagatt cttctccagg gttttaactg   240
ggagtcacat aaatacaagt ggtggccaaa tttggaagaa aagatcccgc acattgctaa   300
agcaggattt acatctgtat ggctgccacc tgcttttgat tctgctgcac cccaaggtta   360
cttgccccga acatttatt ctctgaactc tgcatatggt tcagaatatc agctgaaaag   420
cttacttatg acaatgcgaa agaaaaatgt gagagccatg gctgacatag ttatcaatca   480
tcgcatggga agctctcagg ggtttggagg cttgtataat cgctattatg gttgcctgcc   540
ttgggatgaa cgtgctgtta cacgttgttc tggtggactt ggaaactgga gcacagggga   600
taattttcat ggagtaccaa acgttgatca cacccaagat t                        641
```

<210> SEQ ID NO 186

```
<211> LENGTH: 655
<212> TYPE: DNA
<213> ORGANISM: Pinus radiata

<400> SEQUENCE: 186
agaatggcca agtttcgatc tctgtcttta ttgttatggt tctcctgcat catagtcaat    60
gcagcctctc ctgcacaagc agaagctaca acgcctcctc tgaataccct cttacttcag   120
ggcttcaatt gggattcagc ccagagttct actccttggt ataatgtatt gaagggaatt   180
gtagacgatg cagcggacgc cggcattacg tacgtctggt ttccgccgcc ctcacaatcc   240
ggcgcccctc aaggttattt gccagcgaag ctctatgatt tagactcgtc ctacgggagc   300
gagcaacaac taaaggatgc cgtgaatgcg ttccaccaaa agggaattgc gattatgggc   360
gacatcgtga taaaccatcg gaacgggacg aagcaggacg ataaaggata ttggtgcgtg   420
tttgagggcg ggaaggggga cggtactctg gactggggac cctgggcggt caccgtgaag   480
gaccaaccat atccgttgtg cggctccggc caggcggaca ccgaggggga cttcaagtac   540
gccccggacg tggaccacac caatcccaag atacagcaag atttgtcgga gtggatgaat   600
tggctcaagt ccatgtcgga tttgatggct ggaggttcga ctacgtcaag gctac         655

<210> SEQ ID NO 187
<211> LENGTH: 438
<212> TYPE: DNA
<213> ORGANISM: Eucalyptus grandis

<400> SEQUENCE: 187
ctggggtggg gaggctggtc gacgtgggcg ggagcgcggg ggactgcctc cggatgatca    60
tgggaagca cacgcacgtc cgggaaggga tcaacttcga cttgcccgag gtcgtggcca   120
aagcgcctcc cattcctggg gtgacccatg ttggtggcga catgttcaag tccatccctg   180
ctggtgatgc cattttcatg aggtggatac tgacgacatg gacggacgac gagtgcaagc   240
agatactgga aaactgcttc aaggcactcc ctgcgggagg gaagctgatt gcctgcgagc   300
cggtgctacc gcagcactca gatgatagcc acaggactcg agcacttctt gagggcgaca   360
tcttcgtgat gaccatctac agggccaagg gcaagcatag gactgagcag gaattccagc   420
agctcgggct ctctaccg                                                 438

<210> SEQ ID NO 188
<211> LENGTH: 597
<212> TYPE: DNA
<213> ORGANISM: Eucalyptus grandis

<400> SEQUENCE: 188
acccaacaat ggccgacaac caagaacgcg aagggcgcga tcaagaagag gaagtcggga    60
agctggcggt ccagctggcc agcgcggtgg tgctcccgat gaccctcaag tcggccctcg   120
agctcggcat catcgacgcc ctcgtctccg ccggtgggtt cctctcggct gccgagatag   180
cgagccgggt tggcgccaag aacccggggg ccccagtcct ggtggaccgg atgatgcgcc   240
tcctggcgag ccacggcgtg atcgagtggc ggttgaggag gggcgacggc aacggagatg   300
gaggggagag agagtacggt ccaggaccca tgtgcaggtt ctttgccaag gaccaagaag   360
gtggagatgt tggtcctctg tttctgctaa ttcacgacaa ggtcttcatg gagagttggt   420
accacttgaa cgatgtcatc atggaaggag gggttccgtt cgagagggca tacgggatga   480
cggcgttcga gtatcctgcc gttgacgata ggttcaatca agttttcaac cgggccatgg   540
cgagtcatac ttccctcatc atgaagaaaa tactcgatgt ctacagaggg tttgaag      597
```

<210> SEQ ID NO 189
<211> LENGTH: 470
<212> TYPE: DNA
<213> ORGANISM: Eucalyptus grandis

<400> SEQUENCE: 189

| | |
|---|---:|
| cccgaccccg ctttacatga acaagatcct cgagtcgtac cgtgggtttg agggcgcaaa | 60 |
| gacgattgcc gacctaggtg gcggcgtcgg ccagaacctt cggctcatat tggacaagtt | 120 |
| cccaaatctc aggggcatac tctatgatct gcctcatgtg atcaaagatg cacctgccca | 180 |
| tcctcgtatg gagcgtgtcg gaggagacct gttaaagtct gttccgaaag cagatatact | 240 |
| cttcatgaag tggcttttcc atggtctacg agacgatttc tgcaaaatgc tactccagaa | 300 |
| ctgttacgag gcgctgccac caaatggcaa ggtggtcatc gtggacccga tccttcccga | 360 |
| atacccgag acagacatag tgtcgaggaa ctcgttcacc tccgacatga tcatgctata | 420 |
| cacgagccct ggagaagacc ggacgaggaa agagctggag gtgctcgcac | 470 |

<210> SEQ ID NO 190
<211> LENGTH: 499
<212> TYPE: DNA
<213> ORGANISM: Eucalyptus grandis

<400> SEQUENCE: 190

| | |
|---|---:|
| gtccagtttt cagccgtgct atgaagaagc caacagttta gaccgttgga ttcagcctcc | 60 |
| gtcggatctg cttcataata tgtccgataa agaactattt tggagagcga cccttgttcc | 120 |
| taaaatcaag aagtatccat tcagaagagt tccaaaaatt gctttcatgt tcttgaccaa | 180 |
| gggtccattg ccgctggctc ctctttggga gaggttcttc aagggccatg aggggcttta | 240 |
| ttcgatctat attcattccc atccatcatt ccatgcccac tttcatcctt ggtcggtatt | 300 |
| taacaggaga caaatcccaa gtcaggtgtc tgagtggggc aggatgagca tgtgtgatgc | 360 |
| agagaaaaga ctcctagcca acgcattgct agacatatcc aatgagcggt tcattcttct | 420 |
| ttctgaatca tgcattccgc tgtataactt cagcctcatc tatcactaca ttatgaagtc | 480 |
| cggatatagc ttcatgggt | 499 |

<210> SEQ ID NO 191
<211> LENGTH: 1036
<212> TYPE: DNA
<213> ORGANISM: Eucalyptus grandis

<400> SEQUENCE: 191

| | |
|---|---:|
| ggcaagtggt ggctggaatt cacacccatt gcgctctctc tctctctcta gatcctatct | 60 |
| cgaaagccaa aagaaaagac agtcggaaga aaaaatataa aaaaaaacat gagttcgaag | 120 |
| gaagccccag tcattacaac ttcccatgaa gatgaagaaa ttttgaatgc ctttgaggtc | 180 |
| ccctcaatgg cttttgttcc catggtcttg aaaggcgtcc atgagctggg gattcttgaa | 240 |
| ttgctggcca agggtgacca gctctctccg ttggacatcg tggcccgcct ctctatcgac | 300 |
| aacccggccg caccggacac gatcgaccgg atgctgcggc tccttgcgag ttactccatc | 360 |
| ttatcgtgca ctctcgtgga ggataaagaa ggccgccccc agaggctcta cggcctcggg | 420 |
| cctcggagca agttcttttt ggaccagaat ggagcttcta ctttaccaac tcatatgcta | 480 |
| ctccaagaaa agactctcct ggaatgctgg aactgcctta agatgcagt taaggaagga | 540 |
| ggggcagatc ctttcacccg caggcacggc atgaacgtgt tcgactacat gggccaggac | 600 |

```
ccgagattca acgacctgta caacaagtcg atgaggaccg ggtcggcgat ttacatgccc      660
aagatcgctc agcattatcg tgggttttca aaggcgaaga cggtcgtcaa tgtgggcggt      720
ggcatcggcg agaccctgaa aaccatactc tccaagaatc cccacatccg cgccatcaac      780
tacgacttgc ctcatgtgat cgcaactgct cctcccattc ctggtattac gcatgttgga      840
ggagacattc taaagtccgt ccctaaagcg gatgtccatt tcctgaagtc ggttctccat      900
cgcggggatg atgagttctg cgtgaaggtg ctcaagaatt gctgggaggc attgccgccg      960
acggggaaag tggtgatcgt ggaggaagtg accccggagt atcctgggac cgacgatgtc     1020
tcacagacca cgctct                                                    1036

<210> SEQ ID NO 192
<211> LENGTH: 682
<212> TYPE: DNA
<213> ORGANISM: Pinus radiata

<400> SEQUENCE: 192
agacgttgga ggaggtatag gctctgcctt gtccatcatt gtgaaggaac atccacacat       60
tcgtggcatt aatctcgatc tgcctcatgt cattgccact gcgcctctca taactggggt      120
ggagcacatg gagggaaata tgttcgagca catacctctt gccgatgcag tcatgatgaa      180
gtggatcctc catgactggg cggacgagga gtgtgtgaaa ttgctgagaa aagctacga      240 cgcaacgcca gcgaagggaa aggtgttaat tgtggaagca gttgttgagg gagacaaaga      300
aggtgaaagc atgtcgaggc gattgggatt gttatatgat atatcgatga tggcttacac      360
aactggtggg aaggagagaa cagaggaaga attcaaaggg ttgttccagc gcgcagggtt      420
caagagccac accatcatca agttgccttt ccttcagtcg ctcatagtgc tgtccaaagc      480
ctaataagct attgcgcttc cgattatcgt tacaataacg ttggttttgc tggggttgtt      540
atcatgcagt atatgaccta tgttttatgt tatctggcag tataagattt ctgaagacat      600
ggttgaaatt attgtgagat tttaaagata tttatccatc ataaaaataa tggaatatga      660
taatattttt acaaaaaaaa aa                                              682

<210> SEQ ID NO 193
<211> LENGTH: 399
<212> TYPE: DNA
<213> ORGANISM: Eucalyptus grandis

<400> SEQUENCE: 193
agcgtctaat ggttcctatt tagaagttca gaaagtctct gtctttccta ccttgcgggg       60
tagtctcttc ggacgtactc aaacatggag caaggctggg acaagggcga gatcctggca      120
agcaaagctc tctcgaagta catattggag accaatgcat atccgagaga gcacgagcag      180
ctgaaagaac tcagggaggc cacggtccag aagtaccaaa tccggagtat aatgaacgtg      240
ccggttgatg aggggcagct gatctccatg atgttgaagc tcatgaatgc gaagaagaca      300
atcgagatcg gagtcttcac cggctactct cttctgacca ccgcacttgc acttccggcc      360
gacggcaaga taatagcgat agaccaggat aaggaggcc                            399

<210> SEQ ID NO 194
<211> LENGTH: 399
<212> TYPE: DNA
<213> ORGANISM: Eucalyptus grandis

<400> SEQUENCE: 194
cggacgtact cagacatgga gcgaggcggg gacaagggcg agatcctggc aagcaaagct       60
```

―continued

```
ctctcgaagt acatattgga gacgaatgca tatccgagag agcacgagca gctaaaagaa    120
ctcagggagg ccacggtcca aaagtaccaa atgcggagta taatgagcgt gccggctgat    180
gaggggcagc taatctccat gatgttgaag ctcatgaatg cgaagaaaac aatcgagatc    240
ggagtcttca cgggctattc tcttctcacc accgcacttg cacttccggc cgacggcaag    300
ataatagcaa tagaccccgga taaggaggcc tatgaaattg gcctgccata tcaaaaaa     360
gccggagtcg atcataagat caacttcatc cagtcggat                           399
```

<210> SEQ ID NO 195
<211> LENGTH: 296
<212> TYPE: DNA
<213> ORGANISM: Eucalyptus grandis

<400> SEQUENCE: 195

```
ttgcagtaca tattggagac gaatgcatat ccgagagagc acgagcagct gaaagaactc     60
agggaggcca cagtccagaa gtaccaaatc ggagtataa tgaacgtgcc ggctgacgag    120
gggcagctaa tctccatgat gttgaagctc atgaatgcga agaagacgat cgagatcgga    180
gtcttcaccg gctgttctct tctcaccacc gcacttgcac ttccggccga tggcaagata    240
atagcgatag acccggataa ggaggcctat gaaattggcc taccatatat ccgaaa       296
```

<210> SEQ ID NO 196
<211> LENGTH: 474
<212> TYPE: DNA
<213> ORGANISM: Eucalyptus grandis

<400> SEQUENCE: 196

```
gcgccaccac caaacgctca ccttctcatc atcagccctc tgtctctgtc tctgtctctc     60
gattctccgc cccgccacga caatggaggc gaagccgtcg gagcagcccc gcgagttcat    120
cttccggtcg aagctccccg acatctacat tcccgacaac ctctccctcc acgcctactg    180
cttcgagaac atctccgagt tcgccgaccg ccctgcgtc atcaacgggg ccaccggccg    240
gacctacacc tatgccgagg tcgagctgat ctcccgccgg gtctcagccg gcctcaacgg    300
gctcggcgtc ggacagggcg acgtgatcat gctgctcctc cagaactgcc ctgagttcgt    360
gttcgcgttc ctcggcgcgt cctaccgggg cgccatcagc acgaccgcga cccgttcta    420
caccccgggc gagatcgcca agcaggcctc agctgcccgg gccaagatcg tgat          474
```

<210> SEQ ID NO 197
<211> LENGTH: 543
<212> TYPE: DNA
<213> ORGANISM: Eucalyptus grandis

<400> SEQUENCE: 197

```
gttcgccgac aagtgaggc cgttcgcgga ggagaacggg gtgaaggtcg tgtgcatcga     60
taccgcgccg gagggctgcc tgcacttctc ggaattgatg caggcggacg agaacgccgc    120
ccccgcggcg gacgtcaagc cggacgacgt cttggcgctc ccctattcgt cgggcacgac    180
gggggcttccc aagggagtga tgcttacgca cagggggtcaa gtgaccagcg tggcgcagca    240
ggtcgacgga gacaacccca acttgtactt ccacaaggag gacgtgatcc tgtgcacgct    300
cccgttgttc cacatatact ccctcaactc ggtgatgttc tgcgcgctcc gtgtcggcgc    360
cgccatcctg atcatgcaga gttcgagat cgtggcgctg atggagctcg tgcagcggta    420
ccgggtgacg atcctgccca ttgtcccgcc gatcgtgctg gagatcgcaa agagcgccga    480
```

```
ggtggaccgg tacgacctgt cgtcgatccg gaccatcatg tcgggtgcgg cccgatgggg    540
aag                                                                  543
```

<210> SEQ ID NO 198
<211> LENGTH: 564
<212> TYPE: DNA
<213> ORGANISM: Eucalyptus grandis

<400> SEQUENCE: 198

```
ctggacaact agttgcagga gttgaagctc aagttatcag cgtggataca ctaaaatctc     60 ttcccccta  tcagttaggg gaaatatggg ttcgtggacc taacatgatg aaaggatatt   120
ataacaatcc acaagcaact aaattgacaa ttgataacaa gggttgggtg cacactggag   180
accttggata ttttgatgag aagggcaac  tatatgttgt tgatcgaatc aaagagctca   240
tcaagtacaa aggttttcag attgctccag ctgagcttga aggactcctt ctttcacatc   300
ctgaaatttt agatgctgtt gtcattccat ttcctgatgc tgaagctggt gaagttccta   360
ttgcatatgt cgttcgctca cctaccagct ctctaactga agaggaagtc cagaaattca   420
ttgccaatca ggttgcacca ttcaaaagac taaggagggt gacattcgtc aacagcgtcc   480
caaagtctgc ttccggcaaa attttgagac gtgagctgat tgcaaaagta cgagcaaaga   540
tataactgtg catgctcgat gcgt                                          564
```

<210> SEQ ID NO 199
<211> LENGTH: 455
<212> TYPE: DNA
<213> ORGANISM: Pinus radiata

<400> SEQUENCE: 199

```
ggctactttg atgaggaagg aggattattt attgtggatc gtattaaaga actaatcaaa     60
tacaaaggtt tccaggttgc ccctgctgag ttggagggca tattgttgac acatccccaa   120
attgcagatg ctggagttat tccccttcct gatctaaaag ctggagaggt tccaatagca   180
tatgttgtac gtacccctgg aagctctttg acggaaaagg atgccatgga ttatgttgcc   240
aagcaggtcg caccatttaa aaggttgcat agagtcaatt ttgtagactc tatacccaag   300
tctgcctcag ggaagattct tcgacgagag cttattgcta aggccaaatc aaaattgtaa   360
gcaaagaaat atatcatttt ttctggtatc atgatacaaa gttgcacaaa cttatttgta   420
agtgtcaccc cagatgaaca aggaatttgt tccgc                              455
```

<210> SEQ ID NO 200
<211> LENGTH: 569
<212> TYPE: DNA
<213> ORGANISM: Pinus radiata

<400> SEQUENCE: 200

```
gtcgtctgta aattactctg tgagtgttta gtgttttctt ctcttattga tttcagggga     60
caagtaggtg ggggtggggg agcttaagtc aaatctagtg cttttctctgt aagattttcc   120 ctttttttc  ttgctaagag tagccatgat tgaggtacga tcagctcccc ccatggcacg   180
gtccactgag aacgagaata accagcatga tgccgaagaa gggcggtat  tgaatgaggg   240 cggcatggat tttctgtatc ggtcaaagct tccagacata gatattccat accatcttcc   300
attgcactcg tattgcttcg agaaactgga cgagctcaga gagaagccat gtctgataca   360
ggggtcgaac gggaagattt acagctatgg cgaagtggaa ttgatatctc gcaaggtggc   420
ctcgggtttg gccaaattgg gattcaaaaa gggggacgtg gtcatgctgc tgctgcccaa   480
```

```
ttgccccgaa tttgtctttg ttttcctagg ggcgtccatg gctggtgcca ttgccaccac    540
ggcgaaccct ttttacactc cctccgata                                      569
```

<210> SEQ ID NO 201
<211> LENGTH: 993
<212> TYPE: DNA
<213> ORGANISM: Eucalyptus grandis

<400> SEQUENCE: 201

```
tgaccatcct ccggcaatgg ctcttcacat cctcttcaca tggcttgctc tttcccttcc     60
tctcctcctc ctcctcctcc tctcagtgaa aaacttcaat aacaaaaaga agaacctccc    120
tccagggcct ccatcacttc ccatcatagg caacttccac cagctcggcc ccctgcctca    180
tcagtctctg tggaaactct ccagacgata tggcccccgtc atgctcatcc gcctcggtgg    240 caccccctacc atcgtaatct cctcccctga tgctgccagg gaggtcctca agacccacga    300
ccttgatagt tgcagtcgcc cgcagatggt cggcccggga cgcctctcct atgactccct    360
cgacatggcc ttcgtggagt acggcgatta ctggagggag ttaaggacgc tgtgtgtgct    420
cgagctgttt agcatgaagc gagtccagtc cttccgatac atcagggaag aggaggtggg    480
atctatgatc gaatcgatcg caaaatcagc agagagcgga actccggtta atatgagcga    540
gaagttcatg gctctgacgg ctaacttcac ttgcagggtc gcatttggga agccatttca    600
ggggacggag ttggaagacg aagggttcat ggatatggtt cacgagggaa tggcgatgtt    660
gggaagcttc tcggcatctg attatttccc tcgactcggc tggattgtgg acaggttcac    720
ggggctccat tcgaggttgg agaagagctt tcgcaatttg gacgatctct atcagaaggt    780
gatcgaagag catcggaatg cgaataagag caacgaggga aaggaggaca ttgtcgatgt    840
gctgctgaag atggagaaag atcagactga gctcgcgggg gtccggctca aggaagataa    900
catcaaggcc atcttgatga atatatttct cggaggagtg gacaccggtg cagtgtcatg    960
gactggacaa tggctgagct cgctaggaac ccg                                 993
```

<210> SEQ ID NO 202
<211> LENGTH: 349
<212> TYPE: DNA
<213> ORGANISM: Eucalyptus grandis

<400> SEQUENCE: 202

```
ggacggagtt ggaagacgaa gggttcatgg atatggttca cgagggaatg gcgatgttgg     60
gaagcttctc ggcatctgat tatttccctc gactcggctg gattgtggac aggttcacgg    120
ggctccattc gaggttggag aagagctttc gcaatttgga cgatctctat cagaaggtga    180
tcgaagagca tcggaatgcg aataagagca acgagggaaa ggaggacatt gtcgatgtgc    240
tgctgaagat ggagaaagat cagactgagc tcgcgggtgt ccggctcaag gaagataaca    300
tcaaggccat cttgatggta tatcatacaa tctctacgta ttacttaat                349
```

<210> SEQ ID NO 203
<211> LENGTH: 432
<212> TYPE: DNA
<213> ORGANISM: Eucalyptus grandis

<400> SEQUENCE: 203

```
cttggtcgta gcagctttgc tgattgttct cttgaggagc aagtctagga aagaaagag      60 caacctccca ccgagccctc ctaagttgcc gatcatcggc aatcttcacc agcttggcaa    120
```

| | |
|---|---|
| atcgccacac atatctctcc atcgccttgc gagaaactac gggccaatca tgtccttgca | 180 |
| gctcggcgaa gtcccaacca tagtcgtttc ctcagccgca atggccaagg aggtgatgaa | 240 |
| aacccatgac ctagtgctcg caaaccgccc tcagatcttc tctgccaagc acttgtttta | 300 |
| tgactgcaca gacatggcct tctctcccta tggcgcttat tggaggcaca taaggaaaat | 360 |
| ctgcatactt gaagtgctta gcgcaaaacg ggttcagtca tttagtcatg tcaggagga | 420 |
| agaagttgct cg | 432 |

<210> SEQ ID NO 204
<211> LENGTH: 407
<212> TYPE: DNA
<213> ORGANISM: Eucalyptus grandis

<400> SEQUENCE: 204

| | |
|---|---|
| ctcaccttca aatgcctccg cttcctcttc tcctctgccg ccgctactaa ccttcacctt | 60 |
| ccgccatcac cgccgaagct ccctatcatc gggaacctcc accagctcag tgatcaccct | 120 |
| caccgctcgc tccaagccct gtcgagacgc tatggcccct tgatgatgct ccacttcgga | 180 |
| agcgtgcccg tcctcgtcgt atcttccgcc gactgtgcac gggacatctt gaagacccac | 240 |
| gacctcattt tctccgaccg acccaggtca accctgtcgg agaggctttt gtaccaccgc | 300 |
| aaggacgtgg ctctggcgcc gtttggcgag tactggaggg aaatgaggag catctgtgtc | 360 |
| ctccagctgc tgagcaacaa gagggtccac tcgtttcgga cggtcca | 407 |

<210> SEQ ID NO 205
<211> LENGTH: 384
<212> TYPE: DNA
<213> ORGANISM: Eucalyptus grandis

<400> SEQUENCE: 205

| | |
|---|---|
| gggaaattac cccacaggtc gctggatcga ctctccaaaa catatggccc cctcatgtat | 60 |
| atgagactcg gatccatgcc atgcgtggtc ggctcatccg ctgagatggc ccgagagttt | 120 |
| ctcaagaccc acgatctcac attctcgtcc cgaccccgtg tggcggccgg gaaatacact | 180 |
| gtttacaact actccgacat cacctggtct ccctacggag agcactggcg tctcgccaga | 240 |
| aaaatctgcc tcatggagct cttcagtgcc aaacgcctcg aatctttcga gtacatcaga | 300 |
| gtagaagagg tcgcccggat gctgagttcc gtcttcgaaa ccagccggca gggccttcct | 360 |
| gtagaaatca gggaagagac gact | 384 |

<210> SEQ ID NO 206
<211> LENGTH: 543
<212> TYPE: DNA
<213> ORGANISM: Eucalyptus grandis

<400> SEQUENCE: 206

| | |
|---|---|
| ataaataaga atggtgaacg agttagggtc ggaaaagccc tttctggtat gcctagagtt | 60 |
| ttatatgaaa ctcgctattg ctctagttgc gttggtggtg gcatggagct tcttcgtcaa | 120 |
| gggaagaaat aggaagctgc ccccgggacc gttctctttg cccatcatcg gaaatctcca | 180 |
| tttgctggga cagcttccac accgagcact gaccgctctt tctctcaaat tcgggcctct | 240 |
| tatgtcgctt cgcctcggct ctgctcttac attagtagtc tcttcacctg atatggccaa | 300 |
| ggagtttctg aagacacatg atctgctttt tgctagcaga cctccatccg cggctactaa | 360 |
| ttattttttgg tataattgca ctgacatcgg ttttgctccg tatggcgctt actgaggca | 420 |
| agtgcgtaag gtgtgcgttt tacagttgct gagctccaga cgcttggatt atttccgctt | 480 |

| | | |
|---|---|---|
| tataagagaa gaggaggtct ctgctatgat tcattctatt gctcattccg atcatcctgt | 540 | |
| aaa | 543 | |

<210> SEQ ID NO 207
<211> LENGTH: 1320
<212> TYPE: DNA
<213> ORGANISM: Eucalyptus grandis

<400> SEQUENCE: 207

| | |
|---|---|
| tcatcacttg catttggcca gcacatcata gctacctctt atagctgtaa tcttcaccaa | 60 |
| attggagaga tgagcttcca gaaccagctc ttcatcttct gcacgttgct actagggttt | 120 |
| ctgaagttgg cagaaggcaa aacgaggcac tacaccttcc atatcgattc cataacatg | 180 |
| acgaggctgt gccacacgag gagtgtgctg agtgtaaaca agcagtatcc agggccgccg | 240 |
| cttgtggcga gggaaggcga caacatcctc gtcaaggtgg tgaatcatgt tgccgccaac | 300 |
| gtcacgattc actggcatgg ggttcggcaa ctgaggacgg gatgggcgga tggaccggct | 360 |
| tacgtaaccc agtgtcccat acagaccaac cagagctaca cctacaactt cacccctcacc | 420 |
| ggccagagag gaacgctgct gtggcacgcg cacgtctcgt ggctaagatc gagcatccac | 480 |
| ggccccatca tcatcctccc caagcggaac gagtcctacc cgttcgagaa accctccaag | 540 |
| gaagtcccca taatatttgg agagtggttt aatgtagacc ccgaagcggt catcgcccaa | 600 |
| gctcttcaga gtggaggagg tcccaatgtc tccgatgcct ataccatcaa tggccttcca | 660 |
| ggacccttgt acaattgctc ctctaaagac accttcaagt tgaaggtgaa acctgggaag | 720 |
| acatacctcc tccggctgat caacgctgca ctcaacgacg agctcttctt cagcatagcc | 780 |
| aaccacgcag tcaccgtcgt cgaggttgat gccgtgtaca ctaagccctt ttctgcgggc | 840 |
| tgcctccacc taaccccggg ccaaaccatg aatgtcctcc tcaagacaaa aaccgacttt | 900 |
| cccaactcca ccttcctcat ggcagcgtgg ccctatttca ccggcatggg cactttcgac | 960 |
| aattccaccg tcgccggaat ccttgagtac gaacatccaa agagctcaaa ttacccgccg | 1020 |
| ctcaagaagc tccccaata taaaccaact ctccctccca tgaacagcac cggttttgtc | 1080 |
| gccaaattta cagggcaatt gcgtagtttg ccagcgcta agtttcctgc caacgtgcca | 1140 |
| caaaaggttg acagaaaatt cttcttcacc gtcggccttg ggaccagtcc gtgccccaaa | 1200 |
| aacaccacgt gtcaaggacc aaatggcacg aaattcgccg catcagtcaa caacatatcg | 1260 |
| tttgtgctgc cgtccgtcgc tctcctgcag gctcacttct tcggccagtc caacggagtg | 1320 |

<210> SEQ ID NO 208
<211> LENGTH: 980
<212> TYPE: DNA
<213> ORGANISM: Eucalyptus grandis

<400> SEQUENCE: 208

| | |
|---|---|
| ctccggccgt ggttgagggc agagtccgta actacacatt caatgtggta atgaagaata | 60 |
| ccacgagact gtgttcgagc aagcccatcg tgaccgtgaa cgggatgttc ccggacccca | 120 |
| ctctctatgc tagggaagat gacaccgtgc tcgtgagggt ctctaaccgt gtcaaataca | 180 |
| atgtcaccat ccattggcat ggtatccggc agttgaggac ggggtggggcc gacgggccag | 240 |
| catacattac ccaatgcccg atccagccgg gccaaagcta tgtgtacaat ttcaccatca | 300 |
| cgggccaacg gggcaccctc ctgtggcatg cacacatact ctggctcagg gcaaccctgc | 360 |
| acggagccat tgtcatcttg cccaagcgtg gtgttccata ccctttccct aaaccccaca | 420 |

```
aggaagttgt tgtcgtattg ggcgaatggt ggaaatctga tacagaaggt gtgatcagtc      480
aagccatcaa gtccggatta gcaccgaatg tctccgatgc tcacacgatc aatggccatc      540
cagggccaag ttccaattgc ccttcccagg gtggatttac gttgcctgtt gagagtggca      600
agaagtacat gctgcgaatc atcaacgctg cgctcaatga ggagctcttc ttcaagattg      660
ccgggcacca gctgaccatc gtggaggtcg acgccaccta cgtcaagcct ttcaagaccg      720
acacgatcgt gattgcacct ggccaaacca ccaatgccct catctccacc gaccagagct      780
ctggcaagta catggtcgcc gcctcccctt ttatggactc cccgatcgcc gtcgacaaca      840
tgaccgcgac cgccacatta cactactctg cacgcttgc tgcgacctcc acgaccctca       900
ccaagactcc cccacaaaac gcgaccgctg tggccaacaa tttcgttaac tcgctccgga      960
gcctcaactc gaagaggtac                                                  980

<210> SEQ ID NO 209
<211> LENGTH: 305
<212> TYPE: DNA
<213> ORGANISM: Eucalyptus grandis

<400> SEQUENCE: 209
gaggctgtgt tcgagcaagc ccatcgtgac cgtgaatggg atgttcccgg gacccactct       60
ctacgctagg gaagacgaca ccgtgctcgt gagggtctcc aaccgtgtca aatacaatgt      120
caccatccat tggcatggta ttcggcagct gaggtcgggg tgggccgacg ggccggcata      180
catcacccaa tgcccaattc agccaggcca aagctatgtg tacaatttca ccatcacggg      240
ccaacggggc accctccttt ggcatgcgca catactctgg ctcagggcaa ccctgcacgg      300
agcca                                                                  305

<210> SEQ ID NO 210
<211> LENGTH: 411
<212> TYPE: DNA
<213> ORGANISM: Eucalyptus grandis

<400> SEQUENCE: 210
ttaccgtcga tcacagcctc cttttcacag ttggactagg aatcaaccct tgcccttcct       60
gcaaagctgg caacggaagc agagtcgtgg caagcatgaa caacgtgaca ttcgtgatgc      120
cgacgacagc cattctccaa gcacatttct tcaacaaaag cggcgtcttc acgagcgatt      180
tccccggtaa cccgccaacc attttcaact acacggggtc accgccatca aatttgcgga      240
ccacaagcgg gacaaaggtg taccggttgc gttataactc gacggtccag ctggtgtttc      300
aagacaccgg gattatcgcc ccagagaacc acccaattca tcttcacggg ttcaatttct      360
tcgccattgg gaagggatta ggaaattata atccgaaagt ggatcagaag a              411

<210> SEQ ID NO 211
<211> LENGTH: 311
<212> TYPE: DNA
<213> ORGANISM: Eucalyptus grandis

<400> SEQUENCE: 211
cacaaggaag ttgttgtcgt attgggcgaa tggtggaagt ctgatacaga agctgtgatc       60
aatcaagcca tcaagtccgg attggcaccg aatgtctcgg atgctcacac gatcaatggc      120
catccagggc caagttccaa ttgcccttcc cagggtggat ttacattgcc tgttgagagt      180
ggcaagaagt acatgctccg aatcatcaat gctgcgctca atgaggagct cttcttcaag      240
attgctgggc accagctgac catcgtggag gtcgacgcca cctacgtcaa gccttttcaag      300
```

```
accaacacgg g                                                              311

<210> SEQ ID NO 212
<211> LENGTH: 334
<212> TYPE: DNA
<213> ORGANISM: Eucalyptus grandis

<400> SEQUENCE: 212
agcgtggcgt tccatatcct ttccctaaac cccacaagga agttgttgtc gtattgggcg           60
aatggtggaa gtctgataca gaagctgtga tcaatcaagc catcaagtcc ggattggcac          120
cgaatgtctc ggatgctcac acgatcaatg ccatccagg gccaagttcc aattgccctt          180
cccagggtgg atttacattg cctgttgaga gtggcaagaa gtacatgctc cgaatcatca          240
atgctgcgct caatgaggag ctcttcttca agattgctgg gcaccagctg accatcgtgg          300
aggtcgacgc cacctacgtc aagcctttca agac                                     334

<210> SEQ ID NO 213
<211> LENGTH: 1374
<212> TYPE: DNA
<213> ORGANISM: Eucalyptus grandis

<400> SEQUENCE: 213
accgaacgtg tccgacgctt ataccatcaa cggtcaacct ggagatctct acaactgctc           60
aagcaaagac accgtcatag ttccgatcga ttccggggag acccacctcc tccgagtcat          120
caacgctgcg ctcaatcagg aactcttctt caccgtagcg aaccataggt tcactgtggt          180
cggtgccgac gcctcctacc tgaaacccct caccacctcg gtgatcatgc ttgggccagg          240
ccaaacgacg gatgtattga tctctggaga ccagcccccg gctcggtact acatggcggc          300
cgaaccctac cagagtgctc agggagcgcc ttttgacaac accacgacca cggccatact          360
ggagtacaag tccgccccgt gccccgccaa gggcatatcg agcaagccag tcatgccaac          420
cctaccggct ttcaacgaca cggctaccgt cacagccttc attcagagct caggagccc          480
aaataaggtt gacgtcccga ccgacatcga cgaaaacctc tttatcacgg tcggcctagg          540
actcttcaac tgcccaaaga atttcggtag cagtaggtgc caggggccga atgggacccg          600
tttcacggcc agcatgaaca acgtgtcctt cgtgctgccg tctaatgtct cgatcctgca          660
agcctacaag cagggcgtgc ctggagtttt taccaccgat ttccctgcta accccctgt          720
ccagttcgat tacacgggga acgtgagccg ctcgctgtgg cagcccgttc cggggaccaa          780
ggtgtacaag ttgaagtacg ggtctagagt acagattgtc ttgcaaggaa ccaacataca          840
aacggccgag aaccacccga tccacattca cgggtacgat ttctacatcc tcgccacagg          900
cttcgggaac ttcaaccccc agaaagatac agcgaagttc aaccttgtcg acccgccaat          960
gaggaacaca gttggcgtct ctgtgaacgg gtgggctgtc attagatttg tcgccgacaa         1020
tccaggtgct tggttgatgc actgtcactt ggatgttcac atcacctggg gattggccgt         1080
ggttttcctt gtcgagaatg gagttggcga attgcaatct ctacagcctc tcctgcaga         1140
tttgcctcca tgttaaaaga tctgcggctg acagatagtc ctccacgaga aattcataac         1200
gcccacaaca cgggcctatt ctaattttct tcttcttctt tcaccttccc gttttcgttt         1260
cgcggagttt cagttcagtg attgtttccc ctgaattcag ggagccacca gttgtttgct         1320
tgtctcatac ttttttttat agataaaatt gtcttgcata aaaaaaaaa aaaa                1374

<210> SEQ ID NO 214
```

<211> LENGTH: 418
<212> TYPE: DNA
<213> ORGANISM: Eucalyptus grandis

<400> SEQUENCE: 214

```
atcctgtctc agtctccatc atcacttgcg ccaagtaaca tctgatttcg aggaagacga      60
ggagcgcaaa atgggctccg ctactgctgc tggtgcctcg gtttcgtcgc gaatgattct     120
gatgagagcc gccttcttca cactgtgcgc tctcgtgttc ttgccggctc ttgctcaggc     180
gaagcacgga ggtgtcacca ggcattacaa gtttgatatc aagatgcaga atgtgacgag     240
gttgtgccag acgaagagca ttgtcacggt caatggccag ctcccggggc ctcgaatcat     300
cgctagagaa ggcgaccggc tcctaatcaa agtcgttaac aatgtccagt acaatgtcac     360
aatccactgg catggagtcc gacaactcag aagcgggtgg gctgacggac cggcatac      418
```

<210> SEQ ID NO 215
<211> LENGTH: 466
<212> TYPE: DNA
<213> ORGANISM: Eucalyptus grandis

<400> SEQUENCE: 215

```
ccggatcgag tgattagtac aagttcaatt ttgtatcagg gagagagagg gacgatggga      60
acatttctag ggttcgcagt cactgcgacc ctgctcttct gcgtggctca aggcgaagtc     120
ctcttttatg attttgtggt aaatgagaca cctattgaga tgctatgtga gacaaatcgg     180
agcgtactaa ctgtgaacgg tctatttcct gggccggaga tccatgctca caagggtgac     240
actatttacg ttaatgtcac caacttagga ccttatggag tcactattca ctggcatgga     300
gtgagacaaa tacggtatcc ttggtctgat ggcccagaat atgtcacgca atgccccatc     360
cctacaaact cgagctttct tcaaaaaatc aaactcaccg aggaagaggg cacggtgtgg     420
tggcacgccc acagcgactg gtcacgtgcc acaatacatg gcctat                    466
```

<210> SEQ ID NO 216
<211> LENGTH: 757
<212> TYPE: DNA
<213> ORGANISM: Eucalyptus grandis

<400> SEQUENCE: 216

```
tcgggttctt tgtacaactt aatcggttgt atgtggatac agtgcagaaa ctgcccacga      60
attcagaatc aaatattatg agatgctcca cagttccccg gtttaagtac cttcccatca     120
gtgtacctgc attgtcttca aggaggacat ctaaagcaac tactgtaaga cttggaccg      180
gcacgagcac aagtctcctt ctttgttctg gatcaagtga ttgttacaag ttcatttttc     240
tcttgttgag agagagagag agatgggaac atttctaggg tttgtggtca ccatgaccct     300
gctcttttgc atggctcaag gcgaagtcat ctactatgat ttcgtggtga aggagacacc     360
tattcagatg ttatgtggga cgaatcagac cgtattgact gtgaatggtc tgtttcctgg     420
gccagagatt catgctcaca aggcgacac catctacgtt aatgtcacca acacaggacc     480
ttatggagtc actattcatt ggcatggagt gagacaaata agatatccct ggtccgacgg     540
cccggagtac atcacacaat gcccaatccc tacaaactca gtttccttc aaaaaatcat     600
actcactgaa gaagagggca cactatggtg gcacgctcat agtgactgga cacgtgccac     660
tatacacggc cctataatca ttttgcctgt caacggcacc aactacccctt acaagtttga     720
cgaacaacac acaatcgtga tatctgaatg gtatgca                              757
```

-continued

<210> SEQ ID NO 217
<211> LENGTH: 251
<212> TYPE: DNA
<213> ORGANISM: Eucalyptus grandis

<400> SEQUENCE: 217

| | | | | | |
|---|---|---|---|---|---|
| acacaagtct | ccttctttgt | tctggatcaa | gtgattgtta | caagttcatt | tttctcttgt | 60 |
| tgagagagag | agatgggaac | atttctaggg | tttgtggtca | ccatgaccct | gctcttttgc | 120 |
| atggctcaag | gcgaagtcct | ctactatgat | tcgtggtga | aggagacacc | tattcagatg | 180 |
| ttatgtggga | cgaatcagac | cgtattgact | gtgaatggtc | tgtttcctgg | gccagagatt | 240 |
| catgctcaca | a | | | | | 251 |

<210> SEQ ID NO 218
<211> LENGTH: 762
<212> TYPE: DNA
<213> ORGANISM: Pinus radiata

<400> SEQUENCE: 218

| | | | | | |
|---|---|---|---|---|---|
| gcctggcagt | aatgtctaat | gaacaactcc | tggaatttgc | ttggggattg | gcttccagta | 60 |
| accaatcctt | cttgtgggtt | gtgaggtcag | atatcgtgca | tggtgaatct | gccatattac | 120 |
| ccaaagagtt | cattgaggaa | accaaggata | gaggtatgct | ggtgggttgg | gcgcctcaga | 180 |
| taaaggtact | gtcgcaccca | tctgtgggag | gatttctaac | tcacagcggt | tggaactcta | 240 |
| cattggaaag | cattagtgcg | ggtgtgccaa | tgatgtgctg | gcccttcttt | gccgagcaag | 300 |
| aaacaaatgc | taaatttgtg | tgtgaagagt | ggggaatagg | aatgcaggtg | aagaaaatgg | 360 |
| tgaagagaga | agagttggcg | atactggtga | ggaattcgat | caaaggtgaa | gaggagatg | 420 |
| aaatgaggaa | agaattgga | aaactgaagg | aaactgccaa | gcgagcagtt | agtgaaggag | 480 |
| gctcttctaa | gaacaactta | gacaagttac | tccatcatat | attcctcaag | ggaatgcatc | 540 |
| aaatgatagt | ccagaatgtt | gaagcaaaca | attagttaga | agagaacgtg | taggacgaac | 600 |
| gaaaacatcc | cagtaccccca | agcgttcata | tttctgcatt | tcgcattaaa | tttactttgt | 660 |
| attgttccgc | acatatgtat | tttcaggttg | tcaggtttcc | ccagagttga | acctcatttt | 720 |
| caattagatt | gtttcacgtc | tttacggcgc | aggggggttgt | ga | | 762 |

<210> SEQ ID NO 219
<211> LENGTH: 1144
<212> TYPE: DNA
<213> ORGANISM: Eucalyptus grandis

<400> SEQUENCE: 219

| | | | | | |
|---|---|---|---|---|---|
| aaatagctca | aaggttagtg | tcgcgaccta | aattggtgtc | aacagctagc | caatggagtc | 60 |
| ctgctctatt | tcgctatttt | ggctgggcct | cctcctcccg | gcacttctag | ttttccttct | 120 |
| caaccgtcgg | aagcgcacca | agcttccccc | tcagcccca | gcatggcccg | tgatcggcaa | 180 |
| cattttcgac | ctcgggacca | tgccgcacca | gaacctccac | aacctccgag | ccaagcatgg | 240 |
| gcctgtcttg | tggttgaagc | tcggttccgt | gaacaccatg | gtgatccaat | cagctcgagc | 300 |
| ggccatggag | ttattcaagg | gccatgactt | cgtgttcgca | gaccgcaagt | gttcccaagc | 360 |
| gtttactgct | ctcggctatg | accaaggctc | gctcgctctt | ggtcgtcatg | gtgactactg | 420 |
| gcgcgctctc | cggcgtctct | gctccgcgga | gctcctcgtg | aacaagcgcg | tcaacgatac | 480 |
| ggccccacctc | aggcaaaagt | gtgtcgacag | catgatcatg | tatatagaag | aagaaatggc | 540 |
| agtcaaacaa | gcaacaaaag | ggcaaggaat | cgacttatct | cacttcctct | ttctcctggc | 600 |

-continued

```
atttaatgtg gtgggcaaca tggtgctctc acgggatcta ttggacccaa aatcgaagga      660
tgggcccgag ttctacgacg ccatgaaccg gttcatggag tgggctggca agcccaacgt      720
agccgacttc atgccatggt tgaaatggtt ggatccgcag gggatcaagg caggcatggc      780
gaaggacatg ggtcgagcca tgaggattgc cgaaggcttt gtgaaagaga ggttggagga      840
gcgaaagcta aggggagaga tgagaacaac gaatgatttc ttggacgcag tattggatta      900
tgagggcgat ggaaaagaag gccctcacaa tatctcttcc cagaacataa atataatcat      960
tctggaaatg tttttcgccg atcggagag tacaagtagc accatcgagt gggcgatggc     1020
ggagctactc cgccaacccg agtcaatgaa aaaggccaaa gatgagattg accaggttgt     1080
ggggttgaac agaaagctcg aggaaaatga cacggaaaag atgccatttt tgcaagccgt     1140
ggtg                                                                 1144

<210> SEQ ID NO 220
<211> LENGTH: 563
<212> TYPE: DNA
<213> ORGANISM: Eucalyptus grandis

<400> SEQUENCE: 220
agctcaaagc ttagccaatg gagtcctgct ctatttcgct attttggctg ggcctcctcc       60
tcccggcact tctagttttc cttctcaacc gtcggaagcg caccaagctt ccccctcagc      120
ccccagcatg gcccgtgatc ggcaacattt tcgacctcgg gaccatgccg caccagaacc      180
tccacaacct ccgagccaag catgggcctg tcttgtggtt gaagctcggt tccgtgaaca      240
ccatggtgat ccaatcagct caagcggcca tggagttatt caagggccat gacttcgtgt      300
tcgcggaccg caagtgttcc caagcgttta ctgctcttgg ctatgaccaa ggctcgctcg      360
ctcttggtcg tcatggtgac tactggcgcg ctctccggcg tctctgctcc gcggagctcc      420
tcgtgaacaa gcgcgtcaac gagacggccc acctcaggca aaagtgtgtc gacagcatga      480
tcatgtacat agaggaagaa atggcagtca acaagcaac aaaagggcaa ggaatcgact      540
tatctcactt cctctttctc ctg                                            563

<210> SEQ ID NO 221
<211> LENGTH: 447
<212> TYPE: DNA
<213> ORGANISM: Eucalyptus grandis

<400> SEQUENCE: 221
taatgaaggc ccaagatgag attgattcta tgattggcca tgatagtttg ttagaagaat       60
cggatgtttc aaaactacct taccttcagt gcattatctt ggagacccct cgactaaaca      120
cgacggcacc acttctcctc ccacacgcgt catcggctga ttgcactata ggaggatact      180
tcgtcccacg cgacactatt gtgatggtga atgcatgggc cattcacaaa gaccctcagt      240
tgtgggagga tccattgagc ttcaagcctg aaaggttcga gggcaatggc agcgaaaagc      300
aacaaaagct actattgcct tttggactgg gacggagggc atgccctggt gcccccttgg      360
ctcatcgggt catggggtgg acgttgggct tgttgattca gtgttttgat tggaaaagag      420
taagcgaaga agagattgac atgacgg                                        447

<210> SEQ ID NO 222
<211> LENGTH: 494
<212> TYPE: DNA
<213> ORGANISM: Eucalyptus grandis

<400> SEQUENCE: 222
```

```
ttaccttggc gatttcctgc ccatactaaa gttggtcgat tacaatggag tcaagaagag      60
ggtggttgag ctgaaagaga aattcgatgc gttcattcag ggcttgatca acgagcaccg     120
gaggaagaag ggcgacccag agctcgcaga cagcatgatc agtcatcttc tgcatctaca     180
agaatctcag ccggaagact actcggactc catgatcaaa gggcttgtcc ttgttttgtt     240
agttgcggga acagacacgt catcgcttac attagaatgg ataatgacaa acttactaaa     300
caatcctgaa aagttagaga aggcccgaaa tgagattgat tctgttattg ccacgatcg      360 tctggtagaa gaatcggatg tttcgaatct accttacctt cagtgcatca tcttagagac     420
ccttcgacta aacaccacgg tgccacttct cgtcccgcac gcatcatcag ctgattgcac     480
cattggtgga tact                                                        494

<210> SEQ ID NO 223
<211> LENGTH: 492
<212> TYPE: DNA
<213> ORGANISM: Eucalyptus grandis

<400> SEQUENCE: 223
gttgtcagat gcgatcccgg ctcttggctg gttggactca ggtggctata gacgatcgat      60
ggacgagaca gcgaaagagt tggatgtttt ggctcagggg tggctagagg agcatagaag     120
gaagagattg tcctgcccca agacgacag agagcaagat ttcatggatt ggatgatcaa     180
cgccctcgaa ggtcggaatt ttccagattt tgacgcggat acagttatta aggcgacttg     240
tttgaacatg ataatagcgg ggactgatac ttcgacggtg gcgatcacct gggcgctatc     300
gctgctaatg aacaaccgtc gtgcattgaa gaaggcgcaa caagagctgg acacccatgt     360
tggcaggagt aggcccgtgg aagagtccga tgtgaaaaac ttgacctacc tccaagccat     420
cgtcaaggaa gcactgcgtt tatatcctcc agtaccggtg aacggcctta gaagctccat     480
ggaagagtgc ac                                                         492

<210> SEQ ID NO 224
<211> LENGTH: 391
<212> TYPE: DNA
<213> ORGANISM: Pinus radiata

<400> SEQUENCE: 224
gcaggcttcc tccgggacct ccagggtggc cgattgtggg aaacctgttc cagttgggta      60
acaaacccca cgaagctctc ttccacctcg ctcagaagta cggccctctc atgtgtgtct     120
ctctcggaat gaaaactaca gtggtagtct cctctccggc catggcaaag caagttctca     180
agacccatga ccatgttttt gcgggccgaa cggtcataca gtcagttcag tgcctttctt     240
acgacaagtc ctcagtaatt tgggcccaat atggatccca ctggcgtttg ctcagacgca     300
tatccaatac aaagctcttc agcgtcaaga ggttagaagc cctggaacat ttgagaagag     360
atgaagtatt ccgaacaatc aagcagattc t                                    391

<210> SEQ ID NO 225
<211> LENGTH: 536
<212> TYPE: DNA
<213> ORGANISM: Pinus radiata

<400> SEQUENCE: 225 ctcgttatt tacaagctgc ggtgaaagaa actcttcgac tccatccatc cgggccttta       60
ttggtgcgcc atttatttgg taccgcgtcc tgcaatgtat tggggtatga aatcccgcag     120
```

```
aatactctcg ttctcgtgaa tgtttgggcg attgggagga accctaagtc atgggaggac      180
gccgaagttt tcaagccaga gagattcatg gaaaaagttg ggtctgaagt agatgcaaat      240
ggagatcaaa actttgggtg ccttctcttc ggagcagggc ggagaagatg cccaggacag      300
caattgggaa cgcttcttgt agagtttggg ttggcacagc tgttgcactg cttcaactgg      360
aggcttccct tggatgacat aaatggcgaa atcaagaag tggatatgaa tgaaatgttt       420
aatggagtca cgctgcgcaa agctcgtgag ctctcggcta ttccgacacc acgccttgaa      480
tgcattgctc acctgaaata ggtcatcagg tttcgagtga aacctgtgga gataga          536

<210> SEQ ID NO 226
<211> LENGTH: 463
<212> TYPE: DNA
<213> ORGANISM: Pinus radiata

<400> SEQUENCE: 226
gaaaggtacc gtcccgcttg aaaaatatct acagctttta gattggacgc aattataaac      60 atttattcc agtttgtatg tgttatctct gatcgtgttg gagatgtgtg gctgagccta      120
atcatgcatg gagcaacttg tccaggaaaa gaaaaggcag actgccccg gggccttttct      180 cgttgcccat tatcggcaat cttcacatgc taggaaagat tcctcaccga tcactggcag      240
agctgtctat gaaatacggg cctctcctgt ctctccgcct cggctctact cccgccttag      300
tcgtctcttc tccagaaata gccagtgaat ttctcaaaac ccatgatcag cttttttgcca      360 gcagaattcc ctctgctgct attaaggtat tgacctacaa tttgtccggc ctcatatttt       420
ccccgtatgg cccttgctgg aggcaagtgc gtaaactttg cgt                        463

<210> SEQ ID NO 227
<211> LENGTH: 463
<212> TYPE: DNA
<213> ORGANISM: Pinus radiata

<400> SEQUENCE: 227
ggctgagcct aatcatggtt attacatatc ttgaaccttt gtagtagatg ttgtttgtgg      60
atatagctaa tatcaaattg tttgagatag atgtttgctg gtagatatag ctagattagt      120
acagtgaacc atctaaaaaa ctggcgatgg agtttgtaga gttttgtata acactcgtca      180
ctgctcttct ttttgttgta ttggtagcag catggagcaa cttgttcagg aaaagaaaag      240
gcagactgcc cccgggggcct ttctcgttgc ccattatcgg caatcttcac atgctaggaa      300
agattcctca ccgatcactg gcagagctgt ctatgaaata cgggcctctc ctgtctctcc       360
gcctcggctc tactcccgcc ttagtcgtct cttctccaga aatagccagt gaatttctca      420
aaacccatga tcagcttttt gccagcagaa ttccctctgc tgc                        463

<210> SEQ ID NO 228
<211> LENGTH: 463
<212> TYPE: DNA
<213> ORGANISM: Pinus radiata

<400> SEQUENCE: 228
gaattgcttt ctgcgtgtcc agttcatgaa tgcccatact tttattttaa tctcgctact      60
gttattcttc tgggcgtggt gacgggatgg ggtttcttat tccggggaag aaaacagaag      120
cttcctccgg ggccttttca gtggccgatt gttggaaacc ttcacatgat gggagagctt      180
ccacaccaag caattacagc tctctctatg aaatatgggc ctctcatgtc tctccgcctc      240
ggctcctatc tcactttggt cgtttcttct ccagatgtgg ccgaggagtt cctgaagact      300
```

-continued

```
catgatctgg ctttcgccag cagacctcca accatcggta cgaagtactt ttggtataat    360
tcctccgacg tcgcatttc cccctatggt ccttactgga ggcagatgcg taaaatctgt    420
gtgttacagt tgctgagctc aagacgcata gattccttcc gcc                      463
```

<210> SEQ ID NO 229
<211> LENGTH: 463
<212> TYPE: DNA
<213> ORGANISM: Pinus radiata

<400> SEQUENCE: 229

```
actgtgacca agacctaatt ggtggcattg ggatcaagtc aatgataaag gaaacgtttg     60
tgttagcagg gtcttttgaac atgggagatt ttataccata cttggcatgg attgatcttc   120
aaggtctcaa ccgtcgattg aagaacatac acaagatcca agacgacttg ttagggaaga   180
tactagagga acacgcttcg ccaccgcaga ataaccccaa ctacatgcca gatctcgtgg   240
atgttttgct cgcggcctct gcggatgaag atctggagtt cgaaattact cgagacaata   300
taaaatctgt catctatgta tatattgtcc atgcaattat tagatttcaa tgacttaaat   360
aaaacatgac acggtgatta tatcttgaca tttgttttgg atttgttttg ttggtaggat   420
atcttgtccg ctggttcgga ctcgtcgtct gcaagcatag agt                      463
```

<210> SEQ ID NO 230
<211> LENGTH: 543
<212> TYPE: DNA
<213> ORGANISM: Pinus radiata

<400> SEQUENCE: 230

```
ggcaccagac gagctggaac gtgtcgttgg attgggtcgt atggtaaggg aatctgatct     60
gcctcgtctc gtttattac aagctgtggt gaaagaaact ctgaggctat acccacaggg   120
gccgatttta ttccgccact tgtcttcgga gccctgcaat gtcctgggct atgaaatctc   180
tcaaaacact caagttctgg ttaatatttg ggcgattgga aggaactctg agtcatggga   240
agatgccgga agcttcaaac ctgagagatt catggaaaga gttgggtctg aggtagatac   300
aaatggagat caaaattctg cgtggcttcc cttcggagca gggaggagaa gatgcccagg   360
acagcaattg ggaacgcttg ttgcagaaat tgggctggca cagctcttgc actgtttcaa   420
atggaggctt cccgaagctg atatggatgg cccaaatcaa gaacttgaca tgatggaaag   480
gtttaatgga atcacatcgc cgagggctaa ggaactgttt gcgattccga caccccgcct   540
tga                                                                 543
```

<210> SEQ ID NO 231
<211> LENGTH: 381
<212> TYPE: DNA
<213> ORGANISM: Pinus radiata

<400> SEQUENCE: 231

```
ggaatcctct ttgatatgtt gctcggtggg tcagacacag cgcctacaat aatagagtgg     60
gcaatatcgg aggcgctgat aaaccctcca gtgatgaaga aacttcagga cgagctggaa   120
cgcgtcgttg gattggatcg catggcatgc gaatctgatc tgcctcagct cgtttattta   180
caagctatgg taaaagaaac gcttcgactt cacccagcgg ggcctctttt gaaccgtcgc   240
ttatccgctg agtcctgcaa tgtgttgggg tacgaattcc ctaaaaacac tcgtgttctc   300
gttaatgctt gggcgattgg gaggaaccca agttatggg aggacgctga aactttcaag   360
```

```
ccagaaagat tcacgggaag a                                              381

<210> SEQ ID NO 232
<211> LENGTH: 384
<212> TYPE: DNA
<213> ORGANISM: Pinus radiata

<400> SEQUENCE: 232
ccacttcggc aacagttgaa tgggcaatgg ctgagcttat cagaaaacca acgctactga     60
aaaaggccca ggcagagctg gatgaggttg ttggtcgaga aagagaatg gaggaatcag    120 acatagcaaa attgccctat ctacaagcag tagtgaagga ggtactcaga ttgcacccag    180
cagctccact gataattcct cgaagagcag acaactctgc cgagattggt ggatatgttg    240
tcccagagaa cacgcaggtg tttgtgaata tctggggcat cggaagagat cccaacgttt    300
ggaaggaacc tctgaaattc aaaccggaaa ggtttttaga ctgtaatact gactacagag    360
gccaggattt tgaactgata ccat                                           384

<210> SEQ ID NO 233
<211> LENGTH: 405
<212> TYPE: DNA
<213> ORGANISM: Pinus radiata

<400> SEQUENCE: 233
gagaagatga agtttccgct atgattcgct ctattgttaa ttcagatgcc acaaggact     60 ctcgtcctgt caacatcaag caacttgcgt catcccttgt gacagctata gtcttgagga    120
tgaccttcgg taaaaagtat tcggaccggg attcaggagc attcagttca atgatcaaag    180
aaagtttact gttactcggc tcctttaata ttggagaata cataccttac ttgaactgga    240
tggatttgca aggtctcaac cgccggctga agaagctacg tacaacacaa gaccagttgc    300
tagagaaagt aatagaggaa catgctgccc agaatcggag caacatgacg catgatcttg    360
tggatgcctt acttgcagcc tctgcggata agatagaga gctcc                     405

<210> SEQ ID NO 234
<211> LENGTH: 348
<212> TYPE: DNA
<213> ORGANISM: Eucalyptus grandis

<400> SEQUENCE: 234
catatacgat caagagagtt tgctgaatgc aattaagcag gttgatgtgg taatctctgc     60
tgtggggcaa gcacaaacgg aggaccaaga ccggattgtt gctgccatca aagcagccgg    120
gaatatcaag agattcttgc cttcagagtt tggaaatgat gtggatcgtg tccatgctgt    180
ggagccagta aaaactggat tgctctcaa ggccaagatc cgccgccttg ttgaggccga    240
gggaatccct tatacctatg tgtcttctaa ctcttttgca ggttactacc ttcaaacatt    300
gtcacagccc ggggctacag ctccccctag agataacgtt gttatctt                 348

<210> SEQ ID NO 235
<211> LENGTH: 640
<212> TYPE: DNA
<213> ORGANISM: Eucalyptus grandis

<400> SEQUENCE: 235
ctgtgtgtta agctagtagt cagtcaagca ttgaaggcat gaacacctta aagacatgaa     60
cagatgaaga tttggagtct caattatact gtgtgttaag ctagtagtca gtcaagcatt    120
gaaggcatga acaccttaaa gacatgaaca gatgaagatt tggagtctca atggtattat    180
```

-continued

```
tgcctacctt atctccagtc acagcagagt cgcttctaga aaccgatcga gttcgccgga      240
aaacaccgcg cctccgccgt gaaaaccact cagagatggc tgcgaagagc aaggtcctgg      300
tgatcggagg cactggatac atcggaaagt tcatcgtgga agccagtgct aagtccggtc      360
gccctacctt cgctctcgcg agggagtcca ctctctccaa ccccgccaag gccaagatcg      420
tcgaaggttt caagagcctc ggcgtcactt tagttcacgg agacatatac gatcaagaga      480
gtctattgaa tgcgatcaag caggtcgatg tggtaatctc tgctgtgggg cgagcacaaa      540
tagaggacca agacaggatt gttgctgcca tcaaagcagc cgggaatatc aagagatttg      600
tgccttcaga gtttggaaac aacgtggatc gtgtccatgc                            640

<210> SEQ ID NO 236
<211> LENGTH: 464
<212> TYPE: DNA
<213> ORGANISM: Eucalyptus grandis

<400> SEQUENCE: 236
gtctcgagtt ttttcttatt taattaattt tcttttaga gattcttgcc ttcagagttt       60
ggaaatgatg tggatcgtgt ccatgctgtg gagccagtaa aaactggatt tgctctcaag      120
gccaagatcc gccgcctcgt tgaggccgag ggaatccctt tacctatgt gtcttctaac       180 tcttttgcag gttactacct tcaaacattg tcacagcccg gggctacagc tcccctaga      240 gataacgttg ttatcttagg ggatggaaat gccaaagtgg tgtttaacaa ggaggatgac     300
atcggcacct ataccatcaa agctgtggat gatccaagga ccttgaacaa aattctgtac     360
atcaggcctc ctgccaacac ctactcaatg aatgagctcg tgtctttgtg ggagagaaag    420
atcggcaagg ctctggagag ggtgtatgtt ccagaggagc aaat                      464

<210> SEQ ID NO 237
<211> LENGTH: 315
<212> TYPE: DNA
<213> ORGANISM: Eucalyptus grandis

<400> SEQUENCE: 237
cttctagaaa ccgatcgagt tcgccggaaa acaccgcgcc tccgccgtga aaaccacttc       60
agagatggcc gcgaagagca aggtcctggt gatcggaggc actggttaca tcggaaagtt     120
catcgtggaa gccagtgcta agtccggtcg ccctaccttc gttctcgcga gggagtccac     180
tctctccaac cccgccaagg ccaagatcgt ccaaggtttc aagagcctcg gcgtcacttt     240
agttcacgga gacatatacg atcaagagag tctgttgaat gcgatcaagc aggtcgatgt    300
ggtaatctct gctga                                                      315

<210> SEQ ID NO 238
<211> LENGTH: 376
<212> TYPE: DNA
<213> ORGANISM: Eucalyptus grandis

<400> SEQUENCE: 238
caaagtcacg tcagagaccg atcaagttcg ccggaaaaca ccacgcgcgc tatgaaaaga       60
ccctccaaga tggcagagat gagcagagtc ttggtgattg gaggcgccgg atacatcgga     120
aagttcattg tgaaagcgtg tgctaagtcc ggtcacccta cctttgttct cgagacggag    180
tccactctct ccaaccccgc caacgccgaa atcatcaaag gtttcaagag cttaggcgtg    240
aacctagtcc atggagacat atacgatcaa aaaagtctgt tgagtgcgat taagcaagtt    300
```

```
gatgtggtaa tatctactgt ggggcaagca cagctagaag accaagacag gattgttgca    360
gccatcaaag cagccg                                                    376
```

<210> SEQ ID NO 239
<211> LENGTH: 297
<212> TYPE: DNA
<213> ORGANISM: Eucalyptus grandis

<400> SEQUENCE: 239

```
atcaagttcg ccggaaaaca ccacgcccgc tgtgaaaaga ccctccaaga tggcagagat    60
gagcagagtc ttggtgatcg gaggcgccgg atacatcgga aagttcatcg tgaaagcgtg   120
tgctaagtcc ggtcacccta cctttgttct cgagacggag tccactctct ccaaccccgc   180
caacgccgaa atcatcaaag gtttcaagag cttaggcgtg aacctagtcc atggagacat   240
atacgatcaa aagagtctgt tgagtgcgat taagcaagtt gatgtggtaa tctctac      297
```

<210> SEQ ID NO 240
<211> LENGTH: 951
<212> TYPE: DNA
<213> ORGANISM: Pinus radiata

<400> SEQUENCE: 240

```
tctcgcacag ttgacgacgt tttcttgtat ttgtagcgtt cggcacgatc ggggaaaaac    60
gatggcatgc gctactgatg ttgcacgtca gtttctgcca tgcgtccaac ccgtgccgtc   120
cagcatggga ggagagaccg cccggtcgat caacctcacc tgcaatggcc tctccccgcc   180
tcaaccgcag tacaacgccg agaacaacca tgatcaggac accacagttg ccacaagggt   240
tctcattatt ggcgccaccg ggttcatcgg tcggtttgtt gcagaggcca gtgtgaaatc   300
cgggcgccca acttatgccc ttgtgcggcc gacaacatta agttcgaagc ccaaggtcat   360
tcagtctctg gtggattcgg gtattcaagt tgtttatgga tgtctacatg atcacaattc   420
tttggtgaaa gccatcaggc aggttgacgt tgttatttct actgttggtg agccctaat   480 tcttgatcag ctcaagattg tggatgccat caaggaagtt ggcactgtca agagatttct   540
tccttcagag tttggacacg atgtagaccg agcagatccc gtagagcctg ctcttagttt   600
ttacatagaa aagagaaaag tccggcgtgc agtggaggaa gcaaagattc cttacacata   660
catctgctgc aactccatag ctggctggcc atactattat cacacacatc caactgagct   720
ccccccacca aaggaacagt ttgagatcta tggggatgga agcgttaaag cctttttcgt   780
tactggggac gatattggcg cgtataccat gaaagctgtg gatgaccctc gtactctgaa   840
caagtctatt catttcagac caccaaagaa ttttctcaac ttaaacgaac tcgcagacat   900
atgggagaat aagattaaca gaactctgcc aagagtatct gtctcagcag a            951
```

<210> SEQ ID NO 241
<211> LENGTH: 371
<212> TYPE: DNA
<213> ORGANISM: Pinus radiata

<400> SEQUENCE: 241

```
tttagctgac attttattaa ttcaaagtgg caagatgaca ggtctcaagg actctgctaa    60
tagggttttg ataataggag gcacgggata cattgggaaa tacatggcaa aagccagcgt   120
ttcacagggc tatccaacct acgttcttgt ccgtcctgct acagcagctg cccctgattc   180
cttcaaagca aagctacttc agcaattcaa agatattggc attcatattc ttgaaggatc   240
attagatgat cacaacagcc ttgtggatgc aatcaagcaa gtagacatag taatatccgc   300
```

| | |
|---|---|
| agttgccatt cctcagcatt tggatcagtt taatatcata aacgccatta aggatgttgg | 360 |
| aatggaaata t | 371 |

<210> SEQ ID NO 242
<211> LENGTH: 687
<212> TYPE: DNA
<213> ORGANISM: Eucalyptus grandis

<400> SEQUENCE: 242

| | |
|---|---|
| taatggcgag ctccacccgt ctcactactg tgagagggac ctgctcaaag tggtcgaccg | 60 |
| cgagcatgtg ttcacctacg ctgatgacgc ctgcagcgcc acctacccgc tgatgcagaa | 120 |
| gctgaggcaa gtcctggtcg accaggcact ggtgaatggc gagagcgagc tgaacccgag | 180 |
| cacttcgatc ttccaaaaga tcgtggcctt cgaggaggag ctcaaggccc agttgccgaa | 240 |
| ggacgtcgag ggcgttcgag tccagtacga gacaggcaac ctcgccatcc ccaaccagat | 300 |
| caaggaatgc aggtcctatc cattgtacaa gctggtgagg gaggagctgg ggactgccct | 360 |
| gctcacgggc gagggcgtga tatcccctgg cgaggacttc gacaaggtct tcactgcgat | 420 |
| ctgtgctgga aaactgattg atccgctgct ggagtgccta agcggttgga acggtgctcc | 480 |
| tcttcccatc tcttaggaat tgtcctatat tctttctcct tcttttttccc tttccgttac | 540 |
| ttgccaagta aatctcatgt atccaatctt ttctatcaag agacaattgt atttcttgtt | 600 |
| ttctgttttgg tccttttttgt ctcctcccaa gtgaagaaat tggagaatat aagtaattga | 660 |
| gtaaattttt acatggaaaa aaaaaaa | 687 |

<210> SEQ ID NO 243
<211> LENGTH: 344
<212> TYPE: DNA
<213> ORGANISM: Eucalyptus grandis

<400> SEQUENCE: 243

| | |
|---|---|
| tcctggtcga ccaggcactg gtgaatggcg agagcgagct gaacccgagc acttcgatct | 60 |
| tccaaaagat cgtggccttc gaggaggagc tcaaggccca gttgccgaag gacgtcgagg | 120 |
| gcgttcgagt ccagtacgag acaggaaacc tcgccatccc caaccagatc aaggaatgca | 180 |
| ggtcctatcc attgtacaag ctggtgaggg aggagctggg gactgccctg ctcacgggcg | 240 |
| agggcgtgat atcccctggc gaggacttcg acaaggtctt cactgcgatc tgtgctggaa | 300 |
| aactgattga tccgctgctg gagtgcctaa gcggttggaa cggt | 344 |

<210> SEQ ID NO 244
<211> LENGTH: 681
<212> TYPE: DNA
<213> ORGANISM: Eucalyptus grandis

<400> SEQUENCE: 244

| | |
|---|---|
| cccaagcctg gattacggct tcaagggagc tgagatcgcc atggcctcat actgctcgga | 60 |
| gctgcagttc cttgccaacc ctgtgaccaa ccatgtccag agcgcggagc aacacaacca | 120 |
| ggacgtgaac tccttgggcc tgatctcgtc gaggaagact gccgaggcca tcgatgtgct | 180 |
| gaagctcatg tcctccacct tcctggtcgc cctgtgccag gccatcgacc tgaggcacct | 240 |
| ggaagagaac ctcaagagcg tggtcaagaa cacggtgaac caagtggcca agaaggtcct | 300 |
| ctacgtcggg tccaacggcg agctccaccc gtcgcggttc agcagaaag acctgatcaa | 360 |
| ggtggtcgac cgggagtacg tcttcgccta catcgatgac ccctgcagcg ccacgtaccc | 420 |

| cctgatgcag aaactgaggc aggtcctcgt ggacgatgcg ctggacgacg tcgaccggga | 480 |
| gaagaacccc agcacctcca tcttccagaa gattggggct ttcgaggagg agctcaaggc | 540 |
| actcctcccg aaggaggtcg agaacgcgag agctcagttc gagagcggga actcggcgat | 600 |
| cgctaacaag atcaggggg t gcaggtcgta cccattgtac aggttcgtga gggaagagct | 660 |
| cgggaccggt ttgctcacgg g | 681 |

<210> SEQ ID NO 245
<211> LENGTH: 1455
<212> TYPE: DNA
<213> ORGANISM: Eucalyptus grandis

<400> SEQUENCE: 245

| tttgcaatcc tctgaatttt ccctaactag aaataaagag attatataca tacacgagca | 60 |
| aagcgctctc ctccagttgt cttccttcgt tcgctcatct ctcctcgtac attattagca | 120 |
| tacgacctct tgtatcggac ccggatccgc tatcgttaac gtacacacgt tctagtgctg | 180 |
| aatggagatg gagagcacca ccggcaccgg caacggcctt cacagcctct gcgccgccgg | 240 |
| gagccaccat gccgacccac tgaactgggg gcggcggca gcagcccctca caggagcca | 300 |
| cctcgacgag gtgaagcgga tggtcgagga gtaccggagg ccggcggtgc gcctcggcgg | 360 |
| ggagtccctc acgatagccc aggtggcggc ggtggcgagt caggaggggg taggggtcga | 420 |
| gctctcggag gcggcccgtc ccagggtcaa ggccagcagc gactgggtca tggagagcat | 480 |
| gaacaaggga actgacagct acggggtcac caccgggttc ggcgccactt ctcaccggag | 540 |
| gacgaagcaa ggcggtgctt tgcagaagga acttataagg ttcttgaatg ccgggatctt | 600 |
| cggcaacggc acggagtcgt gccacaccct gcctcaatcc tccacccgag ccgccatgct | 660 |
| cgtccgggtc aacacctcc tccagggcta ctccggcatc cgttttgaga tcctcgaggc | 720 |
| catcaccaag ttcctcaacc acaacatcac cccgtgcctg cccctcaggg gcaccatcac | 780 |
| tgcctcaggc gacttggtcc ccctctccta cattgccggg ctcctgacgg gccggcccaa | 840 |
| ctccaaggcc gtcgggcctg atgggaagtc cctggacgct gtcgaggcct tccggctcgc | 900 |
| cgggattgac acgggcttct tcgagctgca gccaaaggaa gggttggcgc tcgtgaacgg | 960 |
| cacggcagtc gggtctggcc tggcttccat cgtcctcttc gaggccaaca tactcgcggt | 1020 |
| cctgtccgag gtcctgtcag cgatcttcgc agaggtgatg caggggaagc cggagttcac | 1080 |
| agaccacttg acgcataaat tgaagcacca tcccgggcag attgagtctg cggctataat | 1140 |
| ggagcacatt ttggatggaa gcgcttacgt gaaggctgct aaaaagttgc acgagatgga | 1200 |
| tccgctccag aagccaaagc aggacaggta cgctctcagg acttctcccc agtggctagg | 1260 |
| gccccagatt gaggtgatcc gagcggcaac caagatgatt gagagggaaa tcaattcggt | 1320 |
| caatgacaac ccgctgatcg atgtcgcgag gaacaaggcc ctgcacggtg gaacttcca | 1380 |
| ggggaccccg attggtgtct ccatggacaa cactcgcctg gcggttgcgt ccatagggaa | 1440 |
| gctcatgttc gcgca | 1455 |

<210> SEQ ID NO 246
<211> LENGTH: 294
<212> TYPE: DNA
<213> ORGANISM: Eucalyptus grandis

<400> SEQUENCE: 246

| caacagtggc atcacgccgt gcttgccgct ccgcggctcg atctccgcct ctggtgactt | 60 |
| ggtaccctt tcctacatcg cgggtctttt gacgggacgt cccaattcca aagcggtcgg | 120 |

```
acccgctggg gagaccctca cggccaaaca agcctttgag ctcgctggga tcagtggtgg    180
attcttcgag ttgcagccga aggaaggact tgcccttgtg aatgggacgg gagttgggtc    240
tgccttagct gccatagtgc tttttgaagc taatatgctc actgtcctct caga          294
```

<210> SEQ ID NO 247
<211> LENGTH: 1520
<212> TYPE: DNA
<213> ORGANISM: Pinus radiata

<400> SEQUENCE: 247

```
gtgatctggt tcccctgtct tatattgctg ggctcttgac cgggaggcct aattccagag    60
tcagatccag agatggaatt gaaatgagcg gagccgaagc gctcaagaaa gtgggcctgg   120
aaaagccctt tgaattgcag cctaaagaag gtctggccat tgtcaatggc acttcagtgg   180
gagcagcact ggcttccatt gtgtgtttcg atgccaatgt tcttgctctg ctctctgaag   240
taatctctgc catgttctgc gaggttatga atgggaagcc tgagtttaca gatccattaa   300
ctcacaagct gaagcaccat cctggccaaa tggaagctgc agcgatcatg gagtatgtct   360
tggacgggag tcttatatga aacacgctgc taagctccat gagatgaatc ctctgcagaa   420
gccaaagcag gatcgctatg cgcttcgcac ttcgcctcag tggctcggcc tcaggtgga   480 gattatcaga tctgcaactc acatgattga gcggaaatc aattctgtga atgacaatcc   540
agtaattgat gttgccagag acaaagctct acatggaggg aatttccagg gcacacctat   600
tggtgtttcc atggataatc ttcgtctgtc aatttcagca attgggaaat tgatgttcgc   660
tcaattctca gagcttgtga atgattacta caatggaggc ttgccttcga atctgagtgg   720
tgggcctaat cccagcctgg attatggact gaaaggggcc gagatcgcta tggcttctta   780
cacttctgag cttcttttacc tggcaaatcc tgtcaccagc catgtacaga gcgccgaaca   840
gcataaccag gatgtcaatt ctctgggtct cgtttcagct agaaaatctg ccgaggccat   900
cgatattctg aagctgatgc tctccacata cctgacagct ctgtgccagg ctgtggattt   960
aaggcatctg gaggaaaaca tgctggccac tgtgaagcag attgtttctc aggtagccaa  1020
gaaaaccctg agcacagggc tcaacgggga gcttttgcca ggccgtttct gcgaaaagga  1080
tttgctccag gtagtggata cgaacatgt tttctcttac attgacgatc cgtgcaatgc  1140
cagctaccca ttgactcaga aactgagaaa catcctggtg aacatgcct tcaagaacgc  1200 agaaggtgaa aaggatccca acacttccat tttcaataag attcctgtgt ttgaagccga  1260
gctgaaggca cagcttgaac cgcaagttag tctggccaga gaaagttatg acaaagggac  1320
cagccctctg cccaacagga tccaggaatg caggtcttat cctctctatg aatttgtgag  1380
aaaccagctc ggtacccttc aggcatggtt attccatata aatattgtaa tgagatgttt  1440
aattatttac tgctctcttt tttttccgga gcttgcgacc gccttcgatt ccgtgcacta  1500
cgcgaggacg aagcctctgt                                             1520
```

<210> SEQ ID NO 248
<211> LENGTH: 449
<212> TYPE: DNA
<213> ORGANISM: Pinus radiata

<400> SEQUENCE: 248

```
ctctcattct gaggttcatc tggctgaagt ttgaactgtg ctcgaattct gaggttcatc    60
gtgcagaagt ttgattcgtg aattatttgt ttgtttaatt atagtgcaca tggcgcctca   120
```

```
ggaattcaca ggcgaagtga aattctgtgc gggaaatggc ggtacggcgt ctttgaacga    180
tccgctgaat tgggcagccg cagcggagtc catgaaggga tctcacttcg aggaagttaa    240
acgaatgtgg gaggagtttc gttctccagt tgtgaggctc cagggatccg gtctcacgat    300
tgcccaggtg gcagccgtgg ccaggagaac gggatccgtg agagtcgaac ttgagaccgg    360
cgcgaaggcg cgggtagatg agagcagtaa ttgggtgatg gacagtatgg cgaacgggac    420
ggatagctat ggcgttacga cggggttcg                                      449

<210> SEQ ID NO 249
<211> LENGTH: 512
<212> TYPE: DNA
<213> ORGANISM: Eucalyptus grandis

<400> SEQUENCE: 249
gaacttggtg aagttaggaa gtatactagg catggccatc ggtgttgcac tcttcagctc     60
gcttcttgta ctttcatttg tctctccaat ctcttcacta agttccaatt actacgacaa    120
gacctgtccc aatgctgagt tgatcgtcgc aaatgctgtc aagaatgcgg caatgaagga    180
caaaaccgtt ccggctgctc ttctgcggat gcatttccac gactgtttca ttaggggttg    240
cgatgcgtcg gtgcttttaa actccaaagg aagcaacaaa gcggagaagg atggacctcc    300
taatgtctct ctgcactcat tttttgtaat cgacaatgcc aaaaggagt tggaagcttc    360 ttgccccggc gtggtttcat gtgcggacat cttggcacta gctgctagag attccgtcgt    420
actgtccgga ggtccgactt gggatgtgcc caagggaagg aaggatggaa gaacatcaaa    480
agccagcgag acgactcaac tcccagcacc ac                                  512

<210> SEQ ID NO 250
<211> LENGTH: 354
<212> TYPE: DNA
<213> ORGANISM: Eucalyptus grandis

<400> SEQUENCE: 250
ctggtaatca ccatagttgt cttctttggg cacataggag actcagaagg aggggacttg     60
aggaagaatt tctacaagag cgcatgtcct cttgctgagg aaatagtgaa gaatgtcacg    120
tggaagcatg ccgccagtaa ctcagctttg cccgccaagt tcctgaggat gcatttccac    180
gattgcttcg ttaggggttg cgatggctca gttttgctag actcgacggc gaacaacaag    240
gcggagaagg tggcggttcc gaaccagtcg ctaaccgggt tcgacgtaat agacgagatc    300
aaggagaagc tggaggaaac atgccctggg gtcgtctctt gtgccgacat cctg          354

<210> SEQ ID NO 251
<211> LENGTH: 195
<212> TYPE: DNA
<213> ORGANISM: Pinus radiata

<400> SEQUENCE: 251
aacgctgacc ctatcgcggt tatagacgaa gcactcagca ctggtggtgc gcccaatttg     60
tcggatgcat ataccctaaa tggacagcca ggagacctgt ataactgctc tagggcagga    120
acattccggt ttctggtcaa acaaggagaa acttaccttc tacggatggt caatgctgca    180
ctcaatagtg cccac                                                     195

<210> SEQ ID NO 252
<211> LENGTH: 377
<212> TYPE: DNA
<213> ORGANISM: Pinus radiata
```

<400> SEQUENCE: 252

| ccaaacccca | tggagaaact | ccgctcataa | taggagaatg | gtggaacgct | gaccctattg | 60 |
| cggttataga | tgaagcactc | cgcactggtg | gtgcgcccaa | tttgtcggat | gcatataccc | 120 |
| taaatggaca | gccaggagac | ctgtataact | gctctagggc | aggaacattt | cggtttcctg | 180 |
| taaaacaagg | agaaacttac | cttctccgga | tggtcaatgc | tgcactcaat | agtgcccact | 240 |
| ttttcaagat | cgcaggccac | aaatttacag | tagtagctgt | ggatgcttcc | tacaccaagc | 300 |
| catacaaaca | gatgtaatcg | ccattgctcc | cggtcagact | actgatgttc | tcgtcacggc | 360 |
| cgaccaacct | gtgggca | | | | | 377 |

<210> SEQ ID NO 253
<211> LENGTH: 387
<212> TYPE: DNA
<213> ORGANISM: Pinus radiata

<400> SEQUENCE: 253

| gatgcccaca | ccattaatgg | aaagccaggg | ccactcttca | aatgccctac | caaagatact | 60 |
| tttgtggttc | cagtggaaca | tgggaagact | taccttcttc | gaatcatcaa | cgcagctctc | 120 |
| aatgacgagc | tctttttga | tgttgcaaac | catcatctga | agtggtgga | gattgacgca | 180 |
| gtatacacaa | agccactaat | aacgaactca | atagtaattg | ctccaggcca | gaccacaaat | 240 |
| gccttgatcc | acaccaacaa | aaggagtggc | aggtatttca | tggctgctcg | ctcattcatg | 300 |
| gacgcgcccg | tctccgtcga | caataaaacc | gccacagcca | ttttgcagta | cgtcaattca | 360 |
| atacaaattc | tgttataatg | cccagca | | | | 387 |

<210> SEQ ID NO 254
<211> LENGTH: 534
<212> TYPE: DNA
<213> ORGANISM: Pinus radiata

<400> SEQUENCE: 254

| aacatgatgg | cgcccatggc | cggagcagag | tacggaataa | agctgattat | tcagttgctt | 60 |
| gttgtactac | ttgctgttca | acttgttgca | gggaaaacga | ccagacatta | ctcattccat | 120 |
| gtgaggttga | agaacgttac | tcgtctctgc | cacacaaagc | cattgattac | agtcaatggg | 180 |
| aaatctcctg | gacctaaagt | agtcgtccgt | gagggagata | gagtcatcat | caaagttcat | 240 |
| aatcatgtta | gcaataatgt | ctcaattcac | tggcatggag | ttcgacaatt | gaggtctggt | 300 |
| tgggcagatg | gccctgctta | cataacccaa | tgcccaattc | aaacgggaca | gacttatgtt | 360 |
| tataacttca | ctgtcacagg | acagagggga | actctctggt | ggcacgctca | catctcttgg | 420 |
| ctaagagcga | gcgtatatgg | cgctttcatc | atctatccta | aacgccatgt | tccttatcca | 480 |
| tttccaaagc | catacaaaga | agtccctctg | attctcgggg | aatggtggaa | tgca | 534 |

<210> SEQ ID NO 255
<211> LENGTH: 1076
<212> TYPE: DNA
<213> ORGANISM: Pinus radiata

<400> SEQUENCE: 255

| gcccaattcc | accaggtggt | cgttacacat | atagattcaa | catctctggt | caagaaggaa | 60 |
| cggtttggtg | gcatgcccat | tactcatggc | tccgagctac | tgtgcatgga | gcttttgtaa | 120 |
| tccttcctaa | gaaaggaagc | tcatatccct | tttctaaacc | gcatgctgaa | attcctatta | 180 |

```
taataggtga atggtggaac gctaacccca tcgccgttat agacgaagcg gttcgcacag      240
gtggtgcgcc taatttatcc gatgccttca ccataaatgg acagccagga gatctgttta      300
actgctctac ctcgggaaca tttcgcctcc ctgtagaaag cggagaaacg taccttctgc      360
ggattgtgaa tgctgcactc aatagcgggc acttttttcaa gatagcaggc cacgaattta    420
cagtggtagc tgtggatgct tgttacacca agccatacaa acagatgta ctcgtcatat      480 ctgccggcca gacgacagat gttcttatca cggccaacca gtctgtgggc agatactata    540
tggccgcccg agcgtatcaa aatcaggcgg caggcgattt cactaacacc acaacaactg    600
ccattctaga gtacattgga agtgaaaatt ctactcgccc aattttgcct agccttccag    660
cctacaacga cactgccact gtcactagat ttagcagagc actgcgaagt ctggcatccc    720
aggagcaccc tgtgaatgtt ccgcacacaa tagatgaaag cctcatctca actgttggac    780 tgggctact tccgtgtggc gctgggaata cctgtgaagg tcccaacgga acgaggctga     840
gtgcaagtat caacaacata tcgtatgtag agcccacgat ctcgttgctt caagcatatt    900
attacactgc caatggtatc tttacggggg attttccatc aaaacctgaa gttagattca    960
actacacggg ggacgatata ccccgaaaat tttgggctcc ggaccccgca acaaaagtga   1020
aggtgctcga atacaactcc acagtgcagc tcgttttttca gtcaacaaac atcttc       1076

<210> SEQ ID NO 256
<211> LENGTH: 483
<212> TYPE: DNA
<213> ORGANISM: Pinus radiata

<400> SEQUENCE: 256
atttcgcagg gaaactgtaa tacagcatat ttcaagaagc tttctttcga aaatggtgat       60
ctcaaaatat gcagcagcga tgtcgtgctt gctcatcgca gtagttgcat tagaggttgg     120
ggcagaaacg agacattaca aatttgacat aaaattcaag aacgttactc gtttatgcca     180
cacaaagccg atagttacag cgaatggcaa gttcccaggc ccaacaatat atgcacgaga    240
aggagacaca gtcactgtga agtaaccaa tcacgtgaca tacaacgtgt ccatacactg      300
gcacgggata aggcagttgc ggactgggtg ggctgatggg cctgcttata ttacgcagtg    360 cccccattcaa acaggccaaa cttatgtata aactttaca atcacagggc agcgaggcac     420
acttttctgg cacgctcaca ttctctggtt acgtgcaaca ttgaatgggc ccatcgtcat    480
tct                                                                   483

<210> SEQ ID NO 257
<211> LENGTH: 470
<212> TYPE: DNA
<213> ORGANISM: Pinus radiata

<400> SEQUENCE: 257
ggttgttgtt taagtacaag gatgaacatg tcgagatcaa aggcgttgct ctgcccttcc       60
ccagctcatg tgaagtacgt gctaattgtc atcctgttga ttattatgat tcagtgcccg     120
gatatagtag caggaaagca tgcgcagaca accaggcatt acaagttcaa cgtgaggcta    180
agcaatgtga cacgtctttg ccgcacgaaa cctttgatta cagtgaatgg aaagtatcca    240
ggacctacag ttgttgctcg cgagggagat cgggtaatta taaaacttgt aaaccacgtg    300
aaggacaacg tcactattca ctggcatggc gttcgacagc tgagatcggg atgggcggat    360
ggtcctggtt atatcactca atgtccactt caaaccggaa tgagttacgt ttataatttc    420
accatcgtag ggcagagagg aactctatgg tggcacgcac acatttcttg                470
```

-continued

<210> SEQ ID NO 258
<211> LENGTH: 472
<212> TYPE: DNA
<213> ORGANISM: Pinus radiata

<400> SEQUENCE: 258

| agttatccag caggctcttc aaacaggagg tggtccaaat gtatctgatg cctatactat | 60 |
| aaatggactt cctggaccac tttacaactg ttccaatgag acatttgttt tgaaagtgca | 120 |
| tcctggacaa acatatcttc ttcgtatcat caatgctgca ctcaatgatg aactcttcct | 180 |
| tgccattgca aatcacagtt aacagttgt ggaggtggat gcagtgtatg tcaagccttt | 240 |
| ccagacagat actcttctta taccccagg gcagactacc aatgttttac ttactgctaa | 300 |
| tgctactagt ggtaaaaata acaatttgt catagctgct agtccttttg ttaccggttc | 360 |
| agggacattt gataattcca ctgttgcagg aattgtgagt tataattctc ataagtttaa | 420 |
| aaattcttcc accattattc tgccaaaact cccatccttc aatgatacaa at | 472 |

<210> SEQ ID NO 259
<211> LENGTH: 405
<212> TYPE: DNA
<213> ORGANISM: Pinus radiata

<400> SEQUENCE: 259

| caggacaaac cacgaatgtt ttgctcgagg ctaacaaaag atctggaagt tatttcgtgg | 60 |
| ctgctcggcc attcatggat gcacctgtga cagtgaacaa caagaccgca actgccattt | 120 |
| tgcactacat cggcaggaat tctgaatcag atattcccgc cgttaatcct ctcatgccac | 180 |
| gacttcctct cctcaacgac actgcgtttg caacgagttt cacctccaag ctcagaagct | 240 |
| tgaattctgt tcagtttccc gcaaaagtcc cgcagacaat agatcgcaat ctcttcttcg | 300 |
| cagtggggct gcgacggag tcttgtcaga cctgtaacgg tggcctccgt gcttccgcat | 360 |
| caatcaacaa cataagcttc gtcatgccca gcatttctct tctgg | 405 |

<210> SEQ ID NO 260
<211> LENGTH: 1352
<212> TYPE: DNA
<213> ORGANISM: Pinus radiata

<400> SEQUENCE: 260

| acaccactta tccctttacc tttaccaggc cgcatcgcca gattcccatt cttctaggag | 60 |
| aatggtggaa taggaatccc atggacgttg tgaatcaagc aacccaaaca ggagctgccc | 120 |
| ccaacgtttc agatgcattt actataaatg acaaccagg cgacctatac aaatgttcta | 180 |
| cttcagatac cttagcgtg tcgatgaaag gtggggaaac taatcttcta cgtgttatca | 240 |
| acgctgcact caatactgac ctattcttct ccattgctag ccacacaatg acagttgtcg | 300 |
| ctgtggatgc cttgtataca aaaccttttc agacgaatgt tctgatgctc ggccccggcc | 360 |
| agacaacaga catacttctc actgccaatc aggctacagg tagatactac atggctgctc | 420 |
| gagcatattc cagcgggcaa ggagttccct tcgataacac cactaccact gccattttag | 480 |
| aatacgaggg aagctctaag acttcaactc cagtcatgcc taatcttcca ttctataacg | 540 |
| acaccaacag tgctactagc ttcgctaatg gtcttagaag cttgggctca cacgaccacc | 600 |
| cagtcttcgt tcctcagagt gtggaggaga atcgttcta caccatcggt ttggggttga | 660 |
| tcaaatgtcc ggggcagtct tgtggaggtc ccaacggatc aagatttgca gcaagtatga | 720 |

```
ataacatatc atttgtcccg ccaaccactt cttccatcct tcaagctcag cattttggca        780
tgaaaggagt attctccgcg gacttccccg ataacccttc cgtgggattt gattataccg        840
cacagaacat cagcgagaac ctctggtccc ctgtgaaagc cacaagagtg aaagttctta        900
aatataactc gacggtgcaa gtaattcttc aaggaaccaa tatatttgcg ggtgaaagcc        960
atcctatcca tctccatggt tatgacttct acatcgtggg agcaggcttt ggcaattata       1020
acgcacaaac cgatcctcac aagttcaacc tggtggatcc tcctatgcgc aacactgtga       1080
acgttccagt caatggctgg gctgcaataa gattcgtggc tgacaatcct ggagcttggg       1140
tgatgcactg ccacttggac gtgcacataa catgggggatt ggccatggtg tttgtggtta      1200
acaatggacc tgacgctctt ttgagtctcc agtcacctcc cagagatctt ccgctatgct       1260
gaggaaaact gtgatgcata cgatcctct attggtccca cttcattctt tttccttctc        1320
gtcactttgc tccttccatc gtttatgtct at                                     1352

<210> SEQ ID NO 261
<211> LENGTH: 337
<212> TYPE: DNA
<213> ORGANISM: Pinus radiata

<400> SEQUENCE: 261
ttcttaacta taacgcgaca gttcaagtaa ttctccaggg aacaaatata tttgctggtg         60
aaagccatcc tatccatctc catggttatg acttttacat cgtgggagca gggtttggta       120
attataatgc acaaacagat cctcagaagt tcaacctggt ggatcctcct atgcgcaaca       180
ctgtgaacgt tccagtcaat ggctgggctg ccataagatt cgttgctgac aatcctggag       240
cttgggtgat gcactgccac ttagacgtgc acataacatg ggggttggcg atggtttttg       300
tggttaacaa tggacctgat cctctttttga gtctcca                              337

<210> SEQ ID NO 262
<211> LENGTH: 279
<212> TYPE: DNA
<213> ORGANISM: Pinus radiata

<400> SEQUENCE: 262
acaagagtga aagttcttaa ttataacaca acggtgcaag taattcttca aggaacaaat        60
atatttgcgg gtgaaagcca tcctattcat ctccatggtt atgacttcta catagtggga       120
gcaggatttg gcaattataa tccacaaacc gatcctcaaa agttcaacct ggcggatcct       180
cctatgcgca acactgtaaa cgttccagtt aatggctggg ctgcaataag attcgtggcc       240
gacaatcctg gcgcttgggt gatgcactgc cacttggac                             279

<210> SEQ ID NO 263
<211> LENGTH: 279
<212> TYPE: DNA
<213> ORGANISM: Pinus radiata

<400> SEQUENCE: 263
aaaacctttt cagacgaatg ttctgatgct cggccccggc cagacaacag acatagcggc        60
cgcgtcgacc aacttgcaga tacctttagc gtgtcgatga aggtggggaa aactaatctt       120
ctacgtgtta tcaacgctgc actcaatact gacctattct tctccattgc tagccacaca       180
atgacagttg tcgctgtgga tgccttgtat acaaaacctt ttcagacgaa tgttctgatg       240
ctcggccccg gccagacaac agacatagcg gccgcgaat                             279
```

-continued

<210> SEQ ID NO 264
<211> LENGTH: 474
<212> TYPE: DNA
<213> ORGANISM: Pinus radiata

<400> SEQUENCE: 264

| | | | | | |
|---|---|---|---|---|---|
| ccctgactct | acaatcaata | cgtcgttcct | gcaacagtta | caagggcagt | gtcctcgggc | 60 |
| tggtggagac | gagttgcctt | cgtctcttga | ctacgtaacg | ccagcccgtt | ttgataacac | 120 |
| ttactttgcc | aacttgaagc | agcagaaggg | tgttctgcac | tctgatcgca | cgctatacga | 180 |
| tcccgcagcc | tcaggggtctg | taactagcag | tacagttgat | catttctctt | ctgatcagac | 240 |
| tgctttcttc | gaaagcttca | aggagccat | gatcaaaatg | gggaacctca | gcccttcggc | 300 |
| cggaacgcaa | ggagaaatcc | ggcgggactg | cagaaaagta | aattagagag | ctcctagcct | 360 |
| tcatccagag | gcatcaacca | tgaggataag | ttggataaat | tatcttgtct | taatatcagg | 420 |
| ttggatttag | tggtataata | tcgggttgga | tttagtggta | aaaaaaaaaa | aaaa | 474 |

<210> SEQ ID NO 265
<211> LENGTH: 1790
<212> TYPE: DNA
<213> ORGANISM: Pinus radiata

<400> SEQUENCE: 265

| | | | | | |
|---|---|---|---|---|---|
| ggcacgaggc | aaacttggtc | gtttgtttag | gttttgctgc | aggtgaacac | taatatggaa | 60 |
| ggccagattg | cagcattaag | caaagaagat | gagttcattt | ttcacagccc | ttttcctgca | 120 |
| gtacctgttc | cagagaatat | aagtcttttc | cagtttgttc | tggaaggtgc | tgagaaatac | 180 |
| cgtgataagg | tggccctcgt | ggaggcctcc | acagggaagg | agtacaacta | tggtcaggtg | 240 |
| atttcgctca | caaggaatgt | tgcagctggg | ctcgtggaca | aaggcattca | aaagggcgat | 300 |
| gttgtatttg | ttctgcttcc | aaatatggca | gaatacccca | ttattgtgct | gggaataatg | 360 |
| ttggccggcg | cagtgttttc | tggggcaaat | ccttctgcac | acatcaatga | agttgaaaaa | 420 |
| catatccagg | attctggagc | aaagattgtt | gtgacagttg | gtctgctta | tgagaaggtg | 480 |
| aggcaagtga | aactgcctgt | tattattgca | gataacgagc | atgtcatgaa | cacaattcca | 540 |
| ttgcaggaaa | ttttgagag | aaactatgag | gccgcagggc | cttttgtaca | aatttgtcag | 600 |
| gatgatctgt | gtgcactccc | ttattcctct | ggcaccacag | gggcctctaa | aggtgtcatg | 660 |
| ctcactcaca | gaaatctgat | tgcaaatctg | tgctctagct | tgtttgatgt | ccatgaatct | 720 |
| cttgtaggaa | atttcaccac | gttgggggctg | atgccattct | ttcacatata | tggcatcacg | 780 |
| ggcatctgtt | gcgccactct | tcgcaacgga | ggcaaggtcg | tggtcatgtc | cagattcgat | 840 |
| ctccgacact | ttatcagttc | tttgattact | tatgaggtca | acttcgcgcc | tattgtcccg | 900 |
| cctataatgc | tctccctcgt | taaaaatcct | atcgttaacg | agttcgatct | cagccgcttg | 960 |
| aaactcaaag | ctgtcatgac | tgcggctgct | ccactggcgc | cggatctact | gcgagcgttc | 1020 |
| gaggaaaaat | tccctggggt | tgaggttcaa | gaggcctatg | gtcttacgga | acacagttgc | 1080 |
| atcacattga | ctcattgcgc | tcccggaaac | atacgtggga | gagccaagaa | gagttcggtt | 1140 |
| ggttttatta | ttcccaatct | ggaggtgaag | tttattgatc | ccgaaactgg | aaagtcattg | 1200 |
| cccaggaatt | ccatcgggga | ggtgtgcgtc | agaagccaat | gtgtcatgcg | agggtattac | 1260 |
| aagaaaccga | cagaaaccga | gaaaacagtg | gacagcgacg | gctggctgca | tactgggat | 1320 |
| gtcggtttca | tagatgatga | cgacgacgta | ttcatcgtcg | acagaattaa | agagctgatc | 1380 |
| aaatacaaag | gttttcaggt | tgctcctgca | gaactggaag | ccattctact | ttctcatcca | 1440 |

-continued

| | |
|---|---|
| tcagtggaag acgcagcagt ggttcccttta cctgatgagg aagcagggga gattccagcg | 1500 |
| gcgtgcgtgg tgatggcagc cagtgctacg gagacggagg acgacatttc gaagtttgtg | 1560 |
| gcgtcgcagg tggctacata caagagggtg agactggtga agtttgtgtc caccattcct | 1620 |
| aaatcttctt ccggaaagat cctgcgcaga cttctgagag ataatctccg tgaaacgctc | 1680 |
| aaaaaccagc accaaccatt gtccacttag gctttgcagc gttatatata aataaataat | 1740 |
| caaacatcta gggatgggat tatagcccca taacatacat tttgaaattc | 1790 |

<210> SEQ ID NO 266
<211> LENGTH: 2043
<212> TYPE: DNA
<213> ORGANISM: Eucalyptus grandis

<400> SEQUENCE: 266

| | |
|---|---|
| gcgccaccac caaacgctca ccttctcatc atcagccctc tgtctctgtc tctgtctctc | 60 |
| gattctccgc cccgccacga caatggaggc gaagccgtcg gagcagcccc gcgagttcat | 120 |
| cttccggtcg aagctccccg acatctacat tcccgacaac ctctccctcc acgcctactg | 180 |
| cttcgagaac atctccgagt tcgccgaccg cccctgcgtc atcaacgggg ccaccggccg | 240 |
| gacctacacc tatgccgagg tcgagctgat ctcccgccgg gtctcagccg gcctcaacgg | 300 |
| gctcggcgtc ggacagggcg acgtgatcat gctgctcctc cagaactgcc ctgagttcgt | 360 |
| gttcgcgttc ctcggcgcgt cctaccgggg cgccatcagc acgaccgcga acccgttcta | 420 |
| caccccgggc gagatcgcca agcaggcctc agctgcccgg gccaagatcg tgatcacgca | 480 |
| ggccgcgttc gccgacaagg tgaggccgtt cgcggaggag aacggggtga aggtcgtgtg | 540 |
| catcgatacc gcgccggagg gctgcctgca cttctcggaa ttgatgcagg cggacgagaa | 600 |
| cgccgccccc gcggcggacg tcaagccgga cgacgtcttg gcgctcccct attcgtcggg | 660 |
| cacgacgggg cttcccaagg gagtgatgct tacgcacagg ggtcaagtga ccagcgtggc | 720 |
| gcagcaggtc gacggagaca accccaactt gtacttccac aaggaggacg tgatcctgtg | 780 |
| cacgctcccg ttgttccaca tatactccct caactcggtg atgttctgcg cgctccgtgt | 840 |
| cggcgccgcc atcctgatca tgcagaagtt cgagatcgtg gcgctgatgg agctcgtgca | 900 |
| gcggtaccgg gtgacgatcc tgcccattgt cccgccgatc gtgctggaga tcgcaagag | 960 |
| cgccgaggtg gaccggtacg acctgtcgtc gatccggacc atcatgtcgg gtgcggcccc | 1020 |
| gatggggaag gagctcgagg acaccgtgcg agccaagctg cccaatgcca agctcggaca | 1080 |
| gggctatggg atgacggagg cgggcccggt gctggcaatg tgcccggcat ttgcaaagga | 1140 |
| gccgttcgag atcaagtcag gcgcatgcg gaccgtcgtg aggaacgcgg agatgaagat | 1200 |
| cgtcgacccg gagacagggg cctcgctccc gcggaaccag gccggcgaga tctgcatccg | 1260 |
| gggtcaccag atcatgaaag gttatctgaa cgacgccgag gcgaccgcaa ataccataga | 1320 |
| caaagaaggg tggctgcaca ccggcgacat cggctacata gacgatgacg acgagctctt | 1380 |
| cattgtcgat cggttgaagg aactcatcaa gtacaagggc ttccaggttg ctccggccga | 1440 |
| gctagaggca atgctgattg cacacccaag tatctcggat gccgctgttg tgccgatgaa | 1500 |
| ggatgaggtt gccggtgagg ttcctgttgc attcgtggtg aaatccaatg gttccgtaat | 1560 |
| caccgaggac gaaatcaagc aatacatctc gaagcaggtc gtgttttaca agaggatcaa | 1620 |
| gcgggttttc ttcacggacg caattccgaa agcccctcc ggaaaaatct tgaggaagga | 1680 |
| cctaagagca aagttggcct ctggtgttta caattaattt ctcatacct tttcttttc | 1740 |
| aaccctgccc ctgtacttgc ttaaagaccc atgtagttga aatgaatgta acctcttcgg | 1800 |

-continued

```
agggggccaaa tatggaaggg ggaaagaaag acatatggcg atgatttgat ttcacatgct   1860
attgtaatgt atttattgtt tcaattccga attagacaaa gtgcttaaag ctctcttttc   1920
ggattttttt tttcattaat gtataataat tgcggacatt acaatatact gtacaacgtg   1980
atttgagctt gatgaattac aagattggaa gaacttcgaa gacaaaaaaa aaaaaaaaaa   2040
aaa                                                                 2043
```

<210> SEQ ID NO 267
<211> LENGTH: 92
<212> TYPE: PRT
<213> ORGANISM: Pinus radiata

<400> SEQUENCE: 267

```
Lys Glu Thr Gly Leu Leu Asn Gln Phe Val Asp Ile Tyr Gln Glu Met
  1               5                  10                  15

Asp Asp Ser Val Gln Glu Val Ser Lys Glu Gly Asn Gln Trp Ala Gly
                 20                  25                  30

Phe Ile Glu Gly Glu Asn Val Ile Arg Arg Gly Arg Glu Ile Leu Leu
             35                  40                  45

Gln His Asp Asn Arg Glu Ala His Asn Trp Glu Ser His Lys His Lys
         50                  55                  60

Trp Trp Pro His Leu Glu Glu Lys Ile Pro His Ile Ala Lys Ala Gly
 65                  70                  75                  80

Phe Thr Ser Ile Trp Leu Pro Pro Ala Phe Asp Ser
                 85                  90
```

<210> SEQ ID NO 268
<211> LENGTH: 182
<212> TYPE: PRT
<213> ORGANISM: Pinus radiata

<400> SEQUENCE: 268

```
Leu Leu His Gln Phe Val Tyr Ser Phe Arg Lys Met Gly Tyr Pro Val
  1               5                  10                  15

Gln Glu Val Ser Lys Glu His Asp Gln Trp Ala Gly Phe Val Glu Gly
                 20                  25                  30

Glu Ser Val Leu Gln Arg Gly Arg Glu Ile Leu Leu Gln Gly Phe Asn
             35                  40                  45

Trp Glu Ser His Lys Tyr Lys Trp Trp Pro Asn Leu Glu Glu Lys Ile
         50                  55                  60

Pro His Ile Ala Lys Ala Gly Phe Thr Ser Val Trp Leu Pro Pro Ala
 65                  70                  75                  80

Phe Asp Ser Ala Ala Pro Gln Gly Tyr Leu Pro Arg Asn Ile Tyr Ser
                 85                  90                  95

Leu Asn Ser Ala Tyr Gly Ser Glu Tyr Gln Leu Lys Ser Leu Leu Met
                100                 105                 110

Thr Met Arg Lys Lys Asn Val Arg Ala Met Ala Asp Ile Val Ile Asn
            115                 120                 125

His Arg Met Gly Ser Ser Gln Gly Phe Gly Gly Leu Tyr Asn Arg Tyr
        130                 135                 140

Tyr Gly Cys Leu Pro Trp Asp Glu Arg Ala Val Thr Arg Cys Ser Gly
145                 150                 155                 160

Gly Leu Gly Asn Trp Ser Thr Gly Asp Asn Phe His Gly Val Pro Asn
                165                 170                 175

Val Asp His Thr Gln Asp
```

<210> SEQ ID NO 269
<211> LENGTH: 218
<212> TYPE: PRT
<213> ORGANISM: Pinus radiata

<400> SEQUENCE: 269

```
Arg Met Ala Lys Phe Arg Ser Leu Ser Leu Leu Trp Phe Ser Cys
  1               5                  10                  15

Ile Ile Val Asn Ala Ala Ser Pro Ala Gln Ala Glu Ala Thr Thr Pro
                 20                  25                  30

Pro Leu Asn Thr Leu Leu Leu Gln Gly Phe Asn Trp Asp Ser Ala Gln
             35                  40                  45

Ser Ser Thr Pro Trp Tyr Asn Val Leu Lys Gly Ile Val Asp Asp Ala
 50                  55                  60

Ala Asp Ala Gly Ile Thr Tyr Val Trp Phe Pro Pro Ser Gln Ser
 65                  70                  75                  80

Gly Ala Pro Gln Gly Tyr Leu Pro Ala Lys Leu Tyr Asp Leu Asp Ser
                 85                  90                  95

Ser Tyr Gly Ser Glu Gln Leu Lys Asp Ala Val Asn Ala Phe His
            100                 105                 110

Gln Lys Gly Ile Ala Ile Met Gly Asp Ile Val Ile Asn His Arg Asn
        115                 120                 125

Gly Thr Lys Gln Asp Asp Lys Gly Tyr Trp Cys Val Phe Glu Gly Gly
130                 135                 140

Lys Gly Asp Gly Thr Leu Asp Trp Gly Pro Trp Ala Val Thr Val Lys
145                 150                 155                 160

Asp Gln Pro Tyr Pro Leu Cys Gly Ser Gly Gln Ala Asp Thr Gly Gly
                165                 170                 175

Asp Phe Lys Tyr Ala Pro Asp Val Asp His Thr Asn Pro Lys Ile Gln
            180                 185                 190

Gln Asp Leu Ser Glu Trp Met Asn Trp Leu Lys Ser Met Ser Asp Leu
        195                 200                 205

Met Ala Gly Gly Ser Thr Thr Ser Arg Leu
210                 215
```

<210> SEQ ID NO 270
<211> LENGTH: 145
<212> TYPE: PRT
<213> ORGANISM: Eucalyptus grandis

<400> SEQUENCE: 270

```
Gly Val Gly Arg Leu Val Asp Val Gly Gly Ser Ala Gly Asp Cys Leu
  1               5                  10                  15

Arg Met Ile Met Gly Lys His Thr His Val Arg Glu Gly Ile Asn Phe
                 20                  25                  30

Asp Leu Pro Glu Val Val Ala Lys Ala Pro Ile Pro Gly Val Thr
             35                  40                  45

His Val Gly Gly Asp Met Phe Lys Ser Ile Pro Ala Gly Asp Ala Ile
 50                  55                  60

Phe Met Arg Trp Ile Leu Thr Thr Trp Thr Asp Asp Glu Cys Lys Gln
 65                  70                  75                  80

Ile Leu Glu Asn Cys Phe Lys Ala Leu Pro Ala Gly Gly Lys Leu Ile
                 85                  90                  95

Ala Cys Glu Pro Val Leu Pro Gln His Ser Asp Asp Ser His Arg Thr
```

```
                100             105             110
Arg Ala Leu Leu Glu Gly Asp Ile Phe Val Met Thr Ile Tyr Arg Ala
            115                 120                 125
Lys Gly Lys His Arg Thr Glu Gln Glu Phe Gln Gln Leu Gly Leu Ser
        130                 135                 140
Thr
145

<210> SEQ ID NO 271
<211> LENGTH: 198
<212> TYPE: PRT
<213> ORGANISM: Eucalyptus grandis

<400> SEQUENCE: 271

Pro Thr Met Ala Asp Asn Gln Glu Arg Glu Gly Arg Asp Gln Glu Glu
  1               5                  10                  15

Glu Val Gly Lys Leu Ala Val Gln Leu Ala Ser Ala Val Val Leu Pro
              20                  25                  30

Met Thr Leu Lys Ser Ala Leu Glu Leu Gly Ile Ile Asp Ala Leu Val
            35                  40                  45

Ser Ala Gly Gly Phe Leu Ser Ala Ala Glu Ile Ala Ser Arg Val Gly
        50                  55                  60

Ala Lys Asn Pro Gly Ala Pro Val Leu Val Asp Arg Met Met Arg Leu
 65                  70                  75                  80

Leu Ala Ser His Gly Val Ile Glu Trp Arg Leu Arg Arg Gly Asp Gly
                85                  90                  95

Asn Gly Asp Gly Gly Glu Arg Glu Tyr Gly Pro Gly Pro Met Cys Arg
            100                 105                 110

Phe Phe Ala Lys Asp Gln Glu Gly Gly Asp Val Gly Pro Leu Phe Leu
        115                 120                 125

Leu Ile His Asp Lys Val Phe Met Glu Ser Trp Tyr His Leu Asn Asp
    130                 135                 140

Val Ile Met Glu Gly Gly Val Pro Phe Glu Arg Ala Tyr Gly Met Thr
145                 150                 155                 160

Ala Phe Glu Tyr Pro Ala Val Asp Asp Arg Phe Asn Gln Val Phe Asn
                165                 170                 175

Arg Ala Met Ala Ser His Thr Ser Leu Ile Met Lys Lys Ile Leu Asp
            180                 185                 190

Val Tyr Arg Gly Phe Glu
        195

<210> SEQ ID NO 272
<211> LENGTH: 156
<212> TYPE: PRT
<213> ORGANISM: Eucalyptus grandis

<400> SEQUENCE: 272

Pro Thr Pro Leu Tyr Met Asn Lys Ile Leu Glu Ser Tyr Arg Gly Phe
  1               5                  10                  15

Glu Gly Ala Lys Thr Ile Ala Asp Leu Gly Gly Val Gly Gln Asn
              20                  25                  30

Leu Arg Leu Ile Leu Asp Lys Phe Pro Asn Leu Arg Gly Ile Leu Tyr
            35                  40                  45

Asp Leu Pro His Val Ile Lys Asp Ala Pro Ala His Pro Arg Met Glu
        50                  55                  60

Arg Val Gly Gly Asp Leu Leu Lys Ser Val Pro Lys Ala Asp Ile Leu
```

-continued

```
                65                  70                  75                  80
Phe Met Lys Trp Leu Phe His Gly Leu Arg Asp Asp Phe Cys Lys Met
                    85                  90                  95

Leu Leu Gln Asn Cys Tyr Glu Ala Leu Pro Pro Asn Gly Lys Val Val
                100                 105                 110

Ile Val Asp Pro Ile Leu Pro Glu Tyr Pro Glu Thr Asp Ile Val Ser
                115                 120                 125

Arg Asn Ser Phe Thr Ser Asp Met Ile Met Leu Tyr Thr Ser Pro Gly
                130                 135                 140

Glu Asp Arg Thr Arg Lys Glu Leu Glu Val Leu Ala
145                 150                 155

<210> SEQ ID NO 273
<211> LENGTH: 166
<212> TYPE: PRT
<213> ORGANISM: Eucalyptus grandis

<400> SEQUENCE: 273

Ser Ser Phe Gln Pro Cys Tyr Glu Glu Ala Asn Ser Leu Asp Arg Trp
1               5                   10                  15

Ile Gln Pro Pro Ser Asp Leu Leu His Asn Met Ser Asp Lys Glu Leu
                20                  25                  30

Phe Trp Arg Ala Thr Leu Val Pro Lys Ile Lys Lys Tyr Pro Phe Arg
                35                  40                  45

Arg Val Pro Lys Ile Ala Phe Met Phe Leu Thr Lys Gly Pro Leu Pro
            50                  55                  60

Leu Ala Pro Leu Trp Glu Arg Phe Phe Lys Gly His Glu Gly Leu Tyr
65                  70                  75                  80

Ser Ile Tyr Ile His Ser His Pro Ser Phe His Ala His Phe Pro
                85                  90                  95

Trp Ser Val Phe Asn Arg Arg Gln Ile Pro Ser Gln Val Ser Glu Trp
                100                 105                 110

Gly Arg Met Ser Met Cys Asp Ala Glu Lys Arg Leu Leu Ala Asn Ala
                115                 120                 125

Leu Leu Asp Ile Ser Asn Glu Arg Phe Ile Leu Leu Ser Glu Ser Cys
            130                 135                 140

Ile Pro Leu Tyr Asn Phe Ser Leu Ile Tyr His Tyr Ile Met Lys Ser
145                 150                 155                 160

Gly Tyr Ser Phe Met Gly
                165

<210> SEQ ID NO 274
<211> LENGTH: 328
<212> TYPE: PRT
<213> ORGANISM: Eucalyptus grandis

<400> SEQUENCE: 274

Ile Leu Ser Arg Lys Pro Lys Glu Lys Thr Val Gly Arg Lys Asn Ile
1               5                   10                  15

Lys Lys Asn Met Ser Ser Lys Glu Ala Pro Val Ile Thr Thr Ser His
                20                  25                  30

Glu Asp Glu Glu Ile Leu Asn Ala Phe Glu Val Pro Ser Met Ala Phe
                35                  40                  45

Val Pro Met Val Leu Lys Gly Val His Glu Leu Gly Ile Leu Glu Leu
            50                  55                  60

Leu Ala Lys Gly Asp Gln Leu Ser Pro Leu Asp Ile Val Ala Arg Leu
```

-continued

```
                65                   70                 75                  80
Ser Ile Asp Asn Pro Ala Ala Asp Thr Ile Asp Arg Met Leu Arg
                        85                  90                  95
Leu Leu Ala Ser Tyr Ser Ile Leu Ser Cys Thr Leu Val Glu Asp Lys
                100                 105                 110
Glu Gly Arg Pro Gln Arg Leu Tyr Gly Leu Gly Pro Arg Ser Lys Phe
            115                 120                 125
Phe Leu Asp Gln Asn Gly Ala Ser Thr Leu Pro Thr His Met Leu Leu
        130                 135                 140
Gln Glu Lys Thr Leu Leu Glu Cys Trp Asn Cys Leu Lys Asp Ala Val
145                 150                 155                 160
Lys Glu Gly Gly Ala Asp Pro Phe Thr Arg Arg His Gly Met Asn Val
                165                 170                 175
Phe Asp Tyr Met Gly Gln Asp Pro Arg Phe Asn Asp Leu Tyr Asn Lys
                180                 185                 190
Ser Met Arg Thr Gly Ser Ala Ile Tyr Met Pro Lys Ile Ala Gln His
            195                 200                 205
Tyr Arg Gly Phe Ser Lys Ala Lys Thr Val Val Asn Val Gly Gly Gly
    210                 215                 220
Ile Gly Glu Thr Leu Lys Thr Ile Leu Ser Lys Asn Pro His Ile Arg
225                 230                 235                 240
Ala Ile Asn Tyr Asp Leu Pro His Val Ile Ala Thr Ala Pro Pro Ile
                245                 250                 255
Pro Gly Ile Thr His Val Gly Gly Asp Ile Leu Lys Ser Val Pro Lys
                260                 265                 270
Ala Asp Val His Phe Leu Lys Ser Val Leu His Arg Gly Asp Asp Glu
            275                 280                 285
Phe Cys Val Lys Val Leu Lys Asn Cys Trp Glu Ala Leu Pro Pro Thr
        290                 295                 300
Gly Lys Val Val Ile Val Glu Glu Val Thr Pro Glu Tyr Pro Gly Thr
305                 310                 315                 320
Asp Asp Val Ser Gln Thr Thr Leu
                325

<210> SEQ ID NO 275
<211> LENGTH: 160
<212> TYPE: PRT
<213> ORGANISM: Pinus radiata

<400> SEQUENCE: 275

Asp Val Gly Gly Gly Ile Gly Ser Ala Leu Ser Ile Ile Val Lys Glu
  1               5                  10                  15
His Pro His Ile Arg Gly Ile Asn Leu Asp Leu Pro His Val Ile Ala
                 20                  25                  30
Thr Ala Pro Leu Ile Thr Gly Val Glu His Met Glu Gly Asn Met Phe
             35                  40                  45
Glu His Ile Pro Ser Ala Asp Ala Val Met Met Lys Trp Ile Leu His
         50                  55                  60
Asp Trp Ala Asp Glu Glu Cys Val Lys Leu Leu Arg Arg Ser Tyr Asp
 65                  70                  75                  80
Ala Thr Pro Ala Lys Gly Lys Val Leu Ile Val Glu Ala Val Val Glu
                 85                  90                  95
Gly Asp Lys Glu Gly Glu Ser Met Ser Arg Arg Leu Gly Leu Leu Tyr
                100                 105                 110
```

```
Asp Ile Ser Met Met Ala Tyr Thr Thr Gly Gly Lys Glu Arg Thr Glu
            115                 120                 125

Glu Glu Phe Lys Gly Leu Phe Gln Arg Ala Gly Phe Lys Ser His Thr
        130                 135                 140

Ile Ile Lys Leu Pro Phe Leu Gln Ser Leu Ile Val Leu Ser Lys Ala
145                 150                 155                 160

<210> SEQ ID NO 276
<211> LENGTH: 112
<212> TYPE: PRT
<213> ORGANISM: Eucalyptus grandis

<400> SEQUENCE: 276

Ser Leu Arg Thr Tyr Ser Asn Met Glu Gln Gly Trp Asp Lys Gly Glu
1               5                   10                  15

Ile Leu Ala Ser Lys Ala Leu Ser Lys Tyr Ile Leu Glu Thr Asn Ala
            20                  25                  30

Tyr Pro Arg Glu His Glu Gln Leu Lys Glu Leu Arg Glu Ala Thr Val
        35                  40                  45

Gln Lys Tyr Gln Ile Arg Ser Ile Met Asn Val Pro Val Asp Glu Gly
    50                  55                  60

Gln Leu Ile Ser Met Met Leu Lys Leu Met Asn Ala Lys Lys Thr Ile
65                  70                  75                  80

Glu Ile Gly Val Phe Thr Gly Tyr Ser Leu Leu Thr Thr Ala Leu Ala
                85                  90                  95

Leu Pro Ala Asp Gly Lys Ile Ile Ala Ile Asp Gln Asp Lys Glu Ala
            100                 105                 110

<210> SEQ ID NO 277
<211> LENGTH: 133
<212> TYPE: PRT
<213> ORGANISM: Eucalyptus grandis

<400> SEQUENCE: 277

Arg Thr Tyr Ser Asp Met Glu Arg Gly Gly Asp Lys Gly Glu Ile Leu
1               5                   10                  15

Ala Ser Lys Ala Leu Ser Lys Tyr Ile Leu Glu Thr Asn Ala Tyr Pro
            20                  25                  30

Arg Glu His Glu Gln Leu Lys Glu Leu Arg Glu Ala Thr Val Gln Lys
        35                  40                  45

Tyr Gln Met Arg Ser Ile Met Ser Val Pro Ala Asp Glu Gly Gln Leu
    50                  55                  60

Ile Ser Met Met Leu Lys Leu Met Asn Ala Lys Lys Thr Ile Glu Ile
65                  70                  75                  80

Gly Val Phe Thr Gly Tyr Ser Leu Leu Thr Thr Ala Leu Ala Leu Pro
                85                  90                  95

Ala Asp Gly Lys Ile Ile Ala Ile Asp Pro Asp Lys Glu Ala Tyr Glu
            100                 105                 110

Ile Gly Leu Pro Tyr Ile Lys Lys Ala Gly Val Asp His Lys Ile Asn
        115                 120                 125

Phe Ile Gln Ser Asp
    130

<210> SEQ ID NO 278
<211> LENGTH: 98
<212> TYPE: PRT
<213> ORGANISM: Eucalyptus grandis
```

<400> SEQUENCE: 278

```
Leu Gln Tyr Ile Leu Glu Thr Asn Ala Tyr Pro Arg Glu His Glu Gln
1               5                   10                  15

Leu Lys Glu Leu Arg Glu Ala Thr Val Gln Lys Tyr Gln Ile Arg Ser
            20                  25                  30

Ile Met Asn Val Pro Ala Asp Glu Gly Gln Leu Ile Ser Met Met Leu
        35                  40                  45

Lys Leu Met Asn Ala Lys Lys Thr Ile Glu Ile Gly Val Phe Thr Gly
50                  55                  60

Cys Ser Leu Leu Thr Thr Ala Leu Ala Leu Pro Ala Asp Gly Lys Ile
65                  70                  75                  80

Ile Ala Ile Asp Pro Asp Lys Glu Ala Tyr Glu Ile Gly Leu Pro Tyr
                85                  90                  95

Ile Arg
```

<210> SEQ ID NO 279
<211> LENGTH: 157
<212> TYPE: PRT
<213> ORGANISM: Eucalyptus grandis

<400> SEQUENCE: 279

```
Arg His His Gln Thr Leu Thr Phe Ser Ser Ala Leu Cys Leu Cys
1               5                   10                  15

Leu Cys Leu Ser Ile Leu Arg Pro Ala Thr Met Glu Ala Lys Pro
            20                  25                  30

Ser Glu Gln Pro Arg Glu Phe Ile Phe Arg Ser Lys Leu Pro Asp Ile
        35                  40                  45

Tyr Ile Pro Asp Asn Leu Ser Leu His Ala Tyr Cys Phe Glu Asn Ile
    50                  55                  60

Ser Glu Phe Ala Asp Arg Pro Cys Val Ile Asn Gly Ala Thr Gly Arg
65                  70                  75                  80

Thr Tyr Thr Tyr Ala Glu Val Glu Leu Ile Ser Arg Arg Val Ser Ala
                85                  90                  95

Gly Leu Asn Gly Leu Gly Val Gly Gln Gly Asp Val Ile Met Leu Leu
            100                 105                 110

Leu Gln Asn Cys Pro Glu Phe Val Phe Ala Phe Leu Gly Ala Ser Tyr
        115                 120                 125

Arg Gly Ala Ile Ser Thr Thr Ala Asn Pro Phe Tyr Thr Pro Gly Glu
    130                 135                 140

Ile Ala Lys Gln Ala Ser Ala Ala Arg Ala Lys Ile Val
145                 150                 155
```

<210> SEQ ID NO 280
<211> LENGTH: 180
<212> TYPE: PRT
<213> ORGANISM: Eucalyptus grandis

<400> SEQUENCE: 280

```
Phe Ala Asp Lys Val Arg Pro Phe Ala Glu Glu Asn Gly Val Lys Val
1               5                   10                  15

Val Cys Ile Asp Thr Ala Pro Glu Gly Cys Leu His Phe Ser Glu Leu
            20                  25                  30

Met Gln Ala Asp Glu Asn Ala Ala Pro Ala Ala Asp Val Lys Pro Asp
        35                  40                  45

Asp Val Leu Ala Leu Pro Tyr Ser Ser Gly Thr Thr Gly Leu Pro Lys
    50                  55                  60
```

```
Gly Val Met Leu Thr His Arg Gly Gln Val Thr Ser Val Ala Gln Gln
 65                  70                  75                  80

Val Asp Gly Asp Asn Pro Asn Leu Tyr Phe His Lys Glu Asp Val Ile
                 85                  90                  95

Leu Cys Thr Leu Pro Leu Phe His Ile Tyr Ser Leu Asn Ser Val Met
            100                 105                 110

Phe Cys Ala Leu Arg Val Gly Ala Ala Ile Leu Ile Met Gln Lys Phe
            115                 120                 125

Glu Ile Val Ala Leu Met Glu Leu Val Gln Arg Tyr Arg Val Thr Ile
130                 135                 140

Leu Pro Ile Val Pro Pro Ile Val Leu Glu Ile Ala Lys Ser Ala Glu
145                 150                 155                 160

Val Asp Arg Tyr Asp Leu Ser Ser Ile Arg Thr Ile Met Ser Gly Ala
                165                 170                 175

Ala Arg Trp Gly
            180

<210> SEQ ID NO 281
<211> LENGTH: 180
<212> TYPE: PRT
<213> ORGANISM: Eucalyptus grandis

<400> SEQUENCE: 281

Gly Gln Leu Val Ala Gly Val Glu Ala Gln Val Ile Ser Val Asp Thr
 1               5                  10                  15

Leu Lys Ser Leu Pro Pro Asn Gln Leu Gly Glu Ile Trp Val Arg Gly
             20                  25                  30

Pro Asn Met Met Lys Gly Tyr Tyr Asn Asn Pro Gln Ala Thr Lys Leu
         35                  40                  45

Thr Ile Asp Asn Lys Gly Trp Val His Thr Gly Asp Leu Gly Tyr Phe
 50                  55                  60

Asp Glu Glu Gly Gln Leu Tyr Val Val Asp Arg Ile Lys Glu Leu Ile
 65                  70                  75                  80

Lys Tyr Lys Gly Phe Gln Ile Ala Pro Ala Glu Leu Glu Gly Leu Leu
                 85                  90                  95

Leu Ser His Pro Glu Ile Leu Asp Ala Val Val Ile Pro Phe Pro Asp
            100                 105                 110

Ala Glu Ala Gly Glu Val Pro Ile Ala Tyr Val Val Arg Ser Pro Thr
            115                 120                 125

Ser Ser Leu Thr Glu Glu Val Gln Lys Phe Ile Ala Asn Gln Val
            130                 135                 140

Ala Pro Phe Lys Arg Leu Arg Arg Val Thr Phe Val Asn Ser Val Pro
145                 150                 155                 160

Lys Ser Ala Ser Gly Lys Ile Leu Arg Arg Glu Leu Ile Ala Lys Val
                165                 170                 175

Arg Ala Lys Ile
            180

<210> SEQ ID NO 282
<211> LENGTH: 119
<212> TYPE: PRT
<213> ORGANISM: Pinus radiata

<400> SEQUENCE: 282

Gly Tyr Phe Asp Glu Glu Gly Gly Leu Phe Ile Val Asp Arg Ile Lys
 1               5                  10                  15
```

```
Glu Leu Ile Lys Tyr Lys Gly Phe Gln Val Ala Pro Ala Glu Leu Glu
                20                  25                  30

Gly Ile Leu Leu Thr His Pro Gln Ile Ala Asp Ala Gly Val Ile Pro
            35                  40                  45

Leu Pro Asp Leu Lys Ala Gly Glu Val Pro Ile Ala Tyr Val Val Arg
    50                  55                  60

Thr Pro Gly Ser Ser Leu Thr Glu Lys Asp Ala Met Asp Tyr Val Ala
65                  70                  75                  80

Lys Gln Val Ala Pro Phe Lys Arg Leu His Arg Val Asn Phe Val Asp
                85                  90                  95

Ser Ile Pro Lys Ser Ala Ser Gly Lys Ile Leu Arg Arg Glu Leu Ile
                100                 105                 110

Ala Lys Ala Lys Ser Lys Leu
            115

<210> SEQ ID NO 283
<211> LENGTH: 152
<212> TYPE: PRT
<213> ORGANISM: Pinus radiata

<400> SEQUENCE: 283

Asp Phe Pro Phe Phe Phe Leu Leu Arg Val Ala Met Ile Glu Val Gln
1               5                   10                  15

Ser Ala Pro Pro Met Ala Arg Ser Thr Glu Asn Glu Asn Asn Gln His
                20                  25                  30

Asp Ala Glu Glu Gly Ala Val Leu Asn Glu Gly Gly Met Asp Phe Leu
            35                  40                  45

Tyr Arg Ser Lys Leu Pro Asp Ile Asp Ile Pro Tyr His Leu Pro Leu
    50                  55                  60

His Ser Tyr Cys Phe Glu Lys Leu Asp Glu Leu Arg Glu Lys Pro Cys
65                  70                  75                  80

Leu Ile Gln Gly Ser Asn Gly Lys Ile Tyr Ser Tyr Gly Glu Val Glu
                85                  90                  95

Leu Ile Ser Arg Lys Val Ala Ser Gly Leu Ala Lys Leu Gly Phe Lys
                100                 105                 110

Lys Gly Asp Val Val Met Leu Leu Leu Pro Asn Cys Pro Glu Phe Val
            115                 120                 125

Phe Val Phe Leu Gly Ala Ser Met Ala Gly Ala Ile Ala Thr Thr Ala
    130                 135                 140

Asn Pro Phe Tyr Thr Pro Ser Asp
145                 150

<210> SEQ ID NO 284
<211> LENGTH: 330
<212> TYPE: PRT
<213> ORGANISM: Eucalyptus grandis

<400> SEQUENCE: 284

Asp His Pro Pro Ala Met Ala Leu His Ile Leu Phe Thr Trp Leu Ala
1               5                   10                  15

Leu Ser Leu Pro Leu Leu Leu Leu Leu Leu Ser Val Lys Asn Phe
                20                  25                  30

Asn Asn Lys Lys Lys Asn Leu Pro Pro Gly Pro Ser Leu Pro Ile
            35                  40                  45

Ile Gly Asn Phe His Gln Leu Gly Pro Leu Pro His Gln Ser Leu Trp
    50                  55                  60
```

```
Lys Leu Ser Arg Arg Tyr Gly Pro Val Met Leu Ile Arg Leu Gly Gly
 65                  70                  75                  80

Thr Pro Thr Ile Val Ile Ser Ser Pro Asp Ala Ala Arg Glu Val Leu
                 85                  90                  95

Lys Thr His Asp Leu Asp Ser Cys Ser Arg Pro Gln Met Val Gly Pro
            100                 105                 110

Gly Arg Leu Ser Tyr Asp Ser Leu Asp Met Ala Phe Val Glu Tyr Gly
            115                 120                 125

Asp Tyr Trp Arg Glu Leu Arg Thr Leu Cys Val Leu Glu Leu Phe Ser
130                 135                 140

Met Lys Arg Val Gln Ser Phe Arg Tyr Ile Arg Glu Glu Val Gly
145                 150                 155                 160

Ser Met Ile Glu Ser Ile Ala Lys Ser Ala Glu Ser Gly Thr Pro Val
                165                 170                 175

Asn Met Ser Glu Lys Phe Met Ala Leu Thr Ala Asn Phe Thr Cys Arg
            180                 185                 190

Val Ala Phe Gly Lys Pro Phe Gln Gly Thr Glu Leu Glu Asp Glu Gly
            195                 200                 205

Phe Met Asp Met Val His Glu Gly Met Ala Met Leu Gly Ser Phe Ser
210                 215                 220

Ala Ser Asp Tyr Phe Pro Arg Leu Gly Trp Ile Val Asp Arg Phe Thr
225                 230                 235                 240

Gly Leu His Ser Arg Leu Glu Lys Ser Phe Arg Asn Leu Asp Asp Leu
                245                 250                 255

Tyr Gln Lys Val Ile Glu Glu His Arg Asn Ala Asn Lys Ser Asn Glu
            260                 265                 270

Gly Lys Glu Asp Ile Val Asp Val Leu Leu Lys Met Glu Lys Asp Gln
            275                 280                 285

Thr Glu Leu Ala Gly Val Arg Leu Lys Glu Asp Asn Ile Lys Ala Ile
290                 295                 300

Leu Met Asn Ile Phe Leu Gly Gly Val Asp Thr Gly Ala Val Ser Trp
305                 310                 315                 320

Thr Gly Gln Trp Leu Ser Ser Leu Gly Thr
                325                 330

<210> SEQ ID NO 285
<211> LENGTH: 115
<212> TYPE: PRT
<213> ORGANISM: Eucalyptus grandis

<400> SEQUENCE: 285

Thr Glu Leu Glu Asp Glu Gly Phe Met Asp Met Val His Glu Gly Met
 1               5                  10                  15

Ala Met Leu Gly Ser Phe Ser Ala Ser Asp Tyr Phe Pro Arg Leu Gly
                20                  25                  30

Trp Ile Val Asp Arg Phe Thr Gly Leu His Ser Arg Leu Glu Lys Ser
            35                  40                  45

Phe Arg Asn Leu Asp Asp Leu Tyr Gln Lys Val Ile Glu Glu His Arg
 50                  55                  60

Asn Ala Asn Lys Ser Asn Glu Gly Lys Glu Asp Ile Val Asp Val Leu
 65                  70                  75                  80

Leu Lys Met Glu Lys Asp Gln Thr Glu Leu Ala Gly Val Arg Leu Lys
                85                  90                  95

Glu Asp Asn Ile Lys Ala Ile Leu Met Val Tyr His Thr Ile Ser Thr
```

Tyr Tyr Leu
    115

<210> SEQ ID NO 286
<211> LENGTH: 143
<212> TYPE: PRT
<213> ORGANISM: Eucalyptus grandis

<400> SEQUENCE: 286

Leu Val Ala Ala Leu Leu Ile Val Leu Leu Arg Ser Lys Ser Arg
 1               5                  10                  15

Lys Arg Lys Ser Asn Leu Pro Pro Ser Pro Lys Leu Pro Ile Ile
                20                  25                  30

Gly Asn Leu His Gln Leu Gly Lys Ser Pro His Ile Ser Leu His Arg
                35                  40                  45

Leu Ala Arg Asn Tyr Gly Pro Ile Met Ser Leu Gln Leu Gly Glu Val
50                      55                  60

Pro Thr Ile Val Val Ser Ser Ala Ala Met Ala Lys Glu Val Met Lys
65                  70                  75                  80

Thr His Asp Leu Val Leu Ala Asn Arg Pro Gln Ile Phe Ser Ala Lys
                    85                  90                  95

His Leu Phe Tyr Asp Cys Thr Asp Met Ala Phe Ser Pro Tyr Gly Ala
                100                 105                 110

Tyr Trp Arg His Ile Arg Lys Ile Cys Ile Leu Glu Val Leu Ser Ala
                115                 120                 125

Lys Arg Val Gln Ser Phe Ser His Val Arg Glu Glu Val Ala
    130                 135                 140

<210> SEQ ID NO 287
<211> LENGTH: 135
<212> TYPE: PRT
<213> ORGANISM: Eucalyptus grandis

<400> SEQUENCE: 287

Leu Thr Phe Lys Cys Leu Arg Phe Leu Phe Ser Ser Ala Ala Ala Thr
 1               5                  10                  15

Asn Leu His Leu Pro Pro Ser Pro Pro Lys Leu Pro Ile Ile Gly Asn
                20                  25                  30

Leu His Gln Leu Ser Asp His Pro His Arg Ser Leu Gln Ala Leu Ser
                35                  40                  45

Arg Arg Tyr Gly Pro Leu Met Met Leu His Phe Gly Ser Val Pro Val
    50                  55                  60

Leu Val Val Ser Ser Ala Asp Cys Ala Arg Asp Ile Leu Lys Thr His
65                  70                  75                  80

Asp Leu Ile Phe Ser Asp Arg Pro Arg Ser Thr Leu Ser Glu Arg Leu
                85                  90                  95

Leu Tyr His Arg Lys Asp Val Ala Leu Ala Pro Phe Gly Glu Tyr Trp
                100                 105                 110

Arg Glu Met Arg Ser Ile Cys Val Leu Gln Leu Leu Ser Asn Lys Arg
                115                 120                 125

Val His Ser Phe Arg Thr Val
    130                 135

<210> SEQ ID NO 288
<211> LENGTH: 128
<212> TYPE: PRT

<213> ORGANISM: Eucalyptus grandis

<400> SEQUENCE: 288

Gly Lys Leu Pro His Arg Ser Leu Asp Arg Leu Ser Lys Thr Tyr Gly
1               5                   10                  15

Pro Leu Met Tyr Met Arg Leu Gly Ser Met Pro Cys Val Val Gly Ser
            20                  25                  30

Ser Ala Glu Met Ala Arg Glu Phe Leu Lys Thr His Asp Leu Thr Phe
        35                  40                  45

Ser Ser Arg Pro Arg Val Ala Ala Gly Lys Tyr Thr Val Tyr Asn Tyr
    50                  55                  60

Ser Asp Ile Thr Trp Ser Pro Tyr Gly Glu His Trp Arg Leu Ala Arg
65                  70                  75                  80

Lys Ile Cys Leu Met Glu Leu Phe Ser Ala Lys Arg Leu Glu Ser Phe
                85                  90                  95

Glu Tyr Ile Arg Val Glu Glu Val Ala Arg Met Leu Ser Ser Val Phe
            100                 105                 110

Glu Thr Ser Arg Gln Gly Leu Pro Val Glu Ile Arg Glu Glu Thr Thr
        115                 120                 125

<210> SEQ ID NO 289
<211> LENGTH: 179
<212> TYPE: PRT
<213> ORGANISM: Eucalyptus grandis

<400> SEQUENCE: 289

Ile Arg Met Val Asn Glu Leu Gly Ser Glu Lys Pro Phe Leu Val Cys
1               5                   10                  15

Leu Glu Phe Tyr Met Lys Leu Ala Ile Ala Leu Val Ala Leu Val Val
            20                  25                  30

Ala Trp Ser Phe Phe Val Lys Gly Arg Asn Arg Lys Leu Pro Pro Gly
        35                  40                  45

Pro Phe Ser Leu Pro Ile Ile Gly Asn Leu His Leu Leu Gly Gln Leu
    50                  55                  60

Pro His Arg Ala Leu Thr Ala Leu Ser Leu Lys Phe Gly Pro Leu Met
65                  70                  75                  80

Ser Leu Arg Leu Gly Ser Ala Leu Thr Leu Val Val Ser Ser Pro Asp
                85                  90                  95

Met Ala Lys Glu Phe Leu Lys Thr His Asp Leu Leu Phe Ala Ser Arg
            100                 105                 110

Pro Pro Ser Ala Ala Thr Asn Tyr Phe Trp Tyr Asn Cys Thr Asp Ile
        115                 120                 125

Gly Phe Ala Pro Tyr Gly Ala Tyr Trp Arg Gln Val Arg Lys Val Cys
    130                 135                 140

Val Leu Gln Leu Leu Ser Ser Arg Arg Leu Asp Tyr Phe Arg Phe Ile
145                 150                 155                 160

Arg Glu Glu Glu Val Ser Ala Met Ile His Ser Ile Ala His Ser Asp
                165                 170                 175

His Pro Val

<210> SEQ ID NO 290
<211> LENGTH: 440
<212> TYPE: PRT
<213> ORGANISM: Eucalyptus grandis

<400> SEQUENCE: 290

```
Ser Ser Leu Ala Phe Gly Gln His Ile Ile Ala Thr Ser Tyr Ser Cys
 1               5                  10                  15

Asn Leu His Gln Ile Gly Glu Met Ser Phe Gln Asn Gln Leu Phe Ile
            20                  25                  30

Phe Cys Thr Leu Leu Gly Phe Leu Lys Leu Ala Glu Gly Lys Thr
        35                  40                  45

Arg His Tyr Thr Phe His Ile Asp Ser His Asn Met Thr Arg Leu Cys
        50                  55                  60

His Thr Arg Ser Val Leu Ser Val Asn Lys Gln Tyr Pro Gly Pro Pro
65                  70                  75                  80

Leu Val Ala Arg Glu Gly Asp Asn Ile Leu Val Lys Val Val Asn His
                85                  90                  95

Val Ala Ala Asn Val Thr Ile His Trp His Gly Val Arg Gln Leu Arg
            100                 105                 110

Thr Gly Trp Ala Asp Gly Pro Ala Tyr Val Thr Gln Cys Pro Ile Gln
        115                 120                 125

Thr Asn Gln Ser Tyr Thr Tyr Asn Phe Thr Leu Thr Gly Gln Arg Gly
        130                 135                 140

Thr Leu Leu Trp His Ala His Val Ser Trp Leu Arg Ser Ser Ile His
145                 150                 155                 160

Gly Pro Ile Ile Ile Leu Pro Lys Arg Asn Glu Ser Tyr Pro Phe Glu
                165                 170                 175

Lys Pro Ser Lys Glu Val Pro Ile Ile Phe Gly Glu Trp Phe Asn Val
            180                 185                 190

Asp Pro Glu Ala Val Ile Ala Gln Ala Leu Gln Ser Gly Gly Pro
        195                 200                 205

Asn Val Ser Asp Ala Tyr Thr Ile Asn Gly Leu Pro Gly Pro Leu Tyr
    210                 215                 220

Asn Cys Ser Ser Lys Asp Thr Phe Lys Leu Lys Val Lys Pro Gly Lys
225                 230                 235                 240

Thr Tyr Leu Leu Arg Leu Ile Asn Ala Ala Leu Asn Asp Glu Leu Phe
                245                 250                 255

Phe Ser Ile Ala Asn His Ala Val Thr Val Val Glu Val Asp Ala Val
            260                 265                 270

Tyr Thr Lys Pro Phe Ser Ala Gly Cys Leu His Leu Thr Pro Gly Gln
        275                 280                 285

Thr Met Asn Val Leu Leu Lys Thr Lys Thr Asp Phe Pro Asn Ser Thr
    290                 295                 300

Phe Leu Met Ala Ala Trp Pro Tyr Phe Thr Gly Met Gly Thr Phe Asp
305                 310                 315                 320

Asn Ser Thr Val Ala Gly Ile Leu Glu Tyr Glu His Pro Lys Ser Ser
                325                 330                 335

Asn Tyr Pro Pro Leu Lys Lys Leu Pro Gln Tyr Lys Pro Thr Leu Pro
            340                 345                 350

Pro Met Asn Ser Thr Gly Phe Val Ala Lys Phe Thr Gly Gln Leu Arg
        355                 360                 365

Ser Leu Ala Ser Ala Lys Phe Pro Ala Asn Val Pro Gln Lys Val Asp
        370                 375                 380

Arg Lys Phe Phe Phe Thr Val Gly Leu Gly Thr Ser Pro Cys Pro Lys
385                 390                 395                 400

Asn Thr Thr Cys Gln Gly Pro Asn Gly Thr Lys Phe Ala Ala Ser Val
                405                 410                 415

Asn Asn Ile Ser Phe Val Leu Pro Ser Val Ala Leu Leu Gln Ala His
```

```
                    420                 425                 430
Phe Phe Gly Gln Ser Asn Gly Val
        435                 440

<210> SEQ ID NO 291
<211> LENGTH: 326
<212> TYPE: PRT
<213> ORGANISM: Eucalyptus grandis

<400> SEQUENCE: 291

Pro Ala Val Val Glu Gly Arg Val Arg Asn Tyr Thr Phe Asn Val Val
1               5                   10                  15

Met Lys Asn Thr Thr Arg Leu Cys Ser Ser Lys Pro Ile Val Thr Val
            20                  25                  30

Asn Gly Met Phe Pro Gly Pro Thr Leu Tyr Ala Arg Glu Asp Asp Thr
        35                  40                  45

Val Leu Val Arg Val Ser Asn Arg Val Lys Tyr Asn Val Thr Ile His
    50                  55                  60

Trp His Gly Ile Arg Gln Leu Arg Thr Gly Trp Ala Asp Gly Pro Ala
65                  70                  75                  80

Tyr Ile Thr Gln Cys Pro Ile Gln Pro Gly Gln Ser Tyr Val Tyr Asn
                85                  90                  95

Phe Thr Ile Thr Gly Gln Arg Gly Thr Leu Leu Trp His Ala His Ile
            100                 105                 110

Leu Trp Leu Arg Ala Thr Leu His Gly Ala Ile Val Ile Leu Pro Lys
        115                 120                 125

Arg Gly Val Pro Tyr Pro Phe Pro Lys Pro His Lys Glu Val Val Val
    130                 135                 140

Val Leu Gly Glu Trp Trp Lys Ser Asp Thr Glu Gly Val Ile Ser Gln
145                 150                 155                 160

Ala Ile Lys Ser Gly Leu Ala Pro Asn Val Ser Asp Ala His Thr Ile
                165                 170                 175

Asn Gly His Pro Gly Pro Ser Ser Asn Cys Pro Ser Gln Gly Gly Phe
            180                 185                 190

Thr Leu Pro Val Glu Ser Gly Lys Lys Tyr Met Leu Arg Ile Ile Asn
        195                 200                 205

Ala Ala Leu Asn Glu Glu Leu Phe Phe Lys Ile Ala Gly His Gln Leu
    210                 215                 220

Thr Ile Val Glu Val Asp Ala Thr Tyr Val Lys Pro Phe Lys Thr Asp
225                 230                 235                 240

Thr Ile Val Ile Ala Pro Gly Gln Thr Thr Asn Ala Leu Ile Ser Thr
                245                 250                 255

Asp Gln Ser Ser Gly Lys Tyr Met Val Ala Ala Ser Pro Phe Met Asp
            260                 265                 270

Ser Pro Ile Ala Val Asp Asn Met Thr Ala Thr Ala Thr Leu His Tyr
        275                 280                 285

Ser Gly Thr Leu Ala Ala Thr Ser Thr Thr Leu Thr Lys Thr Pro Pro
    290                 295                 300

Gln Asn Ala Thr Ala Val Ala Asn Asn Phe Val Asn Ser Leu Arg Ser
305                 310                 315                 320

Leu Asn Ser Lys Arg Tyr
                325

<210> SEQ ID NO 292
<211> LENGTH: 101
```

```
<212> TYPE: PRT
<213> ORGANISM: Eucalyptus grandis

<400> SEQUENCE: 292

Arg Leu Cys Ser Ser Lys Pro Ile Val Thr Val Asn Gly Met Phe Pro
1               5                   10                  15

Gly Pro Thr Leu Tyr Ala Arg Glu Asp Asp Thr Val Leu Val Arg Val
            20                  25                  30

Ser Asn Arg Val Lys Tyr Asn Val Thr Ile His Trp His Gly Ile Arg
        35                  40                  45

Gln Leu Arg Ser Gly Trp Ala Asp Gly Pro Ala Tyr Ile Thr Gln Cys
    50                  55                  60

Pro Ile Gln Pro Gly Gln Ser Tyr Val Tyr Asn Phe Thr Ile Thr Gly
65                  70                  75                  80

Gln Arg Gly Thr Leu Leu Trp His Ala His Ile Leu Trp Leu Arg Ala
                85                  90                  95

Thr Leu His Gly Ala
            100

<210> SEQ ID NO 293
<211> LENGTH: 136
<212> TYPE: PRT
<213> ORGANISM: Eucalyptus grandis

<400> SEQUENCE: 293

Thr Val Asp His Ser Leu Leu Phe Thr Val Gly Leu Gly Ile Asn Pro
1               5                   10                  15

Cys Pro Ser Cys Lys Ala Gly Asn Gly Ser Arg Val Val Ala Ser Met
            20                  25                  30

Asn Asn Val Thr Phe Val Met Pro Thr Thr Ala Ile Leu Gln Ala His
        35                  40                  45

Phe Phe Asn Lys Ser Gly Val Phe Thr Ser Asp Phe Pro Gly Asn Pro
    50                  55                  60

Pro Thr Ile Phe Asn Tyr Thr Gly Ser Pro Pro Ser Asn Leu Arg Thr
65                  70                  75                  80

Thr Ser Gly Thr Lys Val Tyr Arg Leu Arg Tyr Asn Ser Thr Val Gln
                85                  90                  95

Leu Val Phe Gln Asp Thr Gly Ile Ile Ala Pro Glu Asn His Pro Ile
                100                 105                 110

His Leu His Gly Phe Asn Phe Phe Ala Ile Gly Lys Gly Leu Gly Asn
            115                 120                 125

Tyr Asn Pro Lys Val Asp Gln Lys
    130                 135

<210> SEQ ID NO 294
<211> LENGTH: 104
<212> TYPE: PRT
<213> ORGANISM: Eucalyptus grandis

<400> SEQUENCE: 294

His Lys Glu Val Val Val Leu Gly Glu Trp Trp Lys Ser Asp Thr
1               5                   10                  15

Glu Ala Val Ile Asn Gln Ala Ile Lys Ser Gly Leu Ala Pro Asn Val
            20                  25                  30

Ser Asp Ala His Thr Ile Asn Gly His Pro Gly Pro Ser Ser Asn Cys
        35                  40                  45
```

-continued

Pro Ser Gln Gly Gly Phe Thr Leu Pro Val Glu Ser Gly Lys Lys Tyr
          50                  55                  60

Met Leu Arg Ile Ile Asn Ala Ala Leu Asn Glu Glu Leu Phe Phe Lys
 65                  70                  75                  80

Ile Ala Gly His Gln Leu Thr Ile Val Glu Val Asp Ala Thr Tyr Val
                     85                  90                  95

Lys Pro Phe Lys Thr Asn Thr Gly
                100

<210> SEQ ID NO 295
<211> LENGTH: 110
<212> TYPE: PRT
<213> ORGANISM: Eucalyptus grandis

<400> SEQUENCE: 295

Arg Gly Val Pro Tyr Pro Phe Pro Lys Pro His Lys Glu Val Val Val
 1               5                  10                  15

Val Leu Gly Glu Trp Trp Lys Ser Asp Thr Glu Ala Val Ile Asn Gln
                20                  25                  30

Ala Ile Lys Ser Gly Leu Ala Pro Asn Val Ser Asp Ala His Thr Ile
                35                  40                  45

Asn Gly His Pro Gly Pro Ser Ser Asn Cys Pro Ser Gln Gly Gly Phe
          50                  55                  60

Thr Leu Pro Val Glu Ser Gly Lys Lys Tyr Met Leu Arg Ile Ile Asn
 65                  70                  75                  80

Ala Ala Leu Asn Glu Glu Leu Phe Phe Lys Ile Ala Gly His Gln Leu
                85                  90                  95

Thr Ile Val Glu Val Asp Ala Thr Tyr Val Lys Pro Phe Lys
                100                 105                 110

<210> SEQ ID NO 296
<211> LENGTH: 384
<212> TYPE: PRT
<213> ORGANISM: Eucalyptus grandis

<400> SEQUENCE: 296

Pro Asn Val Ser Asp Ala Tyr Thr Ile Asn Gly Gln Pro Gly Asp Leu
 1               5                  10                  15

Tyr Asn Cys Ser Ser Lys Asp Thr Val Ile Val Pro Ile Asp Ser Gly
                20                  25                  30

Glu Thr His Leu Leu Arg Val Ile Asn Ala Ala Leu Asn Gln Glu Leu
                35                  40                  45

Phe Phe Thr Val Ala Asn His Arg Phe Thr Val Val Gly Ala Asp Ala
          50                  55                  60

Ser Tyr Leu Lys Pro Phe Thr Thr Ser Val Ile Met Leu Gly Pro Gly
 65                  70                  75                  80

Gln Thr Thr Asp Val Leu Ile Ser Gly Asp Gln Pro Pro Ala Arg Tyr
                85                  90                  95

Tyr Met Ala Ala Glu Pro Tyr Gln Ser Ala Gln Gly Ala Pro Phe Asp
                100                 105                 110

Asn Thr Thr Thr Thr Ala Ile Leu Glu Tyr Lys Ser Ala Pro Cys Pro
                115                 120                 125

Ala Lys Gly Ile Ser Ser Lys Pro Val Met Pro Thr Leu Pro Ala Phe
          130                 135                 140

Asn Asp Thr Ala Thr Val Thr Ala Phe Ile Gln Ser Phe Arg Ser Pro
145                 150                 155                 160

```
Asn Lys Val Asp Val Pro Thr Asp Ile Asp Glu Asn Leu Phe Ile Thr
                165                 170                 175
Val Gly Leu Gly Leu Phe Asn Cys Pro Lys Asn Phe Gly Ser Ser Arg
            180                 185                 190
Cys Gln Gly Pro Asn Gly Thr Arg Phe Thr Ala Ser Met Asn Asn Val
        195                 200                 205
Ser Phe Val Leu Pro Ser Asn Val Ser Ile Leu Gln Ala Tyr Lys Gln
    210                 215                 220
Gly Val Pro Gly Val Phe Thr Asp Phe Pro Ala Asn Pro Val
225                 230                 235                 240
Gln Phe Asp Tyr Thr Gly Asn Val Ser Arg Ser Leu Trp Gln Pro Val
                245                 250                 255
Pro Gly Thr Lys Val Tyr Lys Leu Lys Tyr Gly Ser Arg Val Gln Ile
            260                 265                 270
Val Leu Gln Gly Thr Asn Ile Gln Thr Ala Glu Asn His Pro Ile His
        275                 280                 285
Ile His Gly Tyr Asp Phe Tyr Ile Leu Ala Thr Gly Phe Gly Asn Phe
    290                 295                 300
Asn Pro Gln Lys Asp Thr Ala Lys Phe Asn Leu Val Asp Pro Pro Met
305                 310                 315                 320
Arg Asn Thr Val Gly Val Ser Val Asn Gly Trp Ala Val Ile Arg Phe
                325                 330                 335
Val Ala Asp Asn Pro Gly Ala Trp Leu Met His Cys His Leu Asp Val
            340                 345                 350
His Ile Thr Trp Gly Leu Ala Val Val Phe Leu Val Glu Asn Gly Val
        355                 360                 365
Gly Glu Leu Gln Ser Leu Gln Pro Pro Ala Asp Leu Pro Pro Cys
    370                 375                 380

<210> SEQ ID NO 297
<211> LENGTH: 139
<212> TYPE: PRT
<213> ORGANISM: Eucalyptus grandis

<400> SEQUENCE: 297

Ser Cys Leu Ser Leu His His His Leu Arg Gln Val Thr Ser Asp Phe
1               5                   10                  15
Glu Glu Asp Glu Glu Arg Lys Met Gly Ser Ala Thr Ala Ala Gly Ala
                20                  25                  30
Ser Val Ser Ser Arg Met Ile Leu Met Arg Ala Ala Phe Phe Thr Leu
            35                  40                  45
Cys Ala Leu Val Phe Leu Pro Ala Leu Ala Gln Ala Lys His Gly Gly
        50                  55                  60
Val Thr Arg His Tyr Lys Phe Asp Ile Lys Met Gln Asn Val Thr Arg
65                  70                  75                  80
Leu Cys Gln Thr Lys Ser Ile Val Thr Val Asn Gly Gln Leu Pro Gly
                85                  90                  95
Pro Arg Ile Ile Ala Arg Glu Gly Asp Arg Leu Leu Ile Lys Val Val
            100                 105                 110
Asn Asn Val Gln Tyr Asn Val Thr Ile His Trp His Gly Val Arg Gln
        115                 120                 125
Leu Arg Ser Gly Trp Ala Asp Gly Pro Ala Tyr
    130                 135

<210> SEQ ID NO 298
```

<211> LENGTH: 155
<212> TYPE: PRT
<213> ORGANISM: Eucalyptus grandis

<400> SEQUENCE: 298

```
Pro Asp Arg Val Ile Ser Thr Ser Ser Ile Leu Tyr Gln Gly Glu Arg
  1               5                  10                  15

Gly Thr Met Gly Thr Phe Leu Gly Phe Ala Val Thr Ala Thr Leu Leu
             20                  25                  30

Phe Cys Val Ala Gln Gly Glu Val Leu Phe Tyr Asp Phe Val Val Asn
         35                  40                  45

Glu Thr Pro Ile Glu Met Leu Cys Glu Thr Asn Arg Ser Val Leu Thr
     50                  55                  60

Val Asn Gly Leu Phe Pro Gly Pro Glu Ile His Ala His Lys Gly Asp
 65                  70                  75                  80

Thr Ile Tyr Val Asn Val Thr Asn Leu Gly Pro Tyr Gly Val Thr Ile
                 85                  90                  95

His Trp His Gly Val Arg Gln Ile Arg Tyr Pro Trp Ser Asp Gly Pro
            100                 105                 110

Glu Tyr Val Thr Gln Cys Pro Ile Pro Thr Asn Ser Ser Phe Leu Gln
        115                 120                 125

Lys Ile Lys Leu Thr Glu Glu Gly Thr Val Trp Trp His Ala His
130                 135                 140

Ser Asp Trp Ser Arg Ala Thr Ile His Gly Leu
145                 150                 155
```

<210> SEQ ID NO 299
<211> LENGTH: 179
<212> TYPE: PRT
<213> ORGANISM: Eucalyptus grandis

<400> SEQUENCE: 299

```
Leu Leu Gln Val His Phe Ser Leu Val Glu Arg Glu Arg Glu Met Gly
  1               5                  10                  15

Thr Phe Leu Gly Phe Val Val Thr Met Thr Leu Leu Phe Cys Met Ala
             20                  25                  30

Gln Gly Glu Val Ile Tyr Tyr Asp Phe Val Val Lys Glu Thr Pro Ile
         35                  40                  45

Gln Met Leu Cys Gly Thr Asn Gln Thr Val Leu Thr Val Asn Gly Leu
     50                  55                  60

Phe Pro Gly Pro Glu Ile His Ala His Lys Gly Asp Thr Ile Tyr Val
 65                  70                  75                  80

Asn Val Thr Asn Thr Gly Pro Tyr Gly Val Thr Ile His Trp His Gly
                 85                  90                  95

Val Arg Gln Ile Arg Tyr Pro Trp Ser Asp Gly Pro Glu Tyr Ile Thr
            100                 105                 110

Gln Cys Pro Ile Pro Thr Asn Ser Ser Phe Leu Gln Lys Ile Ile Leu
        115                 120                 125

Thr Glu Glu Gly Thr Leu Trp Trp His Ala His Ser Asp Trp Thr
130                 135                 140

Arg Ala Thr Ile His Gly Pro Ile Ile Leu Pro Val Asn Gly Thr
145                 150                 155                 160

Asn Tyr Pro Tyr Lys Phe Asp Glu Gln His Thr Ile Val Ile Ser Glu
                165                 170                 175

Trp Tyr Ala
```

```
<210> SEQ ID NO 300
<211> LENGTH: 62
<212> TYPE: PRT
<213> ORGANISM: Eucalyptus grandis

<400> SEQUENCE: 300

Glu Arg Glu Met Gly Thr Phe Leu Gly Phe Val Thr Met Thr Leu
  1               5                  10                  15

Leu Phe Cys Met Ala Gln Gly Glu Val Leu Tyr Tyr Asp Phe Val Val
                 20                  25                  30

Lys Glu Thr Pro Ile Gln Met Leu Cys Gly Thr Asn Gln Thr Val Leu
                 35                  40                  45

Thr Val Asn Gly Leu Phe Pro Gly Pro Glu Ile His Ala His
             50                  55                  60

<210> SEQ ID NO 301
<211> LENGTH: 190
<212> TYPE: PRT
<213> ORGANISM: Pinus radiata

<400> SEQUENCE: 301

Leu Ala Val Met Ser Asn Glu Gln Leu Leu Glu Phe Ala Trp Gly Leu
  1               5                  10                  15

Ala Ser Ser Asn Gln Ser Phe Leu Trp Val Val Arg Ser Asp Ile Val
                 20                  25                  30

His Gly Glu Ser Ala Ile Leu Pro Lys Glu Phe Ile Glu Glu Thr Lys
                 35                  40                  45

Asp Arg Gly Met Leu Val Gly Trp Ala Pro Gln Ile Lys Val Leu Ser
             50                  55                  60

His Pro Ser Val Gly Gly Phe Leu Thr His Ser Gly Trp Asn Ser Thr
 65                  70                  75                  80

Leu Glu Ser Ile Ser Ala Gly Val Pro Met Met Cys Trp Pro Phe Phe
                 85                  90                  95

Ala Glu Gln Glu Thr Asn Ala Lys Phe Val Cys Glu Glu Trp Gly Ile
                100                 105                 110

Gly Met Gln Val Lys Lys Met Val Lys Arg Glu Glu Leu Ala Ile Leu
                115                 120                 125

Val Arg Asn Ser Ile Lys Gly Glu Glu Gly Asp Glu Met Arg Lys Arg
            130                 135                 140

Ile Gly Lys Leu Lys Glu Thr Ala Lys Arg Ala Val Ser Glu Gly Gly
145                 150                 155                 160

Ser Ser Lys Asn Asn Leu Asp Lys Leu Leu His His Ile Phe Leu Lys
                165                 170                 175

Gly Met His Gln Met Ile Val Gln Asn Val Glu Ala Asn Asn
                180                 185                 190

<210> SEQ ID NO 302
<211> LENGTH: 365
<212> TYPE: PRT
<213> ORGANISM: Eucalyptus grandis

<400> SEQUENCE: 302

Pro Met Glu Ser Cys Ser Ile Ser Leu Phe Trp Leu Gly Leu Leu Leu
  1               5                  10                  15

Pro Ala Leu Leu Val Phe Leu Leu Asn Arg Arg Lys Arg Thr Lys Leu
                 20                  25                  30

Pro Pro Gln Pro Pro Ala Trp Pro Val Ile Gly Asn Ile Phe Asp Leu
```

```
                 35                  40                  45
Gly Thr Met Pro His Gln Asn Leu His Asn Leu Arg Ala Lys His Gly
     50                  55                  60
Pro Val Leu Trp Leu Lys Leu Gly Ser Val Asn Thr Met Val Ile Gln
 65                  70                  75                  80
Ser Ala Arg Ala Ala Met Glu Leu Phe Lys Gly His Asp Phe Val Phe
                 85                  90                  95
Ala Asp Arg Lys Cys Ser Gln Ala Phe Thr Ala Leu Gly Tyr Asp Gln
                100                 105                 110
Gly Ser Leu Ala Leu Gly Arg His Gly Asp Tyr Trp Arg Ala Leu Arg
                115                 120                 125
Arg Leu Cys Ser Ala Glu Leu Leu Val Asn Lys Arg Val Asn Asp Thr
130                 135                 140
Ala His Leu Arg Gln Lys Cys Val Asp Ser Met Ile Met Tyr Ile Glu
145                 150                 155                 160
Glu Glu Met Ala Val Lys Gln Ala Thr Lys Gly Gln Gly Ile Asp Leu
                165                 170                 175
Ser His Phe Leu Phe Leu Leu Ala Phe Asn Val Val Gly Asn Met Val
                180                 185                 190
Leu Ser Arg Asp Leu Leu Asp Pro Lys Ser Lys Asp Gly Pro Glu Phe
                195                 200                 205
Tyr Asp Ala Met Asn Arg Phe Met Glu Trp Ala Gly Lys Pro Asn Val
                210                 215                 220
Ala Asp Phe Met Pro Trp Leu Lys Trp Leu Asp Pro Gln Gly Ile Lys
225                 230                 235                 240
Ala Gly Met Ala Lys Asp Met Gly Arg Ala Met Arg Ile Ala Glu Gly
                245                 250                 255
Phe Val Lys Glu Arg Leu Glu Glu Arg Lys Leu Arg Gly Glu Met Arg
                260                 265                 270
Thr Thr Asn Asp Phe Leu Asp Ala Val Leu Asp Tyr Glu Gly Asp Gly
                275                 280                 285
Lys Glu Gly Pro His Asn Ile Ser Ser Gln Asn Ile Asn Ile Ile
                290                 295                 300
Leu Glu Met Phe Phe Ala Gly Ser Glu Ser Thr Ser Ser Thr Ile Glu
305                 310                 315                 320
Trp Ala Met Ala Glu Leu Leu Arg Gln Pro Glu Ser Met Lys Lys Ala
                325                 330                 335
Lys Asp Glu Ile Asp Gln Val Val Gly Leu Asn Arg Lys Leu Glu Glu
                340                 345                 350
Asn Asp Thr Glu Lys Met Pro Phe Leu Gln Ala Val Val
                355                 360                 365

<210> SEQ ID NO 303
<211> LENGTH: 183
<212> TYPE: PRT
<213> ORGANISM: Eucalyptus grandis

<400> SEQUENCE: 303

Pro Met Glu Ser Cys Ser Ile Ser Leu Phe Trp Leu Gly Leu Leu Leu
 1               5                  10                  15
Pro Ala Leu Leu Val Phe Leu Leu Asn Arg Arg Lys Arg Thr Lys Leu
                20                  25                  30
Pro Pro Gln Pro Pro Ala Trp Pro Val Ile Gly Asn Ile Phe Asp Leu
                35                  40                  45
```

```
Gly Thr Met Pro His Gln Asn Leu His Asn Leu Arg Ala Lys His Gly
        50                  55                  60

Pro Val Leu Trp Leu Lys Leu Gly Ser Val Asn Thr Met Val Ile Gln
 65                  70                  75                  80

Ser Ala Gln Ala Ala Met Glu Leu Phe Lys Gly His Asp Phe Val Phe
                 85                  90                  95

Ala Asp Arg Lys Cys Ser Gln Ala Phe Thr Ala Leu Gly Tyr Asp Gln
                100                 105                 110

Gly Ser Leu Ala Leu Gly Arg His Gly Asp Tyr Trp Arg Ala Leu Arg
            115                 120                 125

Arg Leu Cys Ser Ala Glu Leu Leu Val Asn Lys Arg Val Asn Glu Thr
        130                 135                 140

Ala His Leu Arg Gln Lys Cys Val Asp Ser Met Ile Met Tyr Ile Glu
145                 150                 155                 160

Glu Glu Met Ala Val Lys Gln Ala Thr Lys Gly Gln Gly Ile Asp Leu
                165                 170                 175

Ser His Phe Leu Phe Leu Leu
            180
```

<210> SEQ ID NO 304
<211> LENGTH: 148
<212> TYPE: PRT
<213> ORGANISM: Eucalyptus grandis

<400> SEQUENCE: 304

```
Met Lys Ala Gln Asp Glu Ile Asp Ser Met Ile Gly His Asp Ser Leu
 1               5                  10                  15

Leu Glu Glu Ser Asp Val Ser Lys Leu Pro Tyr Leu Gln Cys Ile Ile
                20                  25                  30

Leu Glu Thr Leu Arg Leu Asn Thr Thr Ala Pro Leu Leu Leu Pro His
            35                  40                  45

Ala Ser Ser Ala Asp Cys Thr Ile Gly Gly Tyr Phe Val Pro Arg Asp
        50                  55                  60

Thr Ile Val Met Val Asn Ala Trp Ala Ile His Lys Asp Pro Gln Leu
 65                  70                  75                  80

Trp Glu Asp Pro Leu Ser Phe Lys Pro Glu Arg Phe Glu Gly Asn Gly
                 85                  90                  95

Ser Glu Lys Gln Gln Lys Leu Leu Pro Phe Gly Leu Gly Arg Arg
                100                 105                 110

Ala Cys Pro Gly Ala Pro Leu Ala His Arg Val Met Gly Trp Thr Leu
            115                 120                 125

Gly Leu Leu Ile Gln Cys Phe Asp Trp Lys Arg Val Ser Glu Glu Glu
        130                 135                 140

Ile Asp Met Thr
145
```

<210> SEQ ID NO 305
<211> LENGTH: 164
<212> TYPE: PRT
<213> ORGANISM: Eucalyptus grandis

<400> SEQUENCE: 305

```
Tyr Leu Gly Asp Phe Leu Pro Ile Leu Lys Leu Val Asp Tyr Asn Gly
 1               5                  10                  15

Val Lys Lys Arg Val Val Glu Leu Lys Glu Lys Phe Asp Ala Phe Ile
                20                  25                  30
```

-continued

```
Gln Gly Leu Ile Asn Glu His Arg Arg Lys Lys Gly Asp Pro Glu Leu
        35                  40                  45

Ala Asp Ser Met Ile Ser His Leu Leu His Leu Gln Glu Ser Gln Pro
 50                  55                  60

Glu Asp Tyr Ser Asp Ser Met Ile Lys Gly Leu Val Leu Val Leu Leu
 65                  70                  75                  80

Val Ala Gly Thr Asp Thr Ser Ser Leu Thr Leu Glu Trp Ile Met Thr
                 85                  90                  95

Asn Leu Leu Asn Asn Pro Glu Lys Leu Glu Lys Ala Arg Asn Glu Ile
                100                 105                 110

Asp Ser Val Ile Gly His Asp Arg Leu Val Glu Glu Ser Asp Val Ser
                115                 120                 125

Asn Leu Pro Tyr Leu Gln Cys Ile Ile Leu Glu Thr Leu Arg Leu Asn
                130                 135                 140

Thr Thr Val Pro Leu Leu Val Pro His Ala Ser Ser Ala Asp Cys Thr
145                 150                 155                 160

Ile Gly Gly Tyr

<210> SEQ ID NO 306
<211> LENGTH: 163
<212> TYPE: PRT
<213> ORGANISM: Eucalyptus grandis

<400> SEQUENCE: 306

Leu Ser Asp Ala Ile Pro Ala Leu Gly Trp Leu Asp Ser Gly Gly Tyr
 1               5                  10                  15

Arg Arg Ser Met Asp Glu Thr Ala Lys Glu Leu Asp Val Leu Ala Gln
                20                  25                  30

Gly Trp Leu Glu Glu His Arg Arg Lys Arg Leu Ser Cys Pro Lys Asp
        35                  40                  45

Asp Arg Glu Gln Asp Phe Met Asp Trp Met Ile Asn Ala Leu Glu Gly
 50                  55                  60

Arg Asn Phe Pro Asp Phe Asp Ala Asp Thr Val Ile Lys Ala Thr Cys
 65                  70                  75                  80

Leu Asn Met Ile Ile Ala Gly Thr Asp Thr Ser Thr Val Ala Ile Thr
                 85                  90                  95

Trp Ala Leu Ser Leu Leu Met Asn Asn Arg Arg Ala Leu Lys Lys Ala
                100                 105                 110

Gln Gln Glu Leu Asp Thr His Val Gly Arg Ser Arg Pro Val Glu Glu
                115                 120                 125

Ser Asp Val Lys Asn Leu Thr Tyr Leu Gln Ala Ile Val Lys Glu Ala
                130                 135                 140

Leu Arg Leu Tyr Pro Pro Val Pro Val Asn Gly Leu Arg Ser Ser Met
145                 150                 155                 160

Glu Glu Cys

<210> SEQ ID NO 307
<211> LENGTH: 129
<212> TYPE: PRT
<213> ORGANISM: Pinus radiata

<400> SEQUENCE: 307

Arg Leu Pro Pro Gly Pro Pro Gly Trp Pro Ile Val Gly Asn Leu Phe
 1               5                  10                  15

Gln Leu Gly Asn Lys Pro His Glu Ala Leu Phe His Leu Ala Gln Lys
                20                  25                  30
```

```
Tyr Gly Pro Leu Met Cys Val Ser Leu Gly Met Lys Thr Thr Val Val
        35                  40                  45

Val Ser Ser Pro Ala Met Ala Lys Gln Val Leu Lys Thr His Asp His
50                  55                  60

Val Phe Ala Gly Arg Thr Val Ile Gln Ser Val Gln Cys Leu Ser Tyr
65                  70                  75                  80

Asp Lys Ser Ser Val Ile Trp Ala Gln Tyr Gly Ser His Trp Arg Leu
                85                  90                  95

Leu Arg Arg Ile Ser Asn Thr Lys Leu Phe Ser Val Lys Arg Leu Glu
            100                 105                 110

Ala Leu Glu His Leu Arg Arg Asp Glu Val Phe Arg Thr Ile Lys Gln
        115                 120                 125

Ile

<210> SEQ ID NO 308
<211> LENGTH: 166
<212> TYPE: PRT
<213> ORGANISM: Pinus radiata

<400> SEQUENCE: 308

Leu Val Tyr Leu Gln Ala Ala Val Lys Glu Thr Leu Arg Leu His Pro
1               5                   10                  15

Ser Gly Pro Leu Leu Val Arg His Leu Phe Gly Thr Ala Ser Cys Asn
            20                  25                  30

Val Leu Gly Tyr Glu Ile Pro Gln Asn Thr Leu Val Leu Val Asn Val
        35                  40                  45

Trp Ala Ile Gly Arg Asn Pro Lys Ser Trp Glu Asp Ala Glu Val Phe
    50                  55                  60

Lys Pro Glu Arg Phe Met Glu Lys Val Gly Ser Glu Val Asp Ala Asn
65                  70                  75                  80

Gly Asp Gln Asn Phe Gly Cys Leu Leu Phe Gly Ala Gly Arg Arg Arg
                85                  90                  95

Cys Pro Gly Gln Gln Leu Gly Thr Leu Leu Val Glu Phe Gly Leu Ala
            100                 105                 110

Gln Leu Leu His Cys Phe Asn Trp Arg Leu Pro Leu Asp Asp Ile Asn
        115                 120                 125

Gly Glu Asn Gln Glu Val Asp Met Asn Glu Met Phe Asn Gly Val Thr
    130                 135                 140

Leu Arg Lys Ala Arg Glu Leu Ser Ala Ile Pro Thr Pro Arg Leu Glu
145                 150                 155                 160

Cys Ile Ala His Leu Lys
                165

<210> SEQ ID NO 309
<211> LENGTH: 123
<212> TYPE: PRT
<213> ORGANISM: Pinus radiata

<400> SEQUENCE: 309

Ser Cys Trp Arg Cys Val Ala Glu Pro Asn His Ala Trp Ser Asn Leu
1               5                   10                  15

Ser Arg Lys Arg Lys Gly Arg Leu Pro Pro Gly Pro Phe Ser Leu Pro
            20                  25                  30

Ile Ile Gly Asn Leu His Met Leu Gly Lys Ile Pro His Arg Ser Leu
        35                  40                  45
```

-continued

Ala Glu Leu Ser Met Lys Tyr Gly Pro Leu Leu Ser Leu Arg Leu Gly
        50                  55                  60

Ser Thr Pro Ala Leu Val Val Ser Ser Pro Glu Ile Ala Ser Glu Phe
 65                  70                  75                  80

Leu Lys Thr His Asp Gln Leu Phe Ala Ser Arg Ile Pro Ser Ala Ala
                85                  90                  95

Ile Lys Val Leu Thr Tyr Asn Leu Ser Gly Leu Ile Phe Ser Pro Tyr
                100                 105                 110

Gly Pro Cys Trp Arg Gln Val Arg Lys Leu Cys
            115                 120

<210> SEQ ID NO 310
<211> LENGTH: 114
<212> TYPE: PRT
<213> ORGANISM: Pinus radiata

<400> SEQUENCE: 310

Tyr Ser Glu Pro Ser Lys Lys Leu Ala Met Glu Phe Val Glu Phe Cys
 1               5                  10                  15

Ile Thr Leu Val Thr Ala Leu Leu Phe Val Leu Val Ala Ala Trp
                20                  25                  30

Ser Asn Leu Phe Arg Lys Arg Lys Gly Arg Leu Pro Pro Gly Pro Phe
                35                  40                  45

Ser Leu Pro Ile Ile Gly Asn Leu His Met Leu Gly Lys Ile Pro His
        50                  55                  60

Arg Ser Leu Ala Glu Leu Ser Met Lys Tyr Gly Pro Leu Leu Ser Leu
 65                  70                  75                  80

Arg Leu Gly Ser Thr Pro Ala Leu Val Val Ser Ser Pro Glu Ile Ala
                85                  90                  95

Ser Glu Phe Leu Lys Thr His Asp Gln Leu Phe Ala Ser Arg Ile Pro
                100                 105                 110

Ser Ala

<210> SEQ ID NO 311
<211> LENGTH: 154
<212> TYPE: PRT
<213> ORGANISM: Pinus radiata

<400> SEQUENCE: 311

Glu Leu Leu Ser Ala Cys Pro Val His Glu Cys Pro Tyr Phe Tyr Phe
 1               5                  10                  15

Asn Leu Ala Thr Val Ile Leu Leu Gly Val Val Thr Gly Trp Gly Phe
                20                  25                  30

Leu Phe Arg Gly Arg Lys Gln Lys Leu Pro Pro Gly Pro Phe Gln Trp
                35                  40                  45

Pro Ile Val Gly Asn Leu His Met Met Gly Glu Leu Pro His Gln Ala
        50                  55                  60

Ile Thr Ala Leu Ser Met Lys Tyr Gly Pro Leu Met Ser Leu Arg Leu
 65                  70                  75                  80

Gly Ser Tyr Leu Thr Leu Val Val Ser Ser Pro Asp Val Ala Glu Glu
                85                  90                  95

Phe Leu Lys Thr His Asp Leu Ala Phe Ala Ser Arg Pro Pro Thr Ile
                100                 105                 110

Gly Thr Lys Tyr Phe Trp Tyr Asn Ser Ser Asp Val Ala Phe Ser Pro
            115                 120                 125

Tyr Gly Pro Tyr Trp Arg Gln Met Arg Lys Ile Cys Val Leu Gln Leu

```
                130                 135                 140
Leu Ser Ser Arg Arg Ile Asp Ser Phe Arg
145                 150
```

<210> SEQ ID NO 312
<211> LENGTH: 116
<212> TYPE: PRT
<213> ORGANISM: Pinus radiata

<400> SEQUENCE: 312

```
Cys Asp Gln Asp Leu Ile Gly Gly Ile Gly Ile Lys Ser Met Ile Lys
1               5                   10                  15

Glu Thr Phe Val Leu Ala Gly Ser Leu Asn Met Gly Asp Phe Ile Pro
            20                  25                  30

Tyr Leu Ala Trp Ile Asp Leu Gln Gly Leu Asn Arg Arg Leu Lys Asn
        35                  40                  45

Ile His Lys Ile Gln Asp Asp Leu Leu Gly Lys Ile Leu Glu Glu His
    50                  55                  60

Ala Ser Pro Pro Gln Asn Asn Pro Asn Tyr Met Pro Asp Leu Val Asp
65                  70                  75                  80

Val Leu Leu Ala Ala Ser Ala Asp Glu Asp Leu Glu Phe Glu Ile Thr
                85                  90                  95

Arg Asp Asn Ile Lys Ser Val Ile Tyr Val Tyr Ile Val His Ala Ile
            100                 105                 110

Ile Arg Phe Gln
        115
```

<210> SEQ ID NO 313
<211> LENGTH: 180
<212> TYPE: PRT
<213> ORGANISM: Pinus radiata

<400> SEQUENCE: 313

```
Ala Pro Asp Glu Leu Glu Arg Val Val Gly Leu Gly Arg Met Val Arg
1               5                   10                  15

Glu Ser Asp Leu Pro Arg Leu Val Tyr Leu Gln Ala Val Val Lys Glu
            20                  25                  30

Thr Leu Arg Leu Tyr Pro Gln Gly Pro Ile Leu Phe Arg His Leu Ser
        35                  40                  45

Ser Glu Pro Cys Asn Val Leu Gly Tyr Glu Ile Ser Gln Asn Thr Gln
    50                  55                  60

Val Leu Val Asn Ile Trp Ala Ile Gly Arg Asn Ser Glu Ser Trp Glu
65                  70                  75                  80

Asp Ala Gly Ser Phe Lys Pro Glu Arg Phe Met Glu Arg Val Gly Ser
                85                  90                  95

Glu Val Asp Thr Asn Gly Asp Gln Asn Ser Ala Trp Leu Pro Phe Gly
            100                 105                 110

Ala Gly Arg Arg Arg Cys Pro Gly Gln Gln Leu Gly Thr Leu Val Ala
        115                 120                 125

Glu Ile Gly Leu Ala Gln Leu His Cys Phe Lys Trp Arg Leu Pro
    130                 135                 140

Glu Ala Asp Met Asp Gly Pro Asn Gln Glu Leu Asp Met Met Glu Arg
145                 150                 155                 160

Phe Asn Gly Ile Thr Ser Pro Arg Ala Lys Glu Leu Phe Ala Ile Pro
                165                 170                 175

Thr Pro Arg Leu
```

-continued

180

<210> SEQ ID NO 314
<211> LENGTH: 127
<212> TYPE: PRT
<213> ORGANISM: Pinus radiata

<400> SEQUENCE: 314

Gly Ile Leu Phe Asp Met Leu Leu Gly Gly Ser Asp Thr Ala Pro Thr
1               5                   10                  15

Ile Ile Glu Trp Ala Ile Ser Glu Ala Leu Ile Asn Pro Pro Val Met
            20                  25                  30

Lys Lys Leu Gln Asp Glu Leu Glu Arg Val Val Gly Leu Asp Arg Met
        35                  40                  45

Ala Cys Glu Ser Asp Leu Pro Gln Leu Val Tyr Leu Gln Ala Met Val
    50                  55                  60

Lys Glu Thr Leu Arg Leu His Pro Ala Gly Pro Leu Leu Asn Arg Arg
65                  70                  75                  80

Leu Ser Ala Glu Ser Cys Asn Val Leu Gly Tyr Glu Phe Pro Lys Asn
                85                  90                  95

Thr Arg Val Leu Val Asn Ala Trp Ala Ile Gly Arg Asn Pro Lys Leu
            100                 105                 110

Trp Glu Asp Ala Glu Thr Phe Lys Pro Glu Arg Phe Thr Gly Arg
        115                 120                 125

<210> SEQ ID NO 315
<211> LENGTH: 127
<212> TYPE: PRT
<213> ORGANISM: Pinus radiata

<400> SEQUENCE: 315

Thr Ser Ala Thr Val Glu Trp Ala Met Ala Glu Leu Ile Arg Lys Pro
1               5                   10                  15

Thr Leu Leu Lys Lys Ala Gln Ala Glu Leu Asp Glu Val Val Gly Arg
            20                  25                  30

Glu Lys Arg Met Glu Glu Ser Asp Ile Ala Lys Leu Pro Tyr Leu Gln
        35                  40                  45

Ala Val Val Lys Glu Val Leu Arg Leu His Pro Ala Ala Pro Leu Ile
    50                  55                  60

Ile Pro Arg Arg Ala Asp Asn Ser Ala Glu Ile Gly Gly Tyr Val Val
65                  70                  75                  80

Pro Glu Asn Thr Gln Val Phe Val Asn Ile Trp Gly Ile Gly Arg Asp
                85                  90                  95

Pro Asn Val Trp Lys Gly Pro Leu Lys Phe Lys Pro Glu Arg Phe Leu
            100                 105                 110

Asp Cys Asn Thr Asp Tyr Arg Gly Gln Asp Phe Glu Leu Ile Pro
        115                 120                 125

<210> SEQ ID NO 316
<211> LENGTH: 134
<212> TYPE: PRT
<213> ORGANISM: Pinus radiata

<400> SEQUENCE: 316

Glu Asp Glu Val Ser Ala Met Ile Arg Ser Ile Val Asn Ser Asp Ala
1               5                   10                  15

His Lys Asp Ser Arg Pro Val Asn Ile Lys Gln Leu Ala Ser Ser Leu
            20                  25                  30

```
Val Thr Ala Ile Val Leu Arg Met Thr Phe Gly Lys Lys Tyr Ser Asp
            35                  40                  45

Arg Asp Ser Gly Ala Phe Ser Ser Met Ile Lys Glu Ser Leu Leu Leu
 50                  55                  60

Leu Gly Ser Phe Asn Ile Gly Glu Tyr Ile Pro Tyr Leu Asn Trp Met
 65                  70                  75                  80

Asp Leu Gln Gly Leu Asn Arg Arg Leu Lys Leu Arg Thr Thr Gln
                85                  90                  95

Asp Gln Leu Leu Glu Lys Val Ile Glu His Ala Ala Gln Asn Arg
            100                 105                 110

Ser Asn Met Thr His Asp Leu Val Asp Ala Leu Leu Ala Ala Ser Ala
            115                 120                 125

Asp Lys Asp Arg Glu Leu
            130
```

```
<210> SEQ ID NO 317
<211> LENGTH: 115
<212> TYPE: PRT
<213> ORGANISM: Eucalyptus grandis

<400> SEQUENCE: 317

Ile Tyr Asp Gln Glu Ser Leu Leu Asn Ala Ile Lys Gln Val Asp Val
 1               5                  10                  15

Val Ile Ser Ala Val Gly Gln Ala Gln Thr Glu Asp Gln Asp Arg Ile
            20                  25                  30

Val Ala Ala Ile Lys Ala Ala Gly Asn Ile Lys Arg Phe Leu Pro Ser
            35                  40                  45

Glu Phe Gly Asn Asp Val Asp Arg Val His Ala Val Glu Pro Val Lys
 50                  55                  60

Thr Gly Phe Ala Leu Lys Ala Lys Ile Arg Arg Leu Val Glu Ala Glu
 65                  70                  75                  80

Gly Ile Pro Tyr Thr Tyr Val Ser Ser Asn Ser Phe Ala Gly Tyr Tyr
                85                  90                  95

Leu Gln Thr Leu Ser Gln Pro Gly Ala Thr Ala Pro Pro Arg Asp Asn
            100                 105                 110

Val Val Ile
    115
```

```
<210> SEQ ID NO 318
<211> LENGTH: 161
<212> TYPE: PRT
<213> ORGANISM: Eucalyptus grandis

<400> SEQUENCE: 318

Arg Phe Gly Val Ser Met Val Leu Leu Pro Thr Leu Ser Pro Val Thr
 1               5                  10                  15

Ala Glu Ser Leu Leu Glu Thr Asp Arg Val Arg Arg Lys Thr Pro Arg
            20                  25                  30

Leu Arg Arg Glu Asn His Ser Glu Met Ala Ala Lys Ser Lys Val Leu
            35                  40                  45

Val Ile Gly Gly Thr Gly Tyr Ile Gly Lys Phe Ile Val Glu Ala Ser
 50                  55                  60

Ala Lys Ser Gly Arg Pro Thr Phe Ala Leu Ala Arg Glu Ser Thr Leu
 65                  70                  75                  80

Ser Asn Pro Ala Lys Ala Lys Ile Val Glu Gly Phe Lys Ser Leu Gly
                85                  90                  95
```

-continued

```
Val Thr Leu Val His Gly Asp Ile Tyr Asp Gln Glu Ser Leu Leu Asn
            100                 105                 110

Ala Ile Lys Gln Val Asp Val Val Ile Ser Ala Val Gly Arg Ala Gln
        115                 120                 125

Ile Glu Asp Gln Asp Arg Ile Val Ala Ala Ile Lys Ala Ala Gly Asn
    130                 135                 140

Ile Lys Arg Phe Val Pro Ser Glu Phe Gly Asn Asn Val Asp Arg Val
145                 150                 155                 160

His

<210> SEQ ID NO 319
<211> LENGTH: 141
<212> TYPE: PRT
<213> ORGANISM: Eucalyptus grandis

<400> SEQUENCE: 319

Arg Phe Leu Pro Ser Glu Phe Gly Asn Asp Val Asp Arg Val His Ala
1               5                   10                  15

Val Glu Pro Val Lys Thr Gly Phe Ala Leu Lys Ala Lys Ile Arg Arg
            20                  25                  30

Leu Val Glu Ala Glu Gly Ile Pro Tyr Thr Tyr Val Ser Ser Asn Ser
        35                  40                  45

Phe Ala Gly Tyr Tyr Leu Gln Thr Leu Ser Gln Pro Gly Ala Thr Ala
    50                  55                  60

Pro Pro Arg Asp Asn Val Val Ile Leu Gly Asp Gly Asn Ala Lys Val
65                  70                  75                  80

Val Phe Asn Lys Glu Asp Asp Ile Gly Thr Tyr Thr Ile Lys Ala Val
                85                  90                  95

Asp Asp Pro Arg Thr Leu Asn Lys Ile Leu Tyr Ile Arg Pro Pro Ala
            100                 105                 110

Asn Thr Tyr Ser Met Asn Glu Leu Val Ser Leu Trp Glu Arg Lys Ile
        115                 120                 125

Gly Lys Ala Leu Glu Arg Val Tyr Val Pro Glu Glu Gln
    130                 135                 140

<210> SEQ ID NO 320
<211> LENGTH: 102
<212> TYPE: PRT
<213> ORGANISM: Eucalyptus grandis

<400> SEQUENCE: 320

Lys Pro Ile Glu Phe Ala Gly Lys His Arg Ala Ser Ala Val Lys Thr
1               5                   10                  15

Thr Ser Glu Met Ala Ala Lys Ser Lys Val Leu Val Ile Gly Gly Thr
            20                  25                  30

Gly Tyr Ile Gly Lys Phe Ile Val Glu Ala Ser Ala Lys Ser Gly Arg
        35                  40                  45

Pro Thr Phe Val Leu Ala Arg Glu Ser Thr Leu Ser Asn Pro Ala Lys
    50                  55                  60

Ala Lys Ile Val Gln Gly Phe Lys Ser Leu Gly Val Thr Leu Val His
65                  70                  75                  80

Gly Asp Ile Tyr Asp Gln Glu Ser Leu Leu Asn Ala Ile Lys Gln Val
                85                  90                  95

Asp Val Val Ile Ser Ala
            100
```

```
<210> SEQ ID NO 321
<211> LENGTH: 125
<212> TYPE: PRT
<213> ORGANISM: Eucalyptus grandis

<400> SEQUENCE: 321

Gln Ser His Val Arg Asp Arg Ser Ser Pro Glu Asn Thr Thr Arg
 1               5                  10                  15

Ala Met Lys Arg Pro Ser Lys Met Ala Glu Met Ser Arg Val Leu Val
             20                  25                  30

Ile Gly Gly Ala Gly Tyr Ile Gly Lys Phe Ile Val Lys Ala Cys Ala
             35                  40                  45

Lys Ser Gly His Pro Thr Phe Val Leu Glu Thr Glu Ser Thr Leu Ser
 50                  55                  60

Asn Pro Ala Asn Ala Glu Ile Ile Lys Gly Phe Lys Ser Leu Gly Val
 65                  70                  75                  80

Asn Leu Val His Gly Asp Ile Tyr Asp Gln Lys Ser Leu Leu Ser Ala
                 85                  90                  95

Ile Lys Gln Val Asp Val Val Ile Ser Thr Val Gly Gln Ala Gln Leu
             100                 105                 110

Glu Asp Gln Asp Arg Ile Val Ala Ala Ile Lys Ala Ala
             115                 120                 125

<210> SEQ ID NO 322
<211> LENGTH: 98
<212> TYPE: PRT
<213> ORGANISM: Eucalyptus grandis

<400> SEQUENCE: 322

Ser Ser Ser Pro Glu Asn Thr Thr Pro Ala Val Lys Arg Pro Ser Lys
 1               5                  10                  15

Met Ala Glu Met Ser Arg Val Leu Val Ile Gly Gly Ala Gly Tyr Ile
             20                  25                  30

Gly Lys Phe Ile Val Lys Ala Cys Ala Lys Ser Gly His Pro Thr Phe
             35                  40                  45

Val Leu Glu Thr Glu Ser Thr Leu Ser Asn Pro Ala Asn Ala Glu Ile
 50                  55                  60

Ile Lys Gly Phe Lys Ser Leu Gly Val Asn Leu Val His Gly Asp Ile
 65                  70                  75                  80

Tyr Asp Gln Lys Ser Leu Leu Ser Ala Ile Lys Gln Val Asp Val Val
                 85                  90                  95

Ile Ser

<210> SEQ ID NO 323
<211> LENGTH: 319
<212> TYPE: PRT
<213> ORGANISM: Pinus radiata

<400> SEQUENCE: 323

Lys Asp Pro Leu Ala Gln Leu Thr Thr Phe Ser Cys Ile Cys Ser Val
 1               5                  10                  15

Arg His Asp Arg Gly Lys Thr Met Ala Cys Ala Thr Asp Val Ala Arg
             20                  25                  30

Gln Phe Leu Pro Cys Val Gln Pro Val Pro Ser Ser Met Gly Gly Glu
             35                  40                  45

Thr Ala Arg Ser Ile Asn Leu Thr Cys Asn Gly Leu Ser Pro Pro Gln
 50                  55                  60
```

```
Pro Gln Tyr Asn Ala Glu Asn Asn His Asp Gln Asp Thr Thr Val Ala
 65                  70                  75                  80

Thr Arg Val Leu Ile Ile Gly Ala Thr Gly Phe Ile Gly Arg Phe Val
                 85                  90                  95

Ala Glu Ala Ser Val Lys Ser Gly Arg Pro Thr Tyr Ala Leu Val Arg
            100                 105                 110

Pro Thr Thr Leu Ser Ser Lys Pro Lys Val Ile Gln Ser Leu Val Asp
            115                 120                 125

Ser Gly Ile Gln Val Val Tyr Gly Cys Leu His Asp His Asn Ser Leu
130                 135                 140

Val Lys Ala Ile Arg Gln Val Asp Val Val Ile Ser Thr Val Gly Gly
145                 150                 155                 160

Ala Leu Ile Leu Asp Gln Leu Lys Ile Val Asp Ala Ile Lys Glu Val
            165                 170                 175

Gly Thr Val Lys Arg Phe Leu Pro Ser Glu Phe Gly His Asp Val Asp
            180                 185                 190

Arg Ala Asp Pro Val Glu Pro Ala Leu Ser Phe Tyr Ile Glu Lys Arg
            195                 200                 205

Lys Val Arg Arg Ala Val Glu Glu Ala Lys Ile Pro Tyr Thr Tyr Ile
210                 215                 220

Cys Cys Asn Ser Ile Ala Gly Trp Pro Tyr Tyr Tyr His Thr His Pro
225                 230                 235                 240

Thr Glu Leu Pro Pro Pro Lys Glu Gln Phe Glu Ile Tyr Gly Asp Gly
            245                 250                 255

Ser Val Lys Ala Phe Phe Val Thr Gly Asp Asp Ile Gly Ala Tyr Thr
            260                 265                 270

Met Lys Ala Val Asp Asp Pro Arg Thr Leu Asn Lys Ser Ile His Phe
            275                 280                 285

Arg Pro Pro Lys Asn Phe Leu Asn Leu Asn Glu Leu Ala Asp Ile Trp
            290                 295                 300

Glu Asn Lys Ile Asn Arg Thr Leu Pro Arg Val Ser Val Ser Ala
305                 310                 315

<210> SEQ ID NO 324
<211> LENGTH: 126
<212> TYPE: PRT
<213> ORGANISM: Pinus radiata

<400> SEQUENCE: 324

Leu Asn Ser Leu Ala Asp Ile Leu Leu Ile Gln Ser Gly Lys Met Thr
 1               5                  10                  15

Gly Leu Lys Asp Ser Ala Asn Arg Val Leu Ile Ile Gly Gly Thr Gly
             20                  25                  30

Tyr Ile Gly Lys Tyr Met Ala Lys Ala Ser Val Ser Gln Gly Tyr Pro
         35                  40                  45

Thr Tyr Val Leu Val Arg Pro Ala Thr Ala Ala Pro Asp Ser Phe
     50                  55                  60

Lys Ala Lys Leu Leu Gln Gln Phe Lys Asp Ile Gly Ile His Ile Leu
 65                  70                  75                  80

Glu Gly Ser Leu Asp Asp His Asn Ser Leu Val Asp Ala Ile Lys Gln
             85                  90                  95

Val Asp Ile Val Ile Ser Ala Val Ala Ile Pro Gln His Leu Asp Gln
            100                 105                 110

Phe Asn Ile Ile Asn Ala Ile Lys Asp Val Gly Met Glu Ile
```

<210> SEQ ID NO 325
<211> LENGTH: 164
<212> TYPE: PRT
<213> ORGANISM: Eucalyptus grandis

<400> SEQUENCE: 325

Asn Gly Glu Leu His Pro Ser His Tyr Cys Glu Arg Asp Leu Leu Lys
1               5                   10                  15

Val Val Asp Arg Glu His Val Phe Thr Tyr Ala Asp Asp Ala Cys Ser
            20                  25                  30

Ala Thr Tyr Pro Leu Met Gln Lys Leu Arg Gln Val Leu Val Asp Gln
        35                  40                  45

Ala Leu Val Asn Gly Glu Ser Glu Leu Asn Pro Ser Thr Ser Ile Phe
    50                  55                  60

Gln Lys Ile Val Ala Phe Glu Glu Leu Lys Ala Gln Leu Pro Lys
65                  70                  75                  80

Asp Val Glu Gly Val Arg Val Gln Tyr Glu Thr Gly Asn Leu Ala Ile
                85                  90                  95

Pro Asn Gln Ile Lys Glu Cys Arg Ser Tyr Pro Leu Tyr Lys Leu Val
            100                 105                 110

Arg Glu Glu Leu Gly Thr Ala Leu Leu Thr Gly Glu Gly Val Ile Ser
        115                 120                 125

Pro Gly Glu Asp Phe Asp Lys Val Phe Thr Ala Ile Cys Ala Gly Lys
    130                 135                 140

Leu Ile Asp Pro Leu Leu Glu Cys Leu Ser Gly Trp Asn Gly Ala Pro
145                 150                 155                 160

Leu Pro Ile Ser

<210> SEQ ID NO 326
<211> LENGTH: 114
<212> TYPE: PRT
<213> ORGANISM: Eucalyptus grandis

<400> SEQUENCE: 326

Leu Val Asp Gln Ala Leu Val Asn Gly Glu Ser Glu Leu Asn Pro Ser
1               5                   10                  15

Thr Ser Ile Phe Gln Lys Ile Val Ala Phe Glu Glu Leu Lys Ala
            20                  25                  30

Gln Leu Pro Lys Asp Val Glu Gly Val Arg Val Gln Tyr Glu Thr Gly
        35                  40                  45

Asn Leu Ala Ile Pro Asn Gln Ile Lys Glu Cys Arg Ser Tyr Pro Leu
    50                  55                  60

Tyr Lys Leu Val Arg Glu Glu Leu Gly Thr Ala Leu Leu Thr Gly Glu
65                  70                  75                  80

Gly Val Ile Ser Pro Gly Glu Asp Phe Asp Lys Val Phe Thr Ala Ile
                85                  90                  95

Cys Ala Gly Lys Leu Ile Asp Pro Leu Leu Glu Cys Leu Ser Gly Trp
            100                 105                 110

Asn Gly

<210> SEQ ID NO 327
<211> LENGTH: 226
<212> TYPE: PRT
<213> ORGANISM: Eucalyptus grandis

```
<400> SEQUENCE: 327

Pro Ser Leu Asp Tyr Gly Phe Lys Gly Ala Glu Ile Ala Met Ala Ser
  1               5                  10                  15

Tyr Cys Ser Glu Leu Gln Phe Leu Ala Asn Pro Val Thr Asn His Val
             20                  25                  30

Gln Ser Ala Glu Gln His Asn Gln Asp Val Asn Ser Leu Gly Leu Ile
         35                  40                  45

Ser Ser Arg Lys Thr Ala Glu Ala Ile Asp Val Leu Lys Leu Met Ser
 50                  55                  60

Ser Thr Phe Leu Val Ala Leu Cys Gln Ala Ile Asp Leu Arg His Leu
 65                  70                  75                  80

Glu Glu Asn Leu Lys Ser Val Val Lys Asn Thr Val Asn Gln Val Ala
                 85                  90                  95

Lys Lys Val Leu Tyr Val Gly Ser Asn Gly Glu Leu His Pro Ser Arg
            100                 105                 110

Phe Ser Glu Lys Asp Leu Ile Lys Val Val Asp Arg Glu Tyr Val Phe
        115                 120                 125

Ala Tyr Ile Asp Asp Pro Cys Ser Ala Thr Tyr Pro Leu Met Gln Lys
130                 135                 140

Leu Arg Gln Val Leu Val Asp Asp Ala Leu Asp Asp Val Asp Arg Glu
145                 150                 155                 160

Lys Asn Pro Ser Thr Ser Ile Phe Gln Lys Ile Gly Ala Phe Glu Glu
                165                 170                 175

Glu Leu Lys Ala Leu Leu Pro Lys Glu Val Glu Asn Ala Arg Ala Gln
            180                 185                 190

Phe Glu Ser Gly Asn Ser Ala Ile Ala Asn Lys Ile Arg Gly Cys Arg
        195                 200                 205

Ser Tyr Pro Leu Tyr Arg Phe Val Arg Glu Glu Leu Gly Thr Gly Leu
    210                 215                 220

Leu Thr
225

<210> SEQ ID NO 328
<211> LENGTH: 424
<212> TYPE: PRT
<213> ORGANISM: Eucalyptus grandis

<400> SEQUENCE: 328

Met Glu Met Glu Ser Thr Thr Gly Thr Gly Asn Gly Leu His Ser Leu
  1               5                  10                  15

Cys Ala Ala Gly Ser His His Ala Asp Pro Leu Asn Trp Gly Ala Ala
             20                  25                  30

Ala Ala Ala Leu Thr Gly Ser His Leu Asp Glu Val Lys Arg Met Val
         35                  40                  45

Glu Glu Tyr Arg Arg Pro Ala Val Arg Leu Gly Gly Glu Ser Leu Thr
 50                  55                  60

Ile Ala Gln Val Ala Ala Val Ala Ser Gln Glu Gly Val Gly Val Glu
 65                  70                  75                  80

Leu Ser Glu Ala Ala Arg Pro Arg Val Lys Ala Ser Ser Asp Trp Val
                 85                  90                  95

Met Glu Ser Met Asn Lys Gly Thr Asp Ser Tyr Gly Val Thr Thr Gly
            100                 105                 110

Phe Gly Ala Thr Ser His Arg Arg Thr Lys Gln Gly Gly Ala Leu Gln
        115                 120                 125
```

```
Lys Glu Leu Ile Arg Phe Leu Asn Ala Gly Ile Phe Gly Asn Gly Thr
    130                 135                 140

Glu Ser Cys His Thr Leu Pro Gln Ser Ser Thr Arg Ala Ala Met Leu
145                 150                 155                 160

Val Arg Val Asn Thr Leu Leu Gln Gly Tyr Ser Gly Ile Arg Phe Glu
                165                 170                 175

Ile Leu Glu Ala Ile Thr Lys Phe Leu Asn His Asn Ile Thr Pro Cys
            180                 185                 190

Leu Pro Leu Arg Gly Thr Ile Thr Ala Ser Gly Asp Leu Val Pro Leu
        195                 200                 205

Ser Tyr Ile Ala Gly Leu Leu Thr Gly Arg Pro Asn Ser Lys Ala Val
    210                 215                 220

Gly Pro Asp Gly Lys Ser Leu Asp Ala Val Glu Ala Phe Arg Leu Ala
225                 230                 235                 240

Gly Ile Asp Thr Gly Phe Phe Glu Leu Gln Pro Lys Glu Gly Leu Ala
                245                 250                 255

Leu Val Asn Gly Thr Ala Val Gly Ser Gly Leu Ala Ser Ile Val Leu
            260                 265                 270

Phe Glu Ala Asn Ile Leu Ala Val Leu Ser Glu Val Leu Ser Ala Ile
        275                 280                 285

Phe Ala Glu Val Met Gln Gly Lys Pro Glu Phe Thr Asp His Leu Thr
    290                 295                 300

His Lys Leu Lys His His Pro Gly Gln Ile Glu Ser Ala Ala Ile Met
305                 310                 315                 320

Glu His Ile Leu Asp Gly Ser Ala Tyr Val Lys Ala Ala Lys Lys Leu
                325                 330                 335

His Glu Met Asp Pro Leu Gln Lys Pro Lys Gln Asp Arg Tyr Ala Leu
            340                 345                 350

Arg Thr Ser Pro Gln Trp Leu Gly Pro Gln Ile Glu Val Ile Arg Ala
        355                 360                 365

Ala Thr Lys Met Ile Glu Arg Glu Ile Asn Ser Val Asn Asp Asn Pro
    370                 375                 380

Leu Ile Asp Val Ala Arg Asn Lys Ala Leu His Gly Gly Asn Phe Gln
385                 390                 395                 400

Gly Thr Pro Ile Gly Val Ser Met Asp Asn Thr Arg Leu Ala Val Ala
                405                 410                 415

Ser Ile Gly Lys Leu Met Phe Ala
            420

<210> SEQ ID NO 329
<211> LENGTH: 97
<212> TYPE: PRT
<213> ORGANISM: Eucalyptus grandis

<400> SEQUENCE: 329

Asn Ser Gly Ile Thr Pro Cys Leu Pro Leu Arg Gly Ser Ile Ser Ala
1               5                   10                  15

Ser Gly Asp Leu Val Pro Phe Ser Tyr Ile Ala Gly Leu Leu Thr Gly
                20                  25                  30

Arg Pro Asn Ser Lys Ala Val Gly Pro Ala Gly Glu Thr Leu Thr Ala
            35                  40                  45

Lys Gln Ala Phe Glu Leu Ala Gly Ile Ser Gly Gly Phe Phe Glu Leu
        50                  55                  60

Gln Pro Lys Glu Gly Leu Ala Leu Val Asn Gly Thr Gly Val Gly Ser
65                  70                  75                  80
```

```
Ala Leu Ala Ala Ile Val Leu Phe Glu Ala Asn Met Leu Thr Val Leu
                85                  90                  95
Ser

<210> SEQ ID NO 330
<211> LENGTH: 412
<212> TYPE: PRT
<213> ORGANISM: Pinus radiata

<400> SEQUENCE: 330

Val Tyr Arg Ser Ile Asn Ser Gln Ala Glu Ala Pro Ser Trp Pro Asn
 1               5                  10                  15

Gly Ser Cys Ser Asp His Gly Val Cys Leu Gly Arg Glu Ser Tyr Met
                20                  25                  30

Lys His Ala Ala Lys Leu His Glu Met Asn Pro Leu Gln Lys Pro Lys
                35                  40                  45

Gln Asp Arg Tyr Ala Leu Arg Thr Ser Pro Gln Trp Leu Gly Pro Gln
50                  55                  60

Val Glu Ile Ile Arg Ser Ala Thr His Met Ile Glu Arg Glu Ile Asn
65                  70                  75                  80

Ser Val Asn Asp Asn Pro Val Ile Asp Val Ala Arg Asp Lys Ala Leu
                85                  90                  95

His Gly Gly Asn Phe Gln Gly Thr Pro Ile Gly Val Ser Met Asp Asn
                100                 105                 110

Leu Arg Leu Ser Ile Ser Ala Ile Gly Lys Leu Met Phe Ala Gln Phe
                115                 120                 125

Ser Glu Leu Val Asn Asp Tyr Tyr Asn Gly Gly Leu Pro Ser Asn Leu
130                 135                 140

Ser Gly Gly Pro Asn Pro Ser Leu Asp Tyr Gly Leu Lys Gly Ala Glu
145                 150                 155                 160

Ile Ala Met Ala Ser Tyr Thr Ser Glu Leu Leu Tyr Leu Ala Asn Pro
                165                 170                 175

Val Thr Ser His Val Gln Ser Ala Glu Gln His Asn Gln Asp Val Asn
                180                 185                 190

Ser Leu Gly Leu Val Ser Ala Arg Lys Ser Ala Glu Ala Ile Asp Ile
                195                 200                 205

Leu Lys Leu Met Leu Ser Thr Tyr Leu Thr Ala Leu Cys Gln Ala Val
                210                 215                 220

Asp Leu Arg His Leu Glu Glu Asn Met Leu Ala Thr Val Lys Gln Ile
225                 230                 235                 240

Val Ser Gln Val Ala Lys Lys Thr Leu Ser Thr Gly Leu Asn Gly Glu
                245                 250                 255

Leu Leu Pro Gly Arg Phe Cys Glu Lys Asp Leu Leu Gln Val Val Asp
                260                 265                 270

Asn Glu His Val Phe Ser Tyr Ile Asp Asp Pro Cys Asn Ala Ser Tyr
                275                 280                 285

Pro Leu Thr Gln Lys Leu Arg Asn Ile Leu Val Glu His Ala Phe Lys
                290                 295                 300

Asn Ala Glu Gly Glu Lys Asp Pro Asn Thr Ser Ile Phe Asn Lys Ile
305                 310                 315                 320

Pro Val Phe Glu Ala Glu Leu Lys Ala Gln Leu Glu Pro Gln Val Ser
                325                 330                 335

Leu Ala Arg Glu Ser Tyr Asp Lys Gly Thr Ser Pro Leu Pro Asn Arg
                340                 345                 350
```

```
Ile Gln Glu Cys Arg Ser Tyr Pro Leu Tyr Glu Phe Val Arg Asn Gln
        355                 360                 365

Leu Gly Thr Leu Gln Ala Trp Leu Phe His Ile Asn Ile Val Met Arg
    370                 375                 380

Cys Leu Ile Ile Tyr Cys Ser Leu Phe Phe Pro Glu Leu Ala Thr Ala
385                 390                 395                 400

Phe Asp Ser Val His Tyr Ala Arg Thr Lys Pro Leu
                405                 410

<210> SEQ ID NO 331
<211> LENGTH: 132
<212> TYPE: PRT
<213> ORGANISM: Pinus radiata

<400> SEQUENCE: 331

Gly Ser Ser Cys Arg Ser Leu Ile Arg Glu Leu Phe Val Cys Leu Ile
1               5                   10                  15

Ile Val His Met Ala Pro Gln Glu Phe Thr Gly Glu Val Lys Phe Cys
            20                  25                  30

Ala Gly Asn Gly Gly Thr Ala Ser Leu Asn Asp Pro Leu Asn Trp Ala
        35                  40                  45

Ala Ala Glu Ser Met Lys Gly Ser His Phe Glu Glu Val Lys Arg
    50                  55                  60

Met Trp Glu Glu Phe Arg Ser Pro Val Val Arg Leu Gln Gly Ser Gly
65              70                  75                  80

Leu Thr Ile Ala Gln Val Ala Ala Val Ala Arg Arg Thr Gly Ser Val
                85                  90                  95

Arg Val Glu Leu Glu Thr Gly Ala Lys Ala Arg Val Asp Glu Ser Ser
            100                 105                 110

Asn Trp Val Met Asp Ser Met Ala Asn Gly Thr Asp Ser Tyr Gly Val
        115                 120                 125

Thr Thr Gly Phe
    130

<210> SEQ ID NO 332
<211> LENGTH: 170
<212> TYPE: PRT
<213> ORGANISM: Eucalyptus grandis

<400> SEQUENCE: 332

Asn Leu Val Lys Leu Gly Ser Ile Leu Gly Met Ala Ile Gly Val Ala
1               5                   10                  15

Leu Phe Ser Ser Leu Leu Val Leu Ser Phe Val Ser Pro Ile Ser Ser
            20                  25                  30

Leu Ser Ser Asn Tyr Tyr Asp Lys Thr Cys Pro Asn Ala Glu Leu Ile
        35                  40                  45

Val Ala Asn Ala Val Lys Asn Ala Ala Met Lys Asp Lys Thr Val Pro
    50                  55                  60

Ala Ala Leu Leu Arg Met His Phe His Asp Cys Phe Ile Arg Gly Cys
65              70                  75                  80

Asp Ala Ser Val Leu Leu Asn Ser Lys Gly Ser Asn Lys Ala Glu Lys
            85                  90                  95

Asp Gly Pro Pro Asn Val Ser Leu His Ser Phe Phe Val Ile Asp Asn
            100                 105                 110

Ala Lys Lys Glu Leu Glu Ala Ser Cys Pro Gly Val Val Ser Cys Ala
        115                 120                 125
```

```
Asp Ile Leu Ala Leu Ala Ala Arg Asp Ser Val Val Leu Ser Gly Gly
        130                 135                 140

Pro Thr Trp Asp Val Pro Lys Gly Arg Lys Asp Gly Arg Thr Ser Lys
145                 150                 155                 160

Ala Ser Glu Thr Thr Gln Leu Pro Ala Pro
                165                 170

<210> SEQ ID NO 333
<211> LENGTH: 118
<212> TYPE: PRT
<213> ORGANISM: Eucalyptus grandis

<400> SEQUENCE: 333

Leu Val Ile Thr Ile Val Val Phe Phe Gly His Ile Gly Asp Ser Glu
1               5                   10                  15

Gly Gly Asp Leu Arg Lys Asn Phe Tyr Lys Ser Ala Cys Pro Leu Ala
            20                  25                  30

Glu Glu Ile Val Lys Asn Val Thr Trp Lys His Ala Ala Ser Asn Ser
        35                  40                  45

Ala Leu Pro Ala Lys Phe Leu Arg Met His Phe His Asp Cys Phe Val
    50                  55                  60

Arg Gly Cys Asp Gly Ser Val Leu Leu Asp Ser Thr Ala Asn Asn Lys
65                  70                  75                  80

Ala Glu Lys Val Ala Val Pro Asn Gln Ser Leu Thr Gly Phe Asp Val
                85                  90                  95

Ile Asp Glu Ile Lys Glu Lys Leu Glu Glu Thr Cys Pro Gly Val Val
            100                 105                 110

Ser Cys Ala Asp Ile Leu
        115

<210> SEQ ID NO 334
<211> LENGTH: 65
<212> TYPE: PRT
<213> ORGANISM: Pinus radiata

<400> SEQUENCE: 334

Asn Ala Asp Pro Ile Ala Val Ile Asp Glu Ala Leu Ser Thr Gly Gly
1               5                   10                  15

Ala Pro Asn Leu Ser Asp Ala Tyr Thr Leu Asn Gly Gln Pro Gly Asp
            20                  25                  30

Leu Tyr Asn Cys Ser Arg Ala Gly Thr Phe Arg Phe Leu Val Lys Gln
        35                  40                  45

Gly Glu Thr Tyr Leu Leu Arg Met Val Asn Ala Ala Leu Asn Ser Ala
    50                  55                  60

His
65

<210> SEQ ID NO 335
<211> LENGTH: 104
<212> TYPE: PRT
<213> ORGANISM: Pinus radiata

<400> SEQUENCE: 335

Lys Pro His Gly Glu Thr Pro Leu Ile Ile Gly Glu Trp Trp Asn Ala
1               5                   10                  15

Asp Pro Ile Ala Val Ile Asp Glu Ala Leu Arg Thr Gly Gly Ala Pro
            20                  25                  30
```

-continued

```
Asn Leu Ser Asp Ala Tyr Thr Leu Asn Gly Gln Pro Gly Asp Leu Tyr
            35                  40                  45

Asn Cys Ser Arg Ala Gly Thr Phe Arg Phe Pro Val Lys Gln Gly Glu
     50                  55                  60

Thr Tyr Leu Leu Arg Met Val Asn Ala Ala Leu Asn Ser Ala His Phe
 65                  70                  75                  80

Phe Lys Ile Ala Gly His Lys Phe Thr Val Val Ala Val Asp Ala Ser
                 85                  90                  95

Tyr Thr Lys Pro Tyr Lys Gln Met
                100

<210> SEQ ID NO 336
<211> LENGTH: 125
<212> TYPE: PRT
<213> ORGANISM: Pinus radiata

<400> SEQUENCE: 336

Asp Ala His Thr Ile Asn Gly Lys Pro Gly Pro Leu Phe Lys Cys Pro
 1               5                  10                  15

Thr Lys Asp Thr Phe Val Val Pro Val Glu His Gly Lys Thr Tyr Leu
             20                  25                  30

Leu Arg Ile Ile Asn Ala Ala Leu Asn Asp Glu Leu Phe Phe Asp Val
            35                  40                  45

Ala Asn His His Leu Lys Val Val Glu Ile Asp Ala Val Tyr Thr Lys
     50                  55                  60

Pro Leu Ile Thr Asn Ser Ile Val Ile Ala Pro Gly Gln Thr Thr Asn
 65                  70                  75                  80

Ala Leu Ile His Thr Asn Lys Arg Ser Gly Arg Tyr Phe Met Ala Ala
                 85                  90                  95

Arg Ser Phe Met Asp Ala Pro Val Ser Val Asp Asn Lys Thr Ala Thr
                100                 105                 110

Ala Ile Leu Gln Tyr Val Asn Ser Ile Gln Ile Leu Leu
            115                 120                 125

<210> SEQ ID NO 337
<211> LENGTH: 178
<212> TYPE: PRT
<213> ORGANISM: Pinus radiata

<400> SEQUENCE: 337

Asn Met Met Ala Pro Met Ala Gly Ala Glu Tyr Gly Ile Lys Leu Ile
 1               5                  10                  15

Ile Gln Leu Leu Val Val Leu Leu Ala Val Gln Leu Val Ala Gly Lys
             20                  25                  30

Thr Thr Arg His Tyr Ser Phe His Val Arg Leu Lys Asn Val Thr Arg
            35                  40                  45

Leu Cys His Thr Lys Pro Leu Ile Thr Val Asn Gly Lys Ser Pro Gly
     50                  55                  60

Pro Lys Val Val Arg Glu Gly Asp Arg Val Ile Ile Lys Val His
 65                  70                  75                  80

Asn His Val Ser Asn Asn Val Ser Ile His Trp His Gly Val Arg Gln
                 85                  90                  95

Leu Arg Ser Gly Trp Ala Asp Gly Pro Ala Tyr Ile Thr Gln Cys Pro
                100                 105                 110

Ile Gln Thr Gly Gln Thr Tyr Val Tyr Asn Phe Thr Val Thr Gly Gln
            115                 120                 125
```

Arg Gly Thr Leu Trp Trp His Ala His Ile Ser Trp Leu Arg Ala Ser
        130                 135                 140

Val Tyr Gly Ala Phe Ile Ile Tyr Pro Lys Arg His Val Pro Tyr Pro
145                 150                 155                 160

Phe Pro Lys Pro Tyr Lys Glu Val Pro Leu Ile Leu Gly Glu Trp Trp
                165                 170                 175

Asn Ala

<210> SEQ ID NO 338
<211> LENGTH: 358
<212> TYPE: PRT
<213> ORGANISM: Pinus radiata

<400> SEQUENCE: 338

Pro Ile Pro Pro Gly Gly Arg Tyr Thr Tyr Arg Phe Asn Ile Ser Gly
1               5                   10                  15

Gln Glu Gly Thr Val Trp Trp His Ala His Tyr Ser Trp Leu Arg Ala
            20                  25                  30

Thr Val His Gly Ala Phe Val Ile Leu Pro Lys Lys Gly Ser Ser Tyr
        35                  40                  45

Pro Phe Ser Lys Pro His Ala Glu Ile Pro Ile Ile Gly Glu Trp
    50                  55                  60

Trp Asn Ala Asn Pro Ile Ala Val Ile Asp Glu Ala Val Arg Thr Gly
65                  70                  75                  80

Gly Ala Pro Asn Leu Ser Asp Ala Phe Thr Ile Asn Gly Gln Pro Gly
                85                  90                  95

Asp Leu Phe Asn Cys Ser Thr Ser Gly Thr Phe Arg Leu Pro Val Glu
            100                 105                 110

Ser Gly Glu Thr Tyr Leu Leu Arg Ile Val Asn Ala Ala Leu Asn Ser
        115                 120                 125

Gly His Phe Phe Lys Ile Ala Gly His Glu Phe Thr Val Val Ala Val
130                 135                 140

Asp Ala Cys Tyr Thr Lys Pro Tyr Lys Thr Asp Val Leu Val Ile Ser
145                 150                 155                 160

Ala Gly Gln Thr Thr Asp Val Leu Ile Thr Ala Asn Gln Ser Val Gly
                165                 170                 175

Arg Tyr Tyr Met Ala Ala Arg Ala Tyr Gln Asn Gln Ala Ala Gly Asp
            180                 185                 190

Phe Thr Asn Thr Thr Thr Thr Ala Ile Leu Glu Tyr Ile Gly Ser Glu
        195                 200                 205

Asn Ser Thr Arg Pro Ile Leu Pro Ser Leu Pro Ala Tyr Asn Asp Thr
    210                 215                 220

Ala Thr Val Thr Arg Phe Ser Arg Ala Leu Arg Ser Leu Ala Ser Gln
225                 230                 235                 240

Glu His Pro Val Asn Val Pro His Thr Ile Asp Glu Ser Leu Ile Ser
                245                 250                 255

Thr Val Gly Leu Gly Leu Leu Pro Cys Gly Ala Gly Asn Thr Cys Glu
            260                 265                 270

Gly Pro Asn Gly Thr Arg Leu Ser Ala Ser Ile Asn Asn Ile Ser Tyr
        275                 280                 285

Val Glu Pro Thr Ile Ser Leu Leu Gln Ala Tyr Tyr Tyr Thr Ala Asn
    290                 295                 300

Gly Ile Phe Thr Gly Asp Phe Pro Ser Lys Pro Glu Val Arg Phe Asn
305                 310                 315                 320

```
Tyr Thr Gly Asp Asp Ile Pro Arg Lys Phe Trp Ala Pro Asp Pro Ala
                325                 330                 335

Thr Lys Val Lys Val Leu Glu Tyr Asn Ser Thr Val Gln Leu Val Phe
            340                 345                 350

Gln Ser Thr Asn Ile Phe
        355

<210> SEQ ID NO 339
<211> LENGTH: 160
<212> TYPE: PRT
<213> ORGANISM: Pinus radiata

<400> SEQUENCE: 339

Phe Arg Arg Glu Thr Val Ile Gln His Ile Ser Arg Ser Phe Leu Ser
1               5                   10                  15

Lys Met Val Ile Ser Lys Tyr Ala Ala Met Ser Cys Leu Leu Ile
            20                  25                  30

Ala Val Ala Leu Glu Val Gly Ala Glu Thr Arg His Tyr Lys Phe
        35                  40                  45

Asp Ile Lys Phe Lys Asn Val Thr Arg Leu Cys His Thr Lys Pro Ile
 50                  55                  60

Val Thr Ala Asn Gly Lys Phe Pro Gly Pro Thr Ile Tyr Ala Arg Glu
65                  70                  75                  80

Gly Asp Thr Val Thr Val Lys Val Thr Asn His Val Thr Tyr Asn Val
                85                  90                  95

Ser Ile His Trp His Gly Ile Arg Gln Leu Arg Thr Gly Trp Ala Asp
            100                 105                 110

Gly Pro Ala Tyr Ile Thr Gln Cys Pro Ile Gln Thr Gly Gln Thr Tyr
        115                 120                 125

Val Tyr Asn Phe Thr Ile Thr Gly Gln Arg Gly Thr Leu Phe Trp His
    130                 135                 140

Ala His Ile Leu Trp Leu Arg Ala Thr Leu Asn Gly Pro Ile Val Ile
145                 150                 155                 160

<210> SEQ ID NO 340
<211> LENGTH: 156
<212> TYPE: PRT
<213> ORGANISM: Pinus radiata

<400> SEQUENCE: 340

Gly Cys Cys Leu Ser Thr Arg Met Asn Met Ser Arg Ser Lys Ala Leu
1               5                   10                  15

Leu Cys Pro Ser Pro Ala His Val Lys Tyr Val Leu Ile Val Ile Leu
            20                  25                  30

Leu Ile Ile Met Ile Gln Cys Pro Asp Ile Val Ala Gly Lys His Ala
        35                  40                  45

Gln Thr Thr Arg His Tyr Lys Phe Asn Val Arg Leu Ser Asn Val Thr
    50                  55                  60

Arg Leu Cys Arg Thr Lys Pro Leu Ile Thr Val Asn Gly Lys Tyr Pro
65                  70                  75                  80

Gly Pro Thr Val Val Ala Arg Glu Gly Asp Arg Val Ile Ile Lys Leu
                85                  90                  95

Val Asn His Val Lys Asp Asn Val Thr Ile His Trp His Gly Val Arg
            100                 105                 110

Gln Leu Arg Ser Gly Trp Ala Asp Gly Pro Gly Tyr Ile Thr Gln Cys
        115                 120                 125
```

-continued

Pro Leu Gln Thr Gly Met Ser Tyr Val Tyr Asn Phe Thr Ile Val Gly
    130                 135                 140

Gln Arg Gly Thr Leu Trp Trp His Ala His Ile Ser
145                 150                 155

<210> SEQ ID NO 341
<211> LENGTH: 157
<212> TYPE: PRT
<213> ORGANISM: Pinus radiata

<400> SEQUENCE: 341

Val Ile Gln Gln Ala Leu Gln Thr Gly Gly Pro Asn Val Ser Asp
1               5                   10                  15

Ala Tyr Thr Ile Asn Gly Leu Pro Gly Pro Leu Tyr Asn Cys Ser Asn
                20                  25                  30

Glu Thr Phe Val Leu Lys Val His Pro Gly Gln Thr Tyr Leu Leu Arg
            35                  40                  45

Ile Ile Asn Ala Ala Leu Asn Asp Glu Leu Phe Leu Ala Ile Ala Asn
        50                  55                  60

His Ser Leu Thr Val Val Glu Val Asp Ala Val Tyr Val Lys Pro Phe
65                  70                  75                  80

Gln Thr Asp Thr Leu Leu Ile Thr Pro Gly Gln Thr Thr Asn Val Leu
                85                  90                  95

Leu Thr Ala Asn Ala Thr Ser Gly Lys Asn Lys Gln Phe Val Ile Ala
            100                 105                 110

Ala Ser Pro Phe Val Thr Gly Ser Gly Thr Phe Asp Asn Ser Thr Val
        115                 120                 125

Ala Gly Ile Val Ser Tyr Asn Ser His Lys Phe Lys Asn Ser Ser Thr
    130                 135                 140

Ile Ile Leu Pro Lys Leu Pro Ser Phe Asn Asp Thr Asn
145                 150                 155

<210> SEQ ID NO 342
<211> LENGTH: 134
<212> TYPE: PRT
<213> ORGANISM: Pinus radiata

<400> SEQUENCE: 342

Gly Gln Thr Thr Asn Val Leu Leu Glu Ala Asn Lys Arg Ser Gly Ser
1               5                   10                  15

Tyr Phe Val Ala Ala Arg Pro Phe Met Asp Ala Pro Val Thr Val Asn
                20                  25                  30

Asn Lys Thr Ala Thr Ala Ile Leu His Tyr Ile Gly Arg Asn Ser Glu
            35                  40                  45

Ser Asp Ile Pro Ala Val Asn Pro Leu Met Pro Arg Leu Pro Leu Leu
        50                  55                  60

Asn Asp Thr Ala Phe Ala Thr Ser Phe Thr Ser Lys Leu Arg Ser Leu
65                  70                  75                  80

Asn Ser Val Gln Phe Pro Ala Lys Val Pro Gln Thr Ile Asp Arg Asn
                85                  90                  95

Leu Phe Phe Ala Val Gly Leu Ala Thr Glu Ser Cys Gln Thr Cys Asn
            100                 105                 110

Gly Gly Leu Arg Ala Ser Ala Ser Ile Asn Asn Ile Ser Phe Val Met
        115                 120                 125

Pro Ser Ile Ser Leu Leu
    130

<210> SEQ ID NO 343
<211> LENGTH: 419
<212> TYPE: PRT
<213> ORGANISM: Pinus radiata

<400> SEQUENCE: 343

```
Thr Thr Tyr Pro Phe Thr Phe Thr Arg Pro His Arg Gln Ile Pro Ile
  1               5                  10                  15

Leu Leu Gly Glu Trp Trp Asn Arg Asn Pro Met Asp Val Val Asn Gln
             20                  25                  30

Ala Thr Gln Thr Gly Ala Ala Pro Asn Val Ser Asp Ala Phe Thr Ile
         35                  40                  45

Asn Gly Gln Pro Gly Asp Leu Tyr Lys Cys Ser Thr Ser Asp Thr Phe
     50                  55                  60

Ser Val Ser Met Lys Gly Gly Glu Thr Asn Leu Leu Arg Val Ile Asn
 65                  70                  75                  80

Ala Ala Leu Asn Thr Asp Leu Phe Phe Ser Ile Ala Ser His Thr Met
                 85                  90                  95

Thr Val Val Ala Val Asp Ala Leu Tyr Thr Lys Pro Phe Gln Thr Asn
            100                 105                 110

Val Leu Met Leu Gly Pro Gly Gln Thr Thr Asp Ile Leu Leu Thr Ala
        115                 120                 125

Asn Gln Ala Thr Gly Arg Tyr Tyr Met Ala Ala Arg Ala Tyr Ser Ser
    130                 135                 140

Gly Gln Gly Val Pro Phe Asp Asn Thr Thr Thr Ala Ile Leu Glu
145                 150                 155                 160

Tyr Glu Gly Ser Ser Lys Thr Ser Thr Pro Val Met Pro Asn Leu Pro
                165                 170                 175

Phe Tyr Asn Asp Thr Asn Ser Ala Thr Ser Phe Ala Asn Gly Leu Arg
            180                 185                 190

Ser Leu Gly Ser His Asp His Pro Val Phe Val Pro Gln Ser Val Glu
        195                 200                 205

Glu Asn Leu Phe Tyr Thr Ile Gly Leu Gly Leu Ile Lys Cys Pro Gly
    210                 215                 220

Gln Ser Cys Gly Gly Pro Asn Gly Ser Arg Phe Ala Ala Ser Met Asn
225                 230                 235                 240

Asn Ile Ser Phe Val Pro Pro Thr Thr Ser Ser Ile Leu Gln Ala Gln
                245                 250                 255

His Phe Gly Met Lys Gly Val Phe Ser Ala Asp Phe Pro Asp Asn Pro
            260                 265                 270

Ser Val Gly Phe Asp Tyr Thr Ala Gln Asn Ile Ser Arg Asp Leu Trp
        275                 280                 285

Ser Pro Val Lys Ala Thr Arg Val Lys Val Leu Lys Tyr Asn Ser Thr
    290                 295                 300

Val Gln Val Ile Leu Gln Gly Thr Asn Ile Phe Ala Gly Glu Ser His
305                 310                 315                 320

Pro Ile His Leu His Gly Tyr Asp Phe Tyr Ile Val Gly Ala Gly Phe
                325                 330                 335

Gly Asn Tyr Asn Ala Gln Thr Asp Pro His Lys Phe Asn Leu Val Asp
            340                 345                 350

Pro Pro Met Arg Asn Thr Val Asn Val Pro Val Asn Gly Trp Ala Ala
        355                 360                 365

Ile Arg Phe Val Ala Asp Asn Pro Gly Ala Trp Val Met His Cys His
    370                 375                 380
```

-continued

Leu Asp Val His Ile Thr Trp Gly Leu Ala Met Val Phe Val Val Asn
385                 390                 395                 400

Asn Gly Pro Asp Ala Leu Leu Ser Leu Gln Ser Pro Pro Arg Asp Leu
            405                 410                 415

Pro Leu Cys

<210> SEQ ID NO 344

<211> LENGTH: 111
<212> TYPE: PRT
<213> ORGANISM: Pinus radiata

<400> SEQUENCE: 344

Leu Asn Tyr Asn Ala Thr Val Gln Val Ile Leu Gln Gly Thr Asn Ile
1               5                   10                  15

Phe Ala Gly Glu Ser His Pro Ile His Leu His Gly Tyr Asp Phe Tyr
            20                  25                  30

Ile Val Gly Ala Gly Phe Gly Asn Tyr Asn Ala Gln Thr Asp Pro Gln
        35                  40                  45

Lys Phe Asn Leu Val Asp Pro Pro Met Arg Asn Thr Val Asn Val Pro
50                  55                  60

Val Asn Gly Trp Ala Ala Ile Arg Phe Val Ala Asp Asn Pro Gly Ala
65                  70                  75                  80

Trp Val Met His Cys His Leu Asp Val His Ile Thr Trp Gly Leu Ala
                85                  90                  95

Met Val Phe Val Val Asn Asn Gly Pro Asp Pro Leu Leu Ser Leu
            100                 105                 110

<210> SEQ ID NO 345
<211> LENGTH: 93
<212> TYPE: PRT
<213> ORGANISM: Pinus radiata

<400> SEQUENCE: 345

Thr Arg Val Lys Val Leu Asn Tyr Asn Thr Thr Val Gln Val Ile Leu
1               5                   10                  15

Gln Gly Thr Asn Ile Phe Ala Gly Glu Ser His Pro Ile His Leu His
            20                  25                  30

Gly Tyr Asp Phe Tyr Ile Val Gly Ala Gly Phe Gly Asn Tyr Asn Pro
        35                  40                  45

Gln Thr Asp Pro Gln Lys Phe Asn Leu Ala Asp Pro Pro Met Arg Asn
50                  55                  60

Thr Val Asn Val Pro Val Asn Gly Trp Ala Ala Ile Arg Phe Val Ala
65                  70                  75                  80

Asp Asn Pro Gly Ala Trp Val Met His Cys His Leu Asp
                85                  90

<210> SEQ ID NO 346
<211> LENGTH: 93
<212> TYPE: PRT
<213> ORGANISM: Pinus radiata

<400> SEQUENCE: 346

Lys Thr Phe Ser Asp Glu Cys Ser Asp Ala Arg Pro Arg Pro Asp Asn
1               5                   10                  15

Arg His Ser Gly Arg Val Asp Gln Leu Ala Asp Thr Phe Ser Val Ser
            20                  25                  30

```
Met Lys Gly Gly Glu Thr Asn Leu Leu Arg Val Ile Asn Ala Ala Leu
          35                  40                  45

Asn Thr Asp Leu Phe Phe Ser Ile Ala Ser His Thr Met Thr Val Val
 50                  55                  60

Ala Val Asp Ala Leu Tyr Thr Lys Pro Phe Gln Thr Asn Val Leu Met
 65                  70                  75                  80

Leu Gly Pro Gly Gln Thr Thr Asp Ile Ala Ala Ala Asn
                 85                  90
```

<210> SEQ ID NO 347
<211> LENGTH: 114
<212> TYPE: PRT
<213> ORGANISM: Pinus radiata

<400> SEQUENCE: 347

```
Pro Asp Ser Thr Ile Asn Thr Ser Phe Leu Gln Gln Leu Gln Gly Gln
 1               5                  10                  15

Cys Pro Arg Ala Gly Asp Glu Leu Pro Ser Ser Leu Asp Tyr Val
                20                  25                  30

Thr Pro Ala Arg Phe Asp Asn Thr Tyr Phe Ala Asn Leu Lys Gln Gln
          35                  40                  45

Lys Gly Val Leu His Ser Asp Arg Thr Leu Tyr Asp Pro Ala Ala Ser
 50                  55                  60

Gly Ser Val Thr Ser Ser Thr Val Asp His Phe Ser Ser Asp Gln Thr
 65                  70                  75                  80

Ala Phe Phe Glu Ser Phe Lys Gly Ala Met Ile Lys Met Gly Asn Leu
                85                  90                  95

Ser Pro Ser Ala Gly Thr Gln Gly Glu Ile Arg Arg Asp Cys Arg Lys
               100                 105                 110

Val Asn
```

<210> SEQ ID NO 348
<211> LENGTH: 551
<212> TYPE: PRT
<213> ORGANISM: Pinus radiata

<400> SEQUENCE: 348

```
Met Glu Gly Gln Ile Ala Ala Leu Ser Lys Glu Asp Glu Phe Ile Phe
 1               5                  10                  15

His Ser Pro Phe Pro Ala Val Pro Val Pro Glu Asn Ile Ser Leu Phe
                20                  25                  30

Gln Phe Val Leu Glu Gly Ala Glu Lys Tyr Arg Asp Lys Val Ala Leu
          35                  40                  45

Val Glu Ala Ser Thr Gly Lys Glu Tyr Asn Tyr Gly Gln Val Ile Ser
 50                  55                  60

Leu Thr Arg Asn Val Ala Ala Gly Leu Val Asp Lys Gly Ile Gln Lys
 65                  70                  75                  80

Gly Asp Val Val Phe Val Leu Leu Pro Asn Met Ala Glu Tyr Pro Ile
                85                  90                  95

Ile Val Leu Gly Ile Met Leu Ala Gly Ala Val Phe Ser Gly Ala Asn
               100                 105                 110

Pro Ser Ala His Ile Asn Glu Val Glu Lys His Ile Gln Asp Ser Gly
           115                 120                 125

Ala Lys Ile Val Val Thr Val Gly Ser Ala Tyr Glu Lys Val Arg Gln
          130                 135                 140

Val Lys Leu Pro Val Ile Ile Ala Asp Asn Glu His Val Met Asn Thr
```

```
            145                 150                 155                 160
Ile Pro Leu Gln Glu Ile Phe Glu Arg Asn Tyr Glu Ala Ala Gly Pro
                    165                 170                 175
Phe Val Gln Ile Cys Gln Asp Asp Leu Cys Ala Leu Pro Tyr Ser Ser
                180                 185                 190
Gly Thr Thr Gly Ala Ser Lys Gly Val Met Leu Thr His Arg Asn Leu
            195                 200                 205
Ile Ala Asn Leu Cys Ser Ser Leu Phe Asp Val His Glu Ser Leu Val
        210                 215                 220
Gly Asn Phe Thr Thr Leu Gly Leu Met Pro Phe His Ile Tyr Gly
225                 230                 235                 240
Ile Thr Gly Ile Cys Cys Ala Thr Leu Arg Asn Gly Gly Lys Val Val
                245                 250                 255
Val Met Ser Arg Phe Asp Leu Arg His Phe Ile Ser Ser Leu Ile Thr
                260                 265                 270
Tyr Glu Val Asn Phe Ala Pro Ile Val Pro Pro Ile Met Leu Ser Leu
            275                 280                 285
Val Lys Asn Pro Ile Val Asn Glu Phe Asp Leu Ser Arg Leu Lys Leu
        290                 295                 300
Lys Ala Val Met Thr Ala Ala Ala Pro Leu Ala Pro Asp Leu Leu Arg
305                 310                 315                 320
Ala Phe Glu Glu Lys Phe Pro Gly Val Glu Val Gln Glu Ala Tyr Gly
                325                 330                 335
Leu Thr Glu His Ser Cys Ile Thr Leu Thr His Cys Ala Pro Gly Asn
            340                 345                 350
Ile Arg Gly Arg Ala Lys Lys Ser Ser Val Gly Phe Ile Ile Pro Asn
            355                 360                 365
Leu Glu Val Lys Phe Ile Asp Pro Glu Thr Gly Lys Ser Leu Pro Arg
        370                 375                 380
Asn Ser Ile Gly Glu Val Cys Val Arg Ser Gln Cys Val Met Arg Gly
385                 390                 395                 400
Tyr Tyr Lys Lys Pro Thr Glu Thr Glu Lys Thr Val Asp Ser Asp Gly
                405                 410                 415
Trp Leu His Thr Gly Asp Val Gly Phe Ile Asp Asp Asp Asp Val
                420                 425                 430
Phe Ile Val Asp Arg Ile Lys Glu Leu Ile Lys Tyr Lys Gly Phe Gln
            435                 440                 445
Val Ala Pro Ala Glu Leu Glu Ala Ile Leu Leu Ser His Pro Ser Val
        450                 455                 460
Glu Asp Ala Ala Val Val Pro Leu Pro Asp Glu Glu Ala Gly Glu Ile
465                 470                 475                 480
Pro Ala Ala Cys Val Val Met Ala Ala Ser Ala Thr Glu Thr Glu Asp
                485                 490                 495
Asp Ile Ser Lys Phe Val Ala Ser Gln Val Ala Thr Tyr Lys Arg Val
            500                 505                 510
Arg Leu Val Lys Phe Val Ser Thr Ile Pro Lys Ser Ser Ser Gly Lys
            515                 520                 525
Ile Leu Arg Arg Leu Leu Arg Asp Asn Leu Arg Glu Thr Leu Lys Asn
        530                 535                 540
Gln His Gln Pro Leu Ser Thr
545                 550

<210> SEQ ID NO 349
```

<211> LENGTH: 544
<212> TYPE: PRT
<213> ORGANISM: Pinus radiata

<400> SEQUENCE: 349

```
Met Glu Ala Lys Pro Ser Glu Gln Pro Arg Glu Phe Ile Phe Arg Ser
 1               5                  10                  15

Lys Leu Pro Asp Ile Tyr Ile Pro Asp Asn Leu Ser Leu His Ala Tyr
            20                  25                  30

Cys Phe Glu Asn Ile Ser Glu Phe Ala Asp Arg Pro Cys Val Ile Asn
        35                  40                  45

Gly Ala Thr Gly Arg Thr Tyr Thr Tyr Ala Glu Val Glu Leu Ile Ser
    50                  55                  60

Arg Arg Val Ser Ala Gly Leu Asn Gly Leu Gly Val Gly Gln Gly Asp
65                  70                  75                  80

Val Ile Met Leu Leu Leu Gln Asn Cys Pro Glu Phe Val Phe Ala Phe
                85                  90                  95

Leu Gly Ala Ser Tyr Arg Gly Ala Ile Ser Thr Thr Ala Asn Pro Phe
            100                 105                 110

Tyr Thr Pro Gly Glu Ile Ala Lys Gln Ala Ser Ala Ala Arg Ala Lys
        115                 120                 125

Ile Val Ile Thr Gln Ala Ala Phe Ala Asp Lys Val Arg Pro Phe Ala
    130                 135                 140

Glu Glu Asn Gly Val Lys Val Val Cys Ile Asp Thr Ala Pro Glu Gly
145                 150                 155                 160

Cys Leu His Phe Ser Glu Leu Met Gln Ala Asp Glu Asn Ala Ala Pro
                165                 170                 175

Ala Ala Asp Val Lys Pro Asp Asp Val Leu Ala Leu Pro Tyr Ser Ser
            180                 185                 190

Gly Thr Thr Gly Leu Pro Lys Gly Val Met Leu Thr His Arg Gly Gln
        195                 200                 205

Val Thr Ser Val Ala Gln Gln Val Asp Gly Asp Asn Pro Asn Leu Tyr
    210                 215                 220

Phe His Lys Glu Asp Val Ile Leu Cys Thr Leu Pro Leu Phe His Ile
225                 230                 235                 240

Tyr Ser Leu Asn Ser Val Met Phe Cys Ala Leu Arg Val Gly Ala Ala
                245                 250                 255

Ile Leu Ile Met Gln Lys Phe Glu Ile Val Ala Leu Met Glu Leu Val
            260                 265                 270

Gln Arg Tyr Arg Val Thr Ile Leu Pro Ile Val Pro Ile Val Leu
        275                 280                 285

Glu Ile Ala Lys Ser Ala Glu Val Asp Arg Tyr Asp Leu Ser Ser Ile
    290                 295                 300

Arg Thr Ile Met Ser Gly Ala Ala Pro Met Gly Lys Glu Leu Glu Asp
305                 310                 315                 320

Thr Val Arg Ala Lys Leu Pro Asn Ala Lys Leu Gly Gln Gly Tyr Gly
                325                 330                 335

Met Thr Glu Ala Gly Pro Val Leu Ala Met Cys Pro Ala Phe Ala Lys
            340                 345                 350

Glu Pro Phe Glu Ile Lys Ser Gly Ala Cys Gly Thr Val Val Arg Asn
        355                 360                 365

Ala Glu Met Lys Ile Val Asp Pro Glu Thr Gly Ala Ser Leu Pro Arg
    370                 375                 380

Asn Gln Ala Gly Glu Ile Cys Ile Arg Gly His Gln Ile Met Lys Gly
```

```
                385                 390                 395                 400
Tyr Leu Asn Asp Ala Glu Ala Thr Ala Asn Thr Ile Asp Lys Glu Gly
                    405                 410                 415
Trp Leu His Thr Gly Asp Ile Gly Tyr Ile Asp Asp Asp Glu Leu
                420                 425                 430
Phe Ile Val Asp Arg Leu Lys Glu Leu Ile Lys Tyr Lys Gly Phe Gln
            435                 440                 445
Val Ala Pro Ala Glu Leu Glu Ala Met Leu Ile Ala His Pro Ser Ile
        450                 455                 460
Ser Asp Ala Ala Val Val Pro Met Lys Asp Glu Val Ala Gly Glu Val
465                 470                 475                 480
Pro Val Ala Phe Val Val Lys Ser Asn Gly Ser Val Ile Thr Glu Asp
                485                 490                 495
Glu Ile Lys Gln Tyr Ile Ser Lys Gln Val Val Phe Tyr Lys Arg Ile
            500                 505                 510
Lys Arg Val Phe Phe Thr Asp Ala Ile Pro Lys Ala Pro Ser Gly Lys
        515                 520                 525
Ile Leu Arg Lys Asp Leu Arg Ala Lys Leu Ala Ser Gly Val Tyr Asn
    530                 535                 540

<210> SEQ ID NO 350
<211> LENGTH: 717
<212> TYPE: DNA
<213> ORGANISM: Eucalyptus grandis

<400> SEQUENCE: 350
cctgttttgg caacaactcc agcagctctc tgctcttttt actataaaaa aacccatctt     60
cacttcttct gtacttgcac acgaacatta agcgcttgat cagaacttgt atcagctccc    120
caccaccacc aaacagaaga gaaacagaag aaaaggaaaa gttcgaacaa cttcgaacga    180
tgcgagccct gctgttgtg ctcggttctg ctatcttgct ggcgtatgtc gcgagcagtg    240
cgggtgcgct gagcttggat tactatgacc agacgtgccc gaagctcgag ttttcggtga    300 gggggggctgt gaagaaagcg atgaagaacg acaacaccgt tcctgctgct ttacttcgca    360
tgcacttcca cgactgcttc atcagaggat gtgacggttc cgtgctcttg aactcgacgg    420
caaagaacac agccgaaaaa gacgggccgc gaacatctc actccacgca ttctatgtga    480
tcgaccttgc gaaggaagcg gtggaagctc agtgccctgg ggtcgtctct tgcgccgaca    540
tcttggcctt ggccgctcgg gatgctgtcg ctctgtctgg aggaccgcat gggatgtgc    600 cgaaaggaag aaaagatggg aggattcgaa agcgaatgac acaaggcaat taccagctcc    660
gaccttcaac atctctcaac tacagcaagc ttctctcaag aggccttcc atggaga       717

<210> SEQ ID NO 351
<211> LENGTH: 369
<212> TYPE: DNA
<213> ORGANISM: Eucalyptus grandis

<400> SEQUENCE: 351
ggcgtctctc ctctgtctag tcatgtttct gaaataccct tccgccgcac tcatctctct     60
tgcaacgatt cgctctgctt acggtgcctc cactccgaag cgaagagcaa catgcgcggg    120
cgggcagacc gtgaaaaacg aggcctgttg cgcctggttc cccgtcctgg aagacattct    180
gcccaacatg ttcgacaacg aatgtggcga cgacgcccat ggcgtctgc gtctgagctt    240 ccacgacgcg atcggtttct ctccttctca aggtggagga ggcgcggacg gatccatttt    300
```

| | |
|---|---:|
| gtcttcagtg acaccgaact gcagttcccc gcgaacgctg gcctcgacga cccgatcgac | 360 |
| actgagctt | 369 |

<210> SEQ ID NO 352
<211> LENGTH: 1391
<212> TYPE: DNA
<213> ORGANISM: Eucalyptus grandis

<400> SEQUENCE: 352

| | |
|---|---:|
| gaaaaactgt ggtggtgaag ctgcctcgca aagatgtgac gttatctaat cagcgtctcc | 60 |
| ctgcccggaa aaagccggaa aaggaactgt tattttcaag cttttatttc accacaatca | 120 |
| cggagttata tattatacca agatttccgc gttaacctta cgccggagaa acttcatctg | 180 |
| agtgtgtgct cttgctggtt ttcaacagga acatatcgat aatttatgtc atggctacac | 240 |
| acgatatggt cggcttttcc gtcgtcgttg tcctccttgc cacttcggtt atcaccactg | 300 |
| cccgttgtaa gctctcaccg agtcattatc aatcaacatg tccgaaagca ttgtcgattg | 360 |
| ttcgagctgg agtagcaaaa gcaatcaaga atgagacccg gacgggcgcg tccttgcttc | 420 |
| ggctgcactt ccatgactgc ttcgtcaatg ggtgcgatgc gtcgatattg ttggatgaca | 480 |
| cgcctagctt cgtgggcgag aaaacagcag ctccgaacaa caattccgtg agagggttcg | 540 |
| aagtgatcga ccgcatcaag gctagtctgg agaaggagtg ccctggagtg gtttcctgtg | 600 |
| cagatatcgt tgccctggct gctcgcgact cagtcgttca tttgggaggt ccttcatgga | 660 |
| ccgtaagctt agggagaaag gattccatta ctgctagcag gagccttgct aacacctcca | 720 |
| tacctccacc tacttctaat ctcagtgctc tcataaccag cttcgctgct cagggtcttt | 780 |
| cagtcaagaa catggtggct cttttctggtt cacataccat tggcctagcg agatgcactt | 840 |
| ccttccgaag acggatctac aacgactcga acatagatac atccttcgcc cataaattgc | 900 |
| agaagatatg tcccaggatt ggaaatgata gtgtccttca aaggctagac atccaaacgc | 960 |
| cgaccttctt tgacaacctt tactaccaca atttactgca gaagaagggc cttcttcact | 1020 |
| ctgatcaaga gctcttcaat ggcagttctg tggattcact ggtcaagaag tatgcatgcg | 1080 |
| acacaggaaa atttttccga gattttgcca aggcaatgat caaaatgagc gaaattaagc | 1140 |
| cccccaaagg aagcaatggt caaataagga aaaattgcag gaaagtgaac taagtatgaa | 1200 |
| gctcatatat gcaatttgaa actgccacat atgaacacgg tagtgaaatc agggctcgat | 1260 |
| aatgtcccct gacaatttgt cgtcatgtat ctgtcttctt gactaatttg tggttgctgc | 1320 |
| ttgaaaaata aaggagctcg tctcagtttc tgtaaaaaaa aaaaaaaaa aaaaaaaaa | 1380 |
| aaaaaaaaaa a | 1391 |

<210> SEQ ID NO 353
<211> LENGTH: 337
<212> TYPE: DNA
<213> ORGANISM: Eucalyptus grandis

<400> SEQUENCE: 353

| | |
|---|---:|
| cagaatgcct agtcgtcatc cgatttgggt aattgtcgcc atagcttttg taaccgcact | 60 |
| cgggtgggga agtgcctccg cacaactctc tacaaacttc tactccaaaa gttgtcccaa | 120 |
| tgttttgagc acggtgaaat ctgttgtccg gtccgcggtg tcgaaagagc gccgcatggg | 180 |
| tgcttctctc ctgcgcctct tctttcatga ttgcttcgtc aatgggtgcg atggctcgat | 240 |
| actcctggac gacacatcct cgttccaagg ggagaagacg gccggcccaa ataataagtc | 300 |
| tttgagagga tacaacgtca ttgaccggat caagtcc | 337 |

```
<210> SEQ ID NO 354
<211> LENGTH: 368
<212> TYPE: DNA
<213> ORGANISM: Eucalyptus grandis

<400> SEQUENCE: 354
ctcacttccg agcgcgccat gcagttcacc ttttccgccg ctttcctcgc tctcgtcaca    60
gtcgcggccg ctatgcccac caagcgtgcg gcgtgcagca acggacgaac ggccactcat   120
gcctcgtgct gtgtgtggtt cgacgtcctc gacgatattc aagagaatct gttcgacggt   180
ggagagtgcg gagaggaaac acgagtctc tgcggctca ctttccacga tgccatcggc   240
ttctccccga gcctgtttct cgagggaaaa ttcggtggtc tcggcgctga tggttccatc   300
atggctcact ctgacatcga gaccgtgttc cccgccaaca atggaattga tgatatcgtc   360
gacgcgca                                                            368

<210> SEQ ID NO 355
<211> LENGTH: 955
<212> TYPE: DNA
<213> ORGANISM: Eucalyptus grandis

<400> SEQUENCE: 355
aagaaactca gacccagacc cagaccacat catggcctcc cgtttcagct ctttcgtttt    60
ggtttctttt cttgtgatag ctgcatcaca tgttcatgtt acgagctctg ctcacttggt   120
gaagggctc tcgtggtcct tctacagaaa gagctgtccc aaggtggagt ccgtcatcaa   180
gaaacatctc aagaaggtgt tcgaggagga tattggccaa gctgctgggc tgcttcgtct   240
gcacttccat gactgctttg ttaagggatg tgatgcttcg gtgttgctgg atggatcagc   300
cagtggacca agtgagcagg acgctccacc gaaccggagc ttgagaccat cagcattcaa   360
gatcatcgat gacctccgtg agctcgtgga caagaagtgt ggtcgagtag tctcttgtgc   420
tgatatcgca gccattgccg ctcgtgactc cgttgtcctg tcaggcggac ctgagtatga   480
tgtgccgttg ggaaggcggg atggactcac gtttgcgact caaaatgtga ccttagagaa   540
tttacctgca ccaactgaga acgccagtgc aattctctcc gccctagcca agaaaaactt   600
agacgctacc gacgtggtgg ccctctctgg aggccacacc atcgggcttg gcactgcac   660
ctcctttgag aatcggctct acccgaccca agaccccacg atggagaaga cctttgccca   720
tgatctcaag ggcgtgtgcc ccaccacaaa ctccaccaac actacggtct tggacatccg   780
atcacccaac cgattcgaca acaagtactt tgtcgatttg gtgaaccgcc aaggcctgtt   840
cacctcagac caagatctgt atgaggatcc cacaaccagg acattgtca ctagctttgc   900
cgaggaccag gaattgttct tgagaagtt tgtcctagcc atgacgaaga tgggg         955

<210> SEQ ID NO 356
<211> LENGTH: 308
<212> TYPE: DNA
<213> ORGANISM: Eucalyptus grandis

<400> SEQUENCE: 356
ctgtgtctag tcatgttcct gaagtatctc tccggcgccc tcgtctccct tgcaacgatc    60
cgcggtgttt gcggtgcttc cgctccgatg cgaagagcaa catgtgcggg tgggcagact   120
gtcaaaaatg cggcatgttg tgcatggttc ccagtactcg acgacatcag ggaaaactt   180
ttcgacaacg aatgcggcga tgacgcccat gctgccctgc gtctgagttt ccacgatgca   240
```

```
atcggtttct ctcgttcgaa aggtggagga ggcgcggacg gatccatcat tgccttcaat    300
aagactga                                                             308
```

<210> SEQ ID NO 357
<211> LENGTH: 373
<212> TYPE: DNA
<213> ORGANISM: Eucalyptus grandis

<400> SEQUENCE: 357

```
tcaggtcctt gtcaacatgg cattcaaact cgtggttaat cttgttagtc ttgctctcgc    60
cgtcagtgct gcaaacttca agcgagttgc ttgcccaggt actacggcca cagctcgcaa   120
tccggcgtgc tgcgcattct tctcactgag agatgacttg cttacaaatc tcttcggggg   180
tgtgtgcggc gaagaggcgc acgagtctct ccgattgtct ttccatgatg ccattgcgtt   240
ttcgcccgca ttaattaggc aaggcaaacc gggaggtgga ggtgctgatg gctctatgat   300
tactttccca aacgtcgagc ccaattttaa tgccaacaac ggcattattg attctgtcga   360
ctttttgaca cca                                                      373
```

<210> SEQ ID NO 358
<211> LENGTH: 417
<212> TYPE: DNA
<213> ORGANISM: Eucalyptus grandis

<400> SEQUENCE: 358

```
ctcttgtcct gggaccgtgt cttgcgccga cattctcgcc ctcggtgctc aagcttctgt    60
cgttctgtca ggaggtccat cttggagggt gctctcgggg aggagggaca gcttgacggc   120
gaaccaagca ggagcgaaca catcgatacc tagcccttt gattccttgg ctaacctcac   180
ttccaaattc gccgctgttg gcttggacac caatgacctt gtcactcttt ccggagctca   240 caccctttgga cgtgcacagt gcaggacatt cagccctagg ctctacaact caacgcgag   300 tggcagccca gatccaacca taagtccttc atacttgacc actctccaac aactttgccc   360
acagaatgga agcggctccg tcctcgccaa cctcgacccg acgaccgtga acacatt     417
```

<210> SEQ ID NO 359
<211> LENGTH: 659
<212> TYPE: DNA
<213> ORGANISM: Pinus radiata

<400> SEQUENCE: 359

```
cacaatggaa atagtttagg tcagtaatgg aacggatgaa acatattccc ggccttacac    60
tgcagtttca gtctgtgctg atcactggag cggcattgtt tctatggatc cagacatcgg   120
atgctcagga ctgtaatggt ctgagtcatc actattatca gaagtcctgt ccaaatgccc   180
aggctatcat taaatctgta gtttcagatg ctgtcaaaaa ggaagcgaga atggctgctt   240
ccttgcttcg tctgcatttt catgactgtt ttgttcaggg ctgtgatgct tcaattctgc   300
ttgatgacac tgctagtttc acaggggaga agacagcatt acctaacaga aattctgtaa   360
gaggctttga ggtagtggat aagatcaaaa gcaaattgga ggaagcatgt cctggagtgg   420
tctcatgtgc tgacattctt gctgtggcag cccgtgattc agtaggcttt agtgtgggtc   480
cgtattggga ggttctactg gcaggaggg actcaaagac tgcaagcaag agcggtgcaa   540
acaacgacat tcctgcaccc aactcaaccc atcagactct ggaaaccaaa ttcaacctca   600
aaggtctcaa tgtgcttgac ctagttgctc tatcaaggtc ccataacaat agggttagc    659
```

<210> SEQ ID NO 360
<211> LENGTH: 669
<212> TYPE: DNA
<213> ORGANISM: Pinus radiata

<400> SEQUENCE: 360

| | | | | | |
|---|---|---|---|---|---|
| gcggcacgag | cggcaaaact | aaagctattc | gcagcctccc | tctatggcga | cattagggat | 60 |
| ccctctcggc | tcactcagcc | tgctcctcct | cttcttctgc | tgcgcacaac | gcagtgtggg | 120 |
| actgaaggaa | aattactacg | caacgtcgtg | tccgagagca | gagcacatag | tgaaggagca | 180 |
| ggtctacaat | ctctaccagg | agcacggcaa | cactgccgtt | tcatggatca | gacttatctt | 240 |
| ccatgactgc | atagttcagt | cgtgcgatgc | ctccattcta | ttagacagta | gtggagacgt | 300 |
| gcagacagaa | aaacaatcgg | accgaaactt | cggaatgcga | aacttcaagt | atgtggacac | 360 |
| cattaaggag | gccatcgagg | tggaatgtcc | tggagtggtg | tcgtgtgctg | acattattgt | 420 |
| tctcgccgca | aaggaggcag | ctgcaatgct | aggaggtcca | cgcatcgcgg | tgaaaacagg | 480 |
| gagacgagac | agcagaaaaa | gcagtgcagc | agtggtggac | aaatacgttc | cgctgcataa | 540 |
| tggcagcatc | tcatctcttc | tctctgcctt | tgcctctgtg | ggcatcgatg | cggaaggagc | 600 |
| tgtggcccctt | ttaggtttga | tacttatcca | ttctgtatta | cattatacat | aaataaaaaa | 660 |
| aaaaaaaaa | | | | | | 669 |

<210> SEQ ID NO 361
<211> LENGTH: 916
<212> TYPE: DNA
<213> ORGANISM: Pinus radiata

<400> SEQUENCE: 361

| | | | | | |
|---|---|---|---|---|---|
| agcaaattgg | ttgcttttgg | agcgcttgtt | ccaacagcaa | aaatggctgt | tttgatgaag | 60 |
| agctttccgt | gcattgctgt | cattgtgttc | attatctgtt | cgattactga | tactgtgaat | 120 |
| gggaaactga | gctccacgtt | ttatgataag | tcttgtccca | aggccctgtc | tatagtgcaa | 180 |
| gccggggtga | agcaagcagt | ggctaaggaa | aaacgtatgg | gggcatcgct | tctccgcctt | 240 |
| catttccacg | actgcttcgt | taatggctgc | gatgggtctg | tactgttgga | caattccacg | 300 |
| accttcacta | gcgagaaata | tgctcttccc | aataacaatt | ccgcgagggg | tttcgaggtg | 360 |
| atcgatagca | taaagagcca | actcgagaat | gcttgcaccg | gcgtcgtttc | ttgtgcagac | 420 |
| attctcacga | ttgctgctcg | tgattctgtt | gttcagttgg | gtggaccttc | gtggaaggtg | 480 |
| atgttgggga | ggcgagactc | aacaacagcg | agcattagcg | gtgcaaacaa | taacattccg | 540 |
| cctcccactt | ccaatctgac | gaaactcatt | tcactatttc | aggcacaggg | cctctccaca | 600 |
| aaggaaatgg | ttgcactctc | tggtggtcat | accatcgggc | aggcgcaatg | caagaatttc | 660 |
| agagcccata | tttacaacga | caccaacata | gatactacgt | acgccacttc | attgcgttca | 720 |
| aagtgtccta | gtaccacagg | ctccggagac | agcaacctgt | cgccactgga | ttatacgact | 780 |
| cccactgtgt | ttgacaaaaa | ctattactac | aatctgaaaa | gcaaagagg | acttctccac | 840 |
| tccgaccagg | aactcttcaa | cggaggctcc | actgattcgc | atgtgactaa | gtacgcctcc | 900 |
| aaccagaata | ccttct | | | | | 916 |

<210> SEQ ID NO 362
<211> LENGTH: 586
<212> TYPE: DNA
<213> ORGANISM: Pinus radiata

<400> SEQUENCE: 362

```
gcaaacagca accttccctc gccagcttcc agtctcagca cactcatgac agcatttcaa    60
aaacagggtc tctctaccaa ggacctcgtc gcactctcag gtgctcatac aattggtcaa   120
gcacggtgca ccacattcag aactcgcatc tacaacgata ccaacattaa cgctgccttc   180
gctacatctg cgaaggcgaa ctgccccagc actggtggcg acaacaccct ctctcccttg   240
gatgttctca cccctaccac atttgacaac aagtattaca ctaatctgaa agccaaaag    300 ggacttttcc actccgatca ggagctattt aatggaggtt ccacagactc tagagttagt   360
atctacagca ccagtcaagc cattttcttt actgactttg cagccgccat ggtgaatatg   420
ggtaatatta gtcccctcac tggcaccaac ggcgagatcc gcacaaactg caggaaagtc   480
aattaaaatt tgtaaagatt gtattatcta tagcttttct ctgaagttat aagcgaagct   540
ttacaagaaa gcaataaatt actgtttaat taaaaaaaaa aaaaaa              586

<210> SEQ ID NO 363
<211> LENGTH: 1224
<212> TYPE: DNA
<213> ORGANISM: Pinus radiata

<400> SEQUENCE: 363
ctaccactca atttcgctct tatcttctgt gtttcatcgt tttcttccaa atatgatgat    60
gaggactcta gtgtgcattg ggttaatggc tgtgtttgta gccttcatac atataaacgc   120
tgtgaatggg cagctgagct caacgtttta tgccaaatcg tgtccgaggt tgccatcgat   180
agtgaaatca gtggtgaagc aagcggtagc taaggagaaa agaatgggag cgtccttggt   240
ccgccttcac tttcacgatt gcttcgtcaa cgggtgcgat ggttcaatct tattggatga   300
caacgctacg tttaccggag aaaagactgc aggcccaaac gccaattctg cgagaggctt   360
cgaggtaatt gacagcatta aaactcaagt ggaggcagcc tgcagtggag tcgtgtcgtg   420
tgcagacatt ctcaccattg ctgctcgtga ctctattgtt gaacttcaag cccaacatg    480 gacggtaatg cttggaaggc gagactccac gactgcgagt ttaagcgctg caaacaacaa   540
cattccatct cccgcttcca gtctgagcac actcatctca tcttttcaag ctcacggtct   600
ttctaccaaa gaccttgttg cactctcagg tgctcataca attggtcaat cacgatgcgc   660 cttttttcaga actcggatct acaacgaaac gaacattaac gctgctttcg ctacatctgt   720
aaaggcaaac tgccccagcg ctggtggcga cagcaacctc tctcccttag atgcggtcac   780
ctcaatcaca tttgacaaca agtattactc taatcttaaa atacagaaag acttctccca   840
ctccgaccag cagctctta atggaggttc tacagattct caggttactg cgtacagcag   900
caatcagaac agcttctttta tagctttac agctgccatg gtgaagatgg gaaatattag   960
ccctctcact ggcactaacg ggcaaatccg caaaaactgc aggaagtcca attagtctct  1020
ctgaagattg tattctccgt actctttcag cttatttttt ctttgtaaca ttgattttcg  1080
atcggctagt gagccttcaa atcgaagctc taaagaaag caataaacta catttctgag   1140
attatgttca gagttgtatg cagttcagac cataattcca attttgcttc ccaaaaaaaa  1200
aagacttgta aaaaaaaaaa aaaa                                         1224

<210> SEQ ID NO 364
<211> LENGTH: 519
<212> TYPE: DNA
<213> ORGANISM: Pinus radiata

<400> SEQUENCE: 364
aaactgccca agtcaggagg cgacaataac ctgtcaccgt tggatctact gactccaaca    60
```

-continued

| acgttcgaca ataaatacta cacaaatctg aagagccaaa agggtcttct ccactcagac | 120 |
| cagcagctgt ttaatggcgg ctctgcagat tcccaggtta ctacctacag caccactcag | 180 |
| agcaccttct ttaccgactt cgcagcttcc atgttgaata tgggtaatat cagtcccctc | 240 |
| actggcacca gcggacaaat ccgcaaaaac tgcagaaaac ctaattgatg cctctcttag | 300 |
| gccatatgta ctttactgtt ctcatgggat tatattttga ttgtagaatt atatagatag | 360 |
| ttgggagacc tacggctgcg ttagacacta gcaagcctcc aattggatct gtgcgtccct | 420 |
| agtttgttga ctatttggtt gatttcgatg taccaagtac aaagtttctc aacagattaa | 480 |
| tccaatgaat taggttttat aaaaaaaaaa aaaaaaaa | 519 |

<210> SEQ ID NO 365
<211> LENGTH: 646
<212> TYPE: DNA
<213> ORGANISM: Pinus radiata

<400> SEQUENCE: 365

| aaaccattca aacccaccga agatttcatt gcgtcgcagc atcatgactt cctttacagc | 60 |
| aatggcgtca gtcgtgtgca tcgctctgct cttttttttcg accgttgctt ttgctcaact | 120 |
| caactcaacg tattatgata cgtcgtgtcc caaactcctg caacggtga aggctgcagt | 180 |
| gaagacggcg gtggccaatg agaaacgcat gggggcatca ttgctccgtc ttcactttca | 240 |
| tgattgtttc gtcaatggtt gcgatgggtc agtgttgttg gacgactctt cgagtctaac | 300 |
| tggggaaaag actgctcttc ccaacaacaa ttcgttgagg ggtttcgacg tcatagacac | 360 |
| catcaaatca caagtggaag cagtttgcag cggaatcgta tcgtgcgctg acattttggc | 420 |
| tattacggct agagattctg tcgtcgaatt gggaggacca acatggacag tgctgcttgg | 480 |
| aaggagagac tcagcaactg ccagcctaag cgccgcaaac accaacattc ccgctcccac | 540 |
| ttccaatctc agtggtctca tctcatcttt tcaagcacag ggccttttcaa ccaaggatat | 600 |
| gattgtccta tcaggtgcac ataccattgg ccaagctcga tgcaca | 646 |

<210> SEQ ID NO 366
<211> LENGTH: 364
<212> TYPE: DNA
<213> ORGANISM: Pinus radiata

<400> SEQUENCE: 366

| ccttaatctc ctcttttaca gcccatggtc tttccacaaa ggatctcggt gcactctcgg | 60 |
| gagctcatac gattggccaa gcgcggtgca ccacattcag agctcgcgtc tacaacgaat | 120 |
| ccaacattga cacttccttc gccacttcgg tgaaggcaaa ctggccaagc gctggtggcg | 180 |
| acaacaccct ctcgccctta gatctggcca cgcctaccac atttgacaac aagtattaca | 240 |
| ctgatttgag aagccaaaag ggacttctgc actccgatca gcaaatgttt agcggagggt | 300 |
| ctacaaattc tcaagtcacc acctatagct ccaatcaaaa acaccttctt tacagacttt | 360 |
| acag | 364 |

<210> SEQ ID NO 367
<211> LENGTH: 364
<212> TYPE: DNA
<213> ORGANISM: Pinus radiata

<400> SEQUENCE: 367

| ggaaaaggat caactttcac ttaaaggagg acatcaccca agcggctggt ttgctgcgcg | 60 |

| | | |
|---|---|---|
| tccatttcca tgactgcttc gttcagggtt gcgacggatc ggttctgttg acggttctg | | 120 |
| ccagcggtcc tagcgaacaa gacgctccac cgaacttaac gctgagagca aaagcctttg | | 180 |
| aaataattaa cgacatcaag aaacatgtgg aaaaggcttg cagcggcgtt gtctcttgcg | | 240 |
| cggacttgac tgctctcgca gctcgcgagt cggtcagagc agttggagga ccagagtatc | | 300 |
| gagtgcctct ggggcgcagg gacagcctga aattcgccac acgaaaagtg acccttgcca | | 360 |
| acct | | 364 |

<210> SEQ ID NO 368
<211> LENGTH: 801
<212> TYPE: DNA
<213> ORGANISM: Pinus radiata

<400> SEQUENCE: 368

| | | |
|---|---|---|
| gtcatggctt cgtttacagc aatgcgatct ctggccttta tcgccttgtt gatgtgttcg | | 60 |
| accgttgcgt acgcgcagct tagcgcaacg ttttataata catcatgtcc caaactactc | | 120 |
| tcaacggtgc aggccgctgt gaagcaagcg gtggccaacg agaagcgcat gggggcatcg | | 180 |
| ctcctccgcc ttcactttca cgactgcttc gttaatggtt cgatgggtc tgtgctgctg | | 240 |
| gacgactctt cgactctaac tggagagaag accgccgttc ccaacaacaa ttcggcaagg | | 300 |
| ggtttcgatg tgatagacac catcaagtct caagtggaag cagtttgcag tggagttgtg | | 360 |
| tcgtgcgcag atattttggc tattgctgct agagattctg ttgtccagtt gggaggccca | | 420 |
| acatggacag tgcagctggg gaggagagac tccaggactg ccagcctaag tggtgcaaac | | 480 |
| aacaacattc cggctcctac ttctaatctc agtgctctca tctcattatt tcaagctcag | | 540 |
| ggtctttcca cgaaggacat ggttgtccta tcaggtgcgc acaccatagg ccaagcgcgg | | 600 |
| tgcacaagct tcagggcccg catctacaac gaatccaaca ttaatgcagc atacgcaact | | 660 |
| tccctgaaga caaactgtcc gactacagga agcgacaaca acctgtcacc attggatcgt | | 720 |
| gttactccca ctacgtttga catcaactac tactcaaatc tgagaagcca aaagggactt | | 780 |
| ctccactccg accagcagct g | | 801 |

<210> SEQ ID NO 369
<211> LENGTH: 1171
<212> TYPE: DNA
<213> ORGANISM: Pinus radiata

<400> SEQUENCE: 369

| | | |
|---|---|---|
| gccaaataaa gttatctttt ggctttattc cacaagaaaa aaatggctta cctaaggaag | | 60 |
| agtttcgcct gtatagctgt aatggtgttt atcgtgtgtt ctattacaga tactgtgaat | | 120 |
| gggcagctga gctccacgtt ttacgacaaa tcttgcccga cggcactgtc ggtagtgaag | | 180 |
| gccgcagtga agcaagcggt cgctaacgag aaacggatgg gtgcgtcttt gctccgcctg | | 240 |
| cactttcacg actgcttcgt taatggttgc gatgggtccg ttctgttgga cgattcttcg | | 300 |
| accattactg gcgagaagac agctaatccc aatgccaatt ctgcgagggg attcgacgta | | 360 |
| atagatacca taaagagcaa tgtcgagaaa gcttgcagtg gagtcgtttc ctgtgcagac | | 420 |
| attctcgcca ttgctgctcg tgattctgtt gttgaactgg gcggtccttc atggacagta | | 480 |
| atgttgggaa ggcgagactc gacaacagct agcaaaagcg gtgcaaacag taatattccg | | 540 |
| cctccgactt ccagtctgag caacctcatc tcactattcc aagcgcaggg actctccgca | | 600 |
| aaggaaatgg ttgcactttc tggcggtcat accatcgggc aggcgcaatg caagaatttc | | 660 |
| agagcccata tttacaacga gaccaacata gacagtgcgt acgccacttc attgcgttca | | 720 |

| | |
|---|---|
| aagtgtccga gtaccacagg ctccggagac agcaacttgt cgccattgga ttatatgact | 780 |
| cccactgtgt ttgacaaaaa ctattacagc gacctgaaaa gccaaaaagg acttctccac | 840 |
| tccgaccagg aactcttcaa cggaggctcc actgattcac aggtgactac gtacgcctcc | 900 |
| aaccagaaca ccttcttctc cgattttgct gcggccatgg ttaagatggg aaatatcaaa | 960 |
| cctcttaccg gcaccagcgg acagatccca agaactgca ggaagccaaa ctaattatga | 1020 |
| tcactgtcga attatcatca ctccgttgca ctgcctttta attgtaaaag taacgtttcg | 1080 |
| actgatttca gtctatggat accatatgct gatggagctt gtcatgaata aataagttca | 1140 |
| taactttacc atcattaaaa aaaaaaaaaa a | 1171 |

<210> SEQ ID NO 370
<211> LENGTH: 1073
<212> TYPE: DNA
<213> ORGANISM: Pinus radiata

<400> SEQUENCE: 370

| | |
|---|---|
| atcagattaa gagtgcactt gagaaggagt gcccaaaaac tgtatcgtgt gcagatattc | 60 |
| tcgctattgc atctcgtgat tcagtggtcc tgagtggagg gctgggctgg aagttttac | 120 |
| tggggaggag agattcgaag agtgcaagtt tgagtgggtc caacaacaat atcccggcgc | 180 |
| ccaactcaac tctgcagacg cttactacca agttcaaact acaaggtcta gatgaggtag | 240 |
| acttggtatc cctttcaggg agtcacacca tcggcctatc tcgatgcaca gtttcaggc | 300 |
| agaggcttta caaccagagt ggaaatgggc tgccagactt cactctaaac agggttact | 360 |
| atgctcggct gaaatccgga tgtccaaaat ctggaggaga taataacttg ttcccattgg | 420 |
| atttcgtgac tcctaccaaa ttcgataact actacttcaa gagcttgctg agcggtcaag | 480 |
| ggctgttgaa cacagacgaa gaattgttcg caaagggctc agggaagacg aaggagctag | 540 |
| ttaaactta tgcagcaaat gaggagctct ttctcaaaca gtttgcatta tctatggtga | 600 |
| agatgggaaa catcaagcct cttacaggca ccgtgggaga atcagggtc aactgtcgta | 660 |
| aggttaacag ttgatcgttt taatttaatc attttccatc tcttgcattg cattttgtta | 720 |
| catctccctt cttagctgcc atcaaattgc attactagat catccttccc atggctttca | 780 |
| gttgtaacag gttgaataaa attgccactt ctgaattatt aaacttctga ttgggctgga | 840 |
| cgatagaggg aaacttcaac gtcccaatca aattgtcatg taagaaatat ctcgggcagt | 900 |
| aaactcagag tggtaaatca agattgttga ataaaatgtt agctcttcgt taatggctgt | 960 |
| ggagaaggtc aacactcctc gtgtgtttag ctatgtgtct gtttattaac gcttgcgagt | 1020 |
| tttgatgtaa tggaaatcgt gtcttcaaca agaataaaaa aaaaaaaaaa aaa | 1073 |

<210> SEQ ID NO 371
<211> LENGTH: 1522
<212> TYPE: DNA
<213> ORGANISM: Pinus radiata

<400> SEQUENCE: 371

| | |
|---|---|
| gaaaggcctg tcgatttcct ccatttgaat cgacaggatc gaagaatcta ttttacatca | 60 |
| aagcaaagcc aaagctgtgg ccgacatggg caagtttatc acggctctgg cttctgttat | 120 |
| tctctgcgtg tttgtgatct atggcggcgc tgtcaatgct ctgcccagtc ccgtggctgg | 180 |
| tctttcttgg acgttctaca gctcgagttg cccgtccttg gagtccatag tgtgggagcg | 240 |
| catggaagcc tatttgagtg cagacatcac acaggctgca ggattgttga ggctccactt | 300 |

| | |
|---|---|
| ccacgactgc tttgtccagg gatgcgatgg gtcggtgttg ttgaacgcaa cgtcaggtga | 360 |
| gcaaacggct cccccaaact tatcactcag agcgcaggct ttaaagatta ttaacgacat | 420 |
| caaagagaac gtcgaagccg cctgcagcgg aattgtgtcg tgtgccgaca ttgttacttt | 480 |
| agcagctcgt gactccgttg taatggctgg aggaccgttc taccccttac cactcggccg | 540 |
| cagggacagc cttaccttcg ccaatcgatc gaccgttctc gccaatttgc catccccaac | 600 |
| ctccaatgta acggggctca tcagtgtttt gggtcccaaa ggcttgaatt tcacagatct | 660 |
| ggtggccctc tcaggaggac atacaattgg cagaagcaac tgctcctcct tcgacaacag | 720 |
| actatataac agcaccaccg gtacacaaat gcgggatccc acgatggacc agagtttcgc | 780 |
| taagaatctt tatctcacct gccctaccag taccaccgtt aacaccacca aattggatat | 840 |
| tcgcactcca aatgtgttcg acaacaaata ctacgtcgat ctcctcaacc gacagaccct | 900 |
| cttcacttct gaccagactc tttacaccga cactcgaacc cgcgacattg tgatcaattt | 960 |
| tgcggtgaat cagagcctct tctttgaaca gtttgtgctg agcatgctca aaatggggca | 1020 |
| gctggatgtg ctcacaggaa gcgagggaga gatccgtaag aactgctggg ctgcgaatcc | 1080 |
| ttcaacattt tcgattatgg atccagaggc gtctcaagaa tcaacatctt actctatgtg | 1140 |
| agattagggt tatgagcgaa tctcaaatat aagcaagcag cgttaattcc cagcaaagtc | 1200 |
| taataaatat atatataacc ggcatcttgt aaacccttg caatgctggt tctacaaatt | 1260 |
| acttttccc ttttgacctt ctgaaagagc agaaatcaag cctgaataca gtgcattctc | 1320 |
| gttgaaaata aatagcgttt cttgttgata atcagatttc caaccgattc cggcaatttc | 1380 |
| caataagaaa ctttactgaa tttaaactca aatgctggcc aattttgttt agggcgtttt | 1440 |
| tgaaatcgtt ggactgttat cttttggaaac ctacattaga cttatattta tctaaaatat | 1500 |
| tgcacccaaa aaaaaaaaaa aa | 1522 |

```
<210> SEQ ID NO 372
<211> LENGTH: 311
<212> TYPE: DNA
<213> ORGANISM: Pinus radiata

<400> SEQUENCE: 372
```

| | |
|---|---|
| ctcaatttcg ctcttatctt ctgtgtttca tcgttttctt cccaatatga tgatgaggac | 60 |
| tctagtgtgc attgggttaa tggctgtgtt tgtagccttc atacatataa acgcttgaat | 120 |
| gggcagctga gctcaacgtt ttatgccaaa tcgtgtccga ggttgccatc gatagtgaaa | 180 |
| tcagtggtga agcaagcggt cgctaaggag aaaagaatgg gagcgtcctt ggtccgcctt | 240 |
| cactttcacg attgcttcgt caatgggtgc gatggttcaa tcttattgga tgacaacgcg | 300 |
| acgtttaccg g | 311 |

```
<210> SEQ ID NO 373
<211> LENGTH: 474
<212> TYPE: DNA
<213> ORGANISM: Pinus radiata

<400> SEQUENCE: 373
```

| | |
|---|---|
| catcgatgct atcaagacag ccctcgagag ttcttgcaac gccactgttt cttgcgcaga | 60 |
| tattctcgct attgcagcgc gggattcagt ataccttagc ggtgggcctt actggcaagt | 120 |
| gcagatgggg agaagagatg gcaccactgc agcaaaagt gcagcaaatg ccgacatccc | 180 |
| ttctcctatt gagtcgcttg gttcactcat atcccaattc caaggtgttg ggctttctgt | 240 |
| tcatgatctt gtagtgcttt caggggctca caccataggc cgtgcccact gtggcaccttt | 300 |

```
cagctcacgc ctattcaatt tcagcggctc aaacagtgcg gacccaacta ttcaccaatc      360
tctactgcaa gacctgcata gtttatgccc agatggaaac agtgatccaa ataccctggc      420
gccactggac cctgtgacca agacaagct ccataatgtg tatttcagaa atct             474
```

<210> SEQ ID NO 374
<211> LENGTH: 353
<212> TYPE: DNA
<213> ORGANISM: Pinus radiata

<400> SEQUENCE: 374

```
ctttctgtta cggatgtcgt tgctttgtca gggggacata caattgggcg agctcggtgc       60
acagtgttca gcggtagact ctacaatttc agcggaacgg gcagtccgga tccgacactg     120
aattcctcct atctatccac cttgcaaagc acgtgcccgc agaatggaag cgcgaatacg     180
ttaacgtcac tggatccagg gactccaaat acgttcgaca caactactt tgcaaatctg     240 cagattgaga tgggtctgct tcagtcgatc aagaacttct ttccacatcg ggagcaagca     300
ccatctctac tgtcaatgat tatgccagta gtcaatccga tttcttcttc aac             353
```

<210> SEQ ID NO 375
<211> LENGTH: 461
<212> TYPE: DNA
<213> ORGANISM: Pinus radiata

<400> SEQUENCE: 375

```
caaagcagag ttgcgtttga agcgcaagaa atggccgctt taatgaaaag ctccgcatgc       60
attgctgtaa ttgtgtttat tgtgtgttcg attaataaca ctgtgcatgg gcagctgagc     120
tcaacatttt atgacaaatc ttgcccgacg gtgctgtcgg tagtgaaagc cggggtgaag     180
caagcggtcg ccaaggagca aaggatgggg gcgtcgcttc tccgacttca cttccacgac     240
tgcttcgtta atggttgcga tgggtccgtt ctgttggatg actcttcgaa aattactggc     300
gagaaaacgg ctattcccaa tgccaattcg gcgaggggt tcgatgtgat cgataccata     360
aagagtcagg tcgagaaatc ttgcagcgca gtcgtttcct gttctgacat tctagccatt     420
gctgctcgtg attctgttgt tgaactgggc ggcccttcat g                         461
```

<210> SEQ ID NO 376
<211> LENGTH: 179
<212> TYPE: PRT
<213> ORGANISM: Eucalyptus grandis

<400> SEQUENCE: 376

```
Met Arg Ala Leu Ala Val Val Leu Gly Ser Ala Ile Leu Leu Ala Tyr
 1               5                  10                  15

Val Ala Ser Ser Ala Gly Ala Leu Ser Leu Asp Tyr Tyr Asp Gln Thr
             20                  25                  30

Cys Pro Lys Leu Glu Phe Ser Arg Gly Ala Val Lys Lys Ala Met
         35                  40                  45

Lys Asn Asp Asn Thr Val Pro Ala Ala Leu Leu Arg Met His Phe His
 50                  55                  60

Asp Cys Phe Ile Arg Gly Cys Asp Gly Ser Val Leu Leu Asn Ser Thr
 65                  70                  75                  80

Ala Lys Asn Thr Ala Glu Lys Asp Gly Pro Pro Asn Ile Ser Leu His
                 85                  90                  95

Ala Phe Tyr Val Ile Asp Leu Ala Lys Glu Ala Val Glu Ala Gln Cys
                100                 105                 110
```

Pro Gly Val Val Ser Cys Ala Asp Ile Leu Ala Leu Ala Ala Arg Asp
        115                 120                 125

Ala Val Ala Leu Ser Gly Gly Pro His Trp Asp Val Pro Lys Gly Arg
    130                 135                 140

Lys Asp Gly Arg Ile Arg Lys Arg Met Thr Gln Gly Asn Tyr Gln Leu
145                 150                 155                 160

Arg Pro Ser Thr Ser Leu Asn Tyr Ser Lys Leu Leu Ser Arg Gly Leu
                165                 170                 175

Ser Met Glu

<210> SEQ ID NO 377
<211> LENGTH: 115
<212> TYPE: PRT
<213> ORGANISM: Eucalyptus grandis

<400> SEQUENCE: 377

Met Phe Leu Lys Tyr Leu Ser Ala Ala Leu Ile Ser Leu Ala Thr Ile
1               5                   10                  15

Arg Ser Ala Tyr Gly Ala Ser Thr Pro Lys Arg Arg Ala Thr Cys Ala
            20                  25                  30

Gly Gly Gln Thr Val Lys Asn Glu Ala Cys Cys Ala Trp Phe Pro Val
        35                  40                  45

Leu Glu Asp Ile Leu Pro Asn Met Phe Asp Asn Glu Cys Gly Asp Asp
    50                  55                  60

Ala His Gly Ala Leu Arg Leu Ser Phe His Asp Ala Ile Gly Phe Ser
65                  70                  75                  80

Pro Ser Gln Gly Gly Gly Gly Ala Asp Gly Ser Ile Leu Ser Ser Val
                85                  90                  95

Thr Pro Asn Cys Ser Ser Pro Arg Thr Leu Ala Ser Thr Thr Arg Ser
            100                 105                 110

Thr Leu Ser
        115

<210> SEQ ID NO 378
<211> LENGTH: 315
<212> TYPE: PRT
<213> ORGANISM: Eucalyptus grandis

<400> SEQUENCE: 378

Met Val Gly Phe Ser Val Val Val Leu Leu Ala Thr Ser Val Ile
1               5                   10                  15

Thr Thr Ala Arg Cys Lys Leu Ser Pro Ser His Tyr Gln Ser Thr Cys
            20                  25                  30

Pro Lys Ala Leu Ser Ile Val Arg Ala Gly Val Ala Lys Ala Ile Lys
        35                  40                  45

Asn Glu Thr Arg Thr Gly Ala Ser Leu Arg Leu His Phe His Asp
    50                  55                  60

Cys Phe Val Asn Gly Cys Asp Ala Ser Ile Leu Leu Asp Asp Thr Pro
65                  70                  75                  80

Ser Phe Val Gly Glu Lys Thr Ala Ala Pro Asn Asn Asn Ser Val Arg
                85                  90                  95

Gly Phe Glu Val Ile Asp Arg Ile Lys Ala Ser Leu Glu Lys Glu Cys
            100                 105                 110

Pro Gly Val Val Ser Cys Ala Asp Ile Val Ala Leu Ala Ala Arg Asp
        115                 120                 125

-continued

```
Ser Val Val His Leu Gly Gly Pro Ser Trp Thr Val Ser Leu Gly Arg
130                 135                 140

Lys Asp Ser Ile Thr Ala Ser Arg Ser Leu Ala Asn Thr Ser Ile Pro
145                 150                 155                 160

Pro Pro Thr Ser Asn Leu Ser Ala Leu Ile Thr Ser Phe Ala Ala Gln
                165                 170                 175

Gly Leu Ser Val Lys Asn Met Val Ala Leu Ser Gly Ser His Thr Ile
            180                 185                 190

Gly Leu Ala Arg Cys Thr Ser Phe Arg Arg Ile Tyr Asn Asp Ser
        195                 200                 205

Asn Ile Asp Thr Ser Phe Ala His Lys Leu Gln Lys Ile Cys Pro Arg
210                 215                 220

Ile Gly Asn Asp Ser Val Leu Gln Arg Leu Asp Ile Gln Thr Pro Thr
225                 230                 235                 240

Phe Phe Asp Asn Leu Tyr Tyr His Asn Leu Leu Gln Lys Lys Gly Leu
                245                 250                 255

Leu His Ser Asp Gln Glu Leu Phe Asn Gly Ser Ser Val Asp Ser Leu
            260                 265                 270

Val Lys Lys Tyr Ala Cys Asp Thr Gly Lys Phe Phe Arg Asp Phe Ala
        275                 280                 285

Lys Ala Met Ile Lys Met Ser Glu Ile Lys Pro Pro Lys Gly Ser Asn
290                 295                 300

Gly Gln Ile Arg Lys Asn Cys Arg Lys Val Asn
305                 310                 315

<210> SEQ ID NO 379
<211> LENGTH: 111
<212> TYPE: PRT
<213> ORGANISM: Eucalyptus grandis

<400> SEQUENCE: 379

Met Pro Ser Arg His Pro Ile Trp Val Ile Val Ala Ile Ala Phe Val
1               5                   10                  15

Thr Ala Leu Gly Trp Gly Ser Ala Ser Ala Gln Leu Ser Thr Asn Phe
            20                  25                  30

Tyr Ser Lys Ser Cys Pro Asn Val Leu Ser Thr Val Lys Ser Val Val
        35                  40                  45

Arg Ser Ala Val Ser Lys Glu Arg Met Gly Ala Ser Leu Leu Arg
    50                  55                  60

Leu Phe Phe His Asp Cys Phe Val Asn Gly Cys Asp Gly Ser Ile Leu
65                  70                  75                  80

Leu Asp Asp Thr Ser Ser Phe Gln Gly Glu Lys Thr Ala Gly Pro Asn
                85                  90                  95

Asn Lys Ser Leu Arg Gly Tyr Asn Val Ile Asp Arg Ile Lys Ser
            100                 105                 110

<210> SEQ ID NO 380
<211> LENGTH: 116
<212> TYPE: PRT
<213> ORGANISM: Eucalyptus grandis

<400> SEQUENCE: 380

Met Gln Phe Thr Phe Ser Ala Ala Phe Leu Ala Leu Val Thr Val Ala
1               5                   10                  15

Ala Ala Met Pro Thr Lys Arg Ala Ala Cys Ser Asn Gly Arg Thr Ala
            20                  25                  30
```

```
Thr His Ala Ser Cys Cys Val Trp Phe Asp Val Leu Asp Asp Ile Gln
        35                  40                  45

Glu Asn Leu Phe Asp Gly Gly Glu Cys Gly Glu Thr His Glu Ser
 50                  55                  60

Leu Arg Leu Thr Phe His Asp Ala Ile Gly Phe Ser Pro Ser Leu Phe
65                   70                  75                  80

Leu Glu Gly Lys Phe Gly Gly Leu Gly Ala Asp Gly Ser Ile Met Ala
                85                  90                  95

His Ser Asp Ile Glu Thr Val Phe Pro Ala Asn Asn Gly Ile Asp Asp
                100                 105                 110

Ile Val Asp Ala
        115

<210> SEQ ID NO 381
<211> LENGTH: 308
<212> TYPE: PRT
<213> ORGANISM: Eucalyptus grandis

<400> SEQUENCE: 381

Met Ala Ser Arg Phe Ser Ser Phe Val Leu Val Ser Phe Leu Val Ile
 1               5                  10                  15

Ala Ala Ser His Val His Val Thr Ser Ser Ala His Leu Val Lys Gly
                20                  25                  30

Leu Ser Trp Ser Phe Tyr Glu Lys Ser Cys Pro Lys Val Glu Ser Val
        35                  40                  45

Ile Lys Lys His Leu Lys Lys Val Phe Glu Glu Asp Ile Gly Gln Ala
 50                  55                  60

Ala Gly Leu Leu Arg Leu His Phe His Asp Cys Phe Val Lys Gly Cys
65                   70                  75                  80

Asp Ala Ser Val Leu Leu Asp Gly Ser Ala Ser Gly Pro Ser Glu Gln
                85                  90                  95

Asp Ala Pro Pro Asn Arg Ser Leu Arg Pro Ser Ala Phe Lys Ile Ile
                100                 105                 110

Asp Asp Leu Arg Glu Leu Val Asp Lys Lys Cys Gly Arg Val Val Ser
                115                 120                 125

Cys Ala Asp Ile Ala Ala Ile Ala Ala Arg Asp Ser Val Val Leu Ser
        130                 135                 140

Gly Gly Pro Glu Tyr Asp Val Pro Leu Gly Arg Arg Asp Gly Leu Thr
145                 150                 155                 160

Phe Ala Thr Gln Asn Val Thr Leu Glu Asn Leu Pro Ala Pro Thr Glu
                165                 170                 175

Asn Ala Ser Ala Ile Leu Ser Ala Leu Ala Lys Lys Asn Leu Asp Ala
                180                 185                 190

Thr Asp Val Val Ala Leu Ser Gly Gly His Thr Ile Gly Leu Gly His
                195                 200                 205

Cys Thr Ser Phe Glu Asn Arg Leu Tyr Pro Thr Gln Asp Pro Thr Met
        210                 215                 220

Glu Lys Thr Phe Ala His Asp Leu Lys Gly Val Cys Pro Thr Thr Asn
225                 230                 235                 240

Ser Thr Asn Thr Thr Val Leu Asp Ile Arg Ser Pro Asn Arg Phe Asp
                245                 250                 255

Asn Lys Tyr Phe Val Asp Leu Val Asn Arg Gln Gly Leu Phe Thr Ser
                260                 265                 270

Asp Gln Asp Leu Tyr Glu Asp Pro Thr Thr Arg Asp Ile Val Thr Ser
                275                 280                 285
```

```
Phe Ala Glu Asp Gln Glu Leu Phe Phe Glu Lys Phe Val Leu Ala Met
    290                 295                 300

Thr Lys Met Gly
305
```

<210> SEQ ID NO 382
<211> LENGTH: 98
<212> TYPE: PRT
<213> ORGANISM: Eucalyptus grandis

<400> SEQUENCE: 382

```
Met Phe Leu Lys Tyr Leu Ser Gly Ala Leu Val Ser Leu Ala Thr Ile
1               5                   10                  15

Arg Gly Val Cys Gly Ala Ser Ala Pro Met Arg Arg Ala Thr Cys Ala
            20                  25                  30

Gly Gly Gln Thr Val Lys Asn Ala Ala Cys Cys Ala Trp Phe Pro Val
        35                  40                  45

Leu Asp Asp Ile Arg Glu Asn Phe Asp Asn Glu Cys Gly Asp Asp
    50                  55                  60

Ala His Ala Ala Leu Arg Leu Ser Phe His Asp Ala Ile Gly Phe Ser
65                  70                  75                  80

Arg Ser Lys Gly Gly Gly Ala Asp Gly Ser Ile Ile Ala Phe Asn
                85                  90                  95

Lys Thr
```

<210> SEQ ID NO 383
<211> LENGTH: 119
<212> TYPE: PRT
<213> ORGANISM: Eucalyptus grandis

<400> SEQUENCE: 383

```
Met Ala Phe Lys Leu Val Val Asn Leu Val Ser Leu Ala Leu Ala Val
1               5                   10                  15

Ser Ala Ala Asn Phe Lys Arg Val Ala Cys Pro Gly Thr Thr Ala Thr
            20                  25                  30

Ala Arg Asn Pro Ala Cys Cys Ala Phe Phe Ser Leu Arg Asp Asp Leu
        35                  40                  45

Leu Thr Asn Leu Phe Gly Gly Val Cys Gly Glu Ala His Glu Ser
    50                  55                  60

Leu Arg Leu Ser Phe His Asp Ala Ile Ala Phe Ser Pro Ala Leu Ile
65                  70                  75                  80

Arg Gln Gly Lys Pro Gly Gly Gly Ala Asp Gly Ser Met Ile Thr
                85                  90                  95

Phe Pro Asn Val Glu Pro Asn Phe Asn Ala Asn Asn Gly Ile Ile Asp
            100                 105                 110

Ser Val Asp Phe Leu Thr Pro
        115
```

<210> SEQ ID NO 384
<211> LENGTH: 138
<212> TYPE: PRT
<213> ORGANISM: Eucalyptus grandis

<400> SEQUENCE: 384

```
Ser Cys Pro Gly Thr Val Ser Cys Ala Asp Ile Leu Ala Leu Gly Ala
1               5                   10                  15

Gln Ala Ser Val Val Leu Ser Gly Gly Pro Ser Trp Arg Val Leu Ser
```

-continued

```
                     20                  25                  30
Gly Arg Arg Asp Ser Leu Thr Ala Asn Gln Ala Gly Asn Thr Ser
         35                  40                  45

Ile Pro Ser Pro Phe Asp Ser Leu Ala Asn Leu Thr Ser Lys Phe Ala
 50                  55                  60

Ala Val Gly Leu Asp Thr Asn Asp Leu Val Thr Leu Ser Gly Ala His
 65                  70                  75                  80

Thr Phe Gly Arg Ala Gln Cys Arg Thr Phe Ser Pro Arg Leu Tyr Asn
                 85                  90                  95

Phe Asn Ala Ser Gly Ser Pro Asp Pro Thr Ile Ser Pro Ser Tyr Leu
                100                 105                 110

Thr Thr Leu Gln Gln Leu Cys Pro Gln Asn Gly Ser Gly Ser Val Leu
                115                 120                 125

Ala Asn Leu Asp Pro Thr Thr Val Asn Thr
                130                 135

<210> SEQ ID NO 385
<211> LENGTH: 208
<212> TYPE: PRT
<213> ORGANISM: Pinus radiata

<400> SEQUENCE: 385

Met Lys His Ile Pro Gly Leu Thr Leu Gln Phe Gln Ser Val Leu Ile
  1               5                  10                  15

Thr Gly Ala Ala Leu Phe Leu Trp Ile Gln Thr Ser Asp Ala Gln Asp
                 20                  25                  30

Cys Asn Gly Leu Ser His His Tyr Tyr Gln Lys Ser Cys Pro Asn Ala
                 35                  40                  45

Gln Ala Ile Ile Lys Ser Val Val Ser Asp Ala Val Lys Lys Glu Ala
 50                  55                  60

Arg Met Ala Ala Ser Leu Leu Arg Leu His Phe His Asp Cys Phe Val
 65                  70                  75                  80

Gln Gly Cys Asp Ala Ser Ile Leu Leu Asp Asp Thr Ala Ser Phe Thr
                 85                  90                  95

Gly Glu Lys Thr Ala Leu Pro Asn Arg Asn Ser Val Arg Gly Phe Glu
                100                 105                 110

Val Val Asp Lys Ile Lys Ser Lys Leu Glu Glu Ala Cys Pro Gly Val
                115                 120                 125

Val Ser Cys Ala Asp Ile Leu Ala Val Ala Ala Arg Asp Ser Val Gly
                130                 135                 140

Phe Ser Val Gly Pro Tyr Trp Glu Val Leu Leu Gly Arg Arg Asp Ser
145                 150                 155                 160

Lys Thr Ala Ser Lys Ser Gly Ala Asn Asn Asp Ile Pro Ala Pro Asn
                165                 170                 175

Ser Thr His Gln Thr Leu Glu Thr Lys Phe Asn Leu Lys Gly Leu Asn
                180                 185                 190

Val Leu Asp Leu Val Ala Leu Ser Arg Ser His Asn Asn Arg Val Ser
                195                 200                 205

<210> SEQ ID NO 386
<211> LENGTH: 202
<212> TYPE: PRT
<213> ORGANISM: Pinus radiata

<400> SEQUENCE: 386

Met Ala Thr Leu Gly Ile Pro Leu Gly Ser Leu Ser Leu Leu Leu Leu
```

-continued

```
            1               5              10              15
Phe Phe Cys Cys Ala Gln Arg Ser Val Gly Leu Lys Glu Asn Tyr Tyr
                 20                  25                  30

Ala Thr Ser Cys Pro Arg Ala Glu His Ile Val Lys Glu Gln Val Tyr
                 35                  40                  45

Asn Leu Tyr Gln Glu His Gly Asn Thr Ala Val Ser Trp Ile Arg Leu
     50                  55                  60

Ile Phe His Asp Cys Ile Val Gln Ser Cys Asp Ala Ser Ile Leu Leu
 65                  70                  75                  80

Asp Ser Ser Gly Asp Val Gln Thr Glu Lys Gln Ser Asp Arg Asn Phe
                 85                  90                  95

Gly Met Arg Asn Phe Lys Tyr Val Asp Thr Ile Lys Glu Ala Ile Glu
                100                 105                 110

Val Glu Cys Pro Gly Val Val Ser Cys Ala Asp Ile Ile Val Leu Ala
                115                 120                 125

Ala Lys Glu Ala Ala Ala Met Leu Gly Gly Pro Arg Ile Ala Val Lys
                130                 135                 140

Thr Gly Arg Arg Asp Ser Arg Lys Ser Ser Ala Ala Val Val Asp Lys
145                 150                 155                 160

Tyr Val Pro Leu His Asn Gly Ser Ile Ser Ser Leu Leu Ser Ala Phe
                165                 170                 175

Ala Ser Val Gly Ile Asp Ala Glu Gly Ala Val Ala Leu Leu Gly Leu
                180                 185                 190

Ile Leu Ile His Ser Val Leu His Tyr Thr
                195                 200

<210> SEQ ID NO 387
<211> LENGTH: 287
<212> TYPE: PRT
<213> ORGANISM: Pinus radiata

<400> SEQUENCE: 387

Met Lys Ser Phe Pro Cys Ile Ala Val Ile Val Phe Ile Ile Cys Ser
 1               5                  10                  15

Ile Thr Asp Thr Val Asn Gly Lys Leu Ser Ser Thr Phe Tyr Asp Lys
                 20                  25                  30

Ser Cys Pro Lys Ala Leu Ser Ile Val Gln Ala Gly Val Lys Gln Ala
                 35                  40                  45

Val Ala Lys Glu Lys Arg Met Gly Ala Ser Leu Leu Arg Leu His Phe
     50                  55                  60

His Asp Cys Phe Val Asn Gly Cys Asp Gly Ser Val Leu Leu Asp Asn
 65                  70                  75                  80

Ser Thr Thr Phe Thr Ser Glu Lys Tyr Ala Leu Pro Asn Asn Asn Ser
                 85                  90                  95

Ala Arg Gly Phe Glu Val Ile Asp Ser Ile Lys Ser Gln Leu Glu Asn
                100                 105                 110

Ala Cys Thr Gly Val Val Ser Cys Ala Asp Ile Leu Thr Ile Ala Ala
                115                 120                 125

Arg Asp Ser Val Val Gln Leu Gly Gly Pro Ser Trp Lys Val Met Leu
                130                 135                 140

Gly Arg Arg Asp Ser Thr Thr Ala Ser Ile Ser Gly Ala Asn Asn Asn
145                 150                 155                 160

Ile Pro Pro Pro Thr Ser Asn Leu Thr Lys Leu Ile Ser Leu Phe Gln
                165                 170                 175
```

```
Ala Gln Gly Leu Ser Thr Lys Glu Met Val Ala Leu Ser Gly Gly His
            180                 185                 190

Thr Ile Gly Gln Ala Gln Cys Lys Asn Phe Arg Ala His Ile Tyr Asn
            195                 200                 205

Asp Thr Asn Ile Asp Thr Thr Tyr Ala Thr Ser Leu Arg Ser Lys Cys
            210                 215                 220

Pro Ser Thr Thr Gly Ser Gly Asp Ser Asn Leu Ser Pro Leu Asp Tyr
225                 230                 235                 240

Thr Thr Pro Thr Val Phe Asp Lys Asn Tyr Tyr Asn Leu Lys Ser
                245                 250                 255

Lys Arg Gly Leu Leu His Ser Asp Gln Glu Leu Phe Asn Gly Gly Ser
                260                 265                 270

Thr Asp Ser His Val Thr Lys Tyr Ala Ser Asn Gln Asn Thr Phe
                275                 280                 285

<210> SEQ ID NO 388
<211> LENGTH: 161
<212> TYPE: PRT
<213> ORGANISM: Pinus radiata

<400> SEQUENCE: 388

Ala Asn Ser Asn Leu Pro Ser Pro Ala Ser Leu Ser Thr Leu Met
1               5                   10                  15

Thr Ala Phe Gln Lys Gln Gly Leu Ser Thr Lys Asp Leu Val Ala Leu
            20                  25                  30

Ser Gly Ala His Thr Ile Gly Gln Ala Arg Cys Thr Thr Phe Arg Thr
            35                  40                  45

Arg Ile Tyr Asn Asp Thr Asn Ile Asn Ala Ala Phe Ala Thr Ser Ala
        50                  55                  60

Lys Ala Asn Cys Pro Ser Thr Gly Gly Asp Asn Thr Leu Ser Pro Leu
65                  70                  75                  80

Asp Val Leu Thr Pro Thr Thr Phe Asp Asn Lys Tyr Tyr Thr Asn Leu
                85                  90                  95

Lys Ser Gln Lys Gly Leu Phe His Ser Asp Gln Glu Leu Phe Asn Gly
            100                 105                 110

Gly Ser Thr Asp Ser Arg Val Ser Ile Tyr Ser Thr Ser Gln Ala Ile
            115                 120                 125

Phe Phe Thr Asp Phe Ala Ala Ala Met Val Asn Met Gly Asn Ile Ser
        130                 135                 140

Pro Leu Thr Gly Thr Asn Gly Glu Ile Arg Thr Asn Cys Arg Lys Val
145                 150                 155                 160

Asn

<210> SEQ ID NO 389
<211> LENGTH: 318
<212> TYPE: PRT
<213> ORGANISM: Pinus radiata

<400> SEQUENCE: 389

Met Arg Thr Leu Val Cys Ile Gly Leu Met Ala Val Phe Val Ala Phe
1               5                   10                  15

Ile His Ile Asn Ala Val Asn Gly Gln Leu Ser Ser Thr Phe Tyr Ala
            20                  25                  30

Lys Ser Cys Pro Arg Leu Pro Ser Ile Val Lys Ser Val Lys Gln
            35                  40                  45

Ala Val Ala Lys Glu Lys Arg Met Gly Ala Ser Leu Val Arg Leu His
```

```
                 50                  55                  60
Phe His Asp Cys Phe Val Asn Gly Cys Asp Gly Ser Ile Leu Leu Asp
 65                  70                  75                  80

Asp Asn Ala Thr Phe Thr Gly Glu Lys Thr Ala Gly Pro Asn Ala Asn
                 85                  90                  95

Ser Ala Arg Gly Phe Glu Val Ile Asp Ser Ile Lys Thr Gln Val Glu
            100                 105                 110

Ala Ala Cys Ser Gly Val Val Ser Cys Ala Asp Ile Leu Thr Ile Ala
            115                 120                 125

Ala Arg Asp Ser Ile Val Glu Leu Gln Gly Pro Thr Trp Thr Val Met
        130                 135                 140

Leu Gly Arg Arg Asp Ser Thr Thr Ala Ser Leu Ser Ala Ala Asn Asn
145                 150                 155                 160

Asn Ile Pro Ser Pro Ala Ser Ser Leu Ser Thr Leu Ile Ser Ser Phe
                165                 170                 175

Gln Ala His Gly Leu Ser Thr Lys Asp Leu Val Ala Leu Ser Gly Ala
            180                 185                 190

His Thr Ile Gly Gln Ser Arg Cys Ala Phe Phe Arg Thr Arg Ile Tyr
        195                 200                 205

Asn Glu Thr Asn Ile Asn Ala Ala Phe Ala Thr Ser Val Lys Ala Asn
    210                 215                 220

Cys Pro Ser Ala Gly Gly Asp Ser Asn Leu Ser Pro Leu Asp Ala Val
225                 230                 235                 240

Thr Ser Ile Thr Phe Asp Asn Lys Tyr Tyr Ser Asn Leu Lys Ile Gln
                245                 250                 255

Lys Gly Leu Leu His Ser Asp Gln Gln Leu Phe Asn Gly Gly Ser Thr
            260                 265                 270

Asp Ser Gln Val Thr Ala Tyr Ser Ser Asn Gln Asn Ser Phe Phe Ile
        275                 280                 285

Asp Phe Thr Ala Ala Met Val Lys Met Gly Asn Ile Ser Pro Leu Thr
    290                 295                 300

Gly Thr Asn Gly Gln Ile Arg Lys Asn Cys Arg Lys Ser Asn
305                 310                 315

<210> SEQ ID NO 390
<211> LENGTH: 95
<212> TYPE: PRT
<213> ORGANISM: Pinus radiata

<400> SEQUENCE: 390

Lys Leu Pro Lys Ser Gly Gly Asp Asn Asn Leu Ser Pro Leu Asp Leu
 1                   5                  10                  15

Leu Thr Pro Thr Thr Phe Asp Asn Lys Tyr Tyr Thr Asn Leu Lys Ser
                 20                  25                  30

Gln Lys Gly Leu Leu His Ser Asp Gln Gln Leu Phe Asn Gly Gly Ser
            35                  40                  45

Ala Asp Ser Gln Val Thr Thr Tyr Ser Thr Thr Gln Ser Thr Phe Phe
        50                  55                  60

Thr Asp Phe Ala Ala Ser Met Leu Asn Met Gly Asn Ile Ser Pro Leu
 65                  70                  75                  80

Thr Gly Thr Ser Gly Gln Ile Arg Lys Asn Cys Arg Lys Pro Asn
                 85                  90                  95

<210> SEQ ID NO 391
<211> LENGTH: 201
```

```
<212> TYPE: PRT
<213> ORGANISM: Pinus radiata

<400> SEQUENCE: 391

Met Thr Ser Phe Thr Ala Met Ala Ser Val Val Cys Ile Ala Leu Leu
  1               5                  10                  15

Phe Phe Ser Thr Val Ala Phe Ala Gln Leu Asn Ser Thr Tyr Tyr Asp
             20                  25                  30

Thr Ser Cys Pro Lys Leu Leu Ala Thr Val Lys Ala Ala Val Lys Thr
         35                  40                  45

Ala Val Ala Asn Glu Lys Arg Met Gly Ala Ser Leu Leu Arg Leu His
     50                  55                  60

Phe His Asp Cys Phe Val Asn Gly Cys Asp Gly Ser Val Leu Leu Asp
 65                  70                  75                  80

Asp Ser Ser Leu Thr Gly Glu Lys Thr Ala Leu Pro Asn Asn Asn
                 85                  90                  95

Ser Leu Arg Gly Phe Asp Val Ile Asp Thr Ile Lys Ser Gln Val Glu
                100                 105                 110

Ala Val Cys Ser Gly Ile Val Ser Cys Ala Asp Ile Leu Ala Ile Thr
            115                 120                 125

Ala Arg Asp Ser Val Val Glu Leu Gly Gly Pro Thr Trp Thr Val Leu
        130                 135                 140

Leu Gly Arg Arg Asp Ser Ala Thr Ala Ser Leu Ser Ala Ala Asn Thr
145                 150                 155                 160

Asn Ile Pro Ala Pro Thr Ser Asn Leu Ser Gly Leu Ile Ser Ser Phe
                165                 170                 175

Gln Ala Gln Gly Leu Ser Thr Lys Asp Met Ile Val Leu Ser Gly Ala
            180                 185                 190

His Thr Ile Gly Gln Ala Arg Cys Thr
            195                 200

<210> SEQ ID NO 392
<211> LENGTH: 120
<212> TYPE: PRT
<213> ORGANISM: Pinus radiata

<400> SEQUENCE: 392

Leu Ile Ser Ser Phe Thr Ala His Gly Leu Ser Thr Lys Asp Leu Gly
  1               5                  10                  15

Ala Leu Ser Gly Ala His Thr Ile Gly Gln Ala Arg Cys Thr Thr Phe
             20                  25                  30

Arg Ala Arg Val Tyr Asn Glu Ser Asn Ile Asp Thr Ser Phe Ala Thr
         35                  40                  45

Ser Val Lys Ala Asn Trp Pro Ser Ala Gly Gly Asp Asn Thr Leu Ser
     50                  55                  60

Pro Leu Asp Leu Ala Thr Pro Thr Thr Phe Asp Asn Lys Tyr Tyr Thr
 65                  70                  75                  80

Asp Leu Arg Ser Gln Lys Gly Leu Leu His Ser Asp Gln Gln Met Phe
                 85                  90                  95

Ser Gly Gly Ser Thr Asn Ser Gln Val Thr Thr Tyr Ser Ser Asn Gln
                100                 105                 110

Lys His Leu Leu Tyr Arg Leu Tyr
            115                 120

<210> SEQ ID NO 393
<211> LENGTH: 120
```

-continued

```
<212> TYPE: PRT
<213> ORGANISM: Pinus radiata

<400> SEQUENCE: 393

Lys Arg Ile Asn Phe His Leu Lys Glu Asp Ile Thr Gln Ala Ala Gly
  1               5                  10                  15

Leu Leu Arg Val His Phe His Asp Cys Phe Val Gln Gly Cys Asp Gly
             20                  25                  30

Ser Val Leu Leu Asp Gly Ser Ala Ser Gly Pro Ser Glu Gln Asp Ala
         35                  40                  45

Pro Pro Asn Leu Thr Leu Arg Ala Lys Ala Phe Glu Ile Ile Asn Asp
     50                  55                  60

Ile Lys Lys His Val Glu Lys Ala Cys Ser Gly Val Val Ser Cys Ala
 65                  70                  75                  80

Asp Leu Thr Ala Leu Ala Ala Arg Glu Ser Val Arg Ala Val Gly Gly
                 85                  90                  95

Pro Glu Tyr Arg Val Pro Leu Gly Arg Arg Asp Ser Leu Lys Phe Ala
            100                 105                 110

Thr Arg Lys Val Thr Leu Ala Asn
            115                 120

<210> SEQ ID NO 394
<211> LENGTH: 266
<212> TYPE: PRT
<213> ORGANISM: Pinus radiata

<400> SEQUENCE: 394

Met Ala Ser Phe Thr Ala Met Arg Ser Leu Ala Phe Ile Ala Leu Leu
  1               5                  10                  15

Met Cys Ser Thr Val Ala Tyr Ala Gln Leu Ser Ala Thr Phe Tyr Asn
             20                  25                  30

Thr Ser Cys Pro Lys Leu Leu Ser Thr Val Gln Ala Ala Val Lys Gln
         35                  40                  45

Ala Val Ala Asn Glu Lys Arg Met Gly Ala Ser Leu Leu Arg Leu His
     50                  55                  60

Phe His Asp Cys Phe Val Asn Gly Cys Asp Gly Ser Val Leu Leu Asp
 65                  70                  75                  80

Asp Ser Ser Thr Leu Thr Gly Glu Lys Thr Ala Val Pro Asn Asn Asn
                 85                  90                  95

Ser Ala Arg Gly Phe Asp Val Ile Asp Thr Ile Lys Ser Gln Val Glu
            100                 105                 110

Ala Val Cys Ser Gly Val Val Ser Cys Ala Asp Ile Leu Ala Ile Ala
            115                 120                 125

Ala Arg Asp Ser Val Val Gln Leu Gly Gly Pro Thr Trp Thr Val Gln
        130                 135                 140

Leu Gly Arg Arg Asp Ser Arg Thr Ala Ser Leu Ser Gly Ala Asn Asn
145                 150                 155                 160

Asn Ile Pro Ala Pro Thr Ser Asn Leu Ser Ala Leu Ile Ser Leu Phe
                165                 170                 175

Gln Ala Gln Gly Leu Ser Thr Lys Asp Met Val Val Leu Ser Gly Ala
            180                 185                 190

His Thr Ile Gly Gln Ala Arg Cys Thr Ser Phe Arg Ala Arg Ile Tyr
            195                 200                 205

Asn Glu Ser Asn Ile Asn Ala Ala Tyr Ala Thr Ser Leu Lys Thr Asn
            210                 215                 220
```

```
Cys Pro Thr Thr Gly Ser Asp Asn Asn Leu Ser Pro Leu Asp Arg Val
225                 230                 235                 240

Thr Pro Thr Thr Phe Asp Ile Asn Tyr Tyr Ser Asn Leu Arg Ser Gln
                245                 250                 255

Lys Gly Leu Leu His Ser Asp Gln Gln Leu
            260                 265
```

<210> SEQ ID NO 395
<211> LENGTH: 323
<212> TYPE: PRT
<213> ORGANISM: Pinus radiata

<400> SEQUENCE: 395

```
Met Ala Tyr Leu Arg Lys Ser Phe Ala Cys Ile Ala Val Met Val Phe
1               5                   10                  15

Ile Val Cys Ser Ile Thr Asp Thr Val Asn Gly Gln Leu Ser Ser Thr
            20                  25                  30

Phe Tyr Asp Lys Ser Cys Pro Thr Ala Leu Ser Val Val Lys Ala Ala
        35                  40                  45

Val Lys Gln Ala Val Ala Asn Glu Lys Arg Met Gly Ala Ser Leu Leu
50                  55                  60

Arg Leu His Phe His Asp Cys Phe Val Asn Gly Cys Asp Gly Ser Val
65                  70                  75                  80

Leu Leu Asp Asp Ser Ser Thr Ile Thr Gly Glu Lys Thr Ala Asn Pro
                85                  90                  95

Asn Ala Asn Ser Ala Arg Gly Phe Asp Val Ile Asp Thr Ile Lys Ser
            100                 105                 110

Asn Val Glu Lys Ala Cys Ser Gly Val Val Ser Cys Ala Asp Ile Leu
        115                 120                 125

Ala Ile Ala Ala Arg Asp Ser Val Val Glu Leu Gly Gly Pro Ser Trp
130                 135                 140

Thr Val Met Leu Gly Arg Arg Asp Ser Thr Thr Ala Ser Lys Ser Gly
145                 150                 155                 160

Ala Asn Ser Asn Ile Pro Pro Thr Ser Leu Ser Asn Leu Ile
                165                 170                 175

Ser Leu Phe Gln Ala Gln Gly Leu Ser Ala Lys Glu Met Val Ala Leu
            180                 185                 190

Ser Gly Gly His Thr Ile Gly Gln Ala Gln Cys Lys Asn Phe Arg Ala
        195                 200                 205

His Ile Tyr Asn Glu Thr Asn Ile Asp Ser Ala Tyr Ala Thr Ser Leu
210                 215                 220

Arg Ser Lys Cys Pro Ser Thr Gly Ser Gly Asp Ser Asn Leu Ser
225                 230                 235                 240

Pro Leu Asp Tyr Met Thr Pro Thr Val Phe Asp Lys Asn Tyr Tyr Ser
                245                 250                 255

Asp Leu Lys Ser Gln Lys Gly Leu Leu His Ser Asp Gln Glu Leu Phe
            260                 265                 270

Asn Gly Gly Ser Thr Asp Ser Gln Val Thr Thr Tyr Ala Ser Asn Gln
        275                 280                 285

Asn Thr Phe Phe Ser Asp Phe Ala Ala Ala Met Val Lys Met Gly Asn
290                 295                 300

Ile Lys Pro Leu Thr Gly Thr Ser Gly Gln Ile Pro Lys Asn Cys Arg
305                 310                 315                 320

Lys Pro Asn
```

-continued

<210> SEQ ID NO 396
<211> LENGTH: 223
<212> TYPE: PRT
<213> ORGANISM: Pinus radiata

<400> SEQUENCE: 396

| Gln | Ile | Lys | Ser | Ala | Leu | Glu | Lys | Glu | Cys | Pro | Lys | Thr | Val | Ser | Cys |
| 1 | | | | 5 | | | | | 10 | | | | | 15 | |

| Ala | Asp | Ile | Leu | Ala | Ile | Ala | Ser | Arg | Asp | Ser | Val | Val | Leu | Ser | Gly |
| | | | 20 | | | | | 25 | | | | | 30 | | |

| Gly | Leu | Gly | Trp | Glu | Val | Leu | Leu | Gly | Arg | Arg | Asp | Ser | Lys | Ser | Ala |
| | | 35 | | | | | 40 | | | | | 45 | | | |

| Ser | Leu | Ser | Gly | Ser | Asn | Asn | Asn | Ile | Pro | Ala | Pro | Asn | Ser | Thr | Leu |
| | 50 | | | | | 55 | | | | | 60 | | | | |

| Gln | Thr | Leu | Thr | Thr | Lys | Phe | Lys | Leu | Gln | Gly | Leu | Asp | Glu | Val | Asp |
| 65 | | | | | 70 | | | | | 75 | | | | | 80 |

| Leu | Val | Ser | Leu | Ser | Gly | Ser | His | Thr | Ile | Gly | Leu | Ser | Arg | Cys | Thr |
| | | | | 85 | | | | | 90 | | | | | 95 | |

| Ser | Phe | Arg | Gln | Arg | Leu | Tyr | Asn | Gln | Ser | Gly | Asn | Gly | Leu | Pro | Asp |
| | | | 100 | | | | | 105 | | | | | 110 | | |

| Phe | Thr | Leu | Asn | Arg | Gly | Tyr | Tyr | Ala | Arg | Leu | Lys | Ser | Gly | Cys | Pro |
| | | | 115 | | | | | 120 | | | | | 125 | | |

| Lys | Ser | Gly | Gly | Asp | Asn | Asn | Leu | Phe | Pro | Leu | Asp | Phe | Val | Thr | Pro |
| | 130 | | | | | 135 | | | | | 140 | | | | |

| Thr | Lys | Phe | Asp | Asn | Tyr | Tyr | Phe | Lys | Ser | Leu | Leu | Ser | Gly | Gln | Gly |
| 145 | | | | | 150 | | | | | 155 | | | | | 160 |

| Leu | Leu | Asn | Thr | Asp | Glu | Glu | Leu | Phe | Ala | Lys | Gly | Ser | Gly | Lys | Thr |
| | | | | 165 | | | | | 170 | | | | | 175 | |

| Lys | Glu | Leu | Val | Lys | Leu | Tyr | Ala | Ala | Asn | Glu | Glu | Leu | Phe | Leu | Lys |
| | | | 180 | | | | | 185 | | | | | 190 | | |

| Gln | Phe | Ala | Leu | Ser | Met | Val | Lys | Met | Gly | Asn | Ile | Lys | Pro | Leu | Thr |
| | | | 195 | | | | | 200 | | | | | 205 | | |

| Gly | Thr | Val | Gly | Glu | Ile | Arg | Val | Asn | Cys | Arg | Lys | Val | Asn | Ser | |
| | 210 | | | | | 215 | | | | | 220 | | | | |

<210> SEQ ID NO 397
<211> LENGTH: 351
<212> TYPE: PRT
<213> ORGANISM: Pinus radiata

<400> SEQUENCE: 397

| Met | Gly | Lys | Phe | Ile | Thr | Ala | Leu | Ala | Ser | Val | Ile | Leu | Cys | Val | Phe |
| 1 | | | | 5 | | | | | 10 | | | | | 15 | |

| Val | Ile | Tyr | Gly | Gly | Ala | Val | Asn | Ala | Leu | Pro | Ser | Pro | Val | Ala | Gly |
| | | | 20 | | | | | 25 | | | | | 30 | | |

| Leu | Ser | Trp | Thr | Phe | Tyr | Ser | Ser | Cys | Pro | Ser | Leu | Glu | Ser | Ile |
| | | 35 | | | | | 40 | | | | | 45 | | | |

| Val | Trp | Glu | Arg | Met | Glu | Ala | Tyr | Leu | Ser | Ala | Asp | Ile | Thr | Gln | Ala |
| | 50 | | | | | 55 | | | | | 60 | | | | |

| Ala | Gly | Leu | Leu | Arg | Leu | His | Phe | His | Asp | Cys | Phe | Val | Gln | Gly | Cys |
| 65 | | | | | 70 | | | | | 75 | | | | | 80 |

| Asp | Gly | Ser | Val | Leu | Leu | Asn | Ala | Thr | Ser | Gly | Glu | Gln | Thr | Ala | Pro |
| | | | | 85 | | | | | 90 | | | | | 95 | |

| Pro | Asn | Leu | Ser | Leu | Arg | Ala | Gln | Ala | Leu | Lys | Ile | Ile | Asn | Asp | Ile |
| | | | 100 | | | | | 105 | | | | | 110 | | |

```
Lys Glu Asn Val Glu Ala Ala Cys Ser Gly Ile Val Ser Cys Ala Asp
        115                 120                 125

Ile Val Thr Leu Ala Ala Arg Asp Ser Val Val Met Ala Gly Gly Pro
130                 135                 140

Phe Tyr Pro Leu Pro Leu Gly Arg Arg Asp Ser Leu Thr Phe Ala Asn
145                 150                 155                 160

Arg Ser Thr Val Leu Ala Asn Leu Pro Ser Pro Thr Ser Asn Val Thr
                165                 170                 175

Gly Leu Ile Ser Val Leu Gly Pro Lys Gly Leu Asn Phe Thr Asp Leu
            180                 185                 190

Val Ala Leu Ser Gly Gly His Thr Ile Gly Arg Ser Asn Cys Ser Ser
        195                 200                 205

Phe Asp Asn Arg Leu Tyr Asn Ser Thr Thr Gly Thr Gln Met Arg Asp
    210                 215                 220

Pro Thr Met Asp Gln Ser Phe Ala Lys Asn Leu Tyr Leu Thr Cys Pro
225                 230                 235                 240

Thr Ser Thr Thr Val Asn Thr Thr Lys Leu Asp Ile Arg Thr Pro Asn
                245                 250                 255

Val Phe Asp Asn Lys Tyr Tyr Val Asp Leu Leu Asn Arg Gln Thr Leu
            260                 265                 270

Phe Thr Ser Asp Gln Thr Leu Tyr Thr Asp Thr Arg Thr Arg Asp Ile
        275                 280                 285

Val Ile Asn Phe Ala Val Asn Gln Ser Leu Phe Phe Glu Gln Phe Val
    290                 295                 300

Leu Ser Met Leu Lys Met Gly Gln Leu Asp Val Leu Thr Gly Ser Glu
305                 310                 315                 320

Gly Glu Ile Arg Lys Asn Cys Trp Ala Ala Asn Pro Ser Thr Phe Ser
                325                 330                 335

Ile Met Asp Pro Glu Ala Ser Gln Glu Ser Thr Ser Tyr Ser Met
            340                 345                 350

<210> SEQ ID NO 398
<211> LENGTH: 103
<212> TYPE: PRT
<213> ORGANISM: Pinus radiata

<400> SEQUENCE: 398

Leu Asn Phe Ala Leu Ile Phe Cys Val Ser Ser Phe Ser Ser Gln Tyr
1               5                   10                  15

Asp Asp Glu Asp Ser Ser Val His Trp Val Asn Gly Cys Val Cys Ser
            20                  25                  30

Leu His Thr Tyr Lys Arg Leu Asn Gly Gln Leu Ser Ser Thr Phe Tyr
        35                  40                  45

Ala Lys Ser Cys Pro Arg Leu Pro Ser Ile Val Lys Ser Val Val Lys
    50                  55                  60

Gln Ala Val Ala Lys Glu Lys Arg Met Gly Ala Ser Leu Val Arg Leu
65                  70                  75                  80

His Phe His Asp Cys Phe Val Asn Gly Cys Asp Gly Ser Ile Leu Leu
                85                  90                  95

Asp Asp Asn Ala Thr Phe Thr
            100

<210> SEQ ID NO 399
<211> LENGTH: 157
<212> TYPE: PRT
<213> ORGANISM: Pinus radiata
```

```
<400> SEQUENCE: 399

Ile Asp Ala Ile Lys Thr Ala Leu Glu Ser Ser Cys Asn Ala Thr Val
 1               5                  10                  15

Ser Cys Ala Asp Ile Leu Ala Ile Ala Arg Asp Ser Val Tyr Leu
            20                  25                  30

Ser Gly Gly Pro Tyr Trp Gln Val Gln Met Gly Arg Arg Asp Gly Thr
        35                  40                  45

Thr Ala Ser Lys Ser Ala Ala Asn Ala Asp Ile Pro Ser Pro Ile Glu
    50                  55                  60

Ser Leu Gly Ser Leu Ile Ser Gln Phe Gln Gly Val Gly Leu Ser Val
65                  70                  75                  80

His Asp Leu Val Val Leu Ser Gly Ala His Thr Ile Gly Arg Ala His
                85                  90                  95

Cys Gly Thr Phe Ser Ser Arg Leu Phe Asn Phe Ser Gly Ser Asn Ser
            100                 105                 110

Ala Asp Pro Thr Ile His Gln Ser Leu Leu Gln Asp Leu His Ser Leu
        115                 120                 125

Cys Pro Asp Gly Asn Ser Asp Pro Asn Thr Leu Ala Pro Leu Asp Pro
    130                 135                 140

Val Thr Lys Asp Lys Leu His Asn Val Tyr Phe Arg Asn
145                 150                 155

<210> SEQ ID NO 400
<211> LENGTH: 117
<212> TYPE: PRT
<213> ORGANISM: Pinus radiata

<400> SEQUENCE: 400

Leu Ser Val Thr Asp Val Val Ala Leu Ser Gly Gly His Thr Ile Gly
 1               5                  10                  15

Arg Ala Arg Cys Thr Val Phe Ser Gly Arg Leu Tyr Asn Phe Ser Gly
            20                  25                  30

Thr Gly Ser Pro Asp Pro Thr Leu Asn Ser Ser Tyr Leu Ser Thr Leu
        35                  40                  45

Gln Ser Thr Cys Pro Gln Asn Gly Ser Ala Asn Thr Leu Thr Ser Leu
    50                  55                  60

Asp Pro Gly Thr Pro Asn Thr Phe Asp Asn Asn Tyr Phe Ala Asn Leu
65                  70                  75                  80

Gln Ile Glu Met Gly Leu Leu Gln Ser Ile Lys Asn Phe Phe Pro His
                85                  90                  95

Arg Glu Gln Ala Pro Ser Leu Leu Ser Met Ile Met Pro Val Val Asn
            100                 105                 110

Pro Ile Ser Ser Ser
        115

<210> SEQ ID NO 401
<211> LENGTH: 143
<212> TYPE: PRT
<213> ORGANISM: Pinus radiata

<400> SEQUENCE: 401

Met Ala Ala Leu Met Lys Ser Ser Ala Cys Ile Ala Val Ile Val Phe
 1               5                  10                  15

Ile Val Cys Ser Ile Asn Asn Thr Val His Gly Gln Leu Ser Ser Thr
            20                  25                  30
```

-continued

```
Phe Tyr Asp Lys Ser Cys Pro Thr Val Leu Ser Val Val Lys Ala Gly
         35                  40                  45

Val Lys Gln Ala Val Ala Lys Glu Gln Arg Met Gly Ala Ser Leu Leu
 50                  55                  60

Arg Leu His Phe His Asp Cys Phe Val Asn Gly Cys Asp Gly Ser Val
 65                  70                  75                  80

Leu Leu Asp Asp Ser Ser Lys Ile Thr Gly Glu Lys Thr Ala Ile Pro
                 85                  90                  95

Asn Ala Asn Ser Ala Arg Gly Phe Asp Val Ile Asp Thr Ile Lys Ser
             100                 105                 110

Gln Val Glu Lys Ser Cys Ser Ala Val Val Ser Cys Ser Asp Ile Leu
         115                 120                 125

Ala Ile Ala Ala Arg Asp Ser Val Val Glu Leu Gly Gly Pro Ser
 130                 135                 140
```

<210> SEQ ID NO 402
<211> LENGTH: 1474
<212> TYPE: DNA
<213> ORGANISM: Pinus radiata

<400> SEQUENCE: 402

| | | | | | |
|---|---|---|---|---|---|
| gaattcggca | cgagaaaacg | tccatagctt | ccttgccaac | tgcaagcaat | acagtacaag | 60 |
| agccagacga | tcgaatcctg | tgaagtggtt | ctgaagtgat | gggaagcttg | gaatctgaaa | 120 |
| aaactgttac | aggatatgca | gctcgggact | ccagtggcca | cttgtcccct | tacacttaca | 180 |
| atctcagaaa | gaaaggacct | gaggatgtaa | ttgtaaaggt | catttactgc | ggaatctgcc | 240 |
| actctgattt | agttcaaatg | cgtaatgaaa | tggacatgtc | tcattaccca | atggtccctg | 300 |
| ggcatgaagt | ggtggggatt | gtaacagaga | ttggcagcga | ggtgaagaaa | ttcaaagtgg | 360 |
| gagagcatgt | aggggttggt | tgcattgttg | ggtcctgtcg | cagttgcggt | aattgcaatc | 420 |
| agagcatgga | acaatactgc | agcaagagga | tttggaccta | caatgatgtg | aaccatgacg | 480 |
| gcacacctac | tcaggggggga | tttgcaagca | gtatggtggt | tgatcagatg | tttgtggttc | 540 |
| gaatcccgga | gaatcttcct | ctggaacaag | cggcccctct | gttatgtgca | ggggttacag | 600 |
| ttttcagccc | aatgaagcat | ttcgccatga | cagagcccgg | gaagaaatgt | gggattttgg | 660 |
| gtttaggagg | cgtggggcac | atgggtgtca | agattgccaa | agcctttgga | ctccacgtga | 720 |
| cggttatcag | ttcgtctgat | aaaagaaag | aagaagccat | ggaagtcctc | ggcgccgatg | 780 |
| cttatcttgt | tagcaaggat | actgaaaaga | tgatggaagc | agcagagagc | ctagattaca | 840 |
| taatggacac | cattccagtt | gctcatcctc | tggaaccata | tcttgcccct | ctgaagacaa | 900 |
| atggaaagct | agtgatgctg | ggcgttgttc | cagagccgtt | gcacttcgtg | actcctctct | 960 |
| taatacttgg | gagaaggagc | atagctggaa | gtttcattgg | cagcatggag | gaaacacagg | 1020 |
| aaactctaga | tttctgtgca | gagaagaagg | tatcatcgat | gattgaggtt | gtgggcctgg | 1080 |
| actacatcaa | cacggccatg | gaaaggttgg | agaagaacga | tgtccgttac | agatttgtgg | 1140 |
| tggatgttgc | tagaagcaag | ttggataatt | agtctgcaat | caatcaatca | gatcaatgcc | 1200 |
| tgcatgcaag | atgaatagat | ctggactagt | agcttaacat | gaaagggaaa | ttaaatttt | 1260 |
| atttaggaac | tcgatactgg | ttttttgttac | tttagtttag | cttttgtgag | gttgaaacaa | 1320 |
| ttcagatgtt | tttttaactt | gtatatgtaa | agatcaattt | ctcgtgacag | taaataataa | 1380 |
| tccaatgtct | tctgccaaat | taatatatgt | attcgtattt | ttatatgaaa | aaaaaaaaa | 1440 |
| aaaaaaaaaa | aaaaaaaaaa | aaaaaaaaaa | aaaa | | | 1474 |

<210> SEQ ID NO 403
<211> LENGTH: 414
<212> TYPE: DNA
<213> ORGANISM: eucalyptus grandis

<400> SEQUENCE: 403

| | | | | | |
|---|---|---|---|---|---|
| cacgctcgac | gaattcggta | ccccgggttc | gaaatcgata | agcttggatc | caaagcaaca | 60 |
| cattgaactc | tctctctctc | tctctctctc | tctctctctc | tcccccaccc | cccttccca | 120 |
| accccaccca | catacagaca | agtagatacg | cgcacacaga | agaagaaaag | atgggggttt | 180 |
| caatgcagtc | aatcgcacta | gcgacggttc | tggccgtcct | aacgacatgg | gcgtggaggg | 240 |
| cggtgaactg | ggtgtggctg | aggccgaaga | ggctcgagag | gcttctgaga | cagcaaggtc | 300 |
| tctccggcaa | gtcctacacc | ttcctggtcg | gcgacctcaa | ggagaacctg | cggatgctca | 360 |
| aggaagccaa | gtccaagccc | atcgccgtct | ccgatgacat | caagcctcgt | ctct | 414 |

<210> SEQ ID NO 404
<211> LENGTH: 2013
<212> TYPE: DNA
<213> ORGANISM: Eucalyptus grandis

<400> SEQUENCE: 404

| | | | | | |
|---|---|---|---|---|---|
| agataagttg | cgcttaaatc | ctctccaaaa | gagctaatcc | atggatattt | tctatttcta | 60 |
| ttcccaactc | cagtctcttg | ttcaaactca | actccagcaa | tctcccatga | ccctcctcct | 120 |
| ctccgtcgtc | cctcttctcc | tcttcctcgg | gctcgtggct | cggctccggc | gcaagccgcc | 180 |
| cttcccaccg | ggcccgaggg | gcctcccggt | catcgggaac | atgctcatga | tgggcgagct | 240 |
| cacccaccgc | ggcctcgcga | gtctggcgaa | gaagtatggc | gggatcttcc | acctccgcat | 300 |
| gggcttcctg | cacatggttg | ccgtgtcgtc | ccccgacgtg | gcccgccagg | tcctccaggt | 360 |
| ccacgacggg | atcttctcga | accggcctgc | caccatcgcg | atcagctacc | tcacgtatga | 420 |
| ccgggccgac | atggccttcg | cgcactacgg | cccgttctgg | cggcagatgc | ggaagctgtg | 480 |
| cgtgatgaag | ctcttcagcc | ggaagcgggc | tgagtcgtgg | gagtcggtcc | gcgatgaggt | 540 |
| ggacacgatg | gtgcgcaccg | tcgcgggcag | cgaggggacc | gccgtgaaca | tcggcgagct | 600 |
| cgtgttcgag | ctcacgcggg | acatcatcta | ccgcgcggcc | ttcggcacga | gctcgaccga | 660 |
| gggccaggac | gagttcatca | gcatactgca | ggagttctcg | aaattatttg | gcgccttcaa | 720 |
| catagccgat | tttatcccgt | acctgagctg | gatcgatccg | caaggctca | ccgccaggct | 780 |
| tgtcaaggcg | cgccagtcgc | tggacgggtt | catcgaccac | attatagatg | atcacatgga | 840 |
| caagaagaga | aacaagacga | gttccggtgg | aggcgatcaa | gatgtcgata | ccgacatggt | 900 |
| cgacgatctg | ctggccttct | acagcgacga | agcgaaggtg | aacgagtccg | acgatttgca | 960 |
| gaactcgatc | aggctaacga | gagacaacat | caaggccatc | atcatggacg | tgatgttcgg | 1020 |
| cgggacggag | actgtggcgt | cggctatcga | gtgggccatg | gcggagctca | tgcgaagccc | 1080 |
| cgaggacctg | aagaaggtcc | agcaagaact | cgcggatgtc | gtgggcctag | accggagagt | 1140 |
| cgaggagagc | gacttcgaga | agctgaccta | tctcaagtgc | tgcctcaaag | agaccctccg | 1200 |
| cctccacccg | ccgatcccgc | tgctcctcca | cgagacggca | gaggacgccg | tgatctccgg | 1260 |
| ctaccgcatc | cccgcacggt | cccgggtcat | gatcaatgca | tgggcatcg | ggcgtgaccc | 1320 |
| cggctcgtgg | accgaacctg | acaagttcaa | accgtcccgg | ttcctggagt | caggcatgcc | 1380 |
| cgactacaag | gggagcaact | tcgagttcat | ccctttcggg | tcgggccgga | ggtcgtgccc | 1440 |
| agggatgcag | ctcgggctct | acgcgctcga | catggccgtg | gcccacctcc | tgcactgctt | 1500 |

-continued

```
cacgtgggaa ctgcccgacg ggatgaagcc gagcgagatg gacatgggcg acgtcttcgg   1560
gctcaccgcg ccgaggtcca cccggctcgt ggcggtgccg actccgaggt tggtggggc    1620 tctatattga gcaagcaaat ggagggtcgg gttggggggt gcgaggaggg gaacgtattt   1680
ttcagctcct ggagggctgc aagatttgga gtgcataaac ccatccatac aagggcaaaa   1740
gagggtggtg ccaaaatgat ttgcatggat ttttcgattt ttgttttgta ttataaaaaa   1800
ggtcaaataa ccgaagagga caagaaagac aagaaaaaga attgagacgg aacttgaatc   1860
aatgttgttc tgttctctct ttctatttct ttgtggatat tacaagactt atctcatttg   1920
gtgggctttt cttttcttgt gatttctttg atcttgtcat acacaaataa atatggaatg   1980 aagaaaacctt tccatcaaaa aaaaaaaaaa aaa                               2013
```

<210> SEQ ID NO 405
<211> LENGTH: 529
<212> TYPE: PRT
<213> ORGANISM: Eucalyptus grandis

<400> SEQUENCE: 405

```
Met Asp Ile Phe Tyr Phe Tyr Ser Gln Leu Gln Ser Leu Val Gln Thr
  1               5                  10                  15

Gln Leu Gln Gln Ser Pro Met Thr Leu Leu Ser Val Val Pro Leu
             20                  25                  30

Leu Leu Phe Leu Gly Leu Val Ala Arg Leu Arg Arg Lys Pro Pro Phe
         35                  40                  45

Pro Pro Gly Pro Arg Gly Leu Pro Val Ile Gly Asn Met Leu Met Met
     50                  55                  60

Gly Glu Leu Thr His Arg Gly Leu Ala Ser Leu Ala Lys Lys Tyr Gly
 65                  70                  75                  80

Gly Ile Phe His Leu Arg Met Gly Phe Leu His Met Val Ala Val Ser
                 85                  90                  95

Ser Pro Asp Val Ala Arg Gln Val Leu Gln Val His Asp Gly Ile Phe
            100                 105                 110

Ser Asn Arg Pro Ala Thr Ile Ala Ile Ser Tyr Leu Thr Tyr Asp Arg
        115                 120                 125

Ala Asp Met Ala Phe Ala His Tyr Gly Pro Phe Trp Arg Gln Met Arg
    130                 135                 140

Lys Leu Cys Val Met Lys Leu Phe Ser Arg Lys Ala Glu Ser Trp
145                 150                 155                 160

Glu Ser Val Arg Asp Glu Val Asp Thr Met Val Arg Thr Val Ala Gly
                165                 170                 175

Ser Glu Gly Thr Ala Val Asn Ile Gly Glu Leu Val Phe Glu Leu Thr
            180                 185                 190

Arg Asp Ile Ile Tyr Arg Ala Ala Phe Gly Thr Ser Ser Thr Glu Gly
        195                 200                 205

Gln Asp Glu Phe Ile Ser Ile Leu Gln Glu Phe Ser Lys Leu Phe Gly
    210                 215                 220

Ala Phe Asn Ile Ala Asp Phe Ile Pro Tyr Leu Ser Trp Ile Asp Pro
225                 230                 235                 240

Gln Gly Leu Thr Ala Arg Leu Val Lys Ala Arg Gln Ser Leu Asp Gly
                245                 250                 255

Phe Ile Asp His Ile Ile Asp Asp His Met Asp Lys Lys Arg Asn Lys
            260                 265                 270

Thr Ser Ser Gly Gly Gly Asp Gln Asp Val Asp Thr Asp Met Val Asp
```

```
                275                 280                 285
Asp Leu Leu Ala Phe Tyr Ser Asp Glu Ala Lys Val Asn Glu Ser Asp
    290                 295                 300

Asp Leu Gln Asn Ser Ile Arg Leu Thr Arg Asp Asn Ile Lys Ala Ile
305                 310                 315                 320

Ile Met Asp Val Met Phe Gly Gly Thr Glu Thr Val Ala Ser Ala Ile
                325                 330                 335

Glu Trp Ala Met Ala Glu Leu Met Arg Ser Pro Glu Asp Leu Lys Lys
            340                 345                 350

Val Gln Gln Glu Leu Ala Asp Val Val Gly Leu Asp Arg Arg Val Glu
        355                 360                 365

Glu Ser Asp Phe Glu Lys Leu Thr Tyr Leu Lys Cys Cys Leu Lys Glu
    370                 375                 380

Thr Leu Arg Leu His Pro Pro Ile Pro Leu Leu Leu His Glu Thr Ala
385                 390                 395                 400

Glu Asp Ala Val Ile Ser Gly Tyr Arg Ile Pro Ala Arg Ser Arg Val
                405                 410                 415

Met Ile Asn Ala Trp Ala Ile Gly Arg Asp Pro Gly Ser Trp Thr Glu
            420                 425                 430

Pro Asp Lys Phe Lys Pro Ser Arg Phe Leu Glu Ser Gly Met Pro Asp
        435                 440                 445

Tyr Lys Gly Ser Asn Phe Glu Phe Ile Pro Phe Gly Ser Gly Arg Arg
    450                 455                 460

Ser Cys Pro Gly Met Gln Leu Gly Leu Tyr Ala Leu Asp Met Ala Val
465                 470                 475                 480

Ala His Leu Leu His Cys Phe Thr Trp Glu Leu Pro Asp Gly Met Lys
                485                 490                 495

Pro Ser Glu Met Asp Met Gly Asp Val Phe Gly Leu Thr Ala Pro Arg
            500                 505                 510

Ser Thr Arg Leu Val Ala Val Pro Thr Pro Arg Leu Val Gly Ala Leu
        515                 520                 525

Tyr

<210> SEQ ID NO 406
<211> LENGTH: 2184
<212> TYPE: DNA
<213> ORGANISM: Pinus radiata

<400> SEQUENCE: 406
gtcgtctgta aattactctg tgagtgttta gtgttttctt ctcttattga tttcagggga      60
caagtaggtg ggggtggggg agcttaagtc aaatctagtg cttttctcgt aagattttcc     120
cttttttttc ttgctaagag tagccatgat tgaggtacag tcagctcccc ccatggcacg     180
gtccactgag aacgagaata accagcatga tgccgaagaa ggggcggtat tgaatgaggg     240
cggcatggat tttctgtatc ggtcaaagct tccagacata gatattccat accatcttcc     300
attgcactcg tattgcttcg agaaactgga cgagctcaga gagaagccat gtctgataca     360
ggggtcgaac gggaagattt acagctatgg cgaagtggaa ttgatatctc gcaaggtggc     420
ctcgggtttg gccaaattgg gattcaaaaa ggggacgtg gtcatgctgc tgctgcccaa     480
ttgccccgaa tttgtctttg ttttcctagg ggcgtccatg gctggtgcca ttgccaccac     540
ggcgaaccct ttttacactc cctccgatat tgccaaacag cggggcgcat cgggcgctcg     600
gctgattgtc acttacgctg cttgcgtaga aaagctgagg gacctaatgg agaatcatgg     660
```

```
ggtccaagtg ataaccatcg acaaccctcc aaagggctgc gaacacattt cacttttgtt      720
ggacggcgac gagaacgaat actgccctgc agactgtatc gtccagcccg acgacacggt      780
cgcgctgcct tattcatcgg gcacgacggg gctccccaag ggtgtcatgt tgacacacaa      840
ggggctcgtc tctagcgtcg cccaacaagt cgatggagaa atcccaatc tgtatttgca       900
ttctgaggat gtggtgctct gcgtactgcc tctgtttcat atctactcgc tcaattctgt      960
gctgctctgc tcgctcaggg ccgggtctgc tattctgctc atgcacaagt ttgagatcgg     1020
gagcctgctg gatctggtgc agaggttcaa ggtcacggta gcgcctgtcg tgcctcccat     1080
tgttctcgcc tttgccaaga acgcgctcgt ggaaagctat gatctgtcgt ccattagggt     1140
tgtgctgtcc ggtgccgcgc ctctcggaaa ggagctggag gatgcattga ggctacgact     1200
tcccaaagcc acttttggtc agggatacgg tatgacagag gcaggaccgg tgctatcaat     1260
gtgtctggcc ttcgctaagg agcccttttcc gatgaagtcc gggtcgtgtg aacggttgt     1320
tcggaatgcc cagatgaaga tcattgaccc cgacacgggc acgtgtcttc cctacaacca     1380
acctggagaa atttgcatca gagggcccca gattatgaaa gggtatctga cgatgctga     1440
gtctacagcc agaactatcg atgaagatgg gtggctgcat actggggata ttggttatat     1500
tgatgacgat gaagaagttt tcattgtgga cagagtgaaa gagattatca aatataaggg     1560
tttttcaggta cctccagctg agttagaagc cattctcatc actcatccat ctattgcaga     1620
tgcagcagtt gtacctcaaa aggatgaagt tgcaggagag gttccagtag cctttgtggt     1680
gagatcaaat ggatttgatc ttacagaaga tgaaatcaaa caatttgtgg ctaaacaggt     1740
ggtgttctac aaaaagctgc acaaggtcta tttcatccac gcaattccca gtctccttc     1800
tggaaaaata ctgcgaaagg atttgagggc gaagctctct gcccccacct ccaccgttga     1860
aatcaaagca tgatattctt ttctctaatc gatttgatca cttcaaccag aatttgtggg     1920
catgccatag acgcatgagg gcggccaata cctgtcactc caataatgtc accgctttct     1980
ggactccttt ttcgagatat atttatggat tcctgcttct ctgtaagggt ggcatgatta     2040
ttaagagtaa ttaggataga gagaaagcca ttgaatagtg tgccatattt ctgattcaca     2100
tcgcttcttt catggtctcc tttacagtta gttgtaagtt tctccacctc cattgcgttt     2160
ggttgttacg tggattatgt gttt                                            2184
```

<210> SEQ ID NO 407
<211> LENGTH: 575
<212> TYPE: PRT
<213> ORGANISM: Pinus radiata

<400> SEQUENCE: 407

```
Met Ile Glu Val Gln Ser Ala Pro Pro Met Ala Arg Ser Thr Glu Asn
 1               5                  10                  15

Glu Asn Asn Gln His Asp Ala Glu Gly Ala Val Leu Asn Glu Gly
            20                  25                  30

Gly Met Asp Phe Leu Tyr Arg Ser Lys Leu Pro Asp Ile Asp Ile Pro
        35                  40                  45

Tyr His Leu Pro Leu His Ser Tyr Cys Phe Glu Lys Leu Asp Glu Leu
    50                  55                  60

Arg Glu Lys Pro Cys Leu Ile Gln Gly Ser Asn Gly Lys Ile Tyr Ser
65                  70                  75                  80

Tyr Gly Glu Val Glu Leu Ile Ser Arg Lys Val Ala Ser Gly Leu Ala
                85                  90                  95

Lys Leu Gly Phe Lys Lys Gly Asp Val Val Met Leu Leu Leu Pro Asn
```

```
            100                 105                 110
Cys Pro Glu Phe Val Phe Val Phe Leu Gly Ala Ser Met Ala Gly Ala
        115                 120                 125

Ile Ala Thr Thr Ala Asn Pro Phe Tyr Thr Pro Ser Asp Ile Ala Lys
        130                 135                 140

Gln Arg Gly Ala Ser Gly Ala Arg Leu Ile Val Thr Tyr Ala Ala Cys
145                 150                 155                 160

Val Glu Lys Leu Arg Asp Leu Met Glu Asn His Gly Val Gln Val Ile
                165                 170                 175

Thr Ile Asp Asn Pro Pro Lys Gly Cys Glu His Ile Ser Leu Leu Leu
            180                 185                 190

Asp Gly Asp Glu Asn Glu Tyr Cys Pro Ala Asp Cys Ile Val Gln Pro
        195                 200                 205

Asp Asp Thr Val Ala Leu Pro Tyr Ser Ser Gly Thr Thr Gly Leu Pro
        210                 215                 220

Lys Gly Val Met Leu Thr His Lys Gly Leu Val Ser Ser Val Ala Gln
225                 230                 235                 240

Gln Val Asp Gly Glu Asn Pro Asn Leu Tyr Leu His Ser Glu Asp Val
                245                 250                 255

Val Leu Cys Val Leu Pro Leu Phe His Ile Tyr Ser Leu Asn Ser Val
            260                 265                 270

Leu Leu Cys Ser Leu Arg Ala Gly Ser Ala Ile Leu Leu Met His Lys
            275                 280                 285

Phe Glu Ile Gly Ser Leu Leu Asp Leu Val Gln Arg Phe Lys Val Thr
        290                 295                 300

Val Ala Pro Val Val Pro Pro Ile Val Leu Ala Phe Ala Lys Asn Ala
305                 310                 315                 320

Leu Val Glu Ser Tyr Asp Leu Ser Ser Ile Arg Val Val Leu Ser Gly
                325                 330                 335

Ala Ala Pro Leu Gly Lys Glu Leu Glu Asp Ala Leu Arg Leu Arg Leu
            340                 345                 350

Pro Lys Ala Thr Phe Gly Gln Gly Tyr Gly Met Thr Glu Ala Gly Pro
        355                 360                 365

Val Leu Ser Met Cys Leu Ala Phe Ala Lys Glu Pro Phe Pro Met Lys
370                 375                 380

Ser Gly Ser Cys Gly Thr Val Val Arg Asn Ala Gln Met Lys Ile Ile
385                 390                 395                 400

Asp Pro Asp Thr Gly Thr Cys Leu Pro Tyr Asn Gln Pro Gly Glu Ile
                405                 410                 415

Cys Ile Arg Gly Pro Gln Ile Met Lys Gly Tyr Leu Asn Asp Ala Glu
            420                 425                 430

Ser Thr Ala Arg Thr Ile Asp Glu Asp Gly Trp Leu His Thr Gly Asp
        435                 440                 445

Ile Gly Tyr Ile Asp Asp Glu Glu Val Phe Ile Val Asp Arg Val
        450                 455                 460

Lys Glu Ile Ile Lys Tyr Lys Gly Phe Gln Val Pro Pro Ala Glu Leu
465                 470                 475                 480

Glu Ala Ile Leu Ile Thr His Pro Ser Ile Ala Asp Ala Ala Val Val
                485                 490                 495

Pro Gln Lys Asp Glu Val Ala Gly Glu Val Pro Val Ala Phe Val Val
            500                 505                 510

Arg Ser Asn Gly Phe Asp Leu Thr Glu Asp Glu Ile Lys Gln Phe Val
            515                 520                 525
```

```
                             -continued

Ala Lys Gln Val Val Phe Tyr Lys Lys Leu His Lys Val Tyr Phe Ile
    530                 535             540
His Ala Ile Pro Lys Ser Pro Ser Gly Lys Ile Leu Arg Lys Asp Leu
545                 550                 555                 560
Arg Ala Lys Leu Ser Ala Pro Thr Ser Thr Val Glu Ile Lys Ala
                565             570                 575
```

MATERIALS AND METHODS FOR THE MODIFICATION OF PLANT LIGNIN CONTENT

CROSS-REFERENCE TO RELATED APPLICATIONS

This application is a continuation-in-part of U.S. application Ser. No. 09/615,192, filed Jul. 12, 2000, now U.S. Pat. No. 6,410,718, which claims priority from U.S. Application No. 60/143,833, filed Jul. 14, 1999 and is a continuation-in-part of U.S. application Ser. No. 09/169,789, filed Oct. 9, 1998, now U.S. Pat. No. 6,653,528, which is a continuation-in-part of U.S. patent application Ser. No. 08/975,316, filed Nov. 21, 1997, now U.S. Pat. No. 5,952,486, which is a continuation-in-part of U.S. patent application Ser. No. 08/713,000, filed Sep. 11, 1996, now U.S. Pat. No. 5,850,020.

REFERENCE TO SEQUENCE LISTING SUBMITTED ON COMPACT DISC

This application incorporates by reference in its entirety the Sequence Listing contained in the accompanying two compact discs, one of which is a duplicate copy. Each CD contains a single file, Name "1003c5 SEQLIST.txt", the size of which is 436 KB, and which was created on Jun. 18, 2002, in IBM-PC MS-Windows format pursuant to 37 CFR 1.52 (e).

TECHNICAL FIELD OF THE INVENTION

This invention relates to polynucleotides, including partial and extended sequences as well as probes and primers, constructs comprising the polynucleotides, biological materials (including plants, microorganisms and multicellular organisms) incorporating the polynucleotides, polypeptides encoded by the polynucleotides, and methods for using the polynucleotides and polypeptides. The invention relates, more particularly, to the modification of lignin content and composition in biological materials including plants, to polypeptides involved in the lignin biosynthetic pathway, and to polynucleotides encoding such enzymes.

BACKGROUND OF THE INVENTION

Lignin is an insoluble polymer that is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols that are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT Publication No. WO 94/23044. Furthermore, it has been shown that antisense expression of sequences encoding CAD in poplar leads to the production of lignin having a modified composition (Grand C et al., *Planta (Berl.)* 163:232–237, 1985).

While polynucleotides encoding some of the enzymes involved in the lignin biosynthetic pathway have been isolated for certain species of plants, genes encoding many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated polynucleotides identified in the attached Sequence Listing as SEQ ID NOS: 1–266, 350–375, 404 and 406, variants of those sequences, genetic constructs comprising such sequences, extended sequences comprising the sequences of SEQ ID NOS: 1–266, 350–375, 404 and 406, and their variants, probes and primers corresponding to the sequences set out in SEQ ID NOS: 1–266, 350–375, 404, 406 and their variants, and polynucleotides comprising at least a specified number of contiguous residues of any of the polynucleotides identified as SEQ ID NOS: 1–266, 350–375, 404 and 406 (x-mers), all of which are referred to herein, collectively, as "polynucleotides of the present invention." Polynucleotides of the present invention are preferably obtainable from *eucalyptus* and pine species, and preferably comprise open reading frames or partial open reading frames encoding enzymes, or functional portions of enzymes, involved in the lignin biosynthetic pathway. Genetic constructs incorporating such polynucleotides, methods for using such polynucleotides and genetic constructs, and biological materials, including plant cells and plants having an altered genomic and/or lignin content and composition are provided. The present invention also provides isolated polypeptide sequences identified in the attached Sequence Listing as SEQ ID NOS: 267–349, 376–401, 405 and 407; polypeptide variants of those sequences; and polypeptides comprising the inventive polypeptide sequences and variants of those sequences.

In one aspect, the present invention provides isolated polynucleotides encoding the following enzymes, or portions of the following enzymes: cinnamate 4-hydroxylase (C4H), coumarate 3-hydroxylase (C3H), phenolase (PNL), O-methyl transferase (OMT), cinnamyl alcohol dehydrogenase (CAD), cinnamoyl-CoA reductase (CCR), phenylalanine ammonia-lyase (PAL), 4-coumarate: CoA ligase (4CL), coniferol glucosyl transferase (CGT), coniferin beta-glucosidase (CBG), laccase (LAC), peroxidase (POX), ferulate-5-hydroxylase (F5H), alpha amylase, caffeic acid methyl transferase, caffeoyl CoA methyl transferase, coumerate 6A ligase, cytochrome P450 LXX1A, diphenol oxidase, flavonol glucosyl transferase, flavonoid hydroxylase, and isoflavone reductase.

In one embodiment, polynucleotides of the present invention encompass polynucleotides comprising a nucleotide sequence selected from the group consisting of: (a) polynucleotides recited in SEQ ID NOS: 1–266, 350–375, 404 and 406; (b) complements of the polynucleotides recited in SEQ ID NOS: 1–266, 350–375, 404 and 406; (c) reverse complements of the sequences recited in SEQ ID NOS: 1–266, 350–375, 404 and 406; (d) reverse sequences of the sequences recited in SEQ ID NOS: 1–266, 350–375, 404 and 406; and (e) variants of the polynucleotides recited in SEQ ID NOS: 1–266, 350–375, 404 and 406. In another embodiment of the present invention, the inventive polynucleotides comprise at least a specified number of contiguous residues (x-mers) of any of the polynucleotides of SEQ ID NOS: 1–266, 350–375, 404 and 406. In yet another aspect, the inventive polynucleotides comprise probes and primers corresponding to any of the polynucleotides of SEQ ID NOS: 1–266, 350–375, 404 and 406.

In a further aspect, the present invention provides genetic constructs comprising a polynucleotide of the present invention, either alone or in combination with one or more of the inventive sequences, or in combination with one or more known polynucleotides; together with host cells and transgenic cells comprising such constructs.

In a related aspect, the present invention provides genetic constructs comprising, in the 5'-3' direction, a gene promoter sequence; an open reading frame coding for at least a functional portion of an enzyme encoded by a polynucleotide of the present invention; and a gene termination sequence. An open reading frame may be orientated in either a sense or antisense direction. Genetic constructs comprising a non-coding region of a gene coding for an enzyme encoded by the above polynucleotides or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. In a preferred embodiment, the gene promoter sequence provides for transcription in xylem. The construct may further include a marker for the identification of transformed cells.

In a further aspect, transgenic cells, such as transgenic plant cells, comprising the genetic constructs of the present invention are provided, together with plants comprising such transgenic cells, and fruits and seeds of such plants.

In yet another aspect, methods for modulating the lignin content and composition of a target organism such as a plant are provided, such methods including stably incorporating into the genome of the target plant a genetic construct comprising a polynucleotide of the present invention. In a preferred embodiment, the target plant is a woody plant, preferably selected from the group consisting of *eucalyptus* and pine species, most preferably from the group consisting of *Eucalyptus grandis* and *Pinus radiata*. In a related aspect, a method for producing a plant having altered lignin content is provided, the method comprising transforming a plant cell with a genetic construct comprising a polynucleotide of the present invention to provide a transgenic cell, and cultivating the transgenic cell under conditions conducive to regeneration and mature plant growth.

In yet a further aspect, the present invention provides methods for modifying the activity of an enzyme in a target organism such as a plant, comprising stably incorporating into the genome of the target organism a genetic construct of the present invention. In a preferred embodiment, the target plant is a woody plant, preferably selected from the group consisting of *eucalyptus* and pine species, most preferably from the group consisting of *Eucalyptus grandis* and *Pinus radiata*.

The present invention also provides polypeptides encoded by the inventive polynucleotides. In certain specific embodiments, such polypeptides comprise a sequence selected from the group consisting of: SEQ ID NOS: 267–349, 376–401, 405 and 407, and variants of those sequences.

BRIEF DESCRIPTION OF THE FIGURES

The above-mentioned and additional features of the present invention and the manner of obtaining them will become apparent, and the invention will be best understood by reference to the following more detailed description, read in conjunction with the accompanying drawing.

DETAILED DESCRIPTION

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies among different plant species and within species. In addition, the composition of lignin may also vary among different tissues within a specific plant. The three monolignols are derived from phenylalanine in a multistep process and are believed to be polymerized into lignin by a free radical mechanism.

Figure 1:
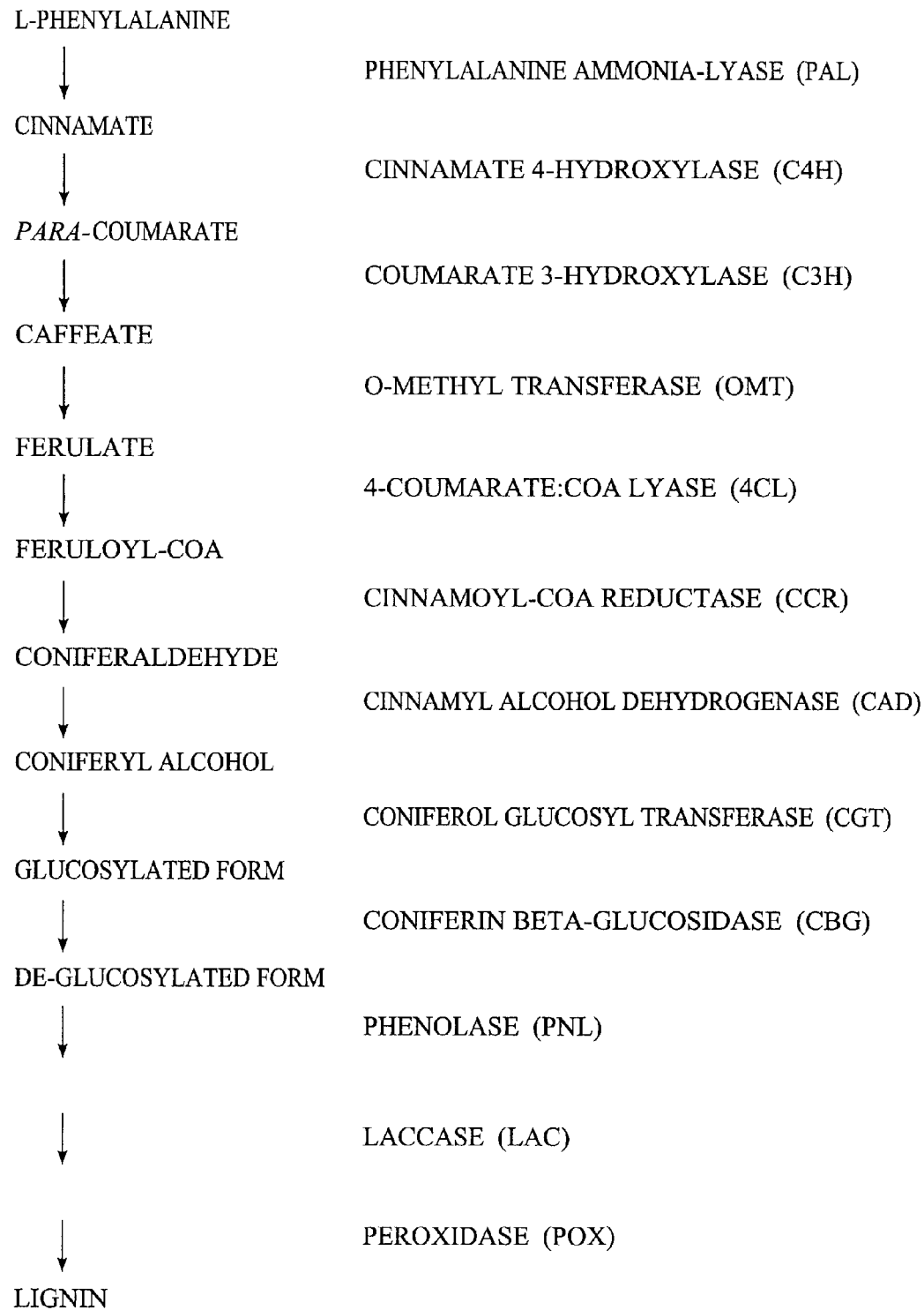
FIG. 1 is a schematic overview of the lignin biosynthetic pathway.

FIG. 1 shows different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX).

The formation of sinapyl alcohol involves an additional enzyme, ferulate-5-hydroxylase (F5H). For a more detailed review of the lignin biosynthetic pathway, see Whetton R and Sederoff R, *The Plant Cell*, 7:1001–1013, 1995.

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H, 4CL and other enzymes involved in the lignin biosynthetic pathway may affect the synthesis of other plant products in addition to lignin.

Using the methods and materials of the present invention, the lignin content of a plant may be modulated by modulating expression of polynucleotides of the present invention, or by modifying the polypeptides encoded by polynucleotides or the polynucleotides. The lignin content of a target organism, such as a plant, may be modified, for example, by incorporating additional copies of genes encoding enzymes involved in the lignin biosynthetic pathway into the genome of the target plant. Similarly, a modified lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in applications of wood processing for paper, and may also be effective in altering the palatability of wood materials to rotting fungi.

In a first aspect, the present invention provides isolated polynucleotide sequences identified in the attached Sequence Listing as SEQ ID NOS: 1–266, 350–375, 404 and 406, variants of those sequences, extended sequences comprising the sequences set out in SEQ ID NOS: 1–266, 350–375, 404 and 406, and their variants, probes and primers corresponding to the sequences set out in SEQ ID NOS: 1–266, 350–375, 404 and 406, and their variants, polynucleotides comprising at least a specified number of contiguous residues of any of the polynucleotides identified as SEQ ID NOS: 1–266, 350–375, 404 and 406 (x-mers), and extended sequences comprising portions of the sequences set out in SEQ ID NOS: 1–266, 350–375, 404 and 406, all of which are referred to herein, collectively, as "polynucleotides of the present invention." The present invention also provides isolated polypeptide sequences identified in the attached Sequence Listing as SEQ ID NOS: 267–349, 376–401, 405 and 407, polypeptide variants of those sequences, and polypeptides comprising the isolated polypeptide sequences and variants of those sequences.

The polynucleotides disclosed herein were derived from forestry plant sources, namely from *Eucalyptus grandis* and *Pinus radiata*. Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NOS: 1–266, 350–375, 404 and 406, or a variant thereof, or a portion of one of the sequences of SEQ ID NOS: 1–266, 350–375, 404 and 406, or a variant thereof, when the extended polynucleotide comprises an identified sequence or its variant, or an identified contiguous portion (x-mer) of one of the sequences of SEQ ID NOS: 1–266, 350–375, 404 and 406, or a variant thereof. Similarly, RNA sequences, reverse sequences, complementary sequences, antisense sequences, and the like, corresponding to the polynucleotides of the present invention, may be routinely ascertained and obtained using the cDNA sequences identified as SEQ ID NOS: 1–266, 350–375, 404 and 406.

The polynucleotides identified as SEQ ID NOS: 1–266, 350–375, 404 and 406 contain open reading frames ("ORFs") or partial open reading frames encoding polypeptides and functional portions of polypeptides. Additionally, open reading frames encoding polypeptides may be identified in extended or full length sequences corresponding to the sequences set out as SEQ ID NOS: 1–266, 350–375, 404 and 406. Open reading frames may be identified using techniques that are well known in the art. These techniques include, for example, analysis for the location of known start and stop codons, most likely reading frame identification based on codon frequencies, etc. . Tools and software for ORF analysis, include, for example, GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tennessee Tenn. Open reading frames and portions of open reading frames are present and may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The present invention also contemplates methods for modulating the polynucleotide and/or polypeptide content and composition of a forestry species, such methods involving stably incorporating into the genome of the organism a genetic construct comprising one or more polynucleotides of the present invention. In one embodiment, the target organism is a forestry species, preferably a woody plant, more preferably a woody plant of the *Pinus* or *Eucalyptus* species, and most preferably *Eucalyptus grandis* or *Pinus radiata*. In a related aspect, a method for producing a forestry plant having an altered genotype or phenotype is provided, the method comprising transforming a plant cell with a genetic construct of the present invention to provide a transgenic cell, and cultivating the transgenic cell under conditions conducive to regeneration and mature plant growth. Forestry plants having an altered genotype or phenotype as a consequence of modulation of the level or content of a polynucleotide or polypeptide of the present invention compared to a wild-type organism, as well as components (seeds, etc.) of such forestry plants, and the progeny of such forestry plants, are contemplated by and encompassed within the present invention.

The isolated polynucleotides of the present invention also have utility in genome mapping, in physical mapping, and in positional cloning of genes. Additionally, the polynucleotide sequences identified as SEQ ID NOS: 1–266, 350–375, 404 and 406, and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology used by Synteni (Palo Alto, Calif.).

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides of the present invention and the polynucleotides encoding the polypeptides have activity in lignin biosynthetic pathways in plants. The polynucleotides were identified by DNA and polypeptide similarity searches. The polynucleotides and polypeptides of the present invention have demonstrated similarity to the following polypeptides that are known to be involved in lignin biosynthetic processes:

TABLE 1

| POLYPEPTIDE IDENTITY | POLYNUCLEOTIDE SEQ ID NO. | POLYPEPTIDE SEQ ID NO. |
|---|---|---|
| Cinnamate 4-hydroxylase (C4H) | 2, 3, 17, 48, 49, 92, 124, 125, 153–163 | |
| Coumarate 3-hydroxylase (C3H) | 4, 18, 50–52, 93, 101, 126, 127, 149–152 | |
| Phenolase (PNL) | 5, 35, 36, 81, 116, 183 | |
| O-methyl transferase (OMT) | 6, 22–25, 53–55, 94, 104–107, 173–175 | |
| Cinnamyl alcohol dehydrogenase (CAD) | 1, 7, 30, 71, 95, 112, 164 | |
| Cinnamoyl-CoA reductase (CCR) | 8, 26–29, 58–70, 96, 108–111, 128–134, 167 | |

TABLE 1-continued

| POLYPEPTIDE IDENTITY | POLYNUCLEOTIDE SEQ ID NO. | POLYPEPTIDE SEQ ID NO. |
|---|---|---|
| Phenylalanine ammonia-lyase (PAL) | 9–11, 16, 45–47, 97, 98, 100, 122, 123, 176 242–248 | 325–331 |
| 4-coumarate:CoA ligase (4CL) | 2, 56–57, 90, 147, 158, 196–200, 265, 266, 406 | 279–283, 348, 349, 407 |
| Coniferol glucosyl transferase (CGT) | 31–33, 72, 113–115, 135, 168 | |
| Coniferin beta-glucosidase (CBG) | 34, 73–80, 136–141, 165, 166 | |
| Laccase (LAC) | 37–41, 82–84, 117, 118, 142–144, 172 | |
| Peroxidase (POX) | 13, 42–44, 85–89, 91, 119–121, 145, 146, 177–182, 249–250, 264, 350–375 | 332–333 347, 376–401 |
| Ferulate-5-hydroxylase (F5H) | 19–21, 102, 103, 169–171, 404 | 405 |
| Alpha amylase | 184–186 | 267–269 |
| Caffeic acid methyl transferase | 187–192 | 270–275 |
| Caffeoyl CoA methyl transferase | 193–195 | 276–278 |
| Cytochrome P450 LXXIA | 201–206 | 284–289 |
| Diphenol oxidase | 207–217 251–263 | 290–300 334–346 |
| Flavonol glucosyl transferase | 218 | 301 |
| Flavonoid hydroxylase | 219–233 | 302–316 |
| Isoflavone reductase | 234–241 | 317–324 |

In one embodiment, isolated polynucleotides of the present invention comprise a sequence selected from the group consisting of: (a) sequences recited in SEQ ID NOS: 1–266, 350–375, 404 and 406; (b) complements of the sequences recited in SEQ ID NOS: 1–266, 350–375, 404 and 406; (c) reverse complements of the sequences recited in SEQ ID NOS: 1–266, 350–375, 404 and 406; (d) reverse sequences of the sequences recited in SEQ ID NOS: 1–266, 350–375, 404 and 406; and (e) sequences having at least 50%, 75%, 90%, 95% or 98% identity, as defined herein, to a sequence of (a)–(d) or a specified region of a sequence of (a)–(d).

In a further aspect, isolated polypeptides encoded by the polynucleotides of the present invention are provided. In one embodiment, such polypeptides comprise an amino acid sequence recited in SEQ ID NOS: 267–349, 376–401, 405 and 407, and variants thereof, as well as polypeptides expressed by polynucleotides of the present invention, including polynucleotides comprising a sequence of SEQ ID NOS: 1–266, 350–375, 404 and 406.

In another aspect, the invention provides genetic constructs comprising a polynucleotide of the present invention, either alone, in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a gene promoter sequence, an open reading frame coding for at least a functional portion of a polypeptide encoded by a polynucleotide of the present invention, and a gene termination sequence. The open reading frame may be oriented in either a sense or antisense direction. Genetic constructs comprising a gene promoter sequence, a polynucleotide of the present invention, and a gene termination sequence are also contemplated, as are genetic constructs comprising a gene promoter sequence, an untranslated region of a polynucleotide of the present invention, or a nucleotide sequence complementary to an untranslated region, and a gene termination sequence. The genetic construct may further include a marker for the identification of transformed cells.

The gene promoter and termination sequences are preferably functional in a host plant and, most preferably, are those native to the host plant. Promoter and termination sequences that are generally used in the art, such as the Cauliflower Mosaic Virus (CMV) promoter, with or without enhancers such as the Kozak sequence or Omega enhancer, and *Agrobacterium tumefaciens* nopaline synthase terminator, are useful. Tissue-specific promoters may be employed in order to target expression to one or more desired tissues.

In a further aspect, methods for producing forestry plants having a modified content of a polynucleotide or polypeptide of the present invention compared to a native organism are provided. The methods involve transforming a target forestry plant with a genetic construct of the present invention to provide a transgenic cell, and cultivating the transgenic cell under conditions conducive to regeneration and mature plant growth. Cells comprising the genetic constructs of the present invention are provided, together with tissues and forestry plants comprising such transgenic cells, and fruits, seeds and other products, derivatives, or progeny of such forestry plants.

The word "polynucleotide(s)," as used herein, means a polymeric collection of nucleotides and includes DNA and corresponding RNA molecules and both single and double stranded molecules, including HnRNA and mRNA molecules, sense and anti-sense strands of DNA and RNA molecules, and cDNA, genomic DNA, and wholly or partially synthesized polynucleotides. An HnRNA molecule contains introns and "corresponds to" a DNA molecule in a generally one-to-one manner. An mRNA molecule "corresponds to" an HnRNA and DNA molecule from which the introns have been excised. A polynucleotide of the present invention may be an entire gene, or any portion thereof. A gene is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., "Antisense techniques," *Methods in Enzymol.* 254(23):363–375, 1995; and Kawasaki et al., *Artific. Organs* 20(8):836–848, 1996.

Complements of such isolated polynucleotides, reverse complements of such isolated polynucleotides, and reverse sequences of such isolated polynucleotides, together with variants of such sequences, are also provided. The definition of the terms "complement", "reverse complement" and "reverse sequence", as used herein, is best illustrated by the following example. For the sequence 5' AGGACC 3', the complement, reverse complement and reverse sequence are as follows:

| | |
|---|---|
| complement | 3' TCCTGG 5' |
| reverse complement | 3' GGTCCT 5' |
| reverse sequence | 5' CCAGGA 3'. |

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesis methods. All of the polynucleotides described herein are isolated and purified, as those terms are commonly used in the art.

In another aspect, the present invention provides isolated polypeptides encoded, or partially encoded, by the above polynucleotides. As used herein, the term "polypeptide" encompasses amino acid chains of any length, including full length proteins, wherein the amino acid residues are linked by covalent peptide bonds. The term "polypeptide encoded by a polynucleotide" as used herein, includes polypeptides encoded by a polynucleotide which comprises an isolated DNA sequence or variant provided herein. In specific embodiments, the inventive polypeptides comprise an amino acid sequence selected from the group consisting of sequences provided in SEQ ID NOS: 267–349, 376–401, 405 and 407, as well as variants of such sequences.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NOS:267–349, 376–401, 405 and 407, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

A functional portion comprising an active site may be made up of separate portions present on one or more polypeptide chains and generally exhibits high substrate specificity. The term "polypeptide encoded by a polynucleotide" as used herein, includes polypeptides encoded by a polynucleotide comprising a partial isolated polynucleotide of the present invention.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85: 2149–2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagensis (Kunkel, T., *Proc. Natl. Acad. Sci. USA* 82: 488–492, 1985). Sections of DNA sequences may also be removed using standard techniques to permit preparation of truncated polypeptides.

In general, the polypeptides disclosed herein are prepared in an isolated, substantially pure form. Preferably, the polypeptides are at least about 80% pure; more preferably at least about 90% pure; and most preferably, at least about 99% pure.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90%, 95% or 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN, BLASTX and BLASTP programs are available on the NCBI anonymous FTP server and from the National Center for Biotechnology Information (NCBI) National Library of Medicine, Building 38A, Room $8N_{805}$, Bethesda, Md. 20894 USA. The BLASTN algorithm Version 2.0.4 [Feb. 24, 1998] and Version 2.0.6 [Sep. 16, 1998], set to the default parameters described in the documentation and distributed with the algorithm, are preferred for use in the determination of polynucleotide variants according to the present invention. The BLASTP algorithm, set to the default parameters described in the documentation and distributed with the program, is preferred for use in the determination of polypeptide variants according to the present invention. The use of the BLAST family of algorithms, including BLASTN, BLASTP, and BLASTX, is described at NCBI's website and in the publication of Altschul Stephen F, et al., "Gapped BLAST and PSI-BLAST: a new generation of protein database search programs," *Nucleic Acids Res.* 25: 3389–3402, 1997.

The computer algorithm FASTA is available on the Internet and from the University of Virginia by contacting David Hudson, Assistant Provost for Research, University of Virginia, PO Box 9025, Charlottesville, Va. 22906-9025 USA. FASTA Version 2.0.4, February 1996, set to the default parameters described in the documentation and distributed with the algorithm, may be used in the determination of variants according to the present invention. The use of the FASTA algorithm is described in Pearson W R and Lipman D J, "Improved Tools for Biological Sequence Analysis," *Proc. Natl. Acad. Sci. USA* 85: 2444–2448, 1988; and Pearson W R, "Rapid and Sensitive Sequence Comparison with FASTP and FASTA," *Methods in Enzymology* 183: 63–98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o BLAST report Output File [File Out] Optional. The following running parameters are preferred for determination of alignments and similarities using BLASTP that contribute to the E values and percentage identity of polypeptide sequences: blastall -p blastp -d swissprotdb -e 10 -G0 -E0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional. The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA, and BLASTP algorithms also produce "Expect" (E) values for alignments. The Expect value (E) indicates the number of hits one can "expect" to see over a certain number of contiguous sequences by chance when searching a database of a certain size.

The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides or polypeptides of the present invention comprise a sequence exhibiting at least 50%; more preferably at least 75%; more preferably yet at least 90%; and most preferably at least 98% similarity to a polynucleotide or polypeptide of the present invention, determined as described below. Polynucleotides and polypeptides having a specified percentage similarity to a polynucleotide or polypeptide specified in one of the SEQ ID NOS. thus share a high degree of similarity in their primary structure. In addition to a specified percentage similarity to a polynucleotide of the present invention, variant polynucleotides and polypeptides preferably have additional structural and/or functional features in common with a polynucleotide of the present invention.

Polynucleotides having a specified degree of identity to, or capable of hybridizing to, a polynucleotide of the present invention preferably additionally have at least one of the following features: (1) they contain an open reading frame or partial open reading frame encoding a polypeptide, or a functional portion of a polypeptide, having substantially the same functional properties as the polypeptide, or functional portion thereof, encoded by a polynucleotide in a recited SEQ ID NO.; or (2) they contain identifiable domains in common. Similarly, polypeptides, or functional portions of polypeptides, having a specified degree of identity to a polypeptide of the present invention shares a high degree of identity in their primary structure and have substantially similar functional properties.

As noted above, the percentage identity is determined by aligning sequences using one of the BLASTN, FASTA, or BLASTP algorithms, set at the running parameters described above, and identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm using the parameters described above. The 23 nucleotide hit includes 21 identical nucleotides, one gap and one different nucleotide. The percentage identity of the polynucleotide of the present invention to the hit in the EMBL library is thus $21/220$ times 100, or 9.5%. The polynucleotide sequence in the EMBL database is thus not a variant of a polynucleotide of the present invention.

Alternatively, variant polynucleotides of the present invention hybridize to the polynucleotide sequences recited in SEQ ID NOS: 1–266, 350–375, 404 and 406, or complements, reverse sequences, or reverse complements of those sequences, under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NOS: 1–266, 350–375, 404 and 406, or complements, reverse sequences, or reverse complements of those sequences as a result of conservative substitutions are contemplated by and encompassed within the present invention.

Additionally. polynucleotides comprising sequences that differ from the polynucleotide sequences recited in SEQ ID NOS: 1–266, 350–375, 404 and 406, or complements, reverse complements, or reverse sequences as a result of deletions and/or insertions totaling less than 10% of the total sequence length are also contemplated by and encompassed within the present invention. Similarly, polypeptides comprising sequences that differ from the polypeptide sequences recited in SEQ ID NOS: 267–349, 376–401, 405 and 407 as a result of amino acid substitutions, insertions, and/or deletions totaling less than 10% of the total sequence length are contemplated by and encompassed within the present invention, provided the variant polypeptide has activity in a lignin biosynthetic pathway.

The polynucleotides of the present invention, including variants, may be isolated from various libraries assembled from plant or non-plant organisms, or may be synthesized using techniques that are well known in the art. Polynucleotides of the present invention may be isolated by high throughput sequencing of cDNA libraries prepared from *Eucalyptus grandis* and *Pinus radiata* as described below in Examples 1 and 2. Alternatively, oligonucleotide probes based on the sequences provided in SEQ ID NO: 1–266, 350–375, 404 and 406 may be synthesized and used to identify positive clones in either cDNA or genomic DNA libraries from *Eucalyptus grandis* and *Pinus radiata* by means of hybridization or PCR techniques. Probes may be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

Variants of the polynucleotides of the present invention derived from other *eucalyptus* and pine species, as well as from other commercially important species utilized by the lumber industry, are contemplated. These include the following gymnosperms, by way of example: loblolly pine *Pinus taeda*, slash pine *Pinus elliotti*, sand pine *Pinus clausa*, longleaf pine *Pinus palustrus*, shortleaf pine *Pinus echinata*, ponderosa pine *Pinus ponderosa*, Jeffrey pine *Pinus jeffrey*, red pine *Pinus resinosa*, pitch pine *Pinus rigida*, jack pine *Pinus hanksiana*, pond pine *Pinus serotina*, Eastern white pine *Pinus strobus*, Western white pine *Pinus monticola*, sugar pine *Pinus lambertiana*, Virginia pine *Pinus virginiana*, lodgepole pine *Pinus contorta*, Caribbean pine *Pinus caribaea*, *P. pinaster*, Calabrian pine *P. brutia*, Afghan pine *P. eldarica*, Coulter pine *P. coulteri*, European pine *P. nigra* and *P. sylvestris*; Douglas-fir *Pseudotsuga menziesii*; the hemlocks which include Western hemlock *Tsuga heterophylla*, Eastern hemlock *Tsuga canadensis*, Mountain hemlock *Tsuga mertensiana*; the spruces which include the Norway spruce *Picea abies*, red spruce *Picea rubens*, white spruce *Picea glauca*, black spruce *Picea mariana*, Sitka spruce *Picea sitchensis*, Englemann spruce *Picea engelmanni*, and blue spruce *Picea pungens*; redwood *Sequoia sempervirens*; the true firs include the Alpine fir *Abies lasiocarpa*, silver fir *Abies amabilis*, grand fir *Abies grandis*, nobel fir *Abies procera*, white fir *Abies concolor*, California red fir *Abies magnifica*, and balsam fir *Abies balsamea*, the cedars which include the Western red cedar *Thuja plicata*, incense cedar *libocedrus decurrens*, Northern white cedar *Thuja occidentalis*, Port Orford cedar *Chamaecyparis lawsoniona*, Atlantic white cedar *Chamaecyparis thyoides*, Alaska yellow-cedar *Chamaecyparis nootkatensis*, and Eastern red cedar *Huniperus virginiana*; the larches which include Eastern larch *Larix laricina*, Western larch *Larix occidentalis*, European larch *Larix decidua*, Japanese larch *Larix leptolepis*, and Siberian larch *Larix siberica*; bold cypress *Taxodium distichum* and Giant sequoia *Sequoia gigantea*; and the following angiosperms, by way of example: *Eucalyptus alba, E. bancroftii, E. botyroides, E. bridgesiana, E. calophylla, E. camaldulensis, E. citriodora, E. cladocalyx, E. coccifera, E. curtisii, E. dalrympleana, E. deglupta, E. delagatensis, E. diversicolor, E. dunnii, E. ficifolia, E. globulus, E. gomphocephala, E. gunnii, E. henryi, E. laevopinea, E. macarthurii, E. macrorhyncha, E. maculata, E. marginata, E. megacarpa, E. melliodora, E. nicholii, E. nitens, E. nova-angelica, E. obliqua, E. obtusiflora, E. oreades, E. pauciflora, E. polybractea, E. regnans, E. resinifera, E. robusta, E. rudis, E. saligna, E. sideroxylon, E. stuartiana, E. tereticornis, E. torelliana, E. urnigera, E. urophylla, E. viminalis, E. viridis, E. wandoo* and *E. youmanni*.

The polynucleotides of the present invention may alternatively be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

The polynucleotides identified as SEQ ID NOS: 1–266, 350–375, 404 and 406 represent both "partial" and full length sequences. Partial sequences do not represent the full coding portion of a gene encoding a naturally occurring polypeptide. The partial polynucleotide sequences disclosed herein may be employed to obtain the corresponding full length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene.

The present invention thus comprehends isolated polynucleotides comprising a sequence identified in SEQ ID NOS: 1–266, 350–375, 404 and 406, or a variant of one of the specified sequences, that encode a functional polypeptide, including full length genes. Such extended polynucleotides may have a length of from about 50 to about 4,000 nucleic acids or base pairs, and preferably have a length of less than about 4,000 nucleic acids or base pairs, more preferably a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Polynucleotides of the present invention also comprehend polynucleotides comprising at least a specified number of contiguous residues (x-mers) of any of the polynucleotides identified as SEQ ID NOS: 1–266, 350–375, 404 and 406 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NOS: 1–266, 350–375, 404 and 406, or a variant of any x-mer. That is, the definitions for variants described above in terms of E values, % similarity and hybridization, apply also to any x-mer of any polynucleotide of the present invention.

Polynucleotide probes and primers complementary to and/or corresponding to SEQ ID NOS: 1–266, 350–375, 404 and 406, and variants of those sequences, are also comprehended by the present invention. Such oligonucleotide probes and primers are substantially complementary to the polynucleotide of interest. An oligonucleotide probe or primer is described as "corresponding to" a polynucleotide of the present invention, including one of the sequences set out as SEQ ID NOS: 1–266, 350–375, 404 and 406 or a variant, if the oligonucleotide probe or primer, or its complement, is contained within one of the sequences set out as SEQ ID NOS: 1–266, 350–375, 404 and 406 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNAs from plants or samples or products containing plant material can be either genomic DNA or DNAs derived by preparing cDNA from the RNAs present in the sample.

In addition to DNA-DNA hybridization, DNA-RNA or RNA-RNA hybridization assays are also possible. In the first case, the mRNAs from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably, from about 10 to 50 base pairs in length or, more preferably, from about 15 to 40 base pairs in length. The probes can be easily selected using procedures well known in the art, taking into account DNA-DNA hybridization stringencies, annealing and melting temperatures, potential for formation of loops and other factors, which are well known in the art. Tools and software suitable for designing probes and PCT primers are well known in the art. Preferred techniques for designing PCR primers are disclosed in Dieffenbach C W and Dvksler G S, *PCR primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to polynucleotides of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–266, 350–375, 404 and 406.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

The significance of high-throughput screening systems is apparent for applications such as plant breeding and quality control operations in which there is a need to identify large numbers of seed lots and plant seedlings, to examine samples or products for unwanted plant materials, to identify plants or samples or products containing plant material for quarantine purposes etc. or to ascertain the true origin of plants or samples or products containing plant material. Screening for the presence or absence of polynucleotides of the present invention used as identifiers for tagging plants is valuable for later detecting the amount of gene flow in plant breeding, introgression of genes via dispersed pollen, etc.

In this manner, oligonucleotide probe kits of the present invention may be employed to examine the presence/absence (or relative amounts in case of mixtures) of polynucleotides of the present invention in different samples or products containing different materials rapidly and in a cost-effective manner. Examples of plant species that may be examined using the present invention, include forestry species, such as pine and *eucalyptus* species, other tree species, agricultural plants including crop and forage plants, and horticultural plants.

Another aspect of the present invention involves collections of polynucleotides of the present invention. A collection of polynucleotides of the present invention, particularly the polynucleotides identified as SEQ ID NOS: 1–266, 350–375, 404 and 406, and variants and x-mers thereof, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–266, 350–375, 404 and 406, and variants thereof, as well as x-mers of the polynucleotides of SEQ ID NOS: 1–266, 350–375, 404 and 406, and extended sequences, probes and primers comprising or correspond to a polynucleotide of SEQ ID NOS: 1–266, 350–375, 404 and 406. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–266, 350–375, 404 and 406, or variants of those polynucleotides.

In another aspect, the present invention provides genetic constructs comprising, in the 5'-3' direction, a gene promoter sequence; an open reading frame coding for at least a functional portion of a polypeptide encoded by a polynucleotide of the present invention; and a gene termination sequence. As used herein, the "functional portion" of an enzyme is a portion that contains an active site essential for affecting a metabolic step, i.e. a portion of the molecule that is capable of binding one or more reactants or is capable of improving or regulating the rate of reaction. An active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated polynucleotides of the present invention.

The open reading frame may be orientated in either a sense or antisense direction. For applications where amplification of lignin synthesis is desired, the open reading frame may be inserted in the construct in a sense orientation, such that transformation of a target organism with the construct will lead to an increase in the number of copies of the gene and therefore an increase in the amount of enzyme. When down-regulation of lignin synthesis is desired, the open reading frame may be inserted in the construct in an antisense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g., DNA or RNA) in ribozyme constructs.

Genetic constructs comprising a non-coding region of a gene coding for an enzyme encoded by the above DNA sequences or a nucleotide sequence complementary to a non-coding region, together with a gene promoter sequence and a gene termination sequence, are also provided. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences. Transformation of a target plant with such a DNA construct may lead to a reduction in the amount of lignin synthesized by the plant by the process of cosuppression, in a manner similar to that discussed, for example, by Napoli et al., *Plant Cell* 2:279–290, 1990; and de Carvalho Niebel et al., *Plant Cell* 7:347–358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen K R, *Mol. Gen. Genet.* 225:81–93, 1991, or in the coding region, as for example in PAL of tomato (Bloksberg, *Studies on the Biology of Phenylalanine Ammonia Lyase and Plant Pathogen Interaction*, Ph.D. Thesis, University of California, Davis, 1991, University Microfilms International Order No. 9217564). When the construct includes an open reading frame in a sense orientation, the gene promoter sequence also initiates translation of the open reading frame. For genetic constructs comprising either an open reading frame in an antisense orientation or a non-coding region, the gene promoter sequence consists only of a transcription initiation site having a RNA polymerase binding site.

A variety of gene promoter sequences which may be usefully employed in the genetic constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With genetic constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as *eucalyptus* or pine are used. Other examples of gene promoters which may be usefully employed in the present invention include, mannopine synthase (mas), octopine synthase (ocs) and those reviewed by Chua et al., *Science* 244:174–181, 1989.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The genetic constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Maniatis et al., (*Molecular cloning: a laboratory manual*, CSHL Press: Cold Spring Harbor, N.Y., 1989). The genetic construct of the present invention may be linked to a vector having at least one replication system, for example, *E. coli*, whereby after each manipulation, the resulting construct can be cloned and sequenced and the correctness of the manipulation determined.

The genetic constructs of the present invention may be used to transform a variety of plants, both monocotyledonous (e.g., grasses, corn, grains, oat, wheat and barley), dicotyledonous (e.g., *Arabidopsis*, tobacco, legumes, alfalfa, oaks, *eucalyptus*, maple), and Gymnosperms (e.g., Scots pine; see Aronen, *Finnish Forest Res. Papers*, Vol. 595, 1996), white spruce (Ellis et al., *Biotechnology* 11:94–92, 1993), and larch (Huang et al., *In Vitro Cell* 27:201–207, 1991). In a preferred embodiment, the inventive genetic constructs are employed to transform woody plants, herein defined as a tree or shrub whose stem lives for a number of years and increases in diameter each year by the addition of woody tissue. Preferably the target plant is selected from the group consisting of *eucalyptus* and pine species, most preferably from the group consisting of *Eucalyptus grandis* and *Pinus radiata*. As discussed above, transformation of a plant with a genetic construct including an open reading frame coding for an enzyme encoded by an inventive polynucleotide wherein the open reading frame is orientated in a sense direction will produce a modified lignin content in the plant. Transformation of a plant with a genetic construct comprising an open reading frame in an antisense orientation or a non-coding (untranslated) region of a gene will also produced a modification in the lignin content of the transformed plant.

Polynucleotides of the present invention may also be used to specifically suppress gene expression by methods that operate post-transcriptionally to block the synthesis of products of targeted genes, such as RNA interference (RNAi) and quelling. Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. Exemplary methods for controlling or modifying gene expression using RNAi are provided in WO 99/49029 and WO 99/53050. In these methods, post-transcriptional gene silencing is brought about by a sequence-specific RNA degradation process which results in the rapid degradation of transcripts of sequence-related genes. Studies have shown that double-stranded RNA may act as a mediator of sequence-specific gene silencing (see, for example, Montgomery and Fire, *Trends in Genetics,* 14:255–258, 1998). Gene constructs that produce transcripts with self-complementary regions are particularly efficient at gene silencing. A unique feature of this post-transcriptional gene silencing pathway is that silencing is not limited to the cells where it is initiated. The gene-silencing effects may be disseminated to other parts of an organism and even transmitted through the germ line to several generations.

The polynucleotides of the present invention may thus be employed to generate gene silencing constructs and/or gene-specific self-complementary RNA sequences that can be delivered by conventional art-known methods to plant tissues, such as forage grass tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. The double-stranded RNA must have sufficient homology to the targeted gene to mediate RNAi and is preferably at least 25 nucleotides in length. Preferably, the double-stranded RNA corresponds specifically to a polynucleotide of the present invention. Gene silencing RNA sequences comprising the polynucleotides of the present invention are useful for creating genetically modified plants with desired phenotypes as well as for characterizing genes (for example, in high-throughput screening of sequences), and studying their functions in intact organisms.

The production of RNA in target cells may be controlled by choice of the promoter sequence, or by selecting the number of functional copies or the site of integration of the polynucleotides incorporated into the genome of the target organism. A target plant may be transformed with more than one construct of the present invention, thereby modulating the lignin biosynthetic pathway for the activity of more than one enzyme, affecting enzyme activity in more than one tissue or affecting enzyme activity at more than one expression time. Similarly, a construct may be assembled containing more than one open reading frame coding for an enzyme encoded by a polynucleotide of the present invention or more than one non-coding region of a gene coding for such an enzyme. The polynucleotides of the present invention may also be employed in combination with other known sequences encoding enzymes involved in the lignin biosynthetic pathway. In this manner, it may be possible to add a lignin biosynthetic pathway to a non-woody plant to produce a new woody plant.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan (*Nucl. Acid Res.* 12:8711–8721, 1984). Targets for the introduction of the genetic constructs of the present invention include tissues, such as leaf tissue, disseminated cells, protoplasts, seeds, embryos, meristematic regions; cotyledons, hypocotyls, and the like. One preferred method for transforming *eucalyptus* and pine is a biolistic method using pollen (see, for example, Aronen, *Finnish Forest Res. Papers*, Vol. 595:53, 1996) or easily regenerable embryonic tissues. Other transformation techniques which may be usefully employed in the inventive methods include those taught by Ellis et al. (*Plant Cell Reports*, 8:16–20, 1989), Wilson et al. (*Plant Cell Reports* 7:704–707, 1989) and Tautorus et al. (*Theor. Appl. Genet.* 78:531–536, 1989).

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees, see Dunstan et al., "Somatic embryogenesis in woody plants," in Thorpe T A, ed., *In vitro embryogenesis of plants*, Current Plant Science and Biotechnology in Agriculture 20(12):471–540, 1995. Specific protocols for the regeneration of spruce are discussed by Roberts et al., ("Somatic embryogenesis of spruce," in Redenbaugh K, ed., *Synseed: applications of synthetic seed to crop improvement*, CRC Press: Chapter 23, pp. 427–449, 1993). The resulting transformed plants may be reproduced sexually or asexually, using methods well known in the art, to give successive generations of transgenic plants.

In yet a further aspect, the present invention provides methods for modifying the level (concentration) or activity of a polypeptide in a host organism, comprising stably incorporating into the genome of the plant a construct comprising a polynucleotide of the present invention. The genetic constructs of the present invention may be used to transform a variety of organisms. Such organisms include plants, such as monocotyledonous angiosperms (e.g., grasses, corn, grains, oat, wheat and barley), and dicotyledonous angiospenns (e.g., *Arabidopsis*, tobacco, legumes, alfalfa, oaks, *eucalyptus*, maple), and gymnosperms (e.g., Scots pine; see Aronen, *Finnish Forest Res. Papers*, Vol. 595, 1996), white spruce (Ellis et al., *Biotechnology* 11:94–92, 1993), and larch (Huang et al., *In Vitro Cell* 27:201–207, 1991).

In preferred embodiments, the genetic constructs of the present invention are employed to transform woody plants, herein defined as a tree or shrub having a stem that lives for a number of years and increases in diameter each year as a consequence of the addition of woody tissue. The target plant is preferably selected from the group consisting of *eucalyptus* and pine species, most preferably from the group consisting of *Eucalyptus grandis* and *Pinus radiata*, but also including any of the species in the following list:

Pines: *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana.*

Other gymnosperms: *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata.*

Eucalypts: *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo, Eucalyptus youmanni*; and hybrids of any of the above species.

Further, the polynucleotides of the present invention have particular application for use as non-disruptive tags for marking organisms, particularly plants. Other organisms may, however, be tagged with the polynucleotides of the present invention, including commercially valuable animals, fish, bacteria and yeasts. Constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material.

Detection of the tag(s) may be accomplished using a variety of conventional techniques, and will generally involve the use of nucleic acid probes. Sensitivity in assaying the presence of probe can be usefully increased by using branched oligonucleotides, as described in Horn T, Chang C A and Urdea M S, "Chemical synthesis and characterization of branched oligodeoxyribonucleotides (bDNA) for use as signal amplifiers in nucleic acid quantification assays," *Nucleic Acids Research* 25(23):4842–4849, 1997), enabling detection of as few as 50 DNA molecules in the sample.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Reporter* 11:113–116, 1993) with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3 HCl) and extracted with chloroform: isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequences for positive clones were obtained using a Perkin Elmer/Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

The determined cDNA sequences were compared to known sequences in the EMBL database (release 46, March 1996) using the FASTA algorithm of February 1996 (Version 2.0.4) or the BLASTN algorithm Version 2.0.4 [Feb. 24, 1998], or Version 2.0.6 [Sep. 16, 1998], set to the preferred parameters described above. Multiple alignments of redundant sequences were used to build up reliable consensus sequences. Based on similarity to known sequences from other plant species, the isolated polynucleotides of the present invention were identified as encoding a specified enzyme.

Using the procedures described above, cDNA sequences derived from the *Eucalyptus grandis* library encoding the following polypeptides were isolated: PAL (SEQ ID NOS: 16, 100, 242–246); C4H (SEQ ID NOS: 17, 153, 154, and 161); C3H (SEQ ID NOS: 18, 101, 149 and 150); F5H (SEQ ID NOS: 19–21, 102, 103, 169–171 and 404); OMT (SEQ ID NOS: 22–25, 104–107, 173 and 174); CCR (SEQ ID NOS: 26–29 and 108–111); CAD (SEQ ID NOS: 1, 30 and 112); CGT (SEQ ID NOS: 31–33 and 113–115); CBG (SEQ ID NOS: 34, 165 and 166); PNL (SEQ ID NOS: 35, 36 and 116); LAC (SEQ ID NOS: 37–41, 117 and 118); POX (SEQ ID NOS: 42–44, 119–121, 179, 249–250 and 350–358); 4CL (SEQ ID NO: 266); caffeic acid methyl transferase (SEQ ID NOS: 187–192); caffeoyl CoA methyl transferase (SEQ ID NOS: 193–195); coumarate Co-A ligase (SEQ ID NOS: 196–198); cytochrome P450 LXX1A (SEQ ID NOS: 201–206); diphenol oxidase (SEQ ID NOS: 207–217); flavonol glucosyl transferase (SEQ ID NO: 218); flavonoid hydroxylase (SEQ ID NOS: 219–223); and isoflavone reductase (SEQ ID NOS: 234–240).

As shown in Table 1, above, the amino acid sequences encoded by SEQ ID NO: 187–191, 193–198, 201–217, 219–223, 234–239, 242–246, 249, 250, 266 and 350–358 are provided in SEQ ID NO: 270–274, 276–281, 284–300, 302–306, 317–322, 325–329, 332, 333, 349 and 376–384, respectively. SEQ ID NO: 107 is a full-length version of SEQ ID NO: 24 and 106; SEQ ID NO: 108 is a full-length version of SEQ ID NO: 26; SEQ ID NO: 266 is a full-length version of SEQ ID NO: 196 and 197; and SEQ ID NO: 404 is a full-length version of SEQ ID NO: 20 and 103.

EXAMPLE 2

Isolation and Characterization of cDNA Clones from *Pinus radiata* a) Isolation of cDNA Clones by High Through-Put Screening

A *Pinus radiata* cDNA expression library was constructed from xylem and screened as described above in Example 1. DNA sequences for positive clones were obtained using forward and reverse primers on a Perkin Elmer/Applied Biosystems Prism 377 sequencer and the determined sequences were compared to known sequences in the EMBL database as described above.

Based on similarity to known sequences from other plant species, the isolated DNA sequences were identified as encoding the enzymes C4H (SEQ ID NOS: 2, 3, 48, 49, 92, 124, 125, 155–160, 162 and 163); C3H (SEQ ID NOS: 4, 50–52, 93, 126, 127, 151 and 152); PNL (SEQ ID NOS: 5, 81 and 183); OMT (SEQ ID NOS: 6, 53–55, 94 and 175); CAD (SEQ ID NOS: 7, 71, 95 and 164); CCR (SEQ ID NOS: 8, 58–70, 96, 128–134 and 167); PAL (SEQ ID NOS: 9–11, 45–47, 97, 98, 122, 123 and 176, 247 and 248); 4CL (SEQ ID NOS: 12, 56, 57, 90, 99, 147, 148, 199, 200, 265 and 406); CGT (SEQ ID NOS: 72, 135 and 168); CBG (SEQ ID NOS: 73–80 and 136–141); LAC (SEQ ID NOS: 82–84, 142–144 and 172); POX (SEQ ID NOS: 85–89, 91, 145, 146, 177, 178, 180–182, 264, 359–375); alpha amylase (SEQ ID NOS: 184–186); flavonoid hydroxylase (SEQ ID NOS: 224–233); isoflavone reductase (SEQ ID NO: 241); and diphenol oxidase (SEQ ID NOS: 251–263).

As shown in Table 1, above, the amino acid sequences encoded by SEQ ID NO: 184–186, 192, 199–200, 218, 224–233, 240–241, 247–248, 251–265, 359–375 and 406 are provided in SEQ ID NO: 267–269, 275, 282–283, 301, 307–316, 323–324, 330–331, 334–348, 385–401 and 407, respectively. SEQ ID NO: 90 is a full-length version of SEQ ID NO: 12 and 56; SEQ ID NO: 94 is a full-length version of SEQ ID NO: 53; SEQ ID NO: 265 is a full-length version of SEQ ID NO: 57; SEQ ID NO: 363 is a full-length version of SEQ ID NO: 372; and SEQ ID NO: 406 is a full-length version of SEQ ID NO: 200.

b) Isolation of cDNA Clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank Accession Nos. D11337, M83671, X56011, X58396, X66125, J02979, D11396, X71593, D11102, L07554, M58381, X57564, Z22920, and Z31011, respectively).

RNA was isolated from pine xylem and first strand cDNA was synthesized as described above. This cDNA was subjected to PCR using 4 µM LNB010, 4 µM LNB011, 1×Kogen's buffer, 0.1 mg/ml BSA, 200 mM dNTP, 2 mM Mg$^{2+}$, and 0.1 U/µl of Taq polymerase (Gibco BRL). Conditions were 2 cycles of 2 min at 94° C., 1 min at 55° C. and 1 min at 72° C.; 25 cycles of 1 min at 94° C., 1 min at 55° C., and 1 min at 72° C.; and 18 cycles of 1 min at 94° C., 1 min at 55° C., and 3 min at 72° C. in a Stratagene Robocycler. The gene was re-amplified in the same manner. A band of about 200 bp was purified from a TAE agarose gel using a Schleicher & Schuell Elu-Quik DNA purification kit and clones into a T-tailed pBluescript vector (Marchuk D et al., *Nucleic Acids Res.* 19:1154, 1991). Based on similarity to known sequences, the isolated gene (SEQ ID NO: 13) was identified as encoding pine peroxidase (POX).

EXAMPLE 3

Use of an O-methyltransferase (OMT) Gene to Modify Lignin Biosynthesis a) Transformation of Tobacco Plants with a *Pinus radiata* OMT Gene Sense and anti-sense constructs containing a polynucleotide including the coding region of OMT (SEQ ID NO: 53) from *Pinus radiata* were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the transgenic constructs were verified by restriction digestion and DNA sequencing.

Tobacco (*Nicotiana tabacum* cv. Samsun) leaf sections were transformed using the method of Horsch et al. (*Science*, 227:1229–1231, 1985). Five independent transformed plant lines were established for the sense construct and eight independent transformed plant lines were established for the anti-sense construct for OMT. Transformed plants containing the appropriate lignin gene construct were verified using Southern blot experiments. A "+" in the column labeled "Southern" in Table 2 below indicates that the transformed plant lines were confirmed as independent transformed lines.

b) Expression of *Pinus* OMT in Transformed Plants

Total RNA was isolated from each independent transformed plant line created with the OMT sense and anti-sense constructs. The RNA samples were analysed in Northern blot experiments to determine the level of expression of the transgene in each transformed line. The data shown in the column labeled "Northern" in Table 2 shows that the transformed plant lines containing the sense and anti-sense constructs for OMT all exhibited high levels of expression, relative to the background on the Northern blots. OMT expression in sense plant line number 2 was not measured because the RNA sample showed signs of degradation. There was no detectable hybridisation to RNA samples from empty vector-transformed control plants.

c) Modulation of OMT Enzyme Activity in Transformed Plants

The total activity of OMT enzyme, encoded by the *Pinus* OMT gene and by the endogenous tobacco OMT gene, in transformed tobacco plants was analysed for each transformed plant line created with the OMT sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 1 shows that the transformed plant lines containing the OMT sense construct generally had elevated OMT enzyme activity, with a maximum of 199%, whereas the transformed plant lines containing the OMT anti-sense construct generally had reduced OMT enzyme activity, with a minimum of 35%, relative to empty vector-transformed control plants. OMT enzyme activity was not estimated in sense plant line number 3.

d) Effects of *Pinus* OMT on Lignin Concentration in Transformed Plants

The concentration of lignin in the transformed tobacco plants was determined using the well-established procedure of thioglycolic acid extraction (see, Freudenberg et al., *Constitution and Biosynthesis of Lignin*, Springer-Verlag: Berlin, 1968). Briefly, whole tobacco plants, of an average age of 38 days, were frozen in liquid nitrogen and ground to a fine powder in a mortar and pestle. 100 mg of frozen powder from one empty vector-transformed control plant line, the five independent transformed plant lines containing the sense construct for OMT and the eight independent transformed plant lines containing the anti-sense construct for OMT were extracted individually with methanol, followed by 10% thioglycolic acid and finally dissolved in 1 M NaOH. The final extracts were assayed for absorbance at 280 nm. The data shown in the column labelled "TGA" in Table 2 shows that the transformed plant lines containing the sense and the anti-sense OMT gene constructs all exhibited significantly decreased levels of lignin, relative to the empty vector-transformed control plant lines.

TABLE 2

| plant line | transgene | orientation | Southern | Northern | Enzyme | TGA |
|---|---|---|---|---|---|---|
| 1 | control | na | + | blank | 100 | 104 |
| 1 | OMT | sense | + | 2.9E+6 | 86 | 55 |
| 2 | OMT | sense | + | na | 162 | 58 |
| 3 | OMT | sense | + | 4.1E+6 | na | 63 |
| 4 | OMT | sense | + | 2.3E+6 | 142 | 66 |
| 5 | OMT | sense | + | 3.6E+5 | 199 | 75 |
| 1 | OMT | anti-sense | + | 1.6E+4 | 189 | 66 |
| 2 | OMT | anti-sense | + | 5.7E+3 | 35 | 70 |
| 3 | OMT | anti-sense | + | 8.0E+3 | 105 | 73 |
| 4 | OMT | anti-sense | + | 1.4E+4 | 109 | 74 |
| 5 | OMT | anti-sense | + | 2.5E+4 | 87 | 78 |
| 6 | OMT | anti-sense | + | 2.5E+4 | 58 | 84 |
| 7 | OMT | anti-sense | + | 2.5E+4 | 97 | 92 |
| 8 | OMT | anti-sense | + | 1.1E+4 | 151 | 94 |

These data clearly indicate that lignin concentration, as measured by the TGA assay, can be directly manipulated by either sense or anti-sense expression of a lignin biosynthetic gene such as OMT.

EXAMPLE 4

Use of a 4-Coumarate:CoA Ligase (4CL) Gene to Modify Lignin Biosynthesis a) Transformation of Tobacco Plants with a *Pinus radiata* 4CL Gene Sense and anti-sense constructs containing a polynucleotide including the coding region of 4CL (SEQ ID NO: 56) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described above. Five independent transformed plant lines were established for the sense construct and eight independent transformed plant lines were established for the anti-sense construct for 4CL. Transformed plants containing the appropriate lignin gene construct were verified using Southern blot experiments. A "+" in the column labeled "Southern" in Table 3 indicates that the transformed plant lines listed were confirmed as independent transformed lines.

b) Expression of *Pinus* 4CL in Transformed Plants

Total RNA was isolated from each independent transformed plant line created with the 4CL sense and anti-sense constructs. The RNA samples were analysed in Northern blot experiments to determine the level of expression of the transgene in each transformed line. The data shown in the column labelled "Northern" in Table 3 below shows that the transformed plant lines containing the sense and anti-sense constructs for 4CL all exhibit high levels of expression, relative to the background on the Northern blots. 4CL expression in anti-sense plant line number 1 was not measured because the RNA was not available at the time of the experiment. There was no detectable hybridisation to RNA samples from empty vector-transformed control plants.

c) Modulation of 4CL Enzyme Activity in Transformed Plants

The total activity of 4CL enzyme, encoded by the *Pinus* 4CL gene and by the endogenous tobacco 4CL gene, in transformed tobacco plants was analysed for each transformed plant line created with the 4CL sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 3 shows that the transformed plant lines containing the 4CL sense construct had elevated 4CL enzyme activity, with a maximum of 258%, and the transformed plant lines containing the 4CL anti-sense construct had reduced 4CL enzyme activity, with a minimum of 59%, relative to empty vector-transformed control plants.

d) Effects of *Pinus* 4CL on Lignin Concentration in Transformed Plants

The concentration of lignin in samples of transformed plant material was determined as described in Example 3. The data shown in the column labelled "TGA" in Table 3 shows that the transformed plant lines containing the sense and the anti-sense 4CL gene constructs all exhibited significantly decreased levels of lignin, relative to the empty vector-transformed control plant lines. These data clearly indicate that lignin concentration, as measured by the TGA assay, can be directly manipulated by either sense or anti-sense expression of a lignin biosynthetic gene such as 4CL.

TABLE 3

| plant line | transgene | orientation | Southern | Northern | Enzyme | TGA |
|---|---|---|---|---|---|---|
| 1 | control | na | + | blank | 100 | 92 |
| 2 | control | na | + | blank | 100 | 104 |
| 1 | 4CL | sense | + | 2.3E+4 | 169 | 64 |
| 2 | 4CL | sense | + | 4.5E+4 | 258 | 73 |
| 3 | 4CL | sense | + | 3.1E+4 | 174 | 77 |
| 4 | 4CL | sense | + | 1.7E+4 | 164 | 80 |
| 5 | 4CL | sense | + | 1.6E+4 | 184 | 92 |
| 1 | 4CL | anti-sense | + | na | 59 | 75 |
| 2 | 4CL | anti-sense | + | 1.0E+4 | 70 | 75 |
| 3 | 4CL | anti-sense | + | 9.6E+3 | 81 | 80 |
| 4 | 4CL | anti-sense | + | 1.2E+4 | 90 | 83 |
| 5 | 4CL | anti-sense | + | 4.7E+3 | 101 | 88 |
| 6 | 4CL | anti-sense | + | 3.9E+3 | 116 | 89 |
| 7 | 4CL | anti-sense | + | 1.8E+3 | 125 | 94 |
| 8 | 4CL | anti-sense | + | 1.7E+4 | 106 | 97 |

EXAMPLE 5

Transformation of Tobacco Using the Inventive Lignin Biosynthetic Genes

Sense and anti-sense constructs containing polynucleotides including the coding regions of C3H (SEQ ID NO: 18), F5H (SEQ ID NO: 19), CCR (SEQ ID NO: 26) and CGT (SEQ ID NO: 31) from *Ecualyptus grandis*, and OMT (SEQ ID NO: 6), PAL (SEQ ID NO: 45 and 47), C4H (SEQ ID NO: 48 and 49), PNL (SEQ ID NO: 81) and LAC (SEQ ID NO: 83) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described in Example 3. Up to twelve independent transformed plant lines were established for each sense construct and each anti-sense construct listed in the preceding paragraph. Transformed plants containing the appropriate lignin gene construct were verified using Southern blot experiments. All of the transformed plant lines analysed were confirmed as independent transformed lines.

EXAMPLE 6

Manipulation of Lignin Content in Transformed Plants a) Determination of Transgene Expression by Northern Blot Experiments Total RNA was isolated from each independent transformed plant line described in Example 5. The RNA samples were analysed in Northern blot experiments to determine the level of expression of the transgene in each transformed line. The column labelled "Northern" in Table 4 shows the level of transgene expression for all plant lines assayed, relative to the background on the Northern blots. There was no detectable hybridisation to RNA samples from empty vector-transformed control plants.

b) Determination of Lignin Concentration in Transformed Plants

The concentration of lignin in empty vector-transformed control plant lines and in up to twelve independent transformed lines for each sense construct and each anti-sense construct described in Example 5 was determined as described in Example 3. The column labelled "TGA" in Table 4 shows the thioglycolic acid extractable lignins for plant lines transformed with C3H, F5H, CCR, PAL, C4H, PNL and LAC, expressed as the average percentage of TGA extractable lignins in transformed plants versus control plants. The range of variation is shown in parentheses.

TABLE 4

| transgene | orientation | no. of lines | Northern | TGA |
|---|---|---|---|---|
| control | na | 3 | blank | 100 (92–104) |
| C3H | sense | 5 | 3.7E+4 | 74 (67–85) |
| F5H | sense | 10 | 5.8E+4 | 70 (63–79) |
| F5H | anti-sense | 9 | 5.8E+4 | 73 (35–93) |
| CCR | sense | 1 | na | 74 |
| CCR | anti-sense | 2 | na | 74 (62–86) |
| PAL | sense | 5 | 1.9E+5 | 77 (71–86) |
| PAL | anti-sense | 4 | 1.5E+4 | 62 (37–77) |
| C4H | anti-sense | 10 | 5.8E+4 | 86 (52–113) |
| PNL | anti-sense | 6 | 1.2E+4 | 88 (70–114) |
| LAC | sense | 5 | 1.7E+5 | na |
| LAC | anti-sense | 12 | 1.7E+5 | 88 (73–114) |

Figure 5:
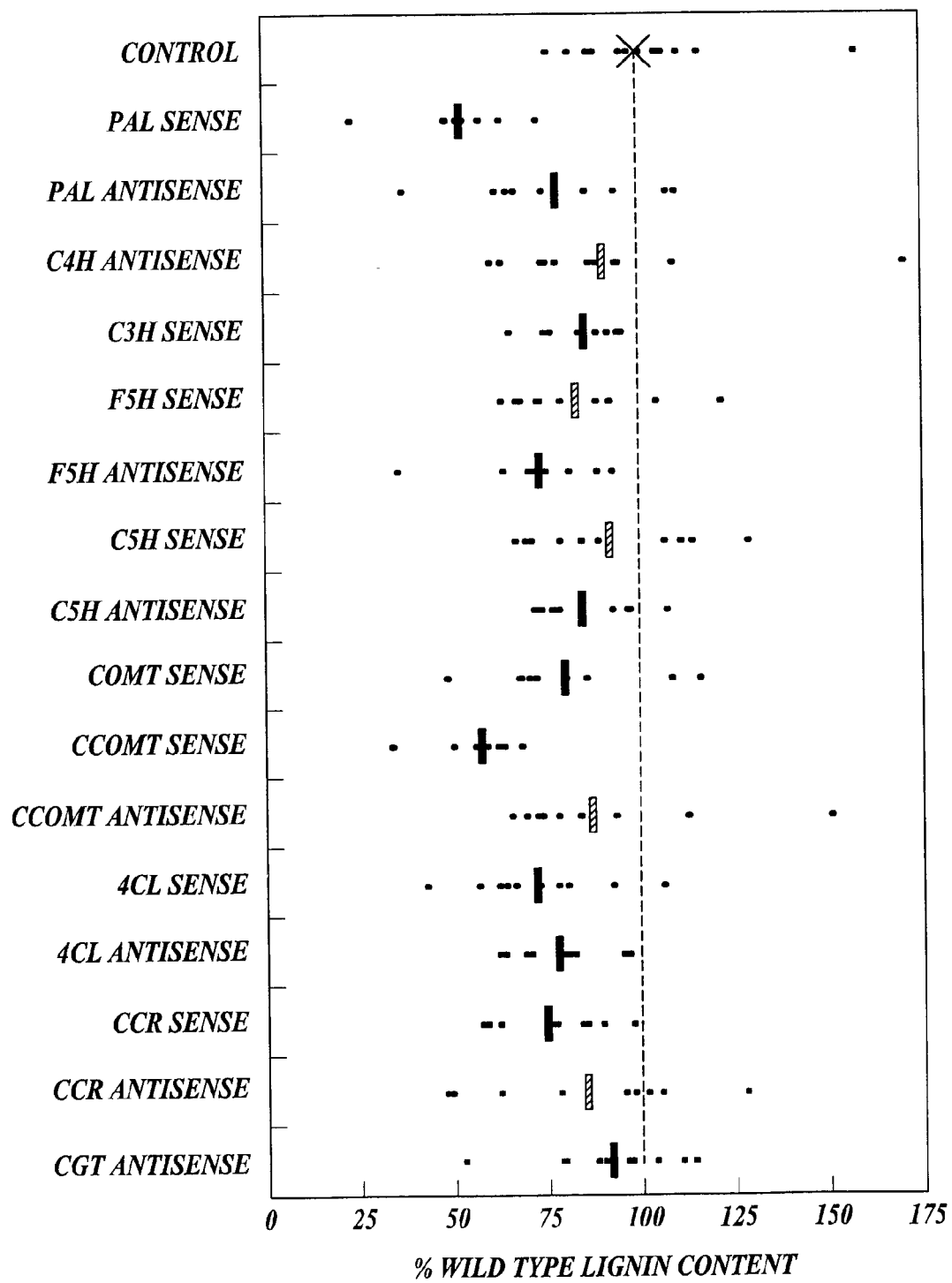
FIG. 5 shows the amount of extractable lignin, as a percentage of wild type lignin content, present in tobacco plants transformed with sense and anti-sense genetic constructs of the present invention.

FIG. 5 illustrates the quantity of extractable lignin, as a percentage of wild type lignin content, in tobacco plants transformed with PAL (sense and anti-sense), C4H (anti-sense), C3H (sense), F5H (sense and antisense), C5H (sense and antisense) C3H (sense; referred to as COMT in FIG. 5), OMT (sense and antisense; referred to as CCOMT in FIG. 5), 4CL (sense and antisense), CCR (sense and antisense) and CGT (antisense) constructs as described in Example 5. Thioglycolic acid-extractable lignin quantities were measured in transgenic plants, normalized to empty-vector control plants. Three extracts were independently derived from each of approximately 10 independently derived transgenic plants. The average of the three extracts is shown by a black dot, as the lignin value for that plant. The average of ten independent transgenic plants transformed with a given cDNA construct is shown as a bar. The average of empty vector transformed control plants is shown as an X. The value for the controls is extrapolated across the field to facilitate comparison. Black bars indicate means which are significantly reduced (p<0.05) in lignin content with respect to control plants. Grey bars indicate means which are not significantly changed from control plants.

Transformed plant lines containing the sense and the anti-sense lignin biosynthetic gene constructs exhibited a mean level of lignin content that was significantly lower than that of empty vector-transformed control plant lines. The most dramatic effects on lignin concentration were seen in the OMT sense plants, and in the PAL sense plants. These data clearly indicate that lignin concentration, as measured by the TGA assay, can be directly manipulated by conventional anti-sense methodology and also by sense over-expression using the inventive lignin biosynthetic genes.

EXAMPLE 7

Modulation of Lignin Enzyme Activity in Transformed Plants

The activities and substrate specificities of selected lignin biosynthetic enzymes were assayed in crude extracts from transformed tobacco plants containing sense and anti-sense constructs for PAL (SEQ ID NO: 45), PNL (SEQ ID NO: 81) and LAC (SEQ ID NO: 83) from *Pinus radiata*, and CGT (SEQ ID NO: 31) from *Eucalyptus grandis*.

Enzyme assays were performed using published methods for PAL (Southerton S G and Deverall B J, *Plant Path.* 39:223–230, 1990), CGT (Vellekoop P et al., *FEBS,* 330: 36–40, 1993), PNL (Espin C J et al., *Phytochemistry* 44:17–22, 1997) and LAC (Bao W et al., *Science,* 260: 672–674, 1993). The data shown in the column labelled "Enzyme" in Table 5 shows the average enzyme activity from replicate measures for all plant lines assayed, expressed as a percent of enzyme activity in empty vector-transformed control plants. The range of variation is shown in parentheses.

TABLE 5

| Transgene | orientation | no. of lines | enzyme |
|---|---|---|---|
| control | na | 3 | 100 |
| PAL | sense | 5 | 87 (60–124) |
| PAL | anti-sense | 3 | 53 (38–80) |
| CGT | anti-sense | 1 | 89 |
| PNL | anti-sense | 6 | 144 (41–279) |
| LAC | sense | 5 | 78 (16–240) |
| LAC | anti-sense | 11 | 64 (14–106) |

All of the transformed plant lines, except the PNL anti-sense transformed plant lines, showed average lignin enzyme activities which were significantly lower than the activities observed in empty vector-transformed control plants. The most dramatic effects on lignin enzyme activities were seen in the PAL anti-sense transformed plant lines in which all of the lines showed reduced PAL activity and in the LAC anti-sense transformed plant lines which showed as little as 14% of the LAC activity in empty vector-transformed control plant lines.

EXAMPLE 8

Functional Identification of Lignin Biosynthetic Genes

Sense constructs containing polynucleotides including the coding regions for PAL (SEQ ID NO: 47), OMT (SEQ ID NO: 53), 4CL (SEQ ID NO: 56 and 57) and POX (SEQ ID NO: 86) from *Pinus radiata*, and OMT (SEQ ID NO: 23 and 24), CCR (SEQ ID NO: 26–28), CGT (SEQ ID NO: 31 and 33) and POX (SEQ ID NO: 42 and 44) from *Ecualyptus grandis* were inserted into the commercially available protein expression vector, pProEX-1 (Gibco BRL). The resultant constructs were transformed into *E. coli* XL1-Blue (Stratagene), which were then induced to produce recombinant protein by the addition of IPTG. Purified proteins were produced for the *Pinus* OMT and 4CL constructs and the Eucalyptus OMT and POX constructs using Ni column chromatography (Janknecht R et al., *Proc. Natl. Acad. Sci.,* 88:8972–8976, 1991). Enzyme assays for each of the purified proteins conclusively demonstrated the expected substrate specificity and enzymatic activity for the genes tested.

The data for two representative enzyme assay experiments, demonstrating the verification of the enzymatic activity of a *Pinus radiata* 4CL gene (SEQ ID NO: 56) and a *Pinus radiata* OMT gene (SEQ ID NO: 53), are shown in Table 6. For the 4CL enzyme, one unit equals the quantity of protein required to convert the substrate into product at the rate of 0.1 absorbance units per minute. For the OMT enzyme, one unit equals the quantity of protein required to convert 1 pmole of substrate to product per minute.

TABLE 6

| transgene | purification step | total ml extract | total mg protein | total units activity | % yield activity | fold purification |
|---|---|---|---|---|---|---|
| 4CL | crude | 10 ml | 51 mg | 4200 | 100 | 1 |
|  | Ni column | 4 ml | 0.84 mg | 3680 | 88 | 53 |
| OMT | crude | 10 ml | 74 mg | 4600 | 100 | 1 |
|  | Ni column | 4 ml | 1.2 mg | 4487 | 98 | 60 |

The data shown in Table 6 indicate that both the purified 4CL enzyme and the purified OMT enzyme show high activity in enzyme assays, confirming the identification of the 4CL and OMT genes described in this application. Crude protein preparations from *E. coli* transformed with empty vector show no activity in either the 4CL or the OMT enzyme assay.

EXAMPLE 9

Demonstration of the Presence/Absence of Unique Sequence Identifiers in Plants

Transgenic tobacco plants were created using unique identifier sequences which are not found in tobacco. The unique identifier sequences inserted were isolated from *Pinus radiata*, SEQ ID NO: 402, and *Ecualyptus grandis*, SEQ ID NO: 403. The unique identifier sequences were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the unique identifier sequences in the *Agrobacterium* transgenic constructs were verified by restriction digestion and DNA sequencing.

Tobacco (*Nicotiana tabacum* cv. Samsun) leaf sections were transformed using the method of Horsch et al. (*Science,* 227:1229–1231, 1985). Three independent transformed plant lines were established for each unique sequence identifier used. Two empty-vector control plant lines were established using an empty gene transfer vector which lacked a unique sequence identifier.

The uniqueness of the sequence identifiers was assayed using Southern blot analyses to test for the presence of the sequence identifier in the genome of the plants. If the sequence identifier is unique and therefore useful as a tag, then the sequence identifier should be clearly absent in plants which have not been tagged and it should be clearly present in plants which have been tagged. In the present example, the unique identifiers would be expected to be absent in the empty-vector transformed control plants. The unique identifier would be expected to be present in the transgenic plants transformed with the unique sequence identifiers.

Figure 2:
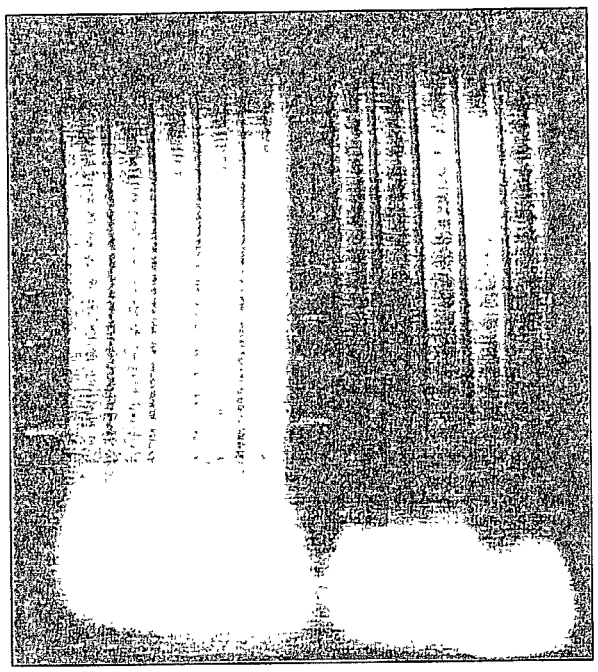
FIG. 2 illustrates genomic DNA samples from tobacco plants created in a tagging experiment using a unique sequence identifier from *Pinus* (left panel) and a unique sequence identifier from Eucalyptus (right panel). In both panels, lanes A and B contain DNA samples from empty-vector transformed control plants and lanes C–E contain DNA samples from plants transformed with a unique sequence identifier.

Genomic DNA was prepared from empty-vector transformed control plants and plants transformed with unique sequence identifiers using the cetyltrimethyl-ammonium bromide (CTAB) extraction method of Murray and Thompson (*Nucleic Acids Research* 8:4321–4325, 1980). The DNA samples were digested with the restriction enzyme EcoRI in the case of the plants transformed with the *Pinus* unique sequence identifier (SEQ ID NO: 402) and the restriction enzyme XbaI in the case of the plants transformed with the Eucalyptus unique sequence identifier (SEQ ID NO: 403). The DNA fragments produced in the restriction digests were resolved on a 1% agarose gel; the left panel of FIG. 2 and the right panel of FIG. 2 show the DNA fragment patterns of the DNA samples from the *Pinus* and Eucalyptus experiments, respectively.

After the agarose gel electrophoresis step, the DNA samples were transferred to Hybond-N+ brand nylon membranes (Amersham Life Science, Little Chalfont, Buckinghamshire, England) using methods established by Southern (*J. Mol. Bio.* 98:503–517). The nylon membranes were probed with radioactively-labeled probes for the unique sequence identifiers identified above and washed at high stringency (final wash: 0.5×salt sodium citrate buffer (SSC) plus 0.1% sodium dodecyl sulfate (SDS), 15 minutes at 65° C.). The hybridisation of the probes to complementary sequences in the genomic DNA samples was detected using auto-radiography. The results are shown in FIGS. 3 and 4.

Figure 3:
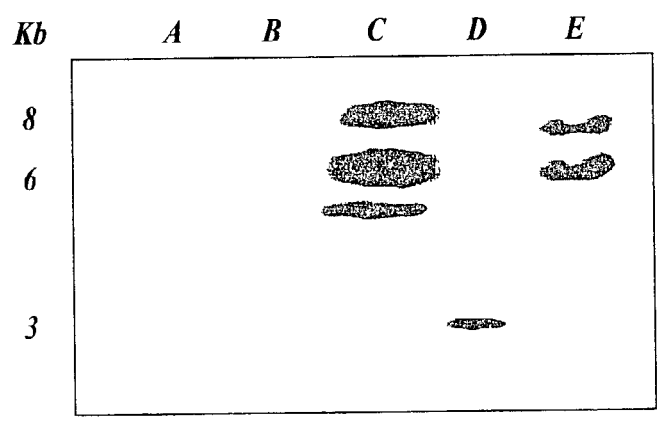
FIG. 3 demonstrates detection of a *Pinus* unique sequence identifier in transformed tobacco plants. Lanes A and B show the hybridization of a probe from SEQ ID NO: 402 to the genomic DNA of tobacco plants which lack the *Pinus* unique sequence identifier (empty-vector transformed control plants). Lanes C–E show the hybridization of the probe to the genomic DNA of tobacco plants containing one to three copies of the *Pinus* unique sequence identifier.

FIG. 3 (corresponding to the left panel of FIG. 2) shows the hybridisation pattern detected in the Southern blot analysis using a probe derived from the *Pinus* sequence identifier (SEQ ID NO: 402). Lanes A–B contain DNA samples from empty-vector transformed control plants and lanes C–E contain DNA from plants transformed with SEQ ID NO: 402. There is no hybridization in lanes A–B indicating that SEQ ID NO: 402 is not present in empty-vector transformed tobacco plants; that is, SEQ ID NO: 402 is a unique tag suitable for unambiguous marking of tobacco plants. There is strong hybridisation in lanes C–E indicating that the plants which received SEQ ID NO: 402 via transformation have been clearly and unambiguously tagged with the unique sequence contained in SEQ ID NO: 402.

Figure 4:
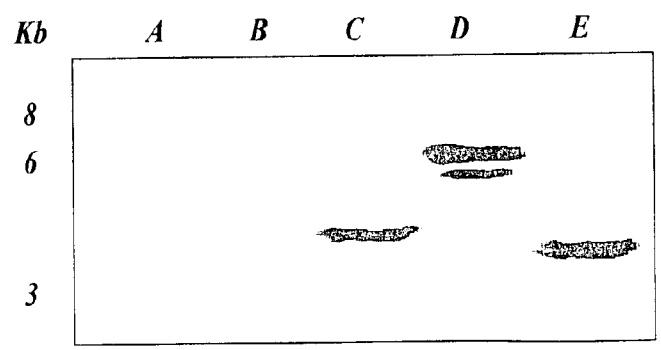
FIG. 4 demonstrates detection of a Eucalyptus unique sequence identifier in transformed tobacco plants. Lanes A and B show the hybridization of a probe from SEQ ID NO: 403 to the genomic DNA of tobacco plants which lack the Eucalyptus unique sequence identifier (empty-vector transformed control plants). Lanes C–E show the hybridization of the probe to the genomic DNA of tobacco plants containing one to two copies of the Eucalyptus unique sequence identifier.

FIG. 4 (corresponding to the right panel of FIG. 2) shows the hybridization pattern detected in the Southern blot analysis using a probe derived from the Eucalyptus sequence identifier (SEQ ID NO: 403). Lanes A–B contain DNA samples from empty-vector transformed control plants and lanes C–E contain DNA from plants transformed with SEQ ID NO: 403. There is no hybridisation in lanes A–B indicating that SEQ ID NO: 403 is not present in empty-vector transformed tobacco plants; that is, SEQ ID NO: 403 is a unique tag suitable for unambiguous marking of tobacco plants. There is strong hybridisation in lanes C–E indicating that the plants which received SEQ ID NO: 403 via transformation have been clearly and unambiguously tagged with the unique sequence contained in SEQ ID NO: 403.

The present example clearly demonstrates the utility of the sequences disclosed in this specification for the purposes of unambiguously tagging transgenic materials. A unique sequence was selected from a large number of potential tags and shown to be absent in the genome of the organism to be tagged. The tag was inserted into the genome of the organism to be tagged and a well-established DNA detection method was used to clearly detect the unique sequence identifier used as the tag.

Because of the sequence-specific detection methods used in the example, a user of the invention disclosed in this specification has both a high likelihood of finding a sequence identifier, among the list which has been disclosed, which will be useful for tagging any given organism and an unequivocal method for demonstrating that a tagged organism could only have acquired a given tag through the deliberate addition of the unique sequence to the genome of the organism to be tagged. If the user of this invention maintains the precise sequence of the tag used in a given organism as a secret, then any disputes as to the origin and history of the organism can be unambiguously resolved using the tag detection techniques demonstrated in the present example.

SEQ ID NOS: 1–407 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polynucleotide comprising a nucleotide sequence selected from the group consisting of: SEQ ID NO: 103 and 404.

2. An isolated polynucleotide comprising a sequence selected from the group consisting of:
 (a) sequences having at least 90% identity to a sequence of SEQ ID NO: 103 or 404; and
 (b) sequences having at least 95% identity to a sequence of SEQ ID NO: 103 or 404,
 wherein the polynucleotide encodes a polypeptide having ferulate-5-hydroxylase activity.

3. An isolated polynucleotide comprising a nucleotide sequence that hybridizes to a sequence of SEQ ID NO: 103 or 404 under stringent hybridization conditions, wherein the polynucleotide encodes a polypeptide having ferulate-5-hydroxylase activity.

4. An isolated polynucleotide comprising a sequence selected from the group consisting of:
 (a) nucleotide sequences that are 200-mers of a sequence recited in SEQ ID NO: 103 or 404
 (b) nucleotide sequences that are 100-mers of a sequence recited in SEQ ID NO: 103 or 404
 (c) nucleotide sequences that are 40-mers of a sequence recited in SEQ ID NO: 103 or 404; and
 (d) nucleotide sequences that are 20-mers of a sequence recited in SEQ ID NO: 103 or 404,
 wherein the polynucleotide encodes a polypeptide having ferulate-5-hydroxylase activity.

5. A genetic construct comprising a polynucleotide of claim 1.

6. A transgenic cell comprising a construct according to claim 5.

7. A construct comprising, in the 5'-3' direction:
 (a) a gene promoter sequence;
 (b) a polynucleotide sequence comprising at least one of the following: (1) a polynucleotide sequence comprising a coding region of a polynucleotide of claim 1 and (2) a polynucleotide sequence comprising a non-coding region of a polynucleotide of claim 1; and
 (c) a gene termination sequence.

8. The construct of claim 7 wherein the polynucleotide is in a sense orientation.

9. The construct of claim 7 wherein the polynucleotide is in an antisense orientation.

10. The construct of claim 7, wherein the gene promoter sequence is functional in a plant host to provide for transcription in xylem.

11. A transgenic plant cell comprising a construct of claim 1.

12. A plant comprising a transgenic plant cell according to claim 11, or fruit or seeds or progeny thereof.

13. A method for modulating one or more of the lignin content, the lignin composition and the lignin structure of a plant, comprising stably incorporating into the genome of the plant a polynucleotide of claim 1.

14. The method of claim 13, wherein the plant is selected from the group consisting of *eucalyptus* and pine species.

15. The method of claim 13, comprising stably incorporating into the genome of the plant a construct of claim 7.

16. A method for producing a plant having one or more of altered lignin content, altered lignin composition and altered lignin structure, comprising:
 (a) transforming a plant cell with a construct of claim 7 to provide a transgenic cell; and
 (b) cultivating the transgenic cell under conditions conducive to regeneration and mature plant growth.

17. A method for modifying the activity of a polypeptide involved in a lignin biosynthetic pathway in a plant comprising stably incorporating into the genome of the plant a construct of claim 7.

18. A method for modifying the activity of a polypeptide involved in a lignin biosynthetic pathway in a plant, comprising introducing into cells of the plant RNA corresponding to a polynucleotide of claim 1, thereby inhibiting expression of a polypeptide encoded by the polynucleotide.

19. A method for modifying the activity of a polypeptide involved in a lignin biosynthetic pathway in a plant, comprising introducing into cells of the plant double stranded RNA corresponding to a polynucleotide of claim 1, thereby inhibiting expression of a polypeptide encoded by the polynucleotide.

20. A genetic construct comprising a polynucleotide of any one of claims 2 and 3.

21. A transgenic cell comprising a construct according to claim 20.

22. A transgenic plant comprising a transgenic cell according to claim 21, or fruit or seeds or progeny thereof.

23. The genetic construct of claim 5, further comprising a promoter operably linked to the polynucleotide.

24. The genetic construct of claim 23, wherein the polynucleotide encodes an RNA transcript coding for a polypeptide having ferulate-5-hydroxylase activity.

* * * * *